US010614724B2

(12) United States Patent
Catani et al.

(10) Patent No.: US 10,614,724 B2
(45) Date of Patent: Apr. 7, 2020

(54) SYSTEMS AND METHODS FOR WELLNESS, HEALTH, AND LIFESTYLE PLANNING, TRACKING, AND MAINTENANCE

(71) Applicant: Johnson & Johnson Consumer Inc., Skillman, NJ (US)

(72) Inventors: Steve Catani, Athens, GA (US); Jeffrey Matthes, Ypsilanti, MI (US); Janeta Nikolovski, Princeton, NJ (US); Richard Bedrosian, Shrewsbury, MA (US); Amy Michelle Bucher, Boston, MA (US); Benjamin C. Wiegand, Yardley, PA (US); Juan L. Navia, Doylestown, PA (US); Kevin Wildenhaus, Skillman, NJ (US); Sanjay Mandloi, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1205 days.

(21) Appl. No.: 14/739,318

(22) Filed: Jun. 15, 2015

(65) Prior Publication Data
US 2015/0364057 A1    Dec. 17, 2015

Related U.S. Application Data

(60) Provisional application No. 62/013,456, filed on Jun. 17, 2014.

(51) Int. Cl.
*G09B 5/02*    (2006.01)
*G06F 19/00*    (2018.01)
(Continued)

(52) U.S. Cl.
CPC .......... *G09B 5/02* (2013.01); *G06F 19/3481* (2013.01); *G06Q 30/0271* (2013.01);
(Continued)

(58) Field of Classification Search
None
See application file for complete search history.

(56) References Cited

U.S. PATENT DOCUMENTS

| 5,673,691 A | 10/1997 | Abrams et al. |
| 6,039,688 A | 3/2000 | Douglas et al. |

(Continued)

OTHER PUBLICATIONS

International Search Report for International Application No. PCT/US2015/036124 dated Sep. 8, 2015.
(Continued)

*Primary Examiner* — Dennis W Ruhl
*Assistant Examiner* — William G Lultschik
(74) *Attorney, Agent, or Firm* — Mintz Levin Cohn Ferris Glovsky and Popeo, P.C.

(57) ABSTRACT

Systems and methods for wellness, health, and lifestyle planning, tracking, and maintenance are provided. In general, the systems and methods described herein can allow a person to manage his/her wellness, health, and lifestyle using a convenient system that can help the person plan strategies for improving and/or maintaining his/her wellness, health, and lifestyle and/or that can help the person track his/her compliance with the strategies. In an exemplary embodiment, the system can be configured to provide recommendations of activities to the person that can positively affect the person's wellness, health, and lifestyle. The recommendations can be tailored to each individual user of the system such that different people can receive different recommendations.

25 Claims, 61 Drawing Sheets

(51) Int. Cl.
*G06Q 30/02* (2012.01)
*G16H 10/60* (2018.01)
*G16H 20/30* (2018.01)
*G16H 20/60* (2018.01)
*G09B 19/00* (2006.01)

(52) U.S. Cl.
CPC ......... *G09B 19/0092* (2013.01); *G16H 10/60* (2018.01); *G16H 20/30* (2018.01); *G16H 20/60* (2018.01)

(56) References Cited

U.S. PATENT DOCUMENTS

| | | |
|---|---|---|
| 7,003,515 B1 | 2/2006 | Glaser et al. |
| 7,962,482 B2 | 6/2011 | Handman et al. |
| 8,075,451 B2 | 12/2011 | Dugan |
| 8,423,380 B1* | 4/2013 | Gelly .............. G06F 19/324 705/2 |
| 8,666,844 B2 | 3/2014 | Shaya et al. |
| 2006/0206478 A1 | 9/2006 | Glaser et al. |
| 2006/0212442 A1 | 9/2006 | Conrad et al. |
| 2006/0212444 A1 | 9/2006 | Handman et al. |
| 2010/0293036 A1* | 11/2010 | Meyer .............. G06Q 30/02 705/14.66 |
| 2011/0054269 A1* | 3/2011 | Lee .............. A61B 5/00 600/300 |
| 2013/0268395 A1* | 10/2013 | Sandow .............. G06Q 30/02 705/26.7 |
| 2014/0074861 A1 | 3/2014 | Bieschke et al. |
| 2014/0115008 A1 | 4/2014 | Stivoric et al. |
| 2014/0156646 A1* | 6/2014 | Brust .............. G06F 17/30554 707/722 |
| 2014/0236622 A1* | 8/2014 | Southam .............. G06Q 30/02 705/2 |
| 2014/0349262 A1 | 11/2014 | Mason et al. |
| 2015/0110387 A1* | 4/2015 | Lienhart .............. G06F 17/30256 382/159 |

OTHER PUBLICATIONS

Song et al. "Online Behavioral Genome Sequencing from Usage Logs: Decoding the Search Behaviors." *Microsoft Research*. Web. Mar. 2014. http://research.microsoft.com/apps/pubs/default.aspx?is=208414.

O'Neil. "Columbia Data Science course, week 7: Hunch.com, recommendation engines, SVD, alternating least squares, convexity, filter bubble." *Mathbabe*. Oct. 18, 2012. <http://mathbabe.org/2012/10/18/columbia-data-science-course-week-7-hunch-com-recommendation-engines-svd-alternating-least-squares-convexity-filter-bubbles/>.

Patel et al., "Wearable devices as facilitators, not drivers, of health behavior change." Journal of American Medical Association E1-E2 (published online Jan. 8, 2015).

* cited by examiner

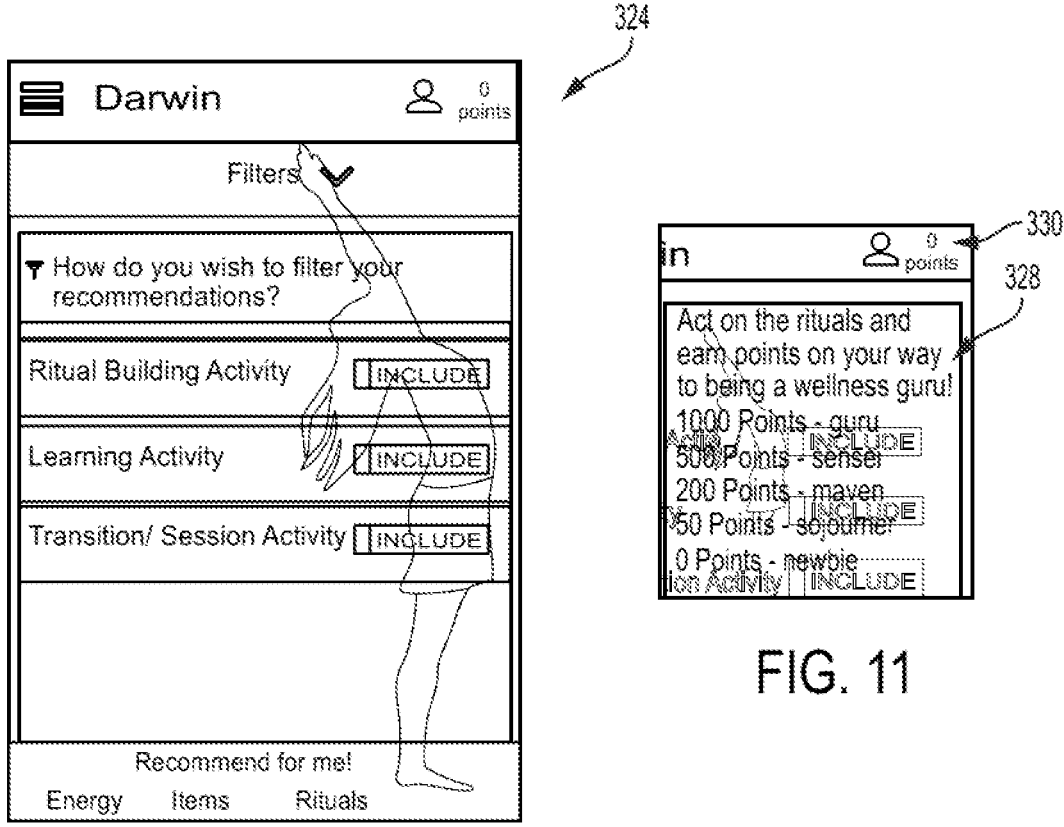
FIG. 10
FIG. 11
FIG. 12

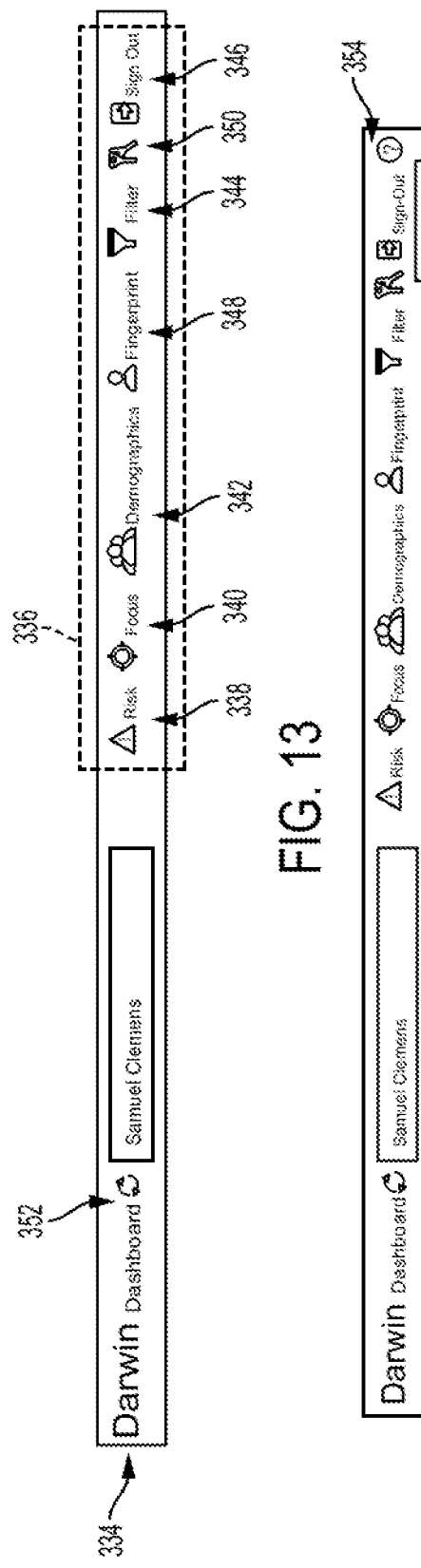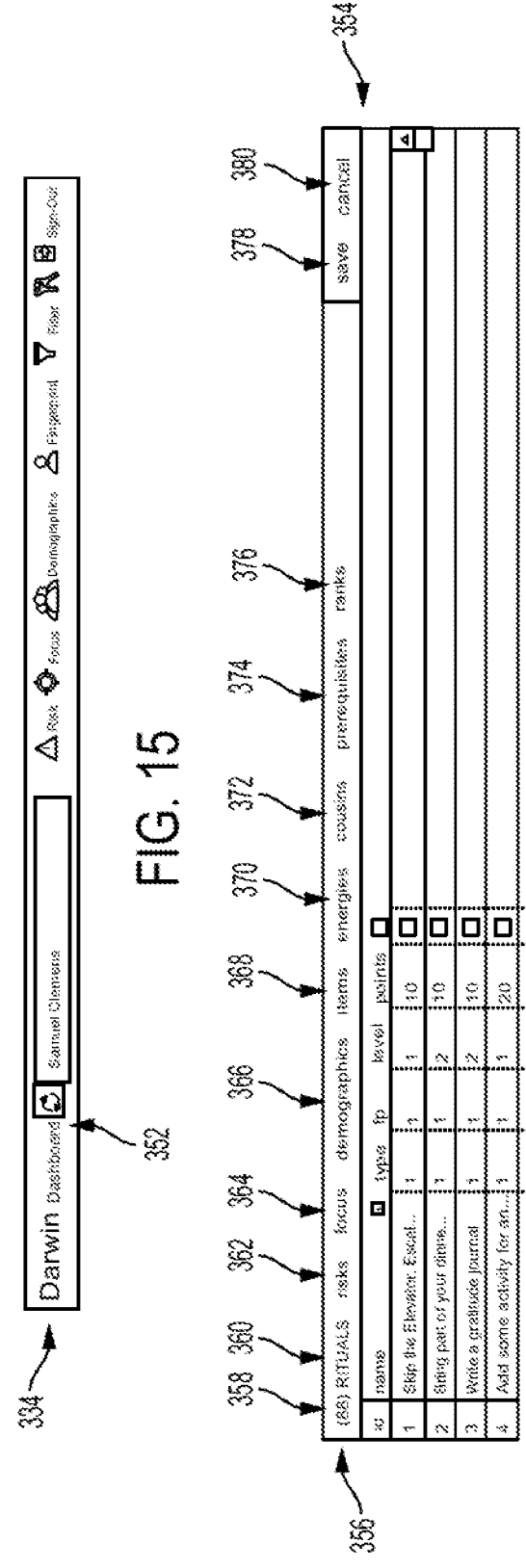

FIG. 20

| (88) RITUALS | risks | | focus | demographics | items | ene |
|---|---|---|---|---|---|---|
| id | name | ◨ | type | fp | level | points | ☐ |
| 1 | Skip the Elevator, Escal... | 1 | 1 | 1 | 10 | ☐ |
| 2 | Bring part of your dinne... | 1 | 1 | 2 | 10 | ☐ |
| 3 | Write a gratitude journal | 1 | 1 | 2 | 10 | ☐ |
| 4 | Add some activity for an... | 1 | 1 | 1 | 20 | ☐ |
| 5 | Quit Drinking coffee aft... | 1 | 1 | 2 | 10 | ☐ |
| 6 | Deep Breathing | 1 | 1 | 1 | 20 | ☐ |
| 7 | Use a standup desk | 1 | 1 | 2 | 10 | ☐ |
| 8 | Plant a garden | 1 | 1 | 2 | 10 | ☐ |
| 9 | Establish a bed time | 1 | 1 | 1 | 10 | ☐ |

FIG. 21

Hi Sam, here is a list of things the system picked to help you achieve your mission...

*Click on any item to learn more about it or just get started!*

Learn about adding a little Activity to your Life

Learn how to build rituals and get more energy to live the life you want

Skip the Elevator, Escalator, or People Mover

Add some activity for an everyday task

Go to the gym with a friend

Play a outdoors with the family

Use an Energy Tracker

Add a recovery break to your day

Have Dinner with the family

Eat Lean Meals

Level 1 Wellness Newbie

You can also look a more choices...

Next List — 400

Previous List — 402

... or filter the list.

Show activities that:

| Expand Energy | Fuel Energy |
| Recover Energy | Focus Energy |
| Preserve Energy | |

... or with certain attributes none

... and include:

Ritual Building | Learning Activities

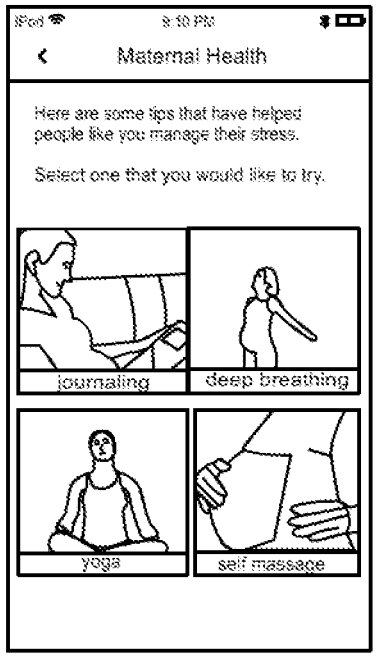
FIG. 89
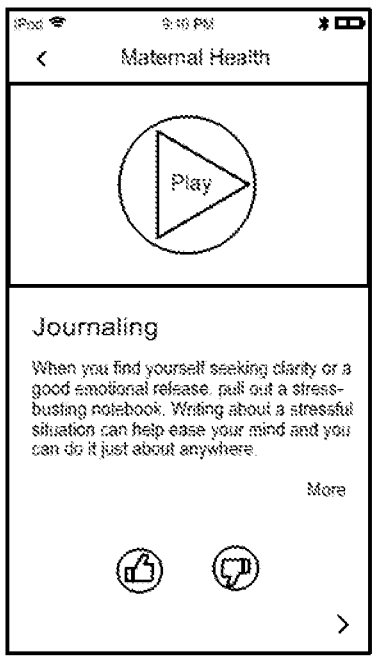
FIG. 90
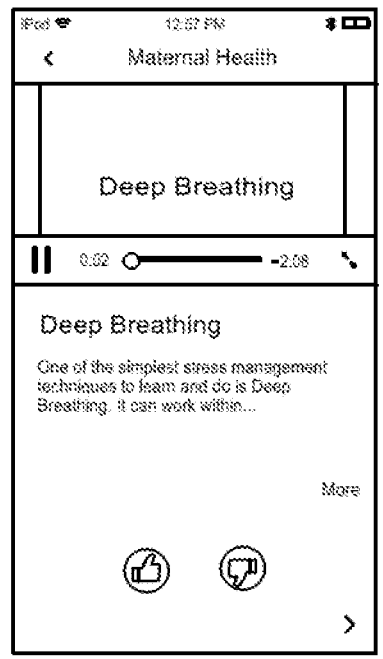
FIG. 91
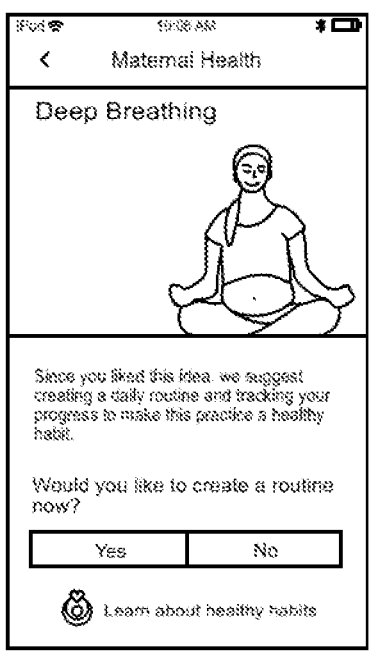
FIG. 92
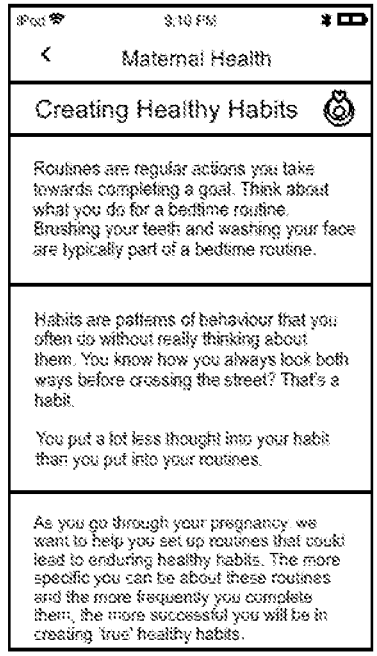
FIG. 93
FIG. 93A

SYSTEMS AND METHODS FOR WELLNESS, HEALTH, AND LIFESTYLE PLANNING, TRACKING, AND MAINTENANCE

CROSS REFERENCE TO RELATED APPLICATIONS

The present application claims priority to U.S. Provisional Application No. 62/013,456 entitled "Systems And Methods For Wellness, Health, And Lifestyle Planning, Tracking, And Maintenance" filed Jun. 17, 2014, which is hereby incorporated by reference in its entirety.

FIELD

The present disclosure relates generally to systems and methods for wellness, health, and lifestyle planning, tracking, and maintenance.

BACKGROUND

A traditional model for managing personal health includes several phases. These phases typically include wellness and prevention, diagnosis, and treatment.

The wellness and prevention phase typically involves a person a monitoring his/her own health and having periodic check-up visits with a care provider. The diagnosis phase typically involves the care provider determining an ailment of the person when the care provider determines that the patient has a health problem. The care provider can reach the diagnosis by consulting any one or more knowledge sources, such as his/her previous experience and knowledge, consultation with colleague(s), review of print and/or electronic literature, and review of diagnostic tests/procedures. During the treatment phase, the care provider typically determines a treatment plan for the person to address the diagnosis, e.g., to relieve the patient of symptom(s).

In the wellness and prevention phase, it can be difficult for people to monitor their health on a continual, long term basis. For non-limiting example, it can be difficult for people to track factors related to their health, such as exercise and diet. Developing their own health tracking tools can be very time consuming, can overlook one or more factors that would be helpful for a care provider to evaluate in the diagnosis and/or treatment phases, and/or can become so burdensome that people reduce their tracking or abandon the tracking altogether. For another non-limiting example, it can be difficult for people to know ways to maintain and/or improve their health without conducting research and/or consulting a care provider. Such resources can be costly, can be unavailable when a person is interested to learn about them, and/or can only provide generalized advice without taking into account a specific person's capabilities, interests, and daily schedule. For yet another non-limiting example, factors relevant to a person's health can change over time, such as by the person aging, the person undergoing a medically significant event (e.g., becoming pregnant, developing diabetes, breaking an arm, etc.), the person moving geographically such that previously available wellness resources are no longer available and/or new wellness resources are available, and/or the person making progress such that his/her abilities and needs have changed. The person may not even be aware when health factors are changing, such as during the aging process, such that the person may not know to vary his/her wellness and prevention habits. Even if the person is aware that health factors are changing, such as when a person moves to university from home, the person can often be unaware of how to change his/her wellness and prevention habits in view of his/her new circumstances, thereby at least temporarily adversely affecting his/her health.

Accordingly, there remains a need for improved systems and methods for wellness, health, and lifestyle planning, tracking, and maintenance.

SUMMARY

The present invention generally provides systems and methods for wellness, health, and lifestyle planning, tracking, and maintenance. In one embodiment, a user management system is provided that in one embodiment includes a storage device and a processor. The storage device can store a fingerprint that includes a plurality of characteristics unique to an individual. Each of the plurality of characteristics can be represented by one of a first variable, a second variable, and a third variable. The first variable can indicate a first condition of the individual with respect to that characteristic, the second variable can indicate a second condition of the individual with respect to that characteristic, and the third variable can indicate a neutral position of the individual with respect to that characteristic. The first and second conditions can be mutually exclusive, and each of the plurality of characteristics can be defaulted to being represented by the third variable. The processor can be configured to perform functions of displaying on a display a prompt to which a user can provide an input in response thereto, receiving the input, and updating one or more of the variables representing the plurality of characteristics based on the received input, thereby updating the fingerprint so as to reflect the user's input.

The system can vary in any number of ways. For example, each of the plurality of characteristics can be limited to being represented by one of the first, second, and third variables. For another example, the storage device can store a profile for each of a plurality of consumable products, and the processor can be configured to perform a function of comparing the profiles of the plurality of consumable products with the fingerprint, thereby identifying at least one consumable product in the plurality of consumable products that has a profile corresponding to the fingerprint. The processor can be configured to perform a function of causing the identified at least one consumable product to be provided to the user. The received input can indicate an opinion of the user with respect to the provided at least one consumable product.

For yet another example, the storage device can store a profile for each of a plurality of activities providing a positive benefit to at least one of wellness, health, and lifestyle, and the processor can be configured to perform a function of comparing the profiles of the plurality of activities with the fingerprint, thereby identifying at least one activity in the plurality of activities that has a profile corresponding to the fingerprint. The processor can be configured to perform a function of causing the identified at least one activity to be indicated on the display. The received input can indicate an opinion of the user with respect to the indicated at least one activity. The plurality of activities can include at least two of an athletic activity, eating a healthy food, drinking a healthy drink, forming a healthy habit, engaging in an individual sport, engaging in a group sport, gardening, taking a walk, jogging, swimming, stretching, yoga, pilates, tai chi, meditation, doing housework, taking an in-person educational course regarding at least one of wellness, health, and lifestyle, taking an online educational course regarding at least one of wellness, health, and lifestyle, deep breathing, martial arts, making art, playing music, writing a handwritten letter, writing an electronic letter, talking on the telephone to a family member, talking on the telephone to a friend, bringing a meal to work, cooking a meal at home, sleeping, walking a dog, quitting smoking, reducing an amount of smoking per day, quitting drinking coffee, reducing an amount of coffee intake per day, stopping drinking coffee after a certain hour of the day, establishing a bed time, purchasing a device that assists in at least one of a wellness, health, or lifestyle behavior, using a device that assists in at least one of a wellness, health, or lifestyle behavior, reducing an intake amount of an unhealthy food, reducing an intake amount of an alcoholic beverage, and establishing a waking time.

For still another example, the updating can include changing the fingerprint by multiplying the variable of the one or more of the plurality of characteristics by a scaling factor that is dependent on a type of the received input. The type of the received input can be selected from the group consisting of an indication of a decision to engage in an activity immediately, an indication of a decision to engage in an activity at a future point in time, engagement in an activity, repeated performance of an activity, an indication of a decision to not engage in an activity previously indicated as an activity that the user would engage in immediately, an indication of a decision to not engage in an activity previously indicated as an activity that the user would engage in at a future time, an indication of a beneficial experience as a result of engaging in an activity, and an indication of a negative experience as a result of engaging in an activity.

For another example, each of the plurality of characteristics can be classified as being of a first type of characteristic that changes over time at a first rate or as being of a second type of characteristic that changes over time at a second rate that is slower than the first rate. The processor can update the one or more of the variables based on whether the characteristics represented by the one or more of the variables are classified as being of the first type or of the second type.

In another aspect, a user management method is provided that in one embodiment includes storing suggestions in at least one storage device, and storing information about a user in the at least one storage device. Each of the suggestions can be described by two or more first factors that each have a value, and the information about the user can be described by two or more second factors that each have a value specific to the user. The method can also include selecting at least one of the suggestions by comparing the values of the second factors with the values of the first factors for each of the suggestions and determining which of the suggestions has first factors with values that most closely match the values of the second factors. The method can also include causing the at least one selected suggestion to be communicated to the user, acquiring an outcome indicative of the user acting on the at least one suggestion, and causing the value of at least one of the second factors to be modified to be closer to the values of the first factors of the acted on suggestion in response to the acquired outcome being a positive outcome.

The method can have any number of variations. For example, the method can include causing the value of at least one of the second factors to be modified to be farther away from the values of the first factors of the acted on suggestion in response to the acquired outcome being a negative outcome. For another example, the values of the second factors can not be modified in response to the acquired outcome being a negative outcome. For yet another example, the method can include, in response to the acquired outcome being the positive outcome, causing the value of at least one of the second factors of suggestions previously acted on by the user to be modified to be closer to the values of the first factors of the acted on suggestion. For still another example, the value for each of the two or more second factors can be one of a first value that represents a first characteristic, a second value that represents a second characteristic that is mutually exclusive to the first characteristic, and a third value that represents a third characteristic that is neutral with respect to the first and second characteristics. The value for each of the two or more first factors can be one of the first, second, and third values. For another example, each of the two or more second factors can represent a different characteristic related to a specific product category, the at least one selected suggestion can include a suggestion for a specific product within the specific product category, and the acquired outcome can include an opinion of the user regarding the suggested specific product. For still another example, each of the two or more second factors can represent a different characteristic related to at least one of the user's health, wellbeing, and lifestyle, the at least one selected suggestion can include a suggestion for a specific activity that provides a positive benefit to the at least one of the user's health, wellbeing, and lifestyle, and the acquired outcome can include an opinion of the user regarding the suggested specific activity. For yet another example, the method can include causing at least one of the suggestions that is not selected to be communicated to the user at a predetermined frequency.

In another embodiment, a user management method includes storing characteristic information for an individual, storing characteristic information forming a profile for each of a plurality of recommendations, and identifying a subset of recommendations from among the plurality of recommendations. The characteristic information can include an array of values, each of the values can represent a characteristic of the individual, and the profile of each recommendation in the subset of recommendations can correspond to the array of values. The method can also include identifying one or more recommendations from among the subset of recommendations that have not been engaged in by the individual, and providing the identified one or more recommendations as suggested recommendations to the individual.

The method can vary in any number of ways. For example, the method can include receiving information indicating that the individual engaged in at least one of the suggested recommendations, and updating the array of values based on the received information, and after the updating, identifying a second subset of recommendations from among the plurality of recommendations, identifying one or more recommendations from among the second subset of recommendations that have not been engaged in by the individual, and providing the one or more recommendations identified from among the second subset of recommendations as suggested recommendations to the individual. For another example, the method can include receiving information indicating the individual's likability of at least one previously performed activity, and filtering the one or more identified recommendations based on the received information. The providing of the identified one or more recommendations as suggested recommendations can include only the filtered identified one or more recommendations. For yet another example, the method can include storing information associated with the individual that indicates one or more personal goals of the individual, determining which of the recommendations in the subset of recommendations are associated with goal factors that correspond to each of the one or more personal goals, and excluding from the suggested recommendations any of the recommendations in the subset of recommendations that are not associated with the goal factors that correspond to each of the one or more personal goals.

For still another example, the plurality of recommendations can include recommendations for specific consumable products that can be used by a person such that the suggested recommendations recommend one or more of the specific consumable products to the individual. The method can include receiving an indication of the individual's interest in one or more of the recommended consumable products, providing the indicated one or more of the recommended consumable products to the individual, receiving an indication of the individual's opinion of the provided one or more recommended consumable products, updating the array of values based on the received indication of the individual's opinion, identifying a second subset of recommendations from among the plurality of recommendations, identifying one or more recommendations from among the second subset of recommendations, providing the identified one or more recommendations from among the second subset of recommendations as suggested recommendations to the individual, receiving an indication of the individual's interest in one or more of the recommended consumable products from among the second subset of recommendations, and providing the indicated one or more of the recommended consumable products from among the second subset of recommendations to the individual.

For yet another example, the plurality of recommendations can include recommendations for activities to be performed by a person that each provide a positive benefit to at least one of health, wellbeing, and lifestyle of the person such that the suggested recommendations recommend one or more of the activities to the individual. The method can include receiving an indication that the individual at least partially performed one or more of the one or more recommended activities, updating the array of values based on the received indication, identifying a second subset of recommendations from among the plurality of recommendations, identifying one or more recommendations from among the second subset of recommendations, and providing the identified one or more recommendations from among the second subset of recommendations as suggested recommendations to the individual.

In another aspect, a system is provided that in one embodiment includes a storage device and an analysis module. The storage device can store characteristic information forming a fingerprint for an individual, and characteristic information forming a fingerprint for each of a plurality of activities. The analysis module can be configured to identify a subset of activities from among the plurality of activities, the fingerprint of each activity in the subset of activities corresponding to the fingerprint of the individual, identify one or more activities from among the subset of activities that have not been performed by the individual, and provide the identified one or more activities as suggested activities to the individual.

The system can vary in any number of ways. For example, the system can include at least one display, and providing the one or more identified activities can include showing the one or more identified activities on the at least one display.

For another example, the system can include an input module configured to receive information indicating the individual's likability of at least one previously performed activity. The analysis module can be configured to filter the one or more identified activities based on the received information, and the providing of the identified one or more activities as suggested activities can include only the filtered identified one or more activities, and/or the analysis module can be configured to predict which of the identified one or more activities that the individual may prefer based on the received information, and the identified one or more activities can be provided to the individual with an indication of the prediction.

For yet another example, the system can include an input module configured to receive information indicating a level of strenuousness for at least one activity previously performed by the user. The analysis module can be configured to filter the one or more identified activities based on the received information, the providing of the identified one or more activities as suggested activities including only the filtered identified one or more activities; the analysis module can be configured to predict which of the identified one or more activities that the individual may prefer based on the received information, the identified one or more activities in at least some embodiments being provided to the individual with an indication of the prediction; the level of strenuousness can be pre-programmed for the at least one activity previously performed by the individual so as to be associated therewith without the individual indicating the level of strenuousness; and/or the input module can be configured to prompt the individual to input the level of strenuousness for the at least one activity previously performed by the individual.

For still another example, the at least one activity can have an associated number of points, and the analysis module can be configured to add the associated number of points to a running total of points accumulated by the individual. The analysis module can be configured to trigger a reward for the individual when the running total of points meets or exceeds a predetermined number of points. The reward can include one or more of an image visible on a display, an increase in user level, an ability to customize a look of the system on an interface that the individual uses to access the system, access to a previously hidden area of the system, virtual money usable for purchase of virtual items provided by the system, non-virtual money usable for purchase of virtual items available from the system, non-virtual money usable for purchase of non-virtual items available from the system, non-virtual money usable for purchase of non-virtual items from a third party and non-virtual money usable for purchase of virtual items from a third party.

For another example, the activity performed by the individual can include at least one athletic activity. The analysis module can be configured to determine whether the activity performed by the individual is an individual athletic activity or a group athletic activity, and filter the one or more identified activities based on the determination of whether the at least one athletic activity is an individual athletic activity or a group athletic activity such that the provided one or more activities exclude individual athletic activities if the at least one athletic activity is a group athletic activity and the provided one or more activities exclude group athletic activities if the at least one athletic activity is an individual athletic activity.

For yet another example, the activity performed by the individual can include at least one of eating a healthy food and drinking a healthy drink. For another example, the activity performed by the individual can include at least one healthy habit. For still another example, the activity performed by the individual can include at least one of engaging in an individual sport, engaging in a group sport, eating a healthy food, drinking a healthy drink, gardening, taking a walk, jogging, swimming, stretching, yoga, pilates, tai chi, meditation, doing housework, taking an in-person educational course regarding at least one of wellness, health, and lifestyle, taking an online educational course regarding at least one of wellness, health, and lifestyle, deep breathing, martial arts, making art, playing music, writing a handwritten letter, writing an electronic letter, talking on the telephone to a family member, talking on the telephone to a friend, bringing a meal to work, cooking a meal at home, sleeping, walking a dog, quitting smoking, reducing an amount of smoking per day, quitting drinking coffee, reducing an amount of coffee intake per day, stopping drinking coffee after a certain hour of the day, establishing a bed time, purchasing a device that assists in at least one of a wellness, health, or lifestyle behavior, using a device that assists in at least one of a wellness, health, or lifestyle behavior, reducing an intake amount of an unhealthy food, reducing an intake amount of an alcoholic beverage, and establishing a waking time. For yet another example, the input module can be configured to cause the received first information and the received second information to be stored in the at least one storage device. For another example, the positive benefit can be to at least one of wellness, health, and lifestyle. For still another example, the system can include at least one display, and providing the one or more identified activities can include showing the one or more identified activities on the at least one display. For yet another example, the system can include at least one processor, and at least one storage device configured to store instructions executable by the at least one processor to execute the functions performed by the analysis module.

A computer-readable storage medium having stored thereon at least one program that when executed causes a computer to perform a method that can include the functions performed by the analysis module of the system. The storage medium can vary in any number of ways. For example, the storage medium can include a tangible storage device included as part of a computer. For another example, the storage medium can include a tangible storage device removably and replaceably attachable to computer via at least one of a disk drive and a data port. The data port can include at least one universal serial bus (USB) port and a 1394 port.

A method can include the functions performed by the analysis module of the system.

In another embodiment, a system includes an input module, a storage device, and an analysis module. The input module can be configured to receive first information indicating an activity selected by a user, and receive second information indicating a demographic for the user such that the user has the first information and second information associated therewith. The activity can provide a positive benefit to the user. The first information can include a plurality of activity factors the second information including a plurality of demographic factors. The storage device can store activity information for a plurality of activities. The activity information for each of the plurality of activities can have associated therewith third information. Each of the plurality of activities can provide a positive benefit to at least one of the user. The third information can include a plurality of predetermined factors. The analysis module can be configured to identify one or more activities from the plurality of activities that a highest number of the plurality of the predetermined factors that match the plurality of activity factors of the user, and provide the identified one or more activities as suggested activities to the user.

The system can have any number of variations. For example, each of the plurality of activity factors can have one of first, second, and third values. The first value can be a default null value indicating no information, the second value can indicate a first condition with respect to the activity, the third value can indicate a second condition with respect to the activity, and the first condition can be mutually exclusive of the second condition. The input module can be configured to receive fourth information indicating a second activity selected by the user such that the user also has the fourth information associated therewith, the second activity providing a positive benefit to the user and the fourth information including a plurality of activity factors, and the analysis module can be configured to automatically change any of the plurality of activity factors from the first value to one of the second value and the third value based on fourth information; and/or the input module can be configured to receive fourth information indicating a second activity selected by the user such that the user also has the fourth information associated therewith, the second activity providing a positive benefit to the user and the fourth information including a plurality of activity factors, and the analysis module can be configured to automatically change any of the plurality of activity factors from its first, second, or third value to a fourth value based on fourth information, the fourth information being related to the first information such that the fourth information indicates that the one or more activity factors changed to the fourth value should be so changed to reflect the fourth information received after the first information.

For another example, each of the plurality of demographic factors can have one of first, second, and third values. The first value can be a default null value indicating no information, the second value can indicate a first condition with respect to the demographic, the third value can indicate a second condition with respect to the demographic, and the first condition can be mutually exclusive of the second condition. The input module can be configured to receive fourth information indicating a second demographic for the user such that the user has the fourth information associated therewith, the fourth information including a plurality of demographic factors, and the analysis module can be configured to automatically change any of the plurality of demographic factors from the first value to one of the second value and the third value based on fourth information; and/or the input module can be configured to receive fourth information indicating a second demographic for the user such that the user also has the fourth information associated therewith, the fourth information including a plurality of demographic factors, and the analysis module can be configured to automatically change any of the plurality of demographic factors from its first, second, or third value to a fourth value based on fourth information, the fourth information being related to the first information such that the fourth information indicates that the one or more demographic factors changed to the fourth value should be so changed to reflect the fourth information received after the first information.

For yet another example, the second information can be a direct input of information from the user in response to a question. For still another example, the positive benefit to the user can be a positive benefit of at least one the user's wellness, health, and lifestyle. For another example, the positive benefit to the user can be a positive benefit with respect to user of a specific product category, e.g., at least one of a vitamin, a cosmetic, a skin care product, computer equipment, and clothing. For yet another example, the system can include at least one display, and providing the suggested activities can include showing the suggested activities on the at least one display.

A method can include the functions performed by the input and analysis modules of the system.

In another embodiment, a system includes at least one storage device storing instructions and storing activity data regarding a plurality of individuals, and at least one processor configured to execute the instructions so as to receive activity data for a user. The activity data for the user can indicate at least one activity performed by the user that positively affects the user. The at least one processor can be configured to execute the instructions so as to compare the activity data for the user with the activity data for the plurality of individuals, determine one or more activities that each positively affect the user should be recommended to the user based on the comparison, and provide the determined one or more activities to the user.

The system can vary in any number of ways. For example, comparing the activity data can include determining a subset of the plurality of individuals who have performed the at least one activity performed by the user, and determining the one or more activities comprises identifying one or more activities that have been performed by the subset and that positively affect the user. The at least one storage device can also store demographic data for each of the individuals, the user data can also include demographic data for the user, the at least one processor can also be configured to execute the instructions so as to compare the demographic data for the user with the demographic data for the plurality of individuals so as to determine a second subset of the plurality of individuals who have demographic data corresponding to the demographic data of the user, and determining the one or more activities can include identifying one or more activities that have been performed by the subset and the second subset.

For another example, the at least one storage device can also store demographic data for each of the individuals, the user data can include demographic data for the user, the at least one processor can also be configured to execute the instructions so as to compare the demographic data for the user with the demographic data for the plurality of individuals, and determining the one or more activities can also be based on the comparison of the demographic data.

For yet another example, the activity data can also indicate a user likability rating of the at least one activity performed by the user. Determining the one or more activities can also be based on the user likability rating of the at least one activity performed by the user, and/or the at least one processor can also be configured to execute the instructions so as to predict which of the determined one or more activities that the user may prefer based on the user likability rating of the at least one activity performed by the user, and the determined one or more activities can be provided to the user with an indication of the prediction.

For still another example, the activity data can also indicate a level of strenuousness for the at least one activity performed by the user. Determining the one or more activities can also be based on the level of strenuousness of the at least one activity performed by the user; the level of strenuousness can be pre-programmed for the at least one activity performed by the user so as to be associated therewith without the user indicating the level of strenuousness; the at least one processor can also be configured to execute the instructions so as to prompt the user to input the level of strenuousness for the at least one activity performed by the user; and/or the at least one processor can also be configured to execute the instructions so as to predict which of the determined one or more activities that the user may prefer based on the level of strenuousness of the at least one activity performed by the user, and the determined one or more activities can be provided to the user with an indication of the prediction.

For another example, the at least one activity can have an associated number of points, and the processor can be configured to execute the instructions so as to add the associated number of points to a running total of points accumulated by the user. The processor can be configured to execute the instructions so as to trigger a reward for the user when the running total of points meets or exceeds a predetermined number of points. The reward can include one or more of an image visible on a display, an increase in user level, an ability to customize a look of the system on an interface that the user uses to access the system, access to a previously hidden area of the system, virtual money usable for purchase of virtual items provided by the system, non-virtual money usable for purchase of virtual items available from the system, non-virtual money usable for purchase of non-virtual items available from the system, non-virtual money usable for purchase of non-virtual items from a third party and non-virtual money usable for purchase of virtual items from a third party.

For still another example, the at least one activity can include at least one athletic activity. The processor can be configured to execute the instructions so as to determine whether the at least one athletic activity is an individual athletic activity or a group athletic activity, and the determining the one or more activities can also be based on whether the at least one athletic activity is determined to be an individual athletic activity or a group athletic activity such that the provided one or more activities exclude individual athletic activities if the at least one athletic activity is a group athletic activity and the provided one or more activities exclude group athletic activities if the at least one athletic activity is an individual athletic activity.

For yet another example, the at least one activity can include at least one of eating a healthy food and drinking a healthy drink. For another example, the at least one activity can include at least one healthy habit. For still another example, the at least one activity can include at least one of engaging in an individual sport, engaging in a group sport, eating a healthy food, drinking a healthy drink, gardening, taking a walk, jogging, swimming, stretching, yoga, pilates, tai chi, meditation, doing housework, taking an in-person educational course regarding at least one of wellness, health, and lifestyle, taking an online educational course regarding at least one of wellness, health, and lifestyle, deep breathing, martial arts, making art, playing music, writing a handwritten letter, writing an electronic letter, talking on the telephone to a family member, talking on the telephone to a friend, bringing a meal to work, cooking a meal at home, sleeping, walking a dog, quitting smoking, reducing an amount of smoking per day, quitting drinking coffee, reducing an amount of coffee intake per day, stopping drinking coffee after a certain hour of the day, establishing a bed time, purchasing a device that assists in at least one of a wellness, health, or lifestyle behavior, using a device that assists in at least one of a wellness, health, or lifestyle behavior, reducing an intake amount of an unhealthy food, reducing an intake amount of an alcoholic beverage, and establishing a waking time. For yet another example, at least one activity performed by the user can positively affect at least one of the user's wellness, health, and lifestyle, and the one or more activities can each positively affect at least one of the user's wellness, health, and lifestyle. For another example, the processor can be configured to execute the instructions so as to cause the received user data to be stored in the at least one storage device. For yet another example, the at least one storage device can be remotely located from the processor. For still another example, the at least one storage device can be located in a same local device as the processor. For another example, the system can include at least one display, and providing the recommendation can include showing the recommendation on the at least one display.

A method can include the functions performed by the at least one processor of the system In another embodiment, a system includes a display, a memory storing instructions, and a processor configured to execute the instructions stored in the memory that cause a plurality of activity options to be displayed on the display. Each of the plurality of activity options can be activities that can be performed by an individual and that each positively benefit the individual. The processor can be configured to execute the instructions stored in the memory that cause the processor to receive information from a user indicating that the user performed one or more of the plurality of activity options, and the user's level of enjoyment of the performed one or more activities. The processor can be configured to execute the instructions stored in the memory that cause a second plurality of activity options to be displayed on the display. Each of the second plurality of options can be activities that can be performed by the individual and that can each positively benefit the individual. Each of the second plurality of activity options can reflect the indicated level of enjoyment of the performed one or more activities such that all of the second plurality of activity options are predicted to be enjoyed by the user based on the indicated level of enjoyment.

The system can have any number of variations. For example, the indicated level of enjoyment can correspond to a category of activities, and the second plurality of activity options can all be included in the category of activities. The category of activities can be based on a strenuousness of the activities in the category, on whether the activities in the category are performed indoors or outdoors, on whether the activities in the category are performed solo or in a group, on a time of day that the activities in the category are performed, on whether the activities in the category are performed with a pet, on whether the activities in the category are performed with a child, on a strenuousness of the activities in the category, and/or on whether the activities in the category require repeated participation, e.g., at least one of multiple times a day, daily, multiple times a week, weekly, multiple times a month, monthly, multiple times a year, and yearly. The second plurality of activity options can be selected from among activities previously performed by a plurality of individuals who also previously performed the one or more activity options performed by the user. The positive benefit can benefit at least one of the individual's wellness, health, and lifestyle. The user can have associated therewith demographic information, the plurality of individuals can each have associated therewith demographic information, and the second plurality of activity options can be selected from among activities previously performed by the plurality of individuals who also have overlapping demographic information with the demographic information associated with the user.

For another example, the user can have associated therewith medical history information indicating one or more medical factors of concern, and the second plurality of activity options can be selected from among activities categorized as being beneficial to one or more medical factors of concern. The one or more medical factors of concern can include at least one of a diagnosed medical condition, a tentatively diagnosed medical condition, being overweight, hypertension, diabetes, a prior surgical procedure, having a family history of a medical condition, and advanced age.

For yet another example, the memory can be remotely located from the processor. For still another example, the memory can be located in a same local device as the processor.

A method can include the functions performed by the at least one processor of the system.

In another embodiment, a system includes a display, a storage device that stores information regarding a plurality of activity options, and at least one processor. Each of the plurality of activity options can be activities that can be performed by an individual and that each positively benefit the individual, and each of the plurality of activity options can be associated with one or more goal factors. The at least one processor can be configured to perform functions of allowing a user to input information indicative of one or more personal goals, determining which of the plurality of activity options are associated with goal factors that correspond to each of the one or more personal goals indicated by the user, displaying on the display the determined plurality of activity options, and allowing the user to input a selection of one or more of the displayed determined plurality of activity options, thereby indicating that the user intends to perform the selected one or more activity options in order to further achievement of the indicated one or more personal goals.

The system can vary in any number of ways. For example, the goal factor being associated with one of the plurality of activity options can be indicative of previous success in achieving the personal goal after performing the one of the plurality of activity options. The previous success can include previous success of the user, the previous success can include previous success of individuals other than the user, or the previous success can include previous success of the user and previous success of individuals other than the user.

For another example, the one or more personal goals can include any one or more of weight loss, improved nutrition, increased physical activity, increased amount of daily sleep, increased quality of sleep, and decreased amount of daily stress. The goal factor corresponding to weight loss can indicate previous achievement of weight loss after performing the corresponding activity option, the goal factor corresponding to improved nutrition can indicate previous achievement of improved nutrition after performing the corresponding activity option, the goal factor corresponding to increased physical activity can indicate previous achievement of increased physical activity after performing the corresponding activity option, the goal factor corresponding to increased amount of daily sleep can indicate previous achievement of increased amount of daily sleep after performing the corresponding activity option, and the goal factor corresponding to decreased amount of daily stress can indicate previous achievement of decreased amount of daily stress after performing the corresponding activity option. The previous achievements can include the user's previous achievements, previous achievements of individuals other than the user, or a combination of the user's previous achievements and previous achievements of individuals other than the user.

For yet another example, the at least one processor can also be configured to perform a function of excluding from the displayed plurality of activity options any of the determined plurality of activity options that the user has previously had displayed thereto on the display a predetermined number of times and that the user has not input a selection thereof any of those predetermined number of times. For still another example, the positive benefit can be related to at least one of the individual's wellness, health, and lifestyle. For another example, the one or more personal goals can be related to at least one of the user's wellness, health, and lifestyle. For yet another example, the system can include a memory that stores instructions configured to cause the processor to execute the functions.

A method can include the functions performed by the at least one processor of the system.

In another embodiment, a system includes a display, a storage device that stores a fingerprint that includes a plurality of characteristics unique to a user, and at least one processor configured to perform functions of displaying on the display a prompt to which a user can provide an input in response thereto, receiving the input, and updating one or more of the plurality of characteristics based on the received input, thereby updating the fingerprint so as to reflect the user's input.

The system can have any number of variations. For example, the prompt can include an overt prompt requesting that the user indicate the user's preference with respect to at least one of the plurality of characteristics. The overt prompt can be associated with a specific one or more of the plurality of characteristics, and the updating can include updating the specific one or more of the plurality of characteristics, and the updating can also include updating an additional one or more of the plurality of characteristics that are not associated with the overt prompt but that are associated with the specific one or more of the plurality of characteristics; and/or the overt prompt can include a direct request to the user asking for the user's preference with respect to at least one of the plurality of characteristics.

For another example, the prompt can include a covert prompt requesting information from the user that is related to at least one of the plurality of characteristics without requesting that the user indicate the user's preference with respect to the at least one of the plurality of characteristics. The covert prompt can be associated with a specific one or more of the plurality of characteristics, and the updating can include updating the specific one or more of the plurality of characteristics. The updating can also include updating an additional one or more of the plurality of characteristics that are not associated with the covert prompt but that are associated with the specific one or more of the plurality of characteristics.

For yet another example, each of the plurality of characteristics can be associated with at least one of the user's wellness, health, and lifestyle.

For still another example, the input can be a type selected from the group consisting of the user indicating a decision to engage in an activity immediately, the user indicating a decision to engage in an activity at a future point in time, the user engaging in an activity, the user repeatedly performing an activity, the user indicating a decision to not engage in an activity previously indicated as an activity that the user would engage in immediately, the user indicating a decision to not engage in an activity previously indicated as an activity that the user would engage in at a future time, the user indicating a beneficial experience as a result of engaging in an activity, and the user indicating a negative experience as a result of engaging in an activity. The updating can include changing the fingerprint using a scaling factor, the scaling factor being dependent on the type of the input.

For yet another example, the at least one processor can also be configured to perform functions of displaying on the display a second prompt to which the user can provide a second input in response thereto, receiving the second input, and updating one or more of the plurality of characteristics based on the received second input, thereby updating the fingerprint so as to reflect the user's second input. The one or more of the plurality of characteristics updated based on the received second input can be the same one or more of the plurality of characteristics updated based on the received input, or the one or more of the plurality of characteristics updated based on the received second input can be different from the one or more of the plurality of characteristics updated based on the received input.

For another example, each of the plurality of characteristics can be classified as being of a first type of characteristic that changes over time at a first rate or as being of a second type of characteristic that changes over time at a second rate that is slower than the first rate. In the updating, the at least one processor can be configured to only update characteristics classified as being of the first type; in the updating, the at least one processor can be configured to more heavily factor the input in updating characteristics classified as being of the first type than in updating characteristics classified as being of the second type; and/or when the prompt includes an overt prompt requesting that the user indicate the user's preference with respect to at least one of the plurality of characteristics, the at least one of the plurality of characteristics can be of the second type, and when the prompt includes a covert prompt requesting information from the user that is related to at least one of the plurality of characteristics without requesting that the user indicate the user's preference with respect to the at least one of the plurality of characteristics, the at least one of the plurality of characteristics can be of the first type.

For still another example, each of the plurality of characteristics can be represented by one of three variables. The three variables can include a first variable indicating a positive position of the user with respect to that characteristic, a second variable indicating a negative position of the user with respect to that characteristic, and a third variable indicating a neutral position of the user with respect to that characteristic. Each of the plurality of characteristics can be defaulted to being represented by the third variable at least until the at least one processor receives the input and updates the one or more of the plurality of characteristics; each of the plurality of characteristics can be limited to being represented by one of the three variables; and/or the updating can include changing the fingerprint by multiplying the variable of the one or more of the plurality of characteristics by a scaling factor that is dependent on a type of the input, and the type of the input can be selected from the group consisting of the user indicating a decision to engage in an activity immediately, the user indicating a decision to engage in an activity at a future point in time, the user engaging in an activity, the user repeatedly performing an activity, the user indicating a decision to not engage in an activity previously indicated as an activity that the user would engage in immediately, the user indicating a decision to not engage in an activity previously indicated as an activity that the user would engage in at a future time, the user indicating a beneficial experience as a result of engaging in an activity, and the user indicating a negative experience as a result of engaging in an activity.

For yet another example, the input can indicate the user's interest in engaging in an activity that provides a positive benefit to at least one of wellness, health, and lifestyle. For another example, each of the plurality of characteristics can be weighted with a weighting factor unique to the user and unique to each of the plurality of characteristics.

For yet another example, the storage device can store a plurality of additional fingerprints that are each associated with a different user and that each include the plurality of characteristics, and the at least one processor can also be configured to perform a function of comparing the fingerprint with the plurality of additional fingerprints so as to determine which one or more of the plurality of additional fingerprints have characteristics that most closely match the characteristics of the fingerprint. The at least one processor can also be configured to perform a function of providing on the display one or more activities as suggested activities to the user, each of the one or more activities providing a positive benefit to at least one of wellness, health, and lifestyle, and each of the one or more activities being provided based on the one or more of the plurality of additional fingerprints having characteristics that most closely match the characteristics of the fingerprint.

For another example, the at least one processor can also be configured to perform a function of providing on the display one or more activities as suggested activities to the user, and each of the one or more activities can provide a positive benefit to at least one of wellness, health, and lifestyle. The at least one processor can also be configured to perform a function of choosing the one or more activities as a subset of a plurality of possible activities that each provide a positive benefit to at least one of wellness, health, and lifestyle, the choosing being based on the stored fingerprint. The at least one processor can also be configured to perform a function of choosing the one or more activities as a subset of a plurality of possible activities that each provide a positive benefit to at least one of wellness, health, and lifestyle, and the choosing can not consider the stored fingerprint so as to be random activity options for the user.

For still another example, the system can include a memory that stores instructions configured to cause the processor to execute the functions.

A method can include the functions performed by the at least one processor of the system.

In another embodiment, a system includes a storage device that stores suggestions and that stores information about a user, a processor, an output device, and an input device. Each of the suggestions can be described by two or more factors that each have a value, and the information about the user can be described by the two or more descriptive factors that each have a value specific to the user. The processor can select at least one of the suggestions by comparing the values of the two or more descriptive factors with the values of the two or more factors for each of the suggestions and determining which of the suggestions has factors with values that most closely match the values of the descriptive factors. The output device can cause the at least one selected suggestion to be communicated to the user. The input device can acquire an outcome from the user acting on the at least one suggestion. The processor can cause the value of at least one of the descriptive factors to be modified to be closer to the values of the factors of the acted on suggestion in response to the acquired outcome being a positive outcome.

The system can have any number of variations. For example, the descriptive factors can include at least one of demographic factors, environmental factors, physiological factors, psychological factors, inspirational factors, aspirational factors, and motivational factors. For another example, the value for each of the descriptive factors can be one of two values that represent mutually exclusive characteristics. For yet another example, the value for each of the descriptive factors can include a first value represented by a positive number and a second value represented by a negative number. For yet another example, the suggestions can each include a specific action to be performed. For still another example, the suggestions can each include informative text that can be read by the user. For another example, the suggestions can each include at least one of a specific action to be performed and informative text that can be read by the user. For still another example, the output device can communicate the at least one selected suggestion to the user only one time. For another example, the processor can cause the value of at least one of the descriptive factors to be modified to be farther away from the values of the factors of the acted on suggestion in response to the acquired outcome being a negative outcome. For still another example, the processor can not cause the values of the descriptive factors to be modified at all in response to the acquired outcome being a negative outcome. For yet another example, the outcome can be related to at least one of the user's health, wellbeing, and lifestyle. For another example, the outcome can be related to at least one of the user's quality of life, preference, and engagement. For yet another example, the processor can also select at least one of the suggestions by weighing each of the factors differently. For still another example, each of the factors can be weighted differently to modify a user's descriptive factors based on the outcome from a suggestion. For yet another example, the processor can select multiple ones of the suggestions, and the output device can cause each of the multiple ones of the suggestions to be communicated to the user. For another example, the output device can cause at least one of the suggestions that is not selected by the processor to be communicated to the user. For still another example, the output device can cause at least one of the suggestions that is not selected by the processor to be communicated to the user at a predetermined frequency. For yet another example, there can be multiple users. For another example, at least one of the suggestions can not be available to the user but are available to at least one other user. For yet another example, the user can choose between different collections of suggestions stored in the storage device, and the processor can select at least one of the suggestions from the chosen collection. For still another example, the outcome can be determined by at least one of biometric, an activity measurement, a device, user self-reporting, and observing the user. For yet another example, in response to the acquired outcome being a positive outcome, the processor can also cause the value of at least one of the descriptive factors of suggestions previously acted on by the user to be modified to be closer to the values of the factors of the acted on suggestion. For another example, the system can include a display that communicates the at least one selected suggestion to the user by displaying the at least one selected suggestion. For yet another example, the system can include a memory that stores instructions configured to cause the processor to select at least one of the suggestions.

For another example, the output device can communicate the at least one selected suggestion to the user multiple times over a period of time. The at least one selected suggestion can be provided to the user each time except the first time without the processor performing the comparison or the determining.

For yet another example, the processor can select a plurality of the suggestions, the processor can filter the plurality of suggestions by one or more secondary criteria to select the at least one of the suggestions, and the output device can cause the filtered suggestion(s) to be communicated to the user. The secondary criteria can include at least one of prior use, current use, inapplicability, an external factor, and a required prerequisite.

A method can include the functions performed by the processor, the output device, and the input device of the system.

In another embodiment, a system includes an input module, a storage device, and an analysis module. The input module can be configured to receive first information indicating an activity performed by a user, and receive second information indicating a demographic for the user. The activity can provide a positive personal benefit to the user. The storage device can store historical activity information for a plurality of individuals and demographic information indicating a demographic for each of the plurality of individuals. The historical activity information can indicate which one or more activities have been performed by each of the plurality of individuals. Each of the one or more activities can provide a positive personal benefit. The analysis module can be configured to identify a first subset of individuals including each of the plurality of individuals who have performed the same activity as the user, and identify a second subset of individuals from among the first subset of individuals. The demographic for each individual in the second subset of individuals can correspond to the demographic for the user. The analysis module can be configured to identify one or more activities that have been performed by each of the individuals in the second subset of individuals, and provide the identified one or more activities as suggested activities to the user.

The system can have any number of variations. For example, if no activities are identified as having been performed by each of the individuals in the second subset of individuals, the analysis module can be configured to identify one or more activities performed by a third subset of individuals from among the second subset of individuals, and provide the one or more identified activities performed by the third subset of individuals to the user. The system can include at least one display, and providing the one or more identified activities performed by the third subset of individuals to the user can include showing the one or more identified activities performed by the third subset of individuals on the at least one display.

For another example, the input module can be configured to receive third information indicating the user's likability of the activity indicated by the first information. The analysis module can be configured to filter the one or more identified activities based on the third information, and the providing of the identified one or more activities as suggested activities to the user can include only the filtered identified one or more activities; and/or the analysis module can be configured to predict which of the identified one or more activities that the user may prefer based on the third information, and the identified one or more activities can be provided to the user with an indication of the prediction.

For yet another example, the input module can be configured to receive third information indicating a level of strenuousness for the at least one activity performed by the user. The analysis module can be configured to filter the one or more identified activities based on the third information, and the providing of the identified one or more activities as suggested activities to the user can include only the filtered identified one or more activities; the analysis module can be configured to predict which of the identified one or more activities that the user may prefer based on the third information, and the identified one or more activities can be provided to the user with an indication of the prediction; the level of strenuousness can be pre-programmed for the at least one activity performed by the user so as to be associated therewith without the user indicating the level of strenuousness; and/or the input module can be configured to prompt the user to input the level of strenuousness for the at least one activity performed by the user.

For still another example, the at least one activity can have an associated number of points, and the analysis module can be configured to add the associated number of points to a running total of points accumulated by the user. The analysis module can be configured to trigger a reward for the user when the running total of points meets or exceeds a predetermined number of points. The reward can include one or more of an image visible on a display, an increase in user level, an ability to customize a look of the system on an interface that the user uses to access the system, access to a previously hidden area of the system, virtual money usable for purchase of virtual items provided by the system, non-virtual money usable for purchase of virtual items available from the system, non-virtual money usable for purchase of non-virtual items available from the system, non-virtual money usable for purchase of non-virtual items from a third party and non-virtual money usable for purchase of virtual items from a third party.

For yet another example, the activity performed by the user can include at least one athletic activity. The analysis module can be configured to determine whether the activity performed by the user is an individual athletic activity or a group athletic activity, and filter the one or more identified activities based on the determination of whether the at least one athletic activity is an individual athletic activity or a group athletic activity such that the provided one or more activities exclude individual athletic activities if the at least one athletic activity is a group athletic activity and the provided one or more activities exclude group athletic activities if the at least one athletic activity is an individual athletic activity.

For another example, the activity performed by the user can include at least one of eating a healthy food and drinking a healthy drink. For yet another example, the activity performed by the user can include at least one healthy habit. For still another example, the activity performed by the user can include at least one of engaging in an individual sport, engaging in a group sport, eating a healthy food, drinking a healthy drink, gardening, taking a walk, jogging, swimming, stretching, yoga, pilates, tai chi, meditation, doing housework, taking an in-person educational course regarding at least one of wellness, health, and lifestyle, taking an online educational course regarding at least one of wellness, health, and lifestyle, deep breathing, martial arts, making art, playing music, writing a handwritten letter, writing an electronic letter, talking on the telephone to a family member, talking on the telephone to a friend, bringing a meal to work, cooking a meal at home, sleeping, walking a dog, quitting smoking, reducing an amount of smoking per day, quitting drinking coffee, reducing an amount of coffee intake per day, stopping drinking coffee after a certain hour of the day, establishing a bed time, purchasing a device that assists in at least one of a wellness, health, or lifestyle behavior, using a device that assists in at least one of a wellness, health, or lifestyle behavior, reducing an intake amount of an unhealthy food, reducing an intake amount of an alcoholic beverage, and establishing a waking time. For another example, the input module can be configured to cause the received first information and the received second information to be stored in the at least one storage device. For yet another example, the positive personal benefit can be to at least one of wellness, health, and lifestyle. For another example, the system can include at least one display, and providing the one or more identified activities can include showing the one or more identified activities on the at least one display. For still another example, the system can include at least one processor, and at least one storage device configured to store instructions executable by the at least one processor to execute the functions performed by the input module and the analysis module.

A computer-readable storage medium can have stored thereon at least one program that when executed causes a computer to perform a method, and the method can include the functions performed by the input module and the analysis module of the system. The storage medium can vary in any number of ways. For example, the storage medium can include a tangible storage device included as part of a computer. For another example, the storage medium can include a tangible storage device removably and replaceably attachable to computer via at least one of a disk drive and a data port. The data port can include at least one USB port and a 1394 port.

A method can include the functions performed by the input module and the analysis module of the system.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF DRAWINGS

This invention will be more fully understood from the following detailed description taken in conjunction with the accompanying drawings, in which:

FIG. 10 is a diagram showing an embodiment of a filters screen of the system of FIG. 4;

FIG. 11 is a diagram showing an embodiment of a points legend of the system of FIG. 4;

FIG. 12 is a diagram showing a portion of an embodiment of a dashboard of a wellness, health, and lifestyle planning, tracking, and maintenance system;

FIG. 13 is a diagram showing another embodiment of a dashboard of a wellness, health, and lifestyle planning, tracking, and maintenance system;

FIG. 14 is a diagram showing the dashboard of FIG. 13 including a help icon and with a key icon of the dashboard selected;

FIG. 15 is a diagram showing the dashboard of FIG. 13 with a dashboard refresh icon of the dashboard selected;

FIG. 16 is a diagram showing another embodiment of a dashboard on a screen of a wellness, health, and lifestyle planning, tracking, and maintenance system with a rituals icon of the dashboard selected;

FIG. 20 is a diagram showing an embodiment of a setup screen of a wellness, health, and lifestyle planning, tracking, and maintenance system;

FIG. 21 is a diagram showing a portion of the dashboard and screen of FIG. 16;

FIG. 24 is a diagram showing another embodiment of an activities input screen of a wellness, health, and lifestyle planning, tracking, and maintenance system;

FIG. 27 is a diagram showing another embodiment of an activities input screen of the system of FIG. 26;

FIG. 32 is a diagram showing an embodiment of a user fingerprint of a wellness, health, and lifestyle planning, tracking, and maintenance system;

FIG. 33 is a diagram showing an updated version of the user fingerprint of FIG. 32;

FIG. 34 is a diagram showing an embodiment of an activity fingerprint of the system of FIG. 32;

FIG. 35 is a diagram showing an embodiment of a distance array of the system of FIG. 32;

FIG. 89 is a diagram showing an embodiment of a stress screen of the system of FIG. 78;

FIG. 90 is a diagram showing an embodiment of a journaling screen of the system of FIG. 78;

FIG. 91 is a diagram showing an embodiment of a deep breathing screen of the system of FIG. 78;

FIG. 92 is a diagram showing a portion of an embodiment of a supplemental deep breathing screen of the system of FIG. 78;

FIG. 93 is a diagram showing a portion of an embodiment of a healthy habits screen of the system of FIG. 78;

FIG. 93A is a diagram showing another portion of the healthy habits screen of FIG. 93;

DETAILED DESCRIPTION

Figure 1:
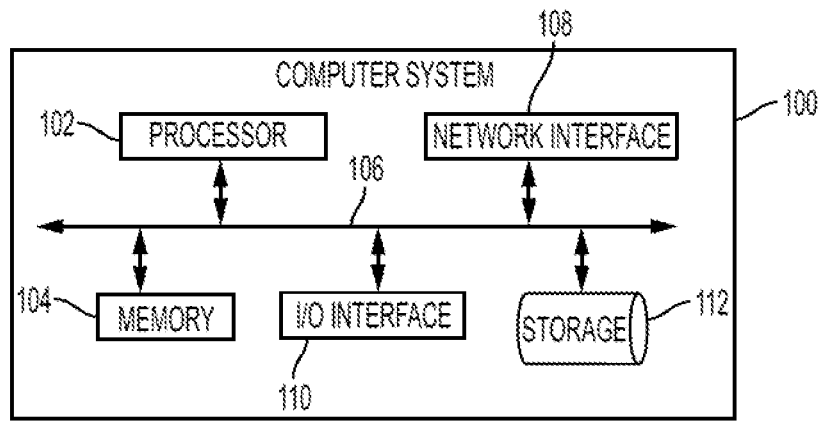
FIG. 1 is a schematic diagram of an embodiment of a computer system.

Certain exemplary embodiments will now be described to provide an overall understanding of the principles of the structure, function, manufacture, and use of the devices and methods described herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon.

Various systems and methods for wellness, health, and lifestyle planning, tracking, and maintenance are provided. Wellness generally refers to physical, mental, and social well-being and is generally directed to preventing illness and injury. Health generally refers to medical state (physical or mental) and is generally directed to treating illness and injury. Lifestyle generally refers to a way of life and is generally directed to engaging in daily life.

In general, the systems and methods described herein can allow a person to manage his/her wellness, health, and/or lifestyle using a convenient system that can help the person plan strategies for improving and/or maintaining his/her wellness, health, and/or lifestyle and/or that can help the person track his/her compliance with the strategies. The systems and methods can thus help the person have awareness of his/her activity related to his/her wellness, health, and/or lifestyle; help the person integrate activities beneficial to wellness, health, and/or lifestyle into his/her daily lives; help the person organize what can be an overwhelming task of planning, tracking, and maintaining his/her wellness, health, and/or lifestyle; help the person achieve his/her personal goals for his/her wellness, health, and/or lifestyle; and/or help the person concretely see his/her progress or lack thereof so as to help the person have awareness of his/her activity related to his/her wellness, health, and/or lifestyle and encourage positive activity related thereto. The systems and methods described herein can be directed to any one or more of wellness, health, and lifestyle, e.g., directed to management of a user's wellness only, directed to management of a user's lifestyle only, directed to management of a user's health only, directed to management of a user's health and lifestyle only, etc.

The systems and methods described herein can allow for documentation and tracking of a person's activities related to wellness, health, and/or lifestyle, such as by storing an electronic record of the person's activities and/or storing a record of the person's compliance therewith. Such documentation and tracking can be beneficial to diagnosing medical conditions for the person in the event of symptom onset by allowing a care provider (e.g., doctor, physical therapist, occupational therapist, chiropractor, psychologist, psychiatrist, licensed counselor, family therapist, spiritualist, etc.) to review the stored data and/or by facilitating the person's recollection of previous activities, can be beneficial to developing medical treatments for the person in the event of illness and/or injury by allowing a care provider to review the stored data and/or by facilitating the person's recollection of previous activities, and/or can help inform decisions regarding planning, tracking, and maintenance of other people's wellness, health, and lifestyle by allowing reference the person's stored data in providing recommendations for other people.

In an exemplary embodiment, a system can be configured to provide recommendations of activities to a person that can positively affect the person's wellness, health, and/or lifestyle. The recommendations can be tailored to each individual user of the system such that different people can receive different recommendations, which can help make the recommendations more likely to be implemented by the person. The recommendations can thus be more likely to improve the person's wellness, health, and/or lifestyle because tailored recommended activities can be more likely to be performed by the person and become part of his/her ingrained behavior. In other words, the recommendations can help improve the person's adherence to recommendations and, accordingly, help positively affect the person's wellness, health, and/or lifestyle. The recommendations can be tailored to a person by being based on the person's past and/or current activities related to wellness, health, and/or lifestyle. By considering the person's past and/or current activities, the system need not have any information regarding any other people in order to provide relevant suggestions to the person. The system can thus be effective regardless of how many users other than the person are using the system and regardless of how similar any of the other users are to the person. By considering the person's past and/or current activities, the system can provide recommendations that are not activities already being performed by the person and/or that are not activities previously indicated by the person as being an activity that the person does not want to incorporate into his/her life. By considering the person's past and/or current activities, the system can provide recommendations similar in type to activities that the person currently engages in and/or has engaged in in the past, thereby indicating that the person enjoys such activities, has access to the resources required for such activities (e.g., certain athletic activities such as swimming, weightlifting, and tennis that require special equipment and/or special facilities, activities that involve a dog or other pet, etc.), etc. and may thus be likely to engage in similar types of activities and have the recommended activity become part of his/her ingrained behavior. By considering the person's past and/or current activities, the system can suggest activities that complement activities already being or already have been performed by the person, such as by focusing on an aspect of the person's wellness, health, and/or lifestyle being addressed less than other aspects of the person's wellness, health, and/or lifestyle, thereby helping to provide a more well-rounded approach for improving and/or maintaining wellness, health, and/or lifestyle. By considering the person's past and/or current activities, the system can provide recommendations based on multiple factors (e.g., multiple comorbid conditions, etc.) related to the patient, which can help the recommendations be complementary to the patient's overall condition.

In at least some embodiments, the recommendations can include a recommendation to use and/or purchase a specific product and/or one or more products in a category of products (e.g., products of a specific type such as lotions, soaps, vitamins, clothing, bedding, computer accessories, mobile phone accessories, apps, exercise products (foam rollers, resistance bands, yoga mats, etc.), etc.; products sold by a same company; products recommended to be used together such as a shampoo and a conditioner, different vitamins, a face wash and a face cream; etc.) to be suggested to a person based on the person's previous activities. The product/product category recommendations can be tailored to each individual user of the system such that different people can receive different product/product category recommendations, which can help make the recommendations more likely to be implemented by the person, e.g., make it more likely that the person will use and/or purchase the product or one or more products in the product category upon receiving the recommendation and/or in the future. In other words, activities related to use and/or purchase of a specific product or product family can be recommended to an individual based on the individual's past actions. Individuals can thus become aware of newly available products, identify products that were previously unknown to them but can be helpful for their wellness, health, and/or lifestyle, and/or be presented with a convenient electronic interface through which the products can be purchased. Sellers of products can thus introduce new products to customers, remind customers about available products, sell directly to consumers via an electronic interface presented to the consumers, encourage product purchase, indicate compatibility of various products, and/or gain loyal customers.

In an exemplary embodiment, the specific product can include a consumable product and the product category can include a category of consumable products. Consumable products generally include products that can be used by an individual and that typically need replacement as part of their normal use, such as because of normal wear and tear (e.g., reduction of elastic band elasticity, worn cosmetic brushes, faded clothing, worn pillows, etc.) or because of supply depletion (e.g., vitamins taken daily from an initial supply, daily use of skin cream from a tube, etc.). Non-limiting examples of consumable product families, with specific products within the categories being non-limiting examples of consumable products, include medications, vitamins, supplements, foods, cosmetics, cosmetics accessories, hair care products, skin care products, pet toys, diapers, shoes, bedding, and clothing.

In another exemplary embodiment, the specific product can include an electronic product and the product category can include a category of electronic products. Electronic products generally include products that can be accessed and used by an individual via a client terminal. Non-limiting examples of electronic product families, with specific products within the categories being non-limiting examples of electronic products, include apps, electronic music (e.g., mp3s, streaming music service, etc.), and electronic video (e.g., AVIs, streaming video service, etc.).

In another exemplary embodiment, the specific product can include an electronic accessory and the product category can include a category of electronic accessories. Electronic accessories generally include devices configured to be used with a client terminal. Non-limiting examples of electronic accessory families, with specific products within the categories being non-limiting examples of electronic accessories, include health monitoring devices (e.g., heart rate monitors, fitness watches, blood pressure measurement devices, glucose meters, etc.), mobile phone headsets, battery chargers, and physical electronic media (e.g., CDs, DVDs, etc.).

In at least some embodiments, the recommendations can be tailored to a person by being based on past and/or current activities of other users of the system in addition to or in alternative to the recommendations being tailored to a person by being based on the person's past and/or current activities. By considering activities of other users of the system, the system can suggest popular activities (e.g., activities engaged in by a relatively large number of users of the system, activities having a relatively large number of newly opened facilities and/or programs in the recent past, etc.), thereby indicating that the person may also be interested in pursuing those activities. By considering activities of other users of the system, the system can provide recommendations to the person based on similarities between the person and other users of the system, such as demographic similarities (e.g., age, age range, geographic area, marital status, number of children, type of pets, etc.) and/or medical history similarities (e.g., disease diagnosis, family history of a certain ailment, prior surgical procedure, etc.), thereby indicating that the person may also be interested in and/or be capable of engaging in such activities.

Computer System

The systems and methods described herein can be implemented using one or more computer systems, which are also referred to herein as digital data processing systems.

FIG. 1 illustrates one exemplary embodiment of a computer system 100. As shown, the computer system 100 can include one or more processors 102 which can control the operation of the computer system 100. The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 106. The illustrated bus system 106 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 108, one or more input/output (I/O) interface(s) 110, and one or more storage device(s) 112.

The network interface(s) 108 can enable the computer system 100 to communicate with remote devices, e.g., other computer systems, over a network, and can be, for non-limiting example, remote desktop connection interfaces, Ethernet adapters, and/or other local area network (LAN) adapters. The I/O interface(s) 110 can include one or more interface components to connect the computer system 100 with other electronic equipment. For non-limiting example, the I/O interface(s) 110 can include high speed data ports, such as universal serial bus (USB) ports, 1394 ports, Wi-Fi, Bluetooth, etc. Additionally, the computer system 100 can be accessible to a human user, and thus the I/O interface(s) 110 can include displays, speakers, keyboards, pointing devices, and/or various other video, audio, or alphanumeric interfaces. The storage device(s) 112 can include any conventional medium for storing data in a non-volatile and/or non-transient manner. The storage device(s) 112 can thus hold data and/or instructions in a persistent state, i.e., the value is retained despite interruption of power to the computer system 100. The storage device(s) 112 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 1 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing Hypertext Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The systems and methods described herein can thus be provided as a singular unit configured to provide the various modules, display the various user interfaces, and capture the data described herein. The singular unit can be modular such that various aspects thereof can be swapped in and out as needed for, e.g., upgrade, replacement, maintenance, etc., without interrupting functionality of any other aspects of the system. The singular unit can thus also be scalable with the ability to be added to as additional modules and/or additional functionality of existing modules are desired and/or improved upon.

While some embodiments are described herein in the context of web pages, it will be appreciated that in other embodiments, one or more of the described functions can be performed without the use of web pages and/or by other than web browser software. A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Planning, Tracking, and Maintenance System Generally

Figure 2:
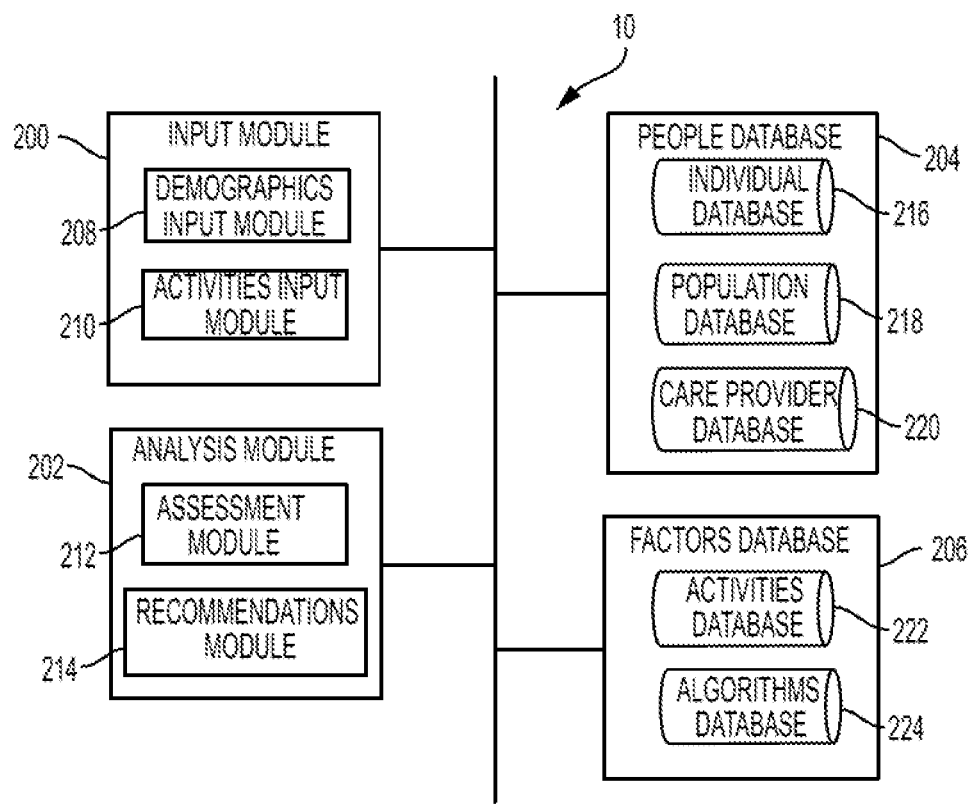
FIG. 2 is a schematic diagram of an embodiment a wellness, health, and lifestyle planning, tracking, and maintenance system.

FIG. 2 is a schematic block diagram of one exemplary embodiment of a planning, tracking, and maintenance system 10. The system 10 can include a plurality of modules, discussed further below, which can each be implemented using one or more digital data processing systems of the type described above, and in particular using one or more web pages which can be viewed, manipulated, and/or interacted with using such digital data processing systems. The system 10 can thus be implemented on a single computer system, or can be distributed across a plurality of computer systems. The system 10 can also include a plurality of databases, which can be stored on and accessed by computer systems. It will be appreciated by a person skilled in the art that any of the modules or databases described herein can be subdivided or can be combined with other modules or databases.

Figure 3:
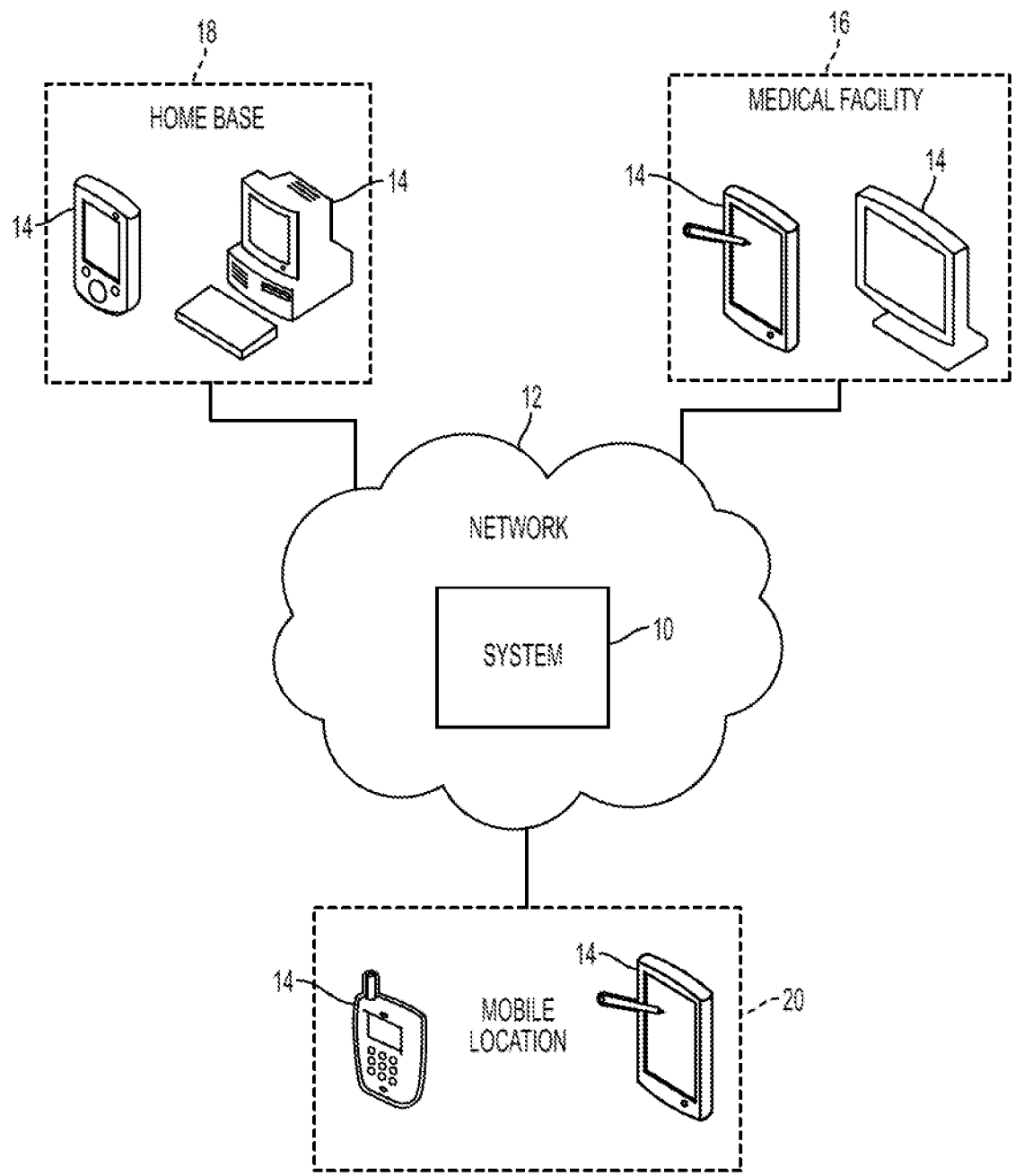
FIG. 3 is a schematic diagram of an embodiment of a network system including the wellness, health, and lifestyle planning, tracking, and maintenance system of FIG. 2.

Any of a variety of parties can access, interact with, control, etc. the system 10 from any of a variety of locations. For non-limiting example, as shown in an embodiment illustrated in FIG. 3, the system 10 can be accessible over a network 12 (e.g., over the Internet via cloud computing, etc.) from any number of client stations, also referred to herein as "client terminals," 14 in any number of locations such as a medical facility 16 (e.g., a hospital, a doctor's office, a medical clinic, a nurse's station, etc.), a home base 18 (e.g., a person's home, a person's work place, etc.), a mobile location 20 (e.g., a public park, a supermarket, a gym, etc.), and so forth. The client station(s) 14 can access the system 10 through a wired and/or wireless connection to the network 12. In an exemplary embodiment, at least some of the client terminal(s) 14 can access the system 10 wirelessly, e.g., through Wi-Fi connection(s), which can facilitate accessibility of the system 10 from almost any location in the world. As shown in FIG. 3, the medical facility 16 includes client stations 14 in the form of a tablet and a computer touch screen, the home base 18 includes client stations 14 in the form of a mobile phone having a touch screen and a desktop computer, and the mobile location 20 includes client stations 14 in the form of a tablet and a mobile phone, but the medical facility 16, the home base 18, and the mobile location 20 can include any number and any type of client stations. In an exemplary embodiment, the system 10 can be accessible by a client terminal via a web address and/or a client application (generally referred to as an "app").

It will be appreciated by a person skilled in the art that the system 10 can include security features such that the aspects of the system available to any particular user can be determined based on the identity of the user and/or the location from which the user is accessing the system. To that end, each user can have a unique username, password, and/or other security credentials to facilitate access to the system 10. The received security parameter information can be checked against a database of authorized users to determine whether the user is authorized and to what extent the user is permitted to interact with the system, view information stored in the system, and so forth. Exemplary, non-limiting examples of parties who can be permitted to access the system 10 include individuals; patients; potential patients; significant others, friends, and family members of patients or potential patients; doctors; nurses; physical therapists; occupational therapists; insurance providers; customers; potential customers; and significant others, friends, and family members of customers or potential customers.

The system 10 can include an input module 200 and an analysis module 202. Any of the input module 200 and the analysis module 202 can be used independently from one another and can be used in combination with any one or more other modules. Each of the modules 200, 202 is discussed further below in turn. In an exemplary embodiment, the input module 200 and the analysis module 202 can be provided as a comprehensive system that can track a patient throughout medical treatment including through initial onset of symptoms, diagnosis, non-surgical treatment, surgical and/or other invasive treatment, and recovery from the invasive treatment. In another exemplary embodiment, the input module 200 and the analysis module 202 can be provided as a comprehensive system that can track an individual through the normal course of daily life until (and if) symptoms of a medical condition manifest in the individual, at which time medical personnel can intervene and stop the individual's use of or modify the individual's use of the system. For non-limiting example, the input module 200 and the analysis module 202 can be part of a system configured to plan, track, and maintain an individual's exercise regimen until (and if) the individual becomes injured such that intervention of medical personnel to tweak or stop the regimen would be beneficial. In yet another exemplary embodiment, the input module 200 and the analysis module 202 can be provided as a comprehensive system that can track an individual through the normal course of daily life without any particular reference to the individual's medical care. For non-limiting example, the input module 200 and the analysis module 202 can be part of a system configured to plan, track, and maintain an individual's beauty regimen as related to, e.g., skin care, hair care, etc.

Although each of the modules 200, 202 is illustrated in FIG. 2 as including a plurality of component modules, each of the modules 200, 202 can include any number of component modules, e.g., one, two, three, etc., the same or different from any of the other modules 200, 202. Further, as mentioned above, it will be appreciated that any of the modules 200, 202, and any of their various component modules, can be subdivided or can be combined with other modules, including modules illustrated in FIG. 2 as being in different ones of the modules 200, 202.

The system 10 can also include a people database 204 and a factors database 206. Any portion of any of the databases 204, 206 can be configured to be accessed by any one or more of the input and analysis modules 200, 202. The people database 204 can be configured to store data regarding one or more people who are using or have used the system 10 and/or to store historical wellness, health, and/or lifestyle data about non-users of the system 10. The factors database 206 can be configured to store data regarding factors relevant to wellness, health, and/or lifestyle planning, tracking, and maintenance. Each of the databases 204, 206 is discussed further below with respect to the modules 200, 202. Each of the databases 204, 206 can include any number of component databases, e.g., one, two, three, etc., the same or different from any of the other databases 204, 206. As mentioned above, it will be appreciated by a person skilled in the art that any of the databases 204, 206, and any of their various component databases, can be subdivided or can be combined with other databases, including databases illustrated in FIG. 2 as being in different ones of the databases 204, 206. Although the system 10 in the illustrated embodiment stores data in database(s), any of the systems described herein can store data in database(s) and/or in other data organization structure(s).

Users of the system 10 can include any person with an interest in wellness, health, and/or lifestyle planning, tracking, and maintenance, such as athletes, generally health conscious individuals, people with one or more diagnosed medical conditions, people with one or more co-morbidities, etc. In some embodiments, the system 10 can be accessible by users other than people using the system 10 to plan, track, and maintain wellness, health, and/or lifestyle, such as doctors who can be given access to data regarding their patients stored by the system 10 in order to more fully assess their patients, insurance providers who can be given access to data regarding their patients stored by the system 10 in order to verify details regarding their insureds for purposes of providing reimbursement, insurance providers who can be given access to population data in order to assess correlations between certain reimbursable treatments and certain individual activities, etc. Different users can have access to different portions of the system 10, as mentioned above regarding security features. For non-limiting example, the system 10 can be configured to allow patients to access only the input module 200, to allow doctors to access only the input module 200, and to allow system administrators to access all of the modules 200, 202. A user can have access to only a portion of a module, e.g., to only a subset of component modules within any one or more of the modules 200, 202.

Input Module

The input module 200 can generally provide users of the system 10 with an interface for inputting data regarding wellness, health, and/or lifestyle planning, tracking, and maintenance. More particularly, the input module 200 can receive user-specific data such as demographics of the user and current activities of the u ser. In this way, the input module 200 can be configured to assist users create and maintain an action plan for managing wellness, health, and/or lifestyle planning, tracking, and maintenance. In one embodiment, the input module 200 can be implemented using one or more web pages which are configured to receive user input and present information to a user. In an exemplary embodiment, the input module 200 can be accessed by users via a web interface, e.g., by connecting to the Internet via a client terminal and accessing a specific web address, by launching an app on a client terminal that accesses the system 10, etc. As mentioned above, the users can wirelessly access the system 10, including the input module 200.

The input module 200 can include a demographics input module 208 and an activities input module 210. Each of the modules 208, 210 of the input module 200 is discussed further below in turn.

The input module 200 can be configured to read information from and write information to the people database 204. The people database 204 can include an individual database 216, a population database 218, and a care provider database 220. Various ones of the input module's component modules 208, 210 can be configured to access one or more of the individual database 216, the population database 218, the care provider database 220, and/or various other databases, e.g., the factors database 206, etc. Each of the individual database 216, the population database 218, and the care provider database 220 is discussed further below in connection with various ones of the input module's component modules 208, 210.

Figures 4, 5:
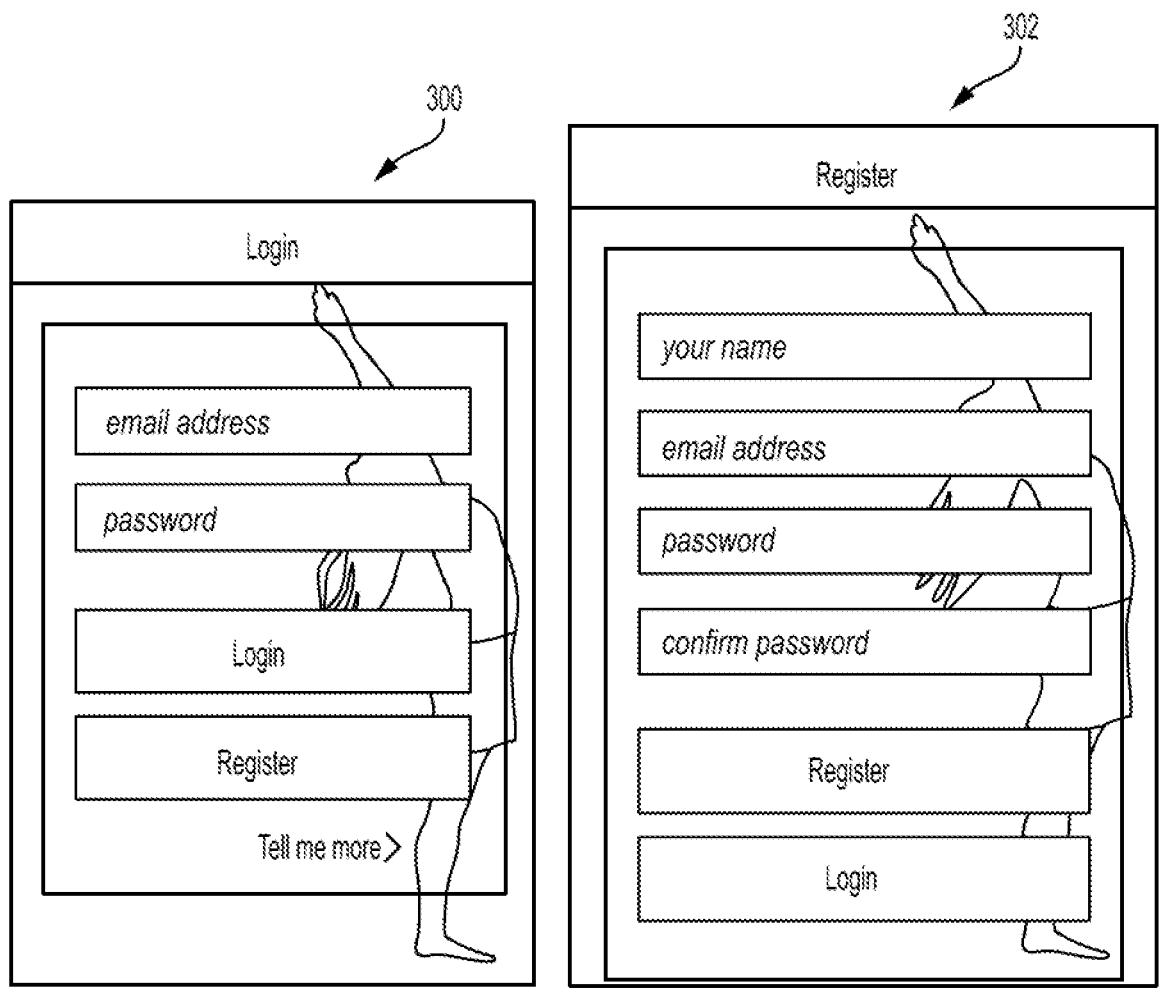
FIG. 4 is a diagram showing an embodiment of a login screen of a wellness, health, and lifestyle planning, tracking, and maintenance system.
FIG. 5 is a diagram showing an embodiment of a registration screen of the system of FIG. 4.

The input module 200 can be configured to allow people to register as users of the system 10 and to allow people to log in as registered users of the system 10. One embodiment of a login screen 300 that can be provided by the system 10 is shown in FIG. 4. One embodiment of a registration screen 302 that can be provided by the system 10 is shown in FIG. 5. FIGS. 4 and 5 show screens 300, 302 that are touchscreens on a mobile phone, but similar screens can be provided on other types of client terminals. Similarly, screens discussed below with respect to various Figures are touchscreens on a mobile phone, but similar screens can be provided on other types of client terminals.

Figures 5A, 6:
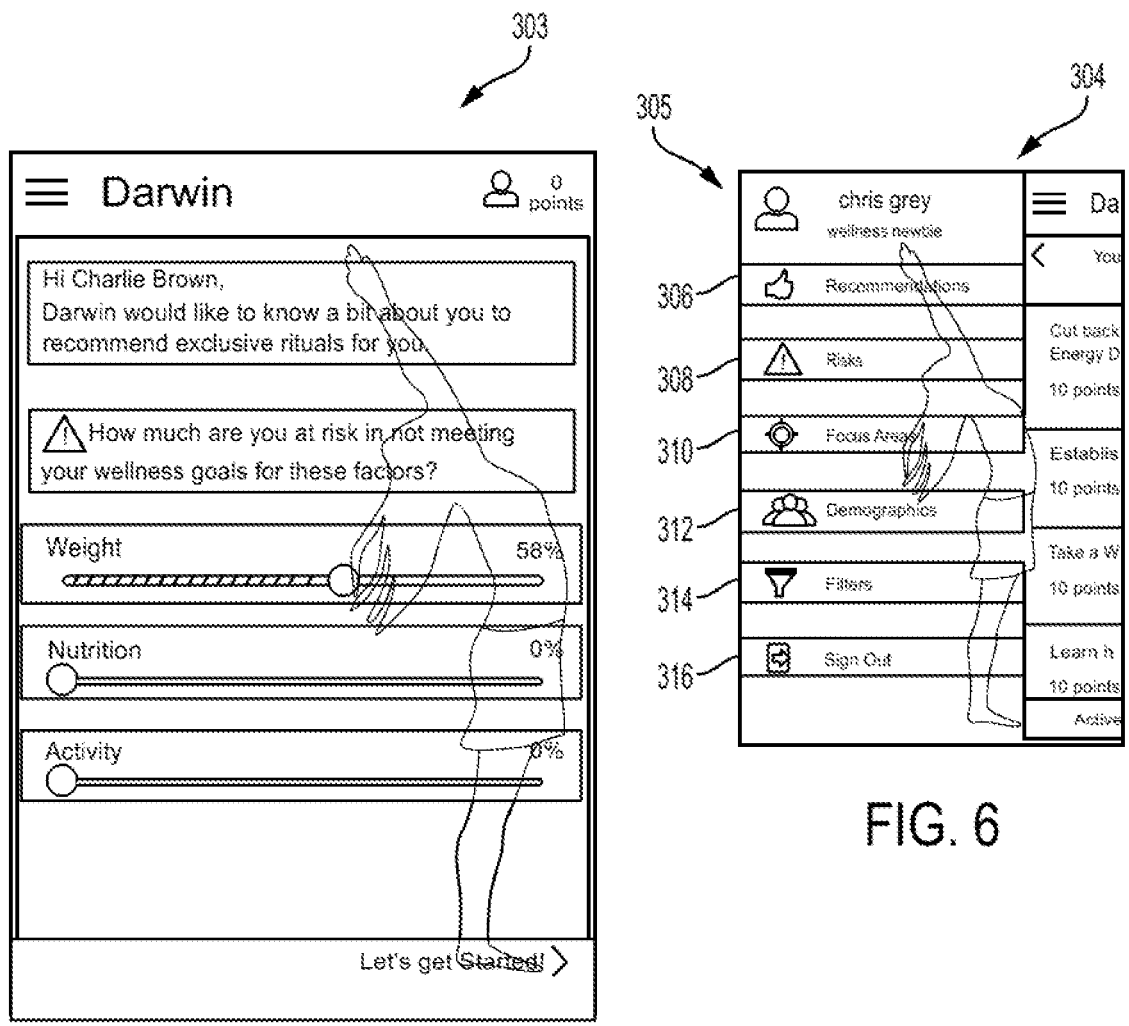
FIG. 5A is a diagram showing an embodiment of an introduction screen of the system of FIG. 4.
FIG. 6 is a diagram showing an embodiment of a menu of the system of FIG. 4.

When a user registers or logs into the system 10 for the first time, the system 10 can be configured to display an introduction screen 303, an embodiment of which is illustrated in FIG. 5A, that queries the user for basic information related to the wellness, health, and/or lifestyle. In this way, the system 10 can provide recommended activities selected for that particular user based on the user's preferences the first time that the user receives recommended activities from the system 10, as discussed further below. The system 10 can be configured to provide the user with access to the introduction screen 303 on demand, thereby allowing the user to adjust his/her introductory information as his/her needs, goals, interests, self-assessment skills, etc. change over time.

The introduction screen 303 can ask the user to input any of a variety of introductory information. As in this illustrated embodiment, the information screen 303 can request that the user indicate on a scale of 0% to 100% how much the believes himself/herself to be at risk of not meeting wellness goals as related to each of weight, nutrition, and activity, with higher percentages indicating that the user is more afraid that the area of concern will not improve. For non-limiting example, the higher the percentage indicated for "Weight," the more concerned that the user is that his/her goal(s) related to weight will not be achieved. The system 10 can be configured to determine which of a plurality of pre-stored possible activities best match the user's selected percentages based on predetermined characteristics associated with each of the activities, as discussed herein, and be configured to provide those activities as recommendations to the user. As also discussed herein, the recommended activities for the user can change over time as the user interacts with the system 10, e.g., by providing inputs regarding completion of activities, abandonment of activities, interest level in recommended activities, how much they believe they are at risk of not achieving certain goals, etc.

When a user logs into the system 10, the system 10 can be configured to display a menu indicating options to the user, as will be appreciated by a person skilled in the art. One embodiment of a menu 304 that can be provided by the system 10 is shown in FIG. 6. The menu 304 of FIG. 6 is configured to be accessible after login via the screen 300 of FIG. 4 or after registration via the screen 302 of FIG. 5, but the menu 304 can be accessed after using another login or registration screen. The menu 304 can include any of a variety of options.

Figure 7:
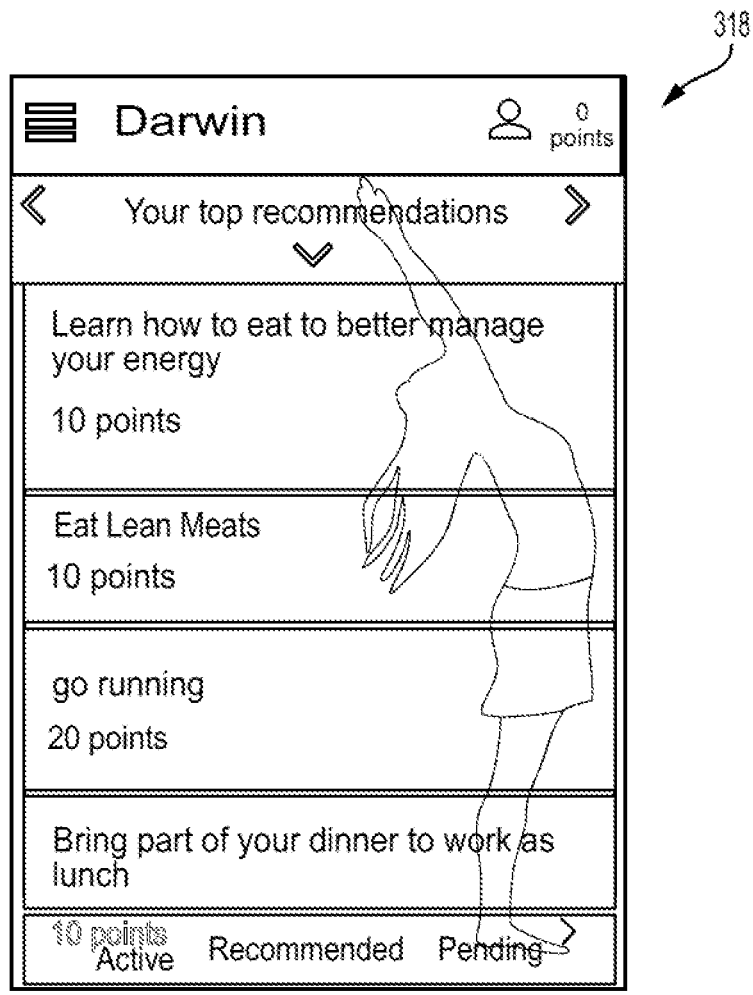
FIG. 7 is a diagram showing an embodiment of a recommendations screen of the system of FIG. 4.
Figures 8, 9:
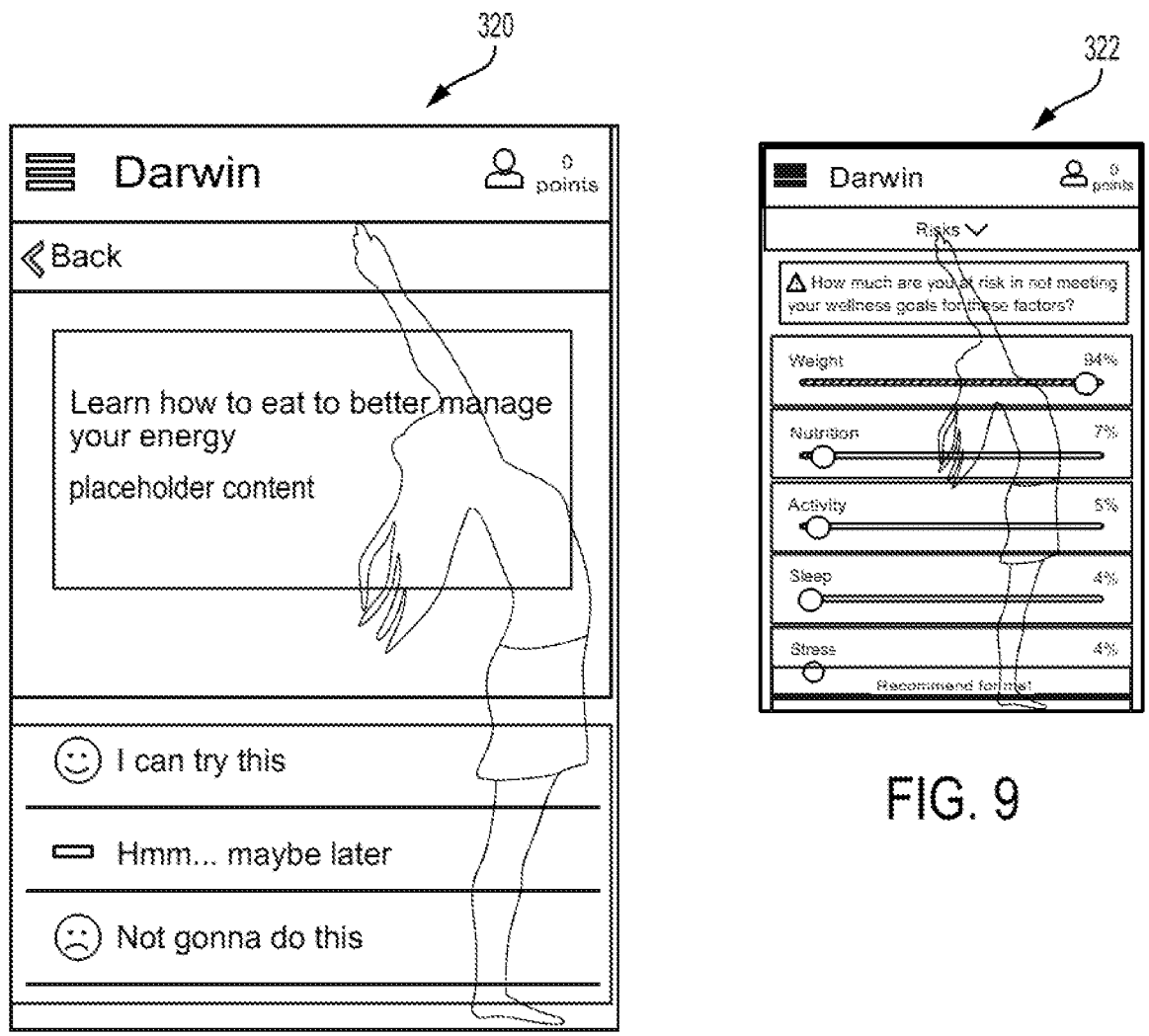
FIG. 8 is a diagram showing an embodiment of a detailed recommendations screen of the system of FIG. 4.
FIG. 9 is a diagram showing an embodiment of a risks screen of the system of FIG. 4.

As in this illustrated embodiment, the menu 304 can include options for "Recommendations" 306 that upon selection thereof can cause the system 10 to display suggested activities to the user that the analysis module 202 has determined to display (with or without customization to the user, as discussed herein), "Risks" 308 that upon selection thereof can cause the system 10 to display the user's goal data and/or to display goal data to the user that allows the user to indicate risks of not achieving goals with respect to one or more general areas of concern, "Focus Areas" 310 that upon selection thereof can cause the system 10 to display the user's focus areas and/or to display one or more general areas of concern that the user can select as being important or de-select as not being important, "Demographics" 312 that upon selection thereof can cause the system 10 to display demographics associated with the user and/or to allow input of demographics data, "Filters" 314 that upon selection thereof can cause the system 10 to allow the user to indicate whether or not the user has interest in one or more classes of activities, and "Sign Out" 316 that upon selection thereof can cause the system 10 to log the user out of the system 10. FIG. 7 shows an embodiment of a recommendations screen 318 that the system 10 can be configured to display upon user selection of the "Recommendations" 306. User selection of any of the recommendations on the recommendations screen 318 can cause the system 10 to display a detailed recommendations screen with further information about the selected recommendation. FIG. 8 shows an embodiment of a detailed recommendations screen 320, displayed in this embodiment in response to user selection of the "Learn how to eat to better manage your energy" recommendation of the recommendations screen 318. FIG. 9 shows an embodiment of a risks screen 322 that the system 10 can be configured to display upon user selection of the "Risks" 308. A focus area screen displayable upon user selection of the "Focus Areas" 310 and a demographics screen displayable upon user selection of the "Demographics" 312 can each be similar to the risks screen 322 by allowing user input thereto indicating focus area preferences and demographics information, respectively. FIG. 10 shows an embodiment of a filters screen 324 that the system 10 can be configured to display upon user selection of the "Filters" 314.

The system 10 can be configured to provide the user with a snapshot indicating his/her progress with recommended activities. Non-limiting examples of such snapshots include graphical representation of progress (e.g., a progress bar, a number of icons, a pie chart, a line graph of achieved recommended activities over time, etc.) and a mood icon indicative of current progress (e.g., a happier face icon for good progress and a sadder face icon for worse progress). As in this illustrated embodiment, the snapshot can be achieved using user levels. The user's actions with respect to the recommendations can allow the user to accumulate points indicative of a user level, which can facilitate the user's tracking of his/her progress, with a higher number of points indicating a higher success in engaging in recommended activities. A user's cumulative number of points can be displayed to the user, such as shown for non-limiting example on the screens 318, 320, 322, 324 of FIGS. 7-10. Different recommendations can be associated with different numbers of points, as shown in the recommendations screen 318. Users can thus receive a sense of each recommendation's relative impact their goals and/or the difficulty in achieving a certain recommended activity, with higher points being associated with activities having bigger and/or more lasting results and/or with activities that are generally more difficult. A user's total number of points can be associated with a certain one of a plurality of predefined levels. The plurality of predefined levels can each be associated with a different range of points and can each have a "name" for ease of identification. The levels can help the user monitor his/her progress and/or give the user repeated encouragement to engage in recommended activities by allowing the user to strive for higher and higher levels. FIG. 11 shows an embodiment of a points legend 328 indicating the system's predefined levels in this illustrated embodiment. The points legend 328 can be configured to be accessible via user selection of a user's displayed current points 330. The "name" can be displayed instead of or in addition to the user's current points level.

The menu 304 can be part of a dashboard 305 shown to the user, as in the illustrated embodiment of FIG. 6. The dashboard 305 can include information uniquely identifying the user (e.g., name, user name, age, etc.), points information (e.g., a total number of virtual points accumulated by the user from performing activities, a goal number of virtual points for the user to achieve within a certain time period, etc.), user level information (e.g., an text and/or image indication of the user's length of time as being a registered user of the system 10, a text and/or image indication of the user's level of involvement with the system 10 such as when users can achieve certain user rank titles based upon a total number of points achieved, a total number of activities performed, and/or other metric), current activity information (e.g., a list of activities that the user is currently trying to achieve, etc.), etc. FIG. 12 shows another embodiment of a user level 332 that can be shown on a dashboard with user levels of different names each being based on different point ranges. In this illustrated embodiment, a user level of "ninja" is associated with user Samuel Clemens's current point total of 135.

FIG. 13 shows another embodiment of a dashboard 334 configured to be shown to a user. FIG. 13's dashboard includes a tool bar 336. The dashboard 334 in this illustrated embodiment includes information uniquely identifying the user (the user's name), "Risk" 338 similar to the "Risks" 308 of FIG. 6, "Focus" 340 similar to the "Focus Areas" 310 of FIG. 6, "Demographics" 342 similar to the "Demographics" 312 of FIG. 6, "Filter" 344 similar to the "Filters" 314 of FIG. 6, "Sign-out" 346 similar to the "Sign Out" 316 of FIG. 6, "Fingerprint" 348 that upon selection thereof can cause the system 10 to allow editing of the user's fingerprint (which, as discussed further below, can reflect the user's unique demographics and/or the user's unique activity preferences), a key icon 350 upon selection thereof can cause the system 10 to grant to or rescind from administrative rights for the user, and a Dashboard refresh 352 that upon selection thereof can cause the system 10 to refresh the currently displayed page. FIG. 14 shows selection of the key icon 350 of FIG. 13. FIG. 14 also shows a help icon 354 that upon selection thereof can provide resources to help the user use the system 10. FIG. 15 shows selection of the Dashboard refresh 352 of FIG. 13. Fingerprints are discussed further below. Fingerprints are also referred to herein as "behavioral DNA" ("B-DNA").

Figure 17:
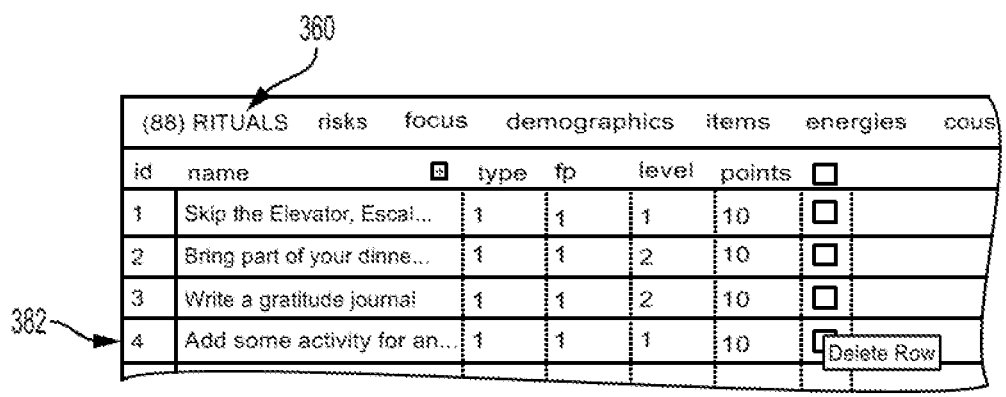
FIG. 17 is a diagram showing a portion of the dashboard and screen of FIG. 16 with a row on the screen selected for deletion.
Figure 18:
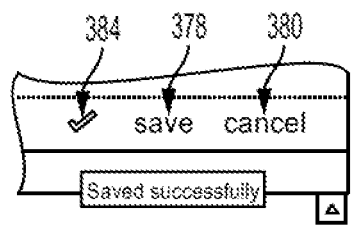
FIG. 18 is a diagram showing a portion of the dashboard of FIG. 16 including an indication that data has not changed since a last save of data.
Figure 19:
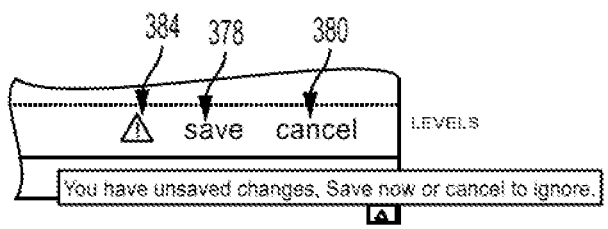
FIG. 19 is a diagram showing a portion of the dashboard of FIG. 16 including an indication that data has changed since a last save of data.

FIG. 16 shows another embodiment of a dashboard 354 shown to the user. The dashboard 354 includes a tool bar 356. The dashboard 354 in this illustrated embodiment includes points information 358 (an 88 point total being shown in this illustrated embodiment), "RITUALS" 360 that upon selection thereof can cause the system 10 to display the user's list of current activities (e.g., activities that the user is currently trying to achieve), "risks" 362 similar to the "Risks" 308 of FIG. 6, "focus" 364 similar to the "Focus Areas" 310 of FIG. 6, "demographics" 366 similar to the "Demographics" 312 of FIG. 6, "items" 368 that upon selection thereof can cause the system 10 to display classes of activities associated with the user, "energies" 370 that upon selection thereof can cause the system 10 to display the user's current activities with an indication of the activities' required energy level (e.g., amount of user exertion), "cousins" 372 that upon selection thereof can cause the system 10 to display activities related to the user's current activities (which can help the user identify one or more new activities that the user would like to pursue based on the user's current activity preferences), "prerequisites" 374 that upon selection thereof can cause the system 10 to display activities that the user must perform before performing other activities, "ranks" 376 that upon selection thereof can cause the system 10 to display the user's current activities with an indication of the activities' priorities (e.g., importance of completion), "save" 378 that upon selection thereof stores any changes made on the currently saved screen and/or since the last save, and "cancel" 380 that allows the user to exit from the currently displayed page without saving any changed made thereon. FIG. 16 shows a display with "RITUALS" 360 selected. FIG. 17 shows an excerpt of the display of FIG. 16 illustrating an embodiment of how current activities can be deleted from the user's current list of activities, which in this embodiment includes deleting a row 382 with the activity to be removed. FIG. 18 shows selection of the "save" option 378 of FIG. 16 to save changed data, with a save status icon 384 showing that data has not changed since the last save, e.g., since the last selection of the "save" option 378 or since the last auto-save of data. FIG. 19 shows the save status icon 384 in the dashboard 356 indicating that the "save" option 378 of FIG. 16 should be selected if the user wants to save changed data since unsaved data exists.

The input module 200 can be configured to allow a user to customize a look and feel of the system 10. As will be appreciated by a person skilled in the art, such customization can include customizable options such as color, background image, screen layout, icon style, avatar, font size, etc. In some embodiments, only a user with administrative rights can be authorized to customize some or all aspects of the look and feel of the system 10.

Figure 20:
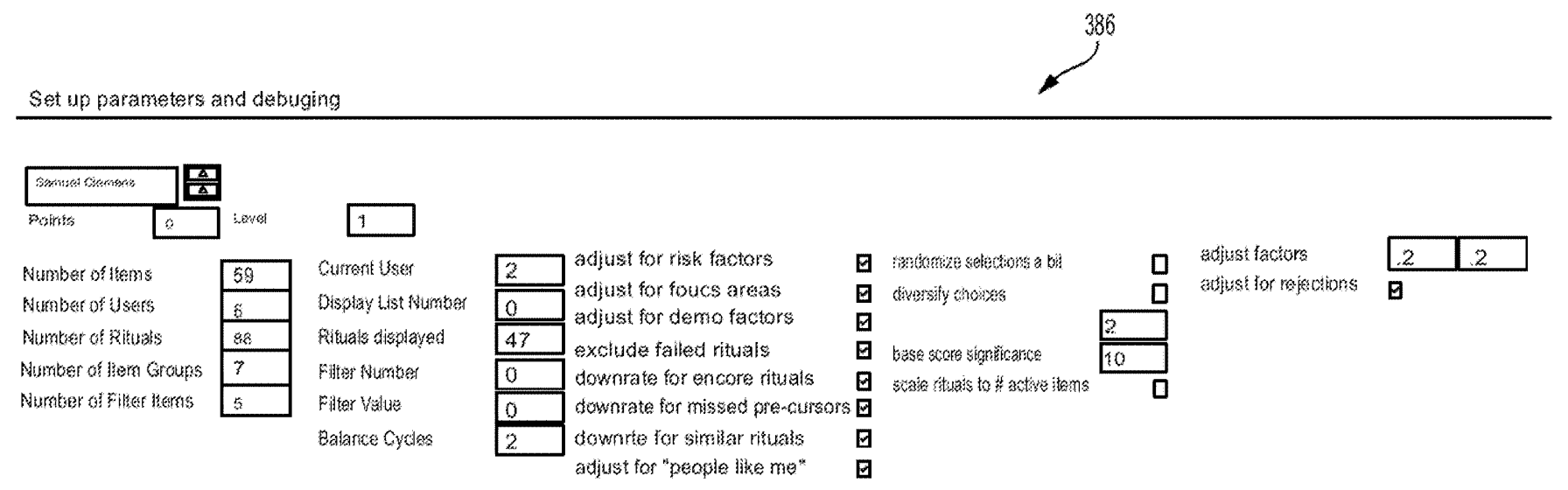

FIG. 20 shows an embodiment of a setup screen 386 that can be provided by the system 10 to allow a user to customize a look and feel of the system 10. In this illustrated embodiment, the user is allowed to change a variety of look and feel elements for a selected user, which is "Samuel Clemens" in this illustrated embodiment. The system 10 can be configured to allow the user to change the look and feel for a plurality of users, such as by selecting one of a plurality of users using arrow scroll buttons, as in this illustrated embodiment. In some embodiments, only a user with administrative rights can be authorized to change the look and feel for a plurality of users. In some embodiments, a user who has been linked by the system 10 with a certain subset of users can be authorized to change the look and feel for any user in that subset. For non-limiting example, a plurality of users can be linked together as being part of the same family, with parent users in the family being authorized to make changes for child users in the family.

Demographics Input Module

The demographics input module 208 can provide users of the system 10 with an interface for inputting demographic information regarding users. Non-limiting examples of demographics information that can be input using the demographics input module 208 include personal identification data (e.g., name, user name, medical record number, mailing address, email address, phone number, etc.) and personal characteristic data (e.g., age, age range, geographic area, marital status, number of children, number of pets, type of pets, existing medical diagnoses, past medical diagnoses, existing injuries, past injuries, past surgical procedures, insurance provider, care provider, occupation, activity level of typical work days, typical work hours, types of available transportation, communication preferences, activity preferences, favorite color, etc.).

The system 10 can be configured to allow only a user to input demographic information regarding the user, thereby helping to ensure that accurate demographic information about the user is input into the system 10. The system 10 can be configured to allow the user to authorize one or more other users to input demographic information about the user, such as authorizing the user's primary care physician (PCP) and/or other medical professional treating the user to input demographic information related to the user's medical care, e.g., medical record number, existing medical diagnoses, past medical diagnoses, existing injuries, past injuries, past surgical procedures, insurance provider, etc.

The system 10 can be configured to allow at least some demographic information to be imported into the system 10 via the demographics input module 208 without the user directly inputting the demographics information into the system 10. For non-limiting example, the demographics input module 208 can be configured to import at least some of a user's demographics information from a third party website (e.g., from a social media website such as Facebook, from another application installed on the user's client terminal, etc.). The system 10 can be configured to require authorization from the user prior to performing the automatic import. For non-limiting example, the demographics input module 208 can be configured to import at least some of a user's demographics information from information associated with the user's connection to the network 12 through which the user is accessing the system 10 (e.g., the user's geographic location, etc.).

The system 10 can be configured to store demographic information input via the demographics input module 208 in the individual database 216. The individual database 216 can be configured to store data about each user of the system 10. The data can include the demographics information received via the demographics input module 208. The data stored in the individual database 216 can be organized such that specific data is associated with a specific user so as to store a user profile for each user. As will be appreciated by a person skilled in the art, the system 10 can be configured to retrieve a user's user profile when the user logs onto the system 10.

The population database 218 can include data gathered from the individual database 216 and/or from other sources, e.g., from other databases, from data input into the system 10 by an administrator, etc. In an exemplary embodiment, the population database 218 can include only information gathered by the system 10, e.g., information about users of the system 10, which can help ensure the integrity of the information used by the system 10 in performing analysis with the analysis module 202.

In an exemplary embodiment, the data stored in the population database 218 can be anonymous, e.g., unable to be associated with a specific user of the system 10. In other words, personal identification data that can be stored in the individual database 216 can be excluded from the population database 218 such that information in the population database 218 that is also stored in some form in the individual database 216 and/or another database can be disassociated from a specific user. This can provide security of information. The analysis module 202 can thus be configured to analyze data, as discussed further below, using data from the population database 218 without compromising a user's privacy.

Activities Input Module

The activities input module 210 can provide users of the system 10 with an interface for inputting activities information regarding users. Non-limiting examples of activities information that can be input using the activities input module 210 include personal activity data (e.g., identification of activities that the user would like to add to his/her list of activities to possibly engage in, identification of activities that the user would like to remove from his/her list of activities to possibly engage in, indication that an activity has been performed, etc.), goal data (e.g., general areas of concern for the user such as weight, nutrition, exercise, stress, social interaction, activity, anxiety, sleep, depression, anxiety, high blood pressure (HBP), heart condition (HC), diabetes, chronic obstructive pulmonary disease (COPD), dementia, smoking, pregnancy, driver safety, infectious disease, eating, binge eating, back pain, emotional health, focus, recovery, happiness, learning, memory, relaxation, mindfulness, willpower, accident prevention, relationships, chronic care, etc.), goal target data (e.g., amount of weight loss, total hour amount of exercise per week, total number of activities outside the home per week, etc.), activity status data (e.g., whether or not a certain scheduled activity has been performed or not), activity likeability data (e.g., whether or not the user has interest in a specific activity (e.g., jogging, playing football, learning about healthy vegetarian diets, etc.), whether or not the user has interest in a class of activities (e.g., sports, spiritual learning, activities that can be performed at work, activities that can be performed at home, activities involving the user's children, activities involving the user's pets, indoor activities, outdoor activities, etc.), and whether or not the user enjoyed a certain performed activity, etc. Activities can be actions intended to be performed once (e.g., registering for an adult education course, getting a pet, etc.), can be actions intended to be performed at multiple, irregular times (e.g., eating more lean meats, deep breathing, etc.), or can be actions intended to be performed at multiple, regular times (e.g., taking a walk during a lunch break, attending weight loss group meetings, etc.). Activities intended to be performed multiple times are also referred to herein as "rituals." Goals can be associated with a particular location (e.g., home, work, away from home, in a car, at a desk), with a particular third party (e.g., with family, with kids, with anyone else, with friends, etc.), with a particular time of day (e.g., morning, lunchtime, evening, on a break, at a controlled time, less than once a day, daily, less than once a week, etc.), with a regularly occurring event, and/or with a certain type (e.g., mental, fun, physical, heavy physical, etc.).

The system 10 can be configured to allow only a user to input activities information regarding the user, thereby helping to ensure that accurate activities information about the user is input into the system 10. The system 10 can be configured to allow the user to authorize one or more other users to input activities information about the user, such as authorizing the user's physical therapist treating the user to input activities information related to activities performed while under the physical therapist's supervision.

The system 10 can be configured to store activities information input via the activities input module 210 in the individual database 216. As mentioned above, the individual database 216 can be configured to store data about each user of the system 10. The data can include the activities information received via the activities input module 210.

The system 10 can be configured to allow a user to indicate whether or not an activity has been performed. In other words, the user can input to the system 10 via the assessment module 212. In response to the indication that the activity has been performed, the analysis module 10 can be configured to update the user's progress snapshot, e.g., the user's point total, the user's progress mood icon, etc. In an embodiment in which points are maintained, such as in the embodiments of FIGS. 5A and 16, the system 10 can be configured to add the completed activity's associated points to the user's total number of points. The points can be numerical points or can be another type of points measurement, such as a progress bar or a number of icons. FIG. 11 shows one embodiment of a points model that can be used by the system 10. FIG. 7 shows one embodiment of points being associated with specific activities. FIG. 16 shows yet another embodiment of points being associated with specific activities. FIG. 21 shows an expanded display of FIG. 16 with "RITUALS" 360 selected, showing more rituals in the list than in FIG. 16. FIG. 17 shows still another embodiment of points being associated with specific activities.

The system 10 can be configured to automatically update an activity as having been performed. In an embodiment in which points are maintained, the analysis module 10 can be configured to update the user's point total by adding the completed activity's associated points to the user's total number of points in response to an automatic determination that an activity has been performed. The system 10 can be configured to not update the user's point total until the user confirms actual performance of the automatically detected activity.

In some embodiments, the system 10 can be configured to use a client terminal's geographic location feature, e.g., a mobile phone's global positioning system (GPS) feature, etc., to automatically determine whether or not a user participated in a certain activity. The system 10 can be configured to ask the user to confirm that the activity was actually performed the next time that the user logs on to the system 10, thereby helping to ensure accuracy. For nonlimiting example, if the geographic location feature indicates that the user was at a particular geographic location at a certain time corresponding to a place and time of a scheduled activity, e.g., at a certain gym at a time of a scheduled exercise class, at a certain dog park at a certain time of scheduled dog walking, etc., the system 10 can be configured to automatically mark that activity as having been performed. For another non-limiting example, if the geographic location feature indicates that the user's geographic location is continually changing within a certain time range, the system 10 can be configured to conclude that an activity scheduled within that time range requiring continual movement has been performed, e.g., a bike ride occurred in the morning before work, a walk occurred during lunch hour, etc.

In some embodiments, the system 10 can be configured to use a client terminal's calling capability (e.g., a tablet's ability to make calls using an Internet calling service such as Skype, a mobile phone's calling capability, etc.) to automatically determine whether or not a user participated in a certain activity that involves making a call. Non-limiting examples of such activities include calling an educational facility to register for an educational course and calling a friend. The system 10 can be configured to determine that the user called a phone number associated with an activity, such as by knowing from the user's electronic contacts stored in or otherwise accessible at the user's client terminal that the user called a phone number associated with the activity (e.g., knowing that the user called his/her mother, knowing that the user called a medical facility associated with the user's physical therapist, etc.).

One embodiment of an activities input screen that can be provided by the system 10 is shown in FIG. 5A. The screen of FIG. 5A is a non-limiting example of goal data input in which a user can identify general areas of concern by moving a slide bar for the area of concern from 0% to a value up to 100%. The analysis module 202 can be configured to use the indicated percentage as a factor in determining with one or more algorithms stored in an algorithms database 224 which one or more activities to suggest to the user as activities that the user may want to engage in to help address one or more of his/her areas of concern. In general, the analysis module 202 can be more likely to suggest activities to the user that address the area(s) of concern that the user associated with the highest percentage.

Another embodiment of an activities input screen that can be provided by the system 10 is shown in FIG. 9. The screen 322 of FIG. 9 is similar to the screen of FIG. 5A and is a non-limiting example of goal data input in which a user can identify general areas of concern by moving a slide bar for the area of concern from 0% to a value up to 100%, with higher percentages indicating that the user is more afraid that the area of concern will not improve.

Another embodiment of an activities input screen that can be provided by the system 10 is shown in FIG. 7. The screen 318 of FIG. 7 is a non-limiting example of personal activity data input in which a user can identify one or more activities that the user would like to add to add to his/her list of activities to possibly engage in. The factors database 206 can configured to store activities that can be provided as suggestions to the user and/or that the user inputs as a user-generated activity in an activities database 222. The analysis module 202 can be configured to customize the activities provided on the personal activity data input screen to the specific user with one or more algorithms stored in an algorithms database 224 that generate activity recommendations with consideration of one or more factors such as the user's goal data, the user's goal target data, goal results for other users of the system 10 who engaged in a specific activity, the user's indicated likeability of previously performed activities, the user's removal of an activity from his/her list of possible activities without the user successfully performing the activity, etc. In other words, the algorithm(s) can include the one or more factors as variables.

Another embodiment of an activities input screen that can be provided by the system 10 is shown in FIG. 8. The screen 320 of FIG. 8 is a non-limiting example of personal activity data input in which a user can indicate whether the user is interested in pursuing a displayed activity, which in this non-limiting example is whether the user is interested in learning how to eat to better manage his/her energy. The screen 320 of FIG. 8 is configured to allow the user to indicate his/her level of interest in the displayed activity. The screen 320 in this illustrated embodiment includes three levels of interest, though another number of levels of interest can be provided. The three levels of interest in this illustrated embodiment include (from highest to lowest) "I can try this," "Hmm . . . maybe later," and "Not gonna do this." The levels of interest can be presented as text, as images, or (as in this illustrated embodiment) both. The analysis module 202 can be configured to use the user's indicated level of interest in executing one or more of the algorithms stored in the algorithms database 224, such as by using the user's indicated level of interest as a variable in an algorithm that determines what one or more activities to show to the user as recommended activities. For non-limiting example, the user selecting the highest level of interest can influence recommended activities shown to the user in the future by being more likely to recommend activities in a same class as the activity that the user showed a high level of interest in, such as by being more likely to suggest an outdoor athletic activity if the user indicating interest in another outdoor athletic activity or by being less likely to suggest a group activity if the user indicated a lowest level of interest in another group activity.

Another embodiment of an activities input screen that can be provided by the system 10 is shown in FIG. 10. The screen 324 of FIG. 10 is a non-limiting example of activity data input in which a user can indicate whether or not the user has interest in a class of activities. A variety of different classes can be provided. In this illustrated embodiment, the classes include filters that the user can use to indicate interest in various types of activities. The analysis module 202 can be configured to consider the user's input filter information in determining suggested activities for the user. In general, the analysis module 202 can be configured to execute algorithm(s) in the algorithms database 224 taking into account the user's interest in certain types of activities as indicated by the filters. For non-limiting example, the analysis module 202 can be configured to be more likely to suggest activities that are ritual building activities (e.g., involve developing a regular daily, weekly, etc. routine, involve establishing good habits, require repeated performance at different days and/or times, etc.) when the user has indicated interest in "Ritual Building Activity," the analysis module 202 can be configured to be more likely to suggest activities that involve learning (e.g., receiving information about relevant care providers in the user's geographic area by referencing care provider data stored in the care provider database 220, taking educational courses at a school, receiving nutritional tips built in to the system 10 and stored in the factors database 206 and/or elsewhere, etc.) when the user has indicated interest in "Learning Activity," and the analysis module 202 can be configured to be more likely to suggest activities that involve taking specific action (e.g., engaging in an athletic activity, making a phone call, etc.) when the user has indicated interest in "Transition/Session Activity." The activities database 222 can be configured to store educational information (e.g., text, images, videos, etc.) that can be provided to the user as a "learning" action and/or the activities database 222 can be configured to provide a link to and/or other access information for educational information that the user can access as a "learning" action.

Figure 22:
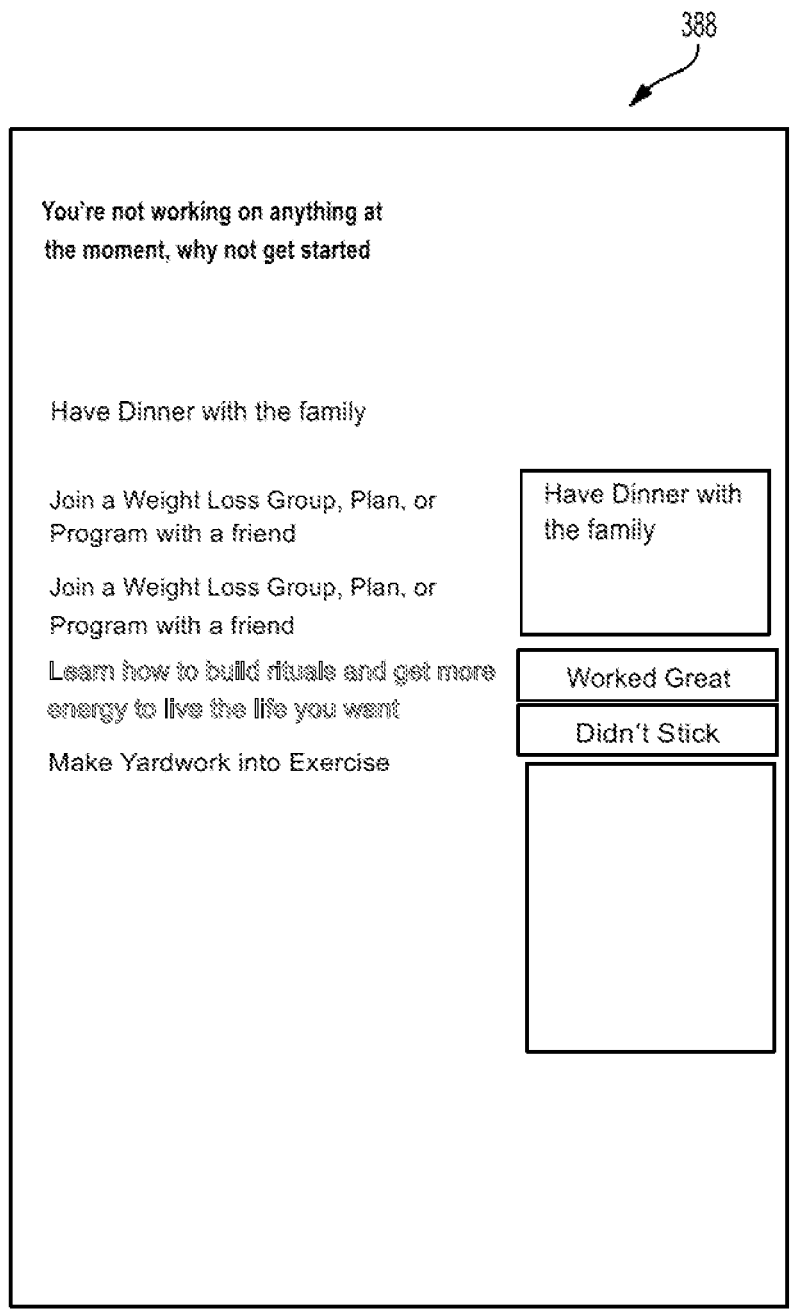
FIG. 22 is a diagram showing an embodiment of an activities input screen of a wellness, health, and lifestyle planning, tracking, and maintenance system.

Another embodiment of an activities input screen 388 that can be provided by the system 10 is shown in FIG. 22. The screen 388 of FIG. 22 is a non-limiting example of personal activity data input in which a user can indicate whether the user is interested in pursuing a displayed activity. Five possible activities are shown as options for selection in this illustrated embodiment. The displayed activities can be customized recommendations for the user, as discussed herein. The screen of FIG. 22 also shows an embodiment of activity status data input in which the user can indicate whether certain activities were performed ("Worked Great") or were not performed ("Didn't Stick").

Figure 23:
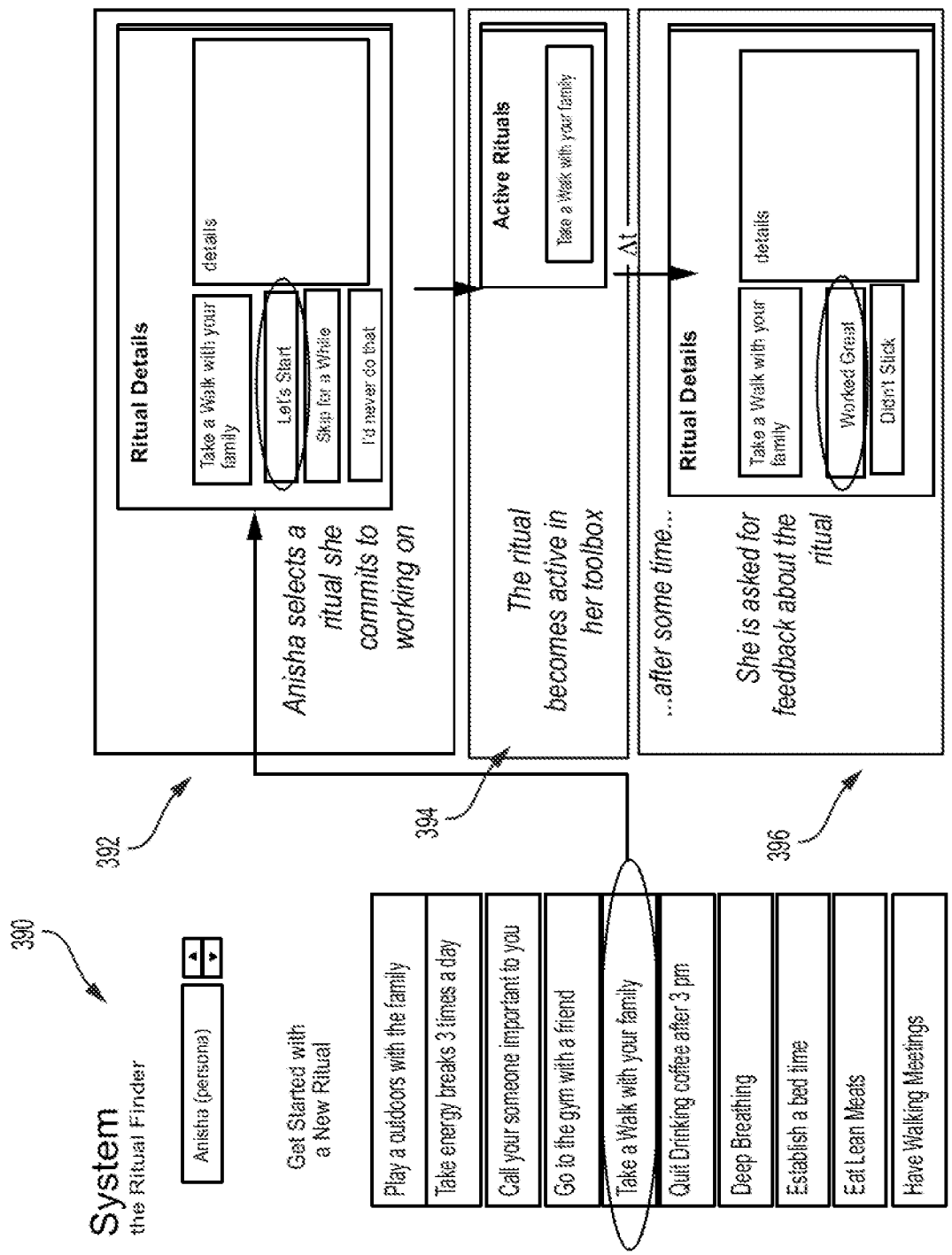
FIG. 23 is a diagram showing another embodiment of an activities input screen, an embodiment of a ritual details screen, an embodiment of an active rituals screen, and an embodiment of an activity status data input screen of a wellness, health, and lifestyle planning, tracking, and maintenance system.

Another embodiment of an activities input screen 390 that can be provided by the system 10 is shown in FIG. 23 on a left side thereof. The screen of FIG. 23 is a non-limiting example of personal activity data input in which a user ("Anisha" in this illustrated embodiment) can indicate whether the user is interested in pursuing a displayed activity. Ten possible activities are shown as options for selection in this illustrated embodiment.

When the user selects one of the displayed activities, "Take a Walk with your family" being selected in this illustrated embodiment, the system 10 can be configured to display a Ritual Details screen 392 as shown in an embodiment thereof on the top right of FIG. 23. The user can then input activity likeability data for the selected activity so as to indicate whether or not the user has interest in that selected activity. The system 10 can allow the user to indicate to the system 10 that a certain activity does not interest the user (e.g., by selecting "I'd never do that"), thereby allowing the analysis module 202 to not suggest that activity to the user in the future. The system 10 can allow the user to indicate to the system 10 that that a certain activity does not currently interest the user but may interest the user at some future time (e.g., by selecting "Skip for a While"), thereby allowing the analysis module 202 to suggest that activity again to the user at some point in the future. The point in the future can be a predetermined amount of time after the user indicates possible interest, e.g., one week, two weeks, three days, one month, three months, etc.), can be after a predetermined number of other activities have been suggested to the user (e.g., after ten other activities have been suggested to the user, after fifty other activities have been suggested to the user, etc.), can be after the user has indicated possible and/or no interest in a predetermined number of other activities (e.g., the user has selected "Skip for a While" for five other activities, the user has selected "Skip for a While" or "I'd never do that" for twenty other activities, etc.). The system 10 can allow the user to indicate to the system 10 that the user would like to add a certain activity to his/her current list of activities (e.g., by selecting "Let's Start"), thereby allowing that activity to be stored in the individual database 216 as part of that user's profile. When the user indicates to the system 10 that the user would like to add a certain activity to his/her current list of activities, the system 10 can be configured to display that selected activity in the user's list of active activities, as shown in an embodiment of an Active Rituals screen 394 in the middle right of FIG. 23.

FIG. 23 also shows, in a bottom right portion thereof, an embodiment of an activity status data input screen 396 that can be provided by the system 10. The activity status data input screen 396 can allow the user to indicate whether or not an activity in the user's current list of activities has been performed ("Worked Great") or not ("Didn't Stick"). The system 10 can be configured to provide the activity status data input screen 396 in response to the user selecting that activity and/or the system 10 can be configured to automatically provide the activity status data input screen 396 after a predetermined amount of time has passed since the user added the activity to his/her active activities list. Automatically asking the user for the status of an active activity can help ensure that the system 10 has accurate information about the user, which can allow the analysis module 202 to perform more accurate analysis and provide more useful and/or more timely data to the user. The predetermined amount of time can be the same for every activity or can vary by activity, e.g., can be a certain amount of predetermined time for habit type activities and a different certain amount of predetermined time after an activity that has a scheduled performance day and/or time. The predetermined amount of time can be, e.g., one week, two weeks, three days, one month, etc.

Another embodiment of an activities input screen 398 that can be provided by the system 10 is shown in FIG. 24. The screen 398 of FIG. 24 is a non-limiting example of personal activity data input in which a user can indicate whether the user is interested in pursuing a displayed activity. Ten possible activities are shown as options for selection in this illustrated embodiment.

The activities input screen 398 of FIG. 24 also illustrates that the system 10 can be configured to allow a user to indicate whether or not the user has interest in a class of activities. In this illustrated embodiment, the classes include activities that expand energy, activities that recover energy, activities that preserve energy, activities that fuel energy, activities that focus energy, and activities that have certain attributes and include ritual building or learning activities. In response to the user's selection of any of the displayed classes, the system 10 can be configured to filter the displayed list of possible activities to activities that are part of that class, e.g., stored in the activities database 222 as being part of that class. The certain attributes can vary. Non-limiting examples of the certain attributes include classes (e.g., sports, spiritual learning, activities that can be performed at work, activities that can be performed at home, activities involving the user's children, activities involving the user's pets, indoor activities, outdoor activities, etc.).

The system 10 can be configured to allow the user to view additional possible activities. As in the illustrated embodiment of FIG. 24, the system 10 can be configured to show additional possible activities to the user in response to the user clicking on a Next List button 400 or a Previous List button 402. As will be appreciated by a person skilled in the art, graphical user interface elements other than buttons can be used for the Next List and Previous List buttons 400, 402, such as a drop-down menu, a scroll bar, etc.

Figure 25:
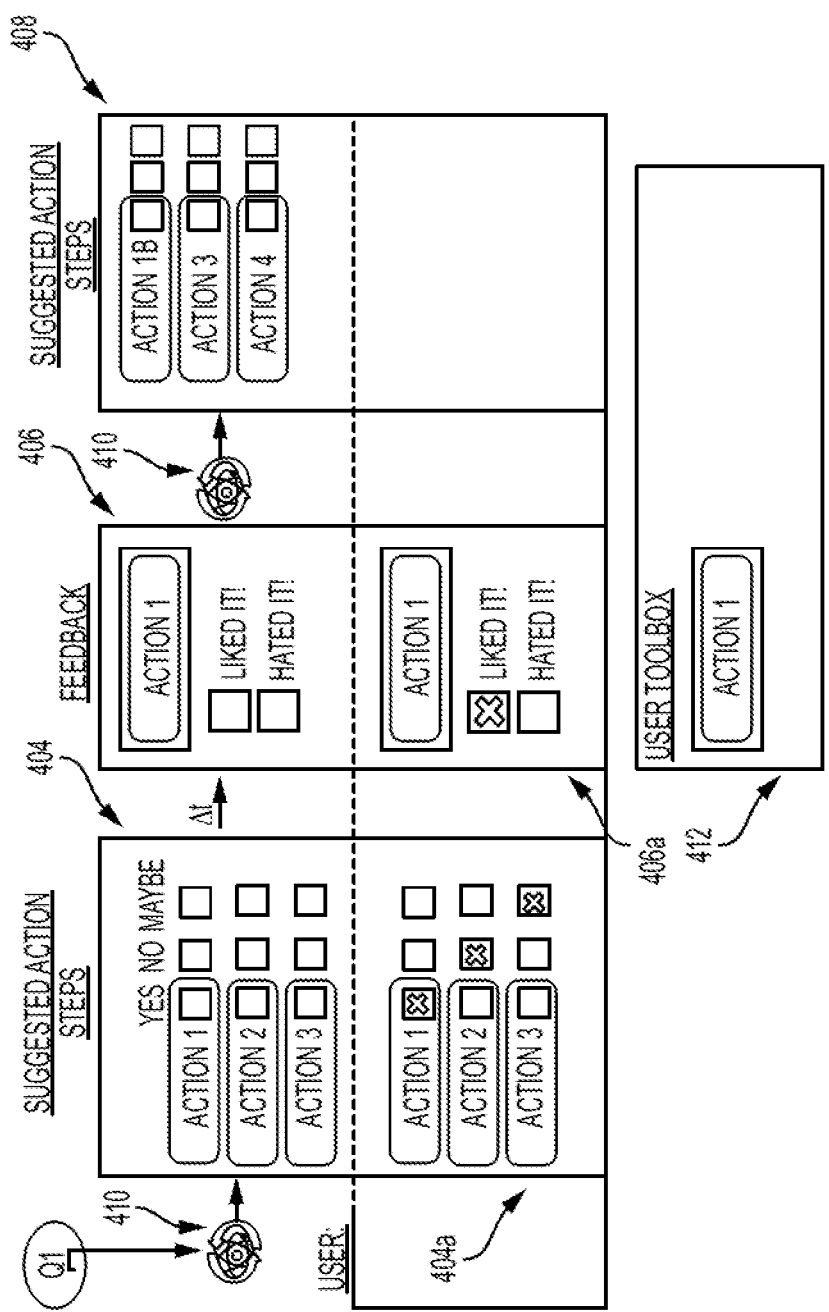
FIG. 25 is a diagram showing another embodiment of an activities input screen of a wellness, health, and lifestyle planning, tracking, and maintenance system.

Another embodiment of an activities input screen 404 that can be provided by the system 10 is shown in FIG. 25. The screen 404 of FIG. 25 is a non-limiting example of personal activity data input in which a user can indicate whether the user is interested in pursuing a displayed activity, which can also be referred to as "actions." Similar to the screen 320 of FIG. 8, the screen 404 of FIG. 25 is configured to allow the user to indicate his/her level of interest in the displayed activity. The screen 404 in this illustrated embodiment includes three levels of interest, though another number of levels of interest can be provided. The three levels of interest in this illustrated embodiment include "yes," "no," and "maybe." A shaded version of the activities input screen 404a in FIG. 25 shows a non-limiting example of user selections of a level of interest for each of the three activities.

The screen of FIG. 25 also shows an embodiment of activity data input screen 406 in which the user can indicate whether or not the user enjoyed certain activities. The system 10 can be configured to automatically provide the activity data input screen 406 to the user after an amount of time $\Delta t$ has passed since the user provided interest level input of "yes" or "maybe" for activities via the activities input screen 404. The amount of time $\Delta t$ can be a predetermined amount of time, e.g., one week, three days, one month, etc., after the interest level is input, independent of what the specific activities marked with "yes" are, which can facilitate regular updating of the system 10 and/or can train a user to regularly input data. The predetermined amount of time $\Delta t$ can instead depend on what the specific activities marked with "yes" are, which can allow shorter term or one-time activities to be updated before too much time has passed since interest was shown in them, and which can prevent the system 10 from asking the user too frequently about longer term or repeatable activities. Additionally or alternatively to automatically providing the activity data input screen 406 at predetermined times, the system 10 can be configured to display the activity data input screen 406 on demand in response to user input to the system 10, thereby allowing the user to input likeability at convenient times and/or very soon after an action is performed while memory of the action is typically most fresh.

As in this illustrated embodiment, the user can indicate enjoyment by selecting "Liked It!" and can indicate a lack of enjoyment by selecting "Hated It!" In other embodiments, the enjoyment levels can have different name identifiers and/or can be more levels than two (e.g., a ranking of enjoyment on a scale of one to ten, a rating of "enjoyed," "neutral enjoyment," and "did not enjoy," etc. A shaded version of the activity data input screen 406a in FIG. 25 shows a non-limiting example of user selections of enjoyment for each of the activities marked with "yes." In at least some embodiments, the system 10 can be configured to activity data input screen 406 for activities marked as "maybe" in addition to those marked with "yes," which can help remind users about activities they may be interested in and/or can allow the system 10 to gather data about activities that the user performed despite previously indicating only a possible, "maybe" interest in them.

The analysis module 202 can be configured to execute algorithm(s) stored in the algorithms database 224 with consideration of the user's input activity likeability data. In general, the analysis module 202 can be more likely to suggest activities to the user that belong to a same class of activities as the user indicated as enjoying and can be less likely to suggest activities to the user that belong to a same class of activities as the user indicated as not enjoying. In some embodiments, the analysis module 202 can be configured to suggest activities that the user has indicated as enjoyable when the user has previously performed the activity, which can help encourage good habits by the user repeatedly performing a beneficial activity. Over time, the user may incorporate the beneficial activity into his/her routine such that the user performs the action without the system 10 even repeatedly suggesting it. As in this illustrated embodiment, the system 10 can be configured to automatically suggest one or more activities to the user based on the user's feedback input, e.g., based on whether the user "Liked It!" or "Hated It!", as indicated by the Suggested Action Steps screen 408 on a right side of FIG. 25. A processing symbol 410 can indicate when the system 10 automatically performs analysis using the analysis module 202 in response to a user input, e.g., generating a list of possible activities in response to the user answering a question Q1 and generating a list of possible actions in response to the user providing feedback on Action 1.

FIG. 25 also illustrates a user toolbox 412 configured to display all of the user's actions selected as "yes" on the activities input screen 404. The user toolbox 412 can help the user keep track of his/her current selected actions. The user toolbox 412 can be configured to allow the user to select an action displayed therein, e.g., by clicking on the name of the action, etc., so as to cause the activity data input screen 406 to be displayed so the user can input his/her likeability of the selected action. The user toolbox 412 can thus be configured to facilitate on demand display of the activity data input screen 406.

FIGS. 26-31 show embodiments of activity input screens 414, 416, 418, 420, 422, 424 for another embodiment of the system 10. The screens of FIGS. 26-31 show screens for display in a browser window of a desktop or laptop computer, but similar screens can be provided on other types of client terminals. The screens of FIGS. 26 and 28-31 each include a dashboard 426 similar to the dashboard 305 of FIG. 6.

Figure 26:
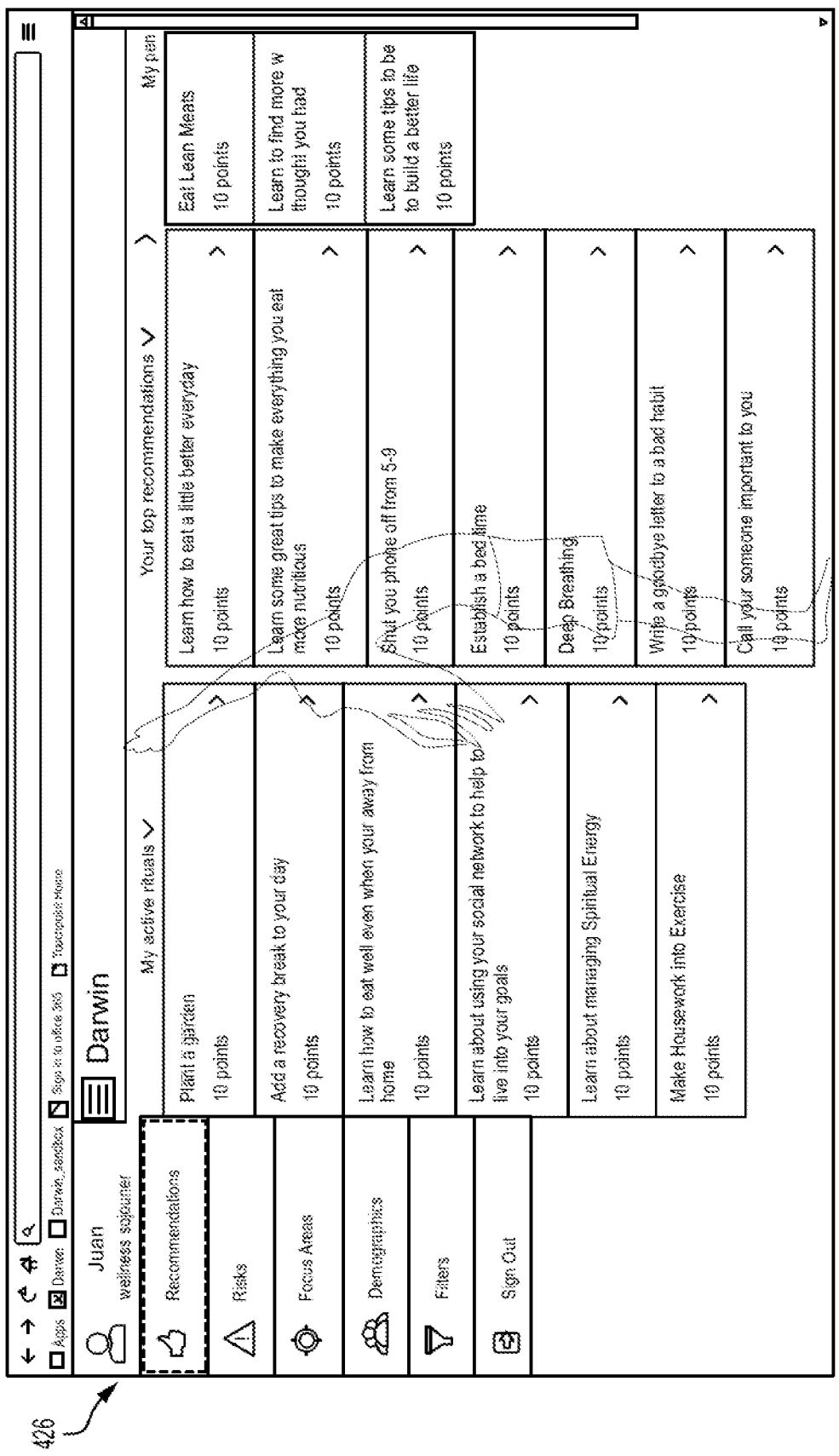
FIG. 26 is a diagram showing another embodiment of an activities input screen of a wellness, health, and lifestyle planning, tracking, and maintenance system.
Figure 27:
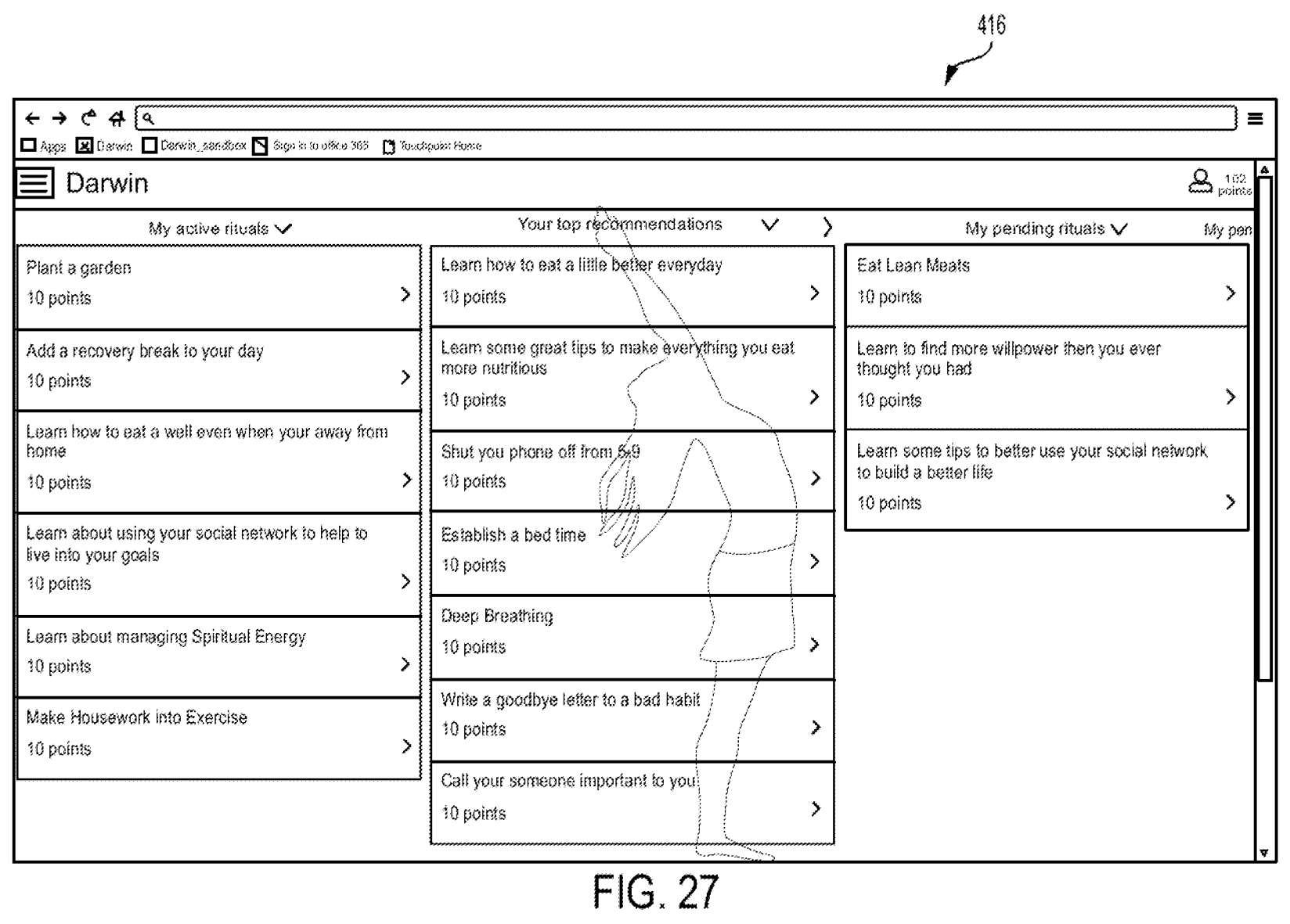
Figure 28:
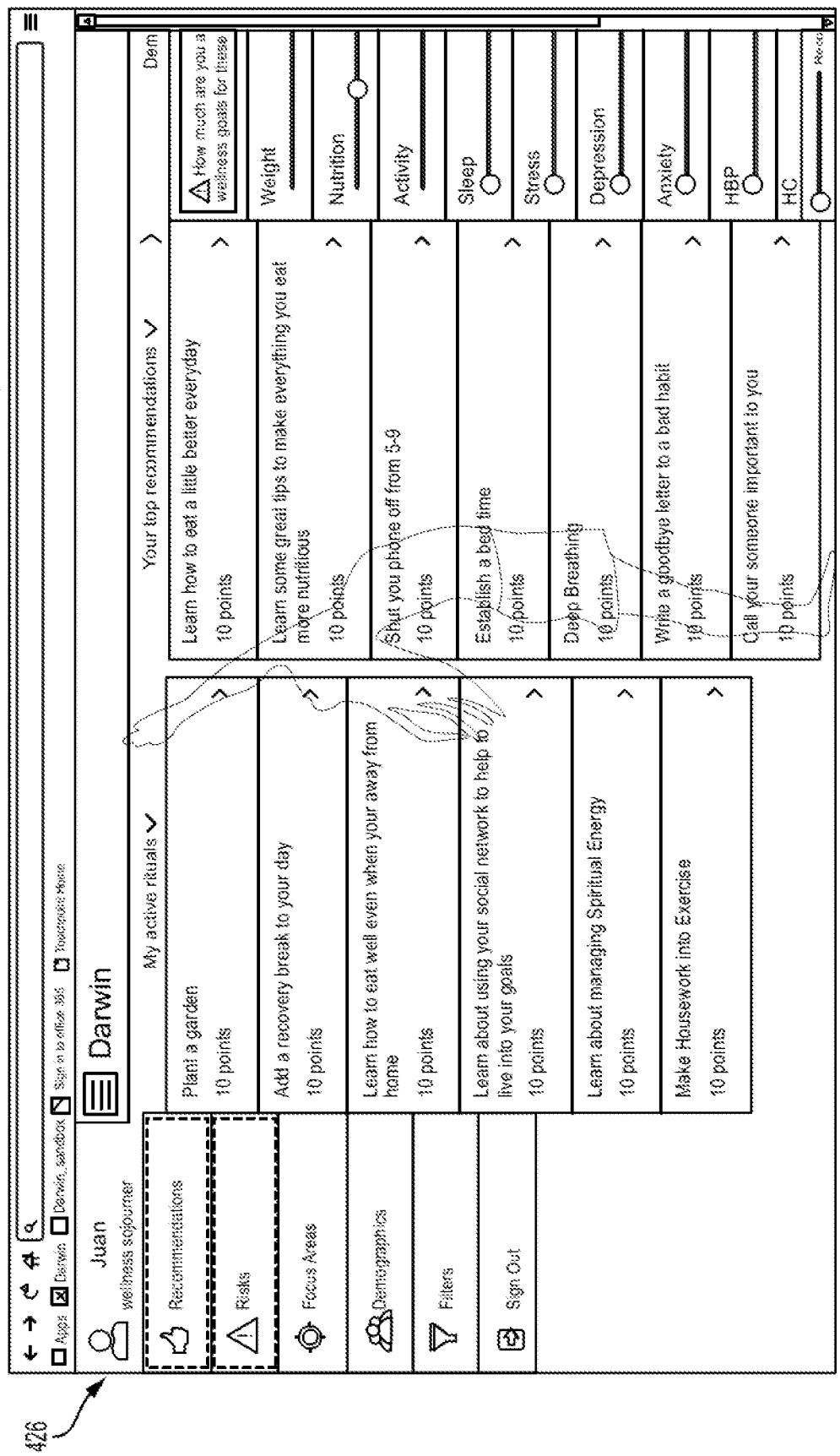
FIG. 28 is a diagram showing another embodiment of an activities input screen of the system of FIG. 26.
Figure 29:
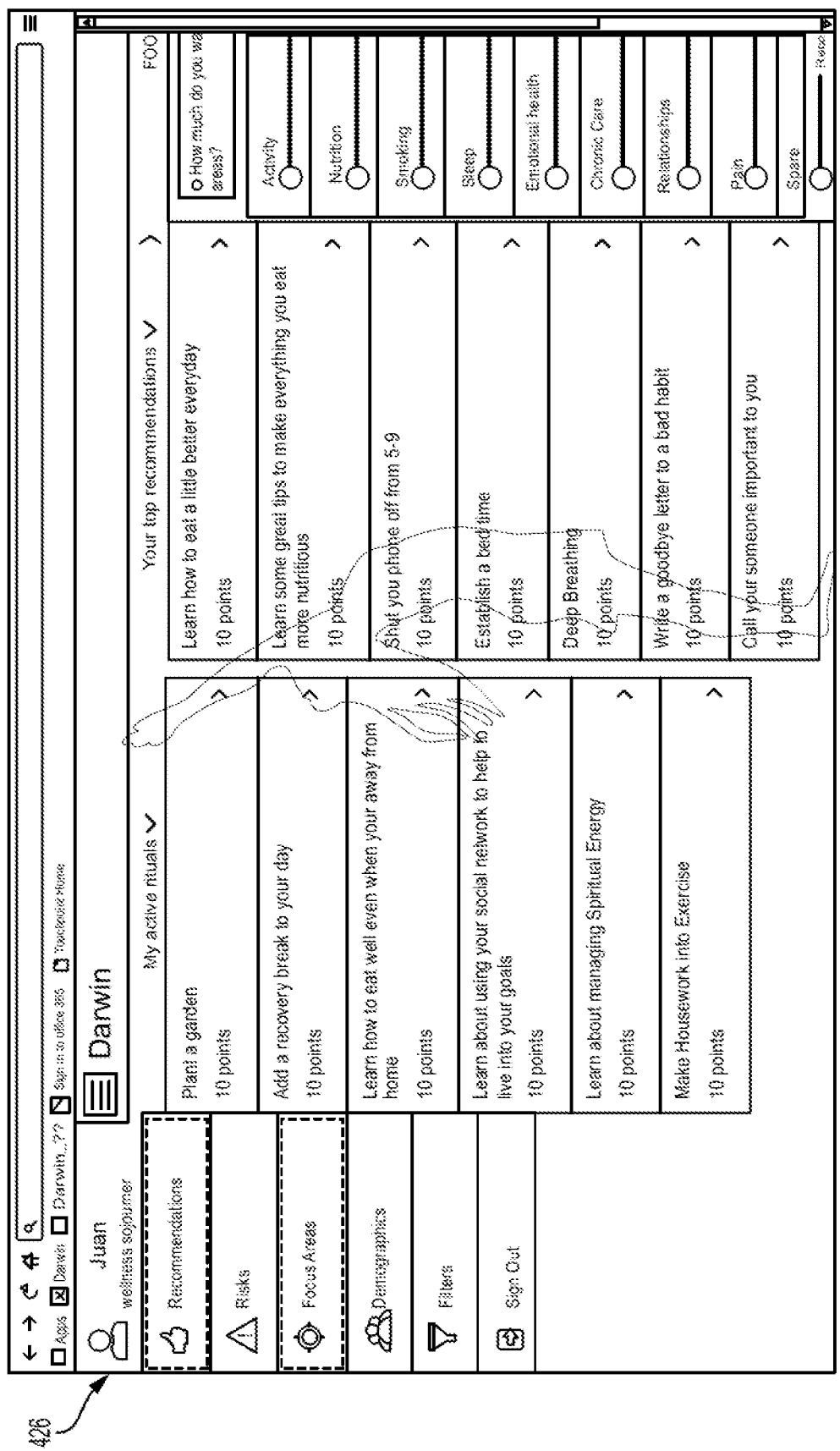
FIG. 29 is a diagram showing another embodiment of an activities input screen of the system of FIG. 26.
Figure 30:
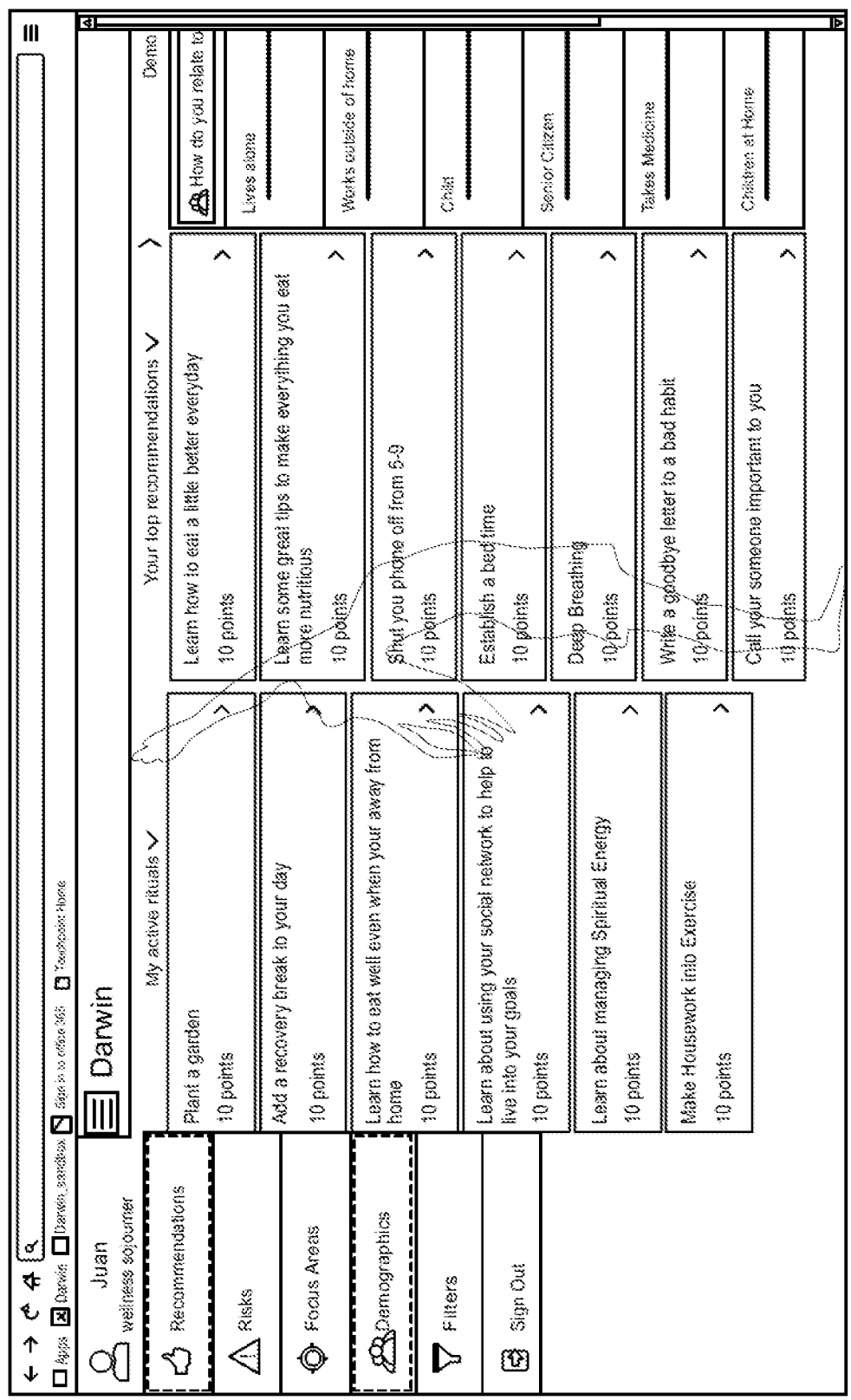
FIG. 30 is a diagram showing another embodiment of an activities input screen of the system of FIG. 26.
Figure 31:
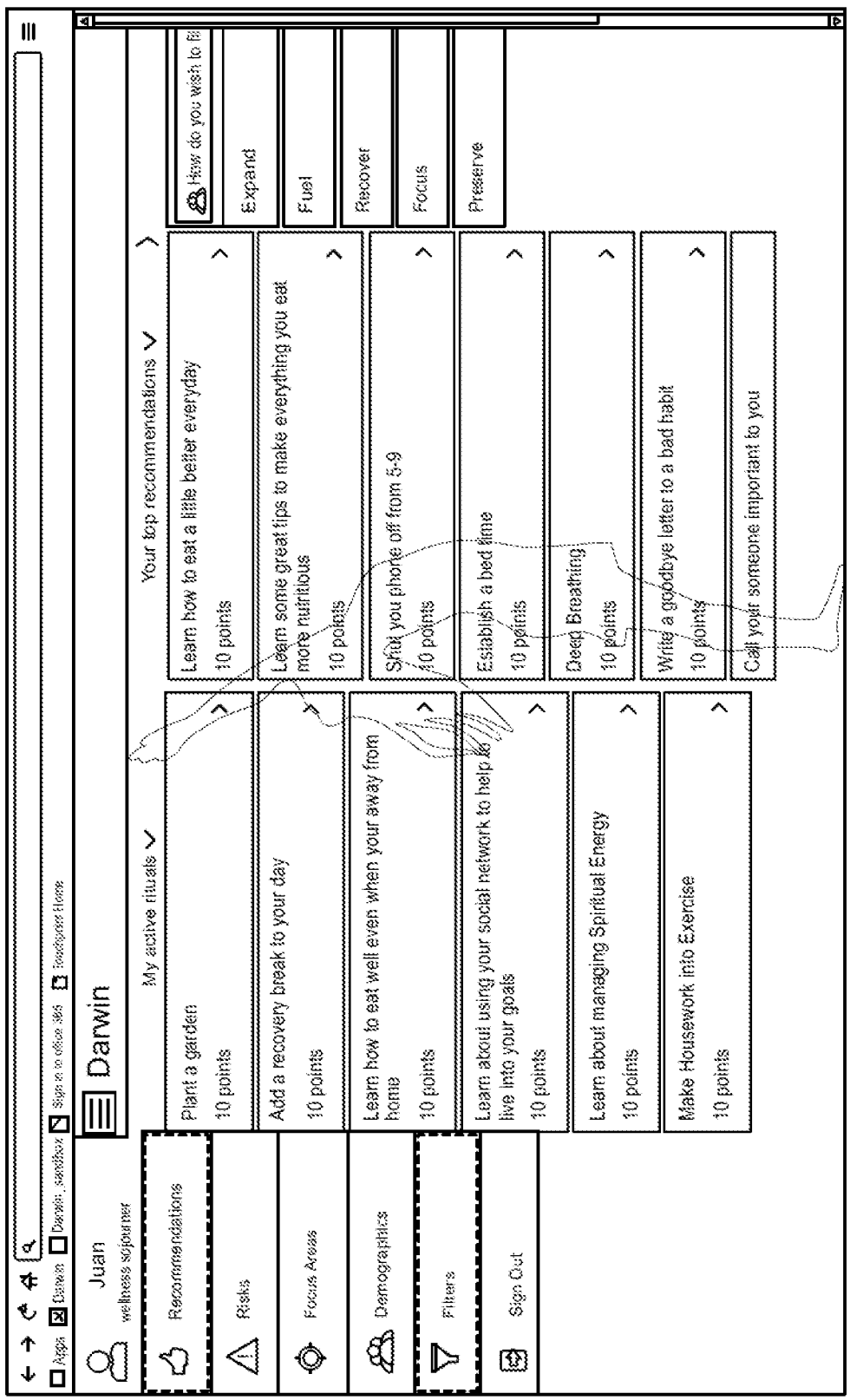
FIG. 31 is a diagram showing another embodiment of an activities input screen of the system of FIG. 26.

FIG. 26 shows the dashboard 426 and shows "Recommendations" selected such that the screen 414 shows suggested activities to the user that the analysis module 202 has determined to display. FIG. 27 shows the "Recommendations" selected as in FIG. 26, but unlike FIG. 26, the screen 416 of FIG. 27 has the dashboard 426 hidden. Hiding the dashboard 426 can maximize an amount of activities information that can be shown at one time to a user. FIG. 28 shows the dashboard 426 and shows "Recommendations" and "Risks" selected such that the screen 426 shows suggested activities to the user that the analysis module 202 has determined to display and shows goal data input similar to FIG. 9. FIG. 29 shows the dashboard 426 and shows "Recommendations" and "Focus Areas" selected such that the screen 420 shows suggested activities to the user that the analysis module 202 has determined to display and shows focus areas that the user can select as being important or de-select as not being important along a continuum of importance via slide bars for each focus area. FIG. 30 shows the dashboard 426 and shows "Recommendations" and "Demographics" selected such that the screen 422 shows suggested activities to the user that the analysis module 202 has determined to display and shows demographics data for the user that the user can edit (e.g., indicate whether or not the user is a senior citizen, whether or not the user has children at home, whether the user takes medicine or not, whether the user lives alone or with other people, whether the user works at home or outside the home, whether the user is a child or an adult, etc.). FIG. 31 shows the dashboard 426 and shows "Recommendations" and "Filters" selected such that the screen 424 shows suggested activities to the user that the analysis module 202 has determined to display and shows filters that the user can manipulate to indicate whether or not the user has interest in one or more classes of activities.

Analysis Module

The analysis module 202 can generally be configured to analyze data input into the system via the input module 200, data stored in the people database 204, data stored in the factors database 206, and/or data stored outside the system 10. More particularly, the analysis module 202 can be configured to perform analysis related to activities that can aim to improve and/or maintain a person's wellness, health, and/or lifestyle in order to help maximize positive wellness, health, and/or lifestyle benefits to users of the system 10. In an exemplary embodiment, the analysis module 202 can be configured to execute one or more algorithms stored in the algorithm database 224 to perform analysis.

Activities, also called "actions" herein, are generally discussed herein as being related to at least one of wellness, health, and lifestyle. Non-limiting examples of activities include exercise; sport; substituting physical activity for couch time once this week; monitor and keep a daily blood pressure log; include a serving of vegetables with every meal; drink more water; drink a glass of water before giving in to a food craving; wait ten minutes before giving in to a food craving; use the 80/20 rule when snacking (snack healthy 80% of the time and treat yourself with less healthy snacks 20% of the time); use the 80/20 rule for meals; add protein to your salads; improve ergonomics in your home office and/or work office; at your next medical appointment try listening critically to help understand and remember what the doctor says; get a pill container to organize medications and to remember to take them; sign up for automatic medication refills; sign up for automatic bill payment; consider buying a meditation CD or download or make one of your own; add more nuts, seeds, and legumes to your diet; every ninety minutes get up and take a 5-10 minute standing/walking/stretching/movement break; add planned workouts to your work calendar and respect them like work meetings; use a step tracker daily; decide on a reward for yourself for achieving a goal like not smoking for one week; get a "worry notebook" and write down your worries every day and then imagine closing the book on your worries as you close the notebook daily; stay in hotels with exercise facilities and use them; fill your water bottle only halfway with water so you have to get up to refill it more frequently; eat breakfast daily; ensure that your bedroom is dark, quiet, and cool during sleep times; make yourself note cards that say, "I choose not to smoke today regardless of any situation," "I am a non-smoker," "I enjoy breathing fresh, clean air," and anything else you wish to remind yourself of on a daily basis, and read them every morning when you wake up and throughout the day when you need encouragement; come prepared to your medical appointments with your recent blood sugar results and a list of issues you want to discuss; check out the American Diabetes Association website for more information about support groups, online communities, and message boards; to help deal with pain, complete a pain and visualization exercise; sprinkle exercise throughout your day by taking quick walks whenever you can; make down time active time: try simple exercises like sit-ups and push-ups while you watch your favorite television shows; bring portable workout equipment like resistance bands when you travel, and ask your hotel desk about safe walking or running routes; be mindful during meals, eat slowly and chew each bite, pay attention to your feelings of fullness, and stop eating when you're full; evaluate your mattress and pillows, try out different levels of firmness, and if your mattress is more than 9-10 years old, it may need to be replaced; when you notice yourself tensing your muscles or grinding your jaw, go for a quick walk and clear your mind; when your mood changes, notice your thoughts, and when you feel a bad mood coming on, ask yourself, "What is that little voice in my head saying to me right now?" and try to work backward and see if you can identify what you were thinking right before the symptom hit; talk to someone you trust when something is bothering you and as you talk, listen to your own words to identify any thinking errors; try doing something unexpected and nice for someone else; if you're having trouble identifying your warning signs, ask someone close to you what symptoms they noticed in the early stages of your last episode; identify and work on other negative thoughts that may contribute to concentration (and memory) problems; learn to make amends if you act out your anger and take ownership of your behavior in a sincere, non-defensive manner; laugh out loud even If you might not feel like laughing right now; remember that sometimes sadness can be useful; identify and challenge distorted beliefs about nutrition; create a binge eating plan—reach out for support; create a binge eating plan—remember the costs; create a binge eating plan—visualize waking up tomorrow; create a binge eating plan—use affirmations; create a binge eating plan—reward yourself; write a list of the ways in which your life would be different if guilt and shame over your weight or shape did not have as big a role in it, and keep the list handy to review when you feel badly about yourself; go to the NIH website for more information on medications; plan around pain and be realistic and expect that pain will affect life at times; schedule breaks, rest, and pain relief activities; try not to be wary of digital health coaching (DHC) techniques even though they are not "in person" techniques; schedule the tough tasks when you're in the least pain; get a blood glucose meter and learn how to use it, find out the best time to test, and ask your doctor for signs that you medication is working; check out a support organization online for people with your medical ailment; challenge one negative thought this week; write down daily one simple happiness experienced; share daily via social media one simple happiness experienced; practice muscle relaxation; perform a muscle relaxation exercise daily before falling asleep; skip the elevator, escalator, or people mover; bring part of your dinner to work as lunch; write a gratitude journal; add some activity for an everyday task; quit drinking coffee after 3 pm; deep breathing; use a standup desk; plant a garden; establish a bed time; eat lean meats; use medicine reminders; keep an HCP question list; take a warm bath before bed; have dinner with the family; shut your phone off from 5-9; go to the gym; add a recovery break to your day; do a puzzle; play outdoors with the family; join a sports team; go to the gym with a friend; read a book; call someone important to you; write a note to a friend; coach a team; learn about adding a little activity to your life; learn some ways to get activity into your everyday life; learn some more way to get more active; learn how to build rituals and get more energy to live the life you want; learn how to eat to better manage your energy learn how to eat a little better every day; learn how to eat a well even when you are away from home; learn some tips to make everything you eat more nutritious; learn how to get a good night's sleep; learn some everyday ways to sleep better tonight; learn how to make a good night's sleep even easier; learn some more sleep tips; learn about nutrition for people with high blood pressure; learn about nutrition for people with high cholesterol; learn about nutrition for people with diabetes; learn how to talk to your doctor; learn to build the willpower to stick with you plan; learn to find more willpower than you ever thought you had; learn about using your social network to help to live into your goals; learn some tips to better use your social network to build a better life; learn why emotional health is important; learn how to be happier; learn to manage your moods; learn tips to everyday emotional health; learn to manage anxiety; learn to manage stress; learn to turn stress into resilience with recovery; learn some stress management tips; learn how to have a healthy pregnancy; learn how to manage sleep during pregnancy; learn how to manage stress during pregnancy; learn how to manage nausea during pregnancy; learn about nutrition during pregnancy; learn about exercise during pregnancy; learn to drive safer; learn to prevent foodborne illness; learn to prevent catching an infection; learn to the first steps to quit smoking; learn some tips to quit smoking; learn how to make your success stick; take a walk with your family; take a walk after dinner; take a walk for your break; walk while you do something else; walk to someplace you would normally drive; use a food tracking tool; cut back on caffeine in coffee, tea, energy drinks, and soda; incorporate back strengthening exercises into everyday routine; join a weight loss plan or program; form a weight loss group; join a weight loss group; join a weight loss group, plan, or program with a friend; sign up for an online weight loss plan; learn about managing physical energy; learn about managing mental energy; learn about managing emotional energy; learn about managing spiritual energy; use an activity tracker; use a mood tracker; use an energy tracker; make housework into exercise; make yard work into exercise; review restaurant menu's before you go to the restaurant; set a date to quit smoking; use a smoking quit kit; reward yourself every week for not smoking; get rid of your smoking stuff; and write a goodbye letter to a bad habit.

In one embodiment, the analysis module 202 can be implemented using one or more web pages which are configured to receive user input and present information to a user. In an exemplary embodiment, the analysis module 202 can be accessed by users via a web interface, e.g., by connecting to the Internet via a client terminal and accessing a specific web address, by launching an app on a client terminal that accesses the system 10, etc. As mentioned above, the users can wirelessly access the system 10, including the analysis module 202.

The analysis module 202 can be configured to determine activities to recommend to the user based on the user's demographics information, e.g., the demographics information regarding the user input via the demographics input module 208 and/or the demographics information regarding the user stored in the individual database 216. Activities recommended to the user can thus be more likely to be attractive to the user and/or more likely to actually be performed by the user, thereby providing a better chance of improving the user's wellness, health, and/or lifestyle. The analysis module 202 can be configured to determine activities to recommend to the user based on the user's demographics information in a variety of ways. In an exemplary embodiment, the analysis module 202 can be configured to determine activities to recommend to the user based on the user's demographics information by comparing the user's demographic information, e.g., the user's demographic information as reflected in the user's B-DNA, with demographics information corresponding to activities stored in the activities database 222. In other words, activities stored in the activities database 222 can be stored therein with associations to one or more demographic characteristics, thereby allowing the analysis module 202 to identify which the activities are associated with one or more demographic characteristics of the user. For non-limiting example, the analysis module 202 can be configured to filter activity suggestions based on a user's medical history as indicated by the user's demographic information, e.g., the analysis module 202 can be configured to limit activity suggestions to a user having a medical history of heart problems to those activities tagged in the activities database 222 as being safe for people with heart issues. For another non-limiting example, the analysis module 202 can be configured to filter activity suggestions based on a user's age, e.g., filter activity suggestions to those associated with an age range including the user's age. For yet another non-limiting example, the analysis module can be configured to eliminate activity suggestions for a user based on the user's geographic location, e.g., eliminate winter sport activities requiring snow to users located in places where it does not snow.

The analysis module 202 can be configured to consider any number of demographics factors when analyzing activities. In general, the more factors considered, the more likely that activities will be relevant to a user. The analysis module can be configured to weigh one or more demographics factors more than one or more other demographics factors. In this way, a user's indicated preference for certain goals can be better addressed.

The analysis module 202 can be configured to determine activities to recommend to the user based on the user's activity information, e.g., the activities information regarding the user input via the activities input module 210 and/or the activities information regarding the user stored in the individual database 216 that is not specifically input by a user but that is learned by the system 10 as the user makes choices and/or performs actions. Activities recommended to the user can thus be more likely to be attractive to the user and/or more likely to actually be performed by the user, thereby providing a better chance of improving the user's wellness, health, and/or lifestyle. The analysis module 202 can be configured to determine activities to recommend to the user based on the user's activity information in a variety of ways. In an exemplary embodiment, the analysis module 202 can be configured to determine activities to recommend to the user based on the user's activity information by comparing the user's activity information, e.g., the user's activity information as reflected in the user's B-DNA, with activity information corresponding to activities stored in the activities database 222. In other words, activities stored in the activities database 222 can be stored therein with associations to one or more activity characteristics, thereby allowing the analysis module 202 to identify which the activities are associated with one or more activity characteristics of the user. For non-limiting example, the analysis module 202 can be configured to filter activity suggestions based on a user's preference for indoor or outdoor activities, e.g., the analysis module 202 can be configured to limit activity suggestions to a user preferring outdoor activities to those activities tagged in the activities database 222 as being able to be performed outdoors. For another non-limiting example, the analysis module 202 can be configured to filter activity suggestions based on a user's strong concern that weight loss will not be achieved, e.g., the analysis module 202 can be configured to limit activity suggestions to a user who marked weight loss as a risk to those activities tagged in the activities database 222 as having effectively caused users to lose weight.

The analysis module 202 can be configured to consider any number of activity factors when analyzing activities. In general, the more factors considered, the more likely that activities will be relevant to a user. The analysis module can be configured to weigh one or more activity factors more than one or more other demographics factors. In this way, a user's indicated preference for certain goals can be better addressed.

The analysis module 202 can be configured to determine activities to recommend to the user based on a fingerprint of the user, e.g., based on the user's unique demographics and/or the user's unique activity preferences. In general, a user's fingerprint indicates the user's preferences for a plurality of factors that the analysis module 202 can use in evaluating activities for the user, e.g., in determining activities to recommend to the user. In an exemplary embodiment, a user's fingerprint can be stored in the individual database 216 for the user so as to be specifically associated with the user, and every user's fingerprint can be stored in the population database 218 without being specifically associated with a specific user. In other words, the population database 218 can store anonymous fingerprints of actual users of the system 10. Similarly, an activity's fingerprint can indicate characteristics for each of the plurality of factors that the analysis module 202 can use in evaluating activities for the user, e.g., in determining activities to recommend to the user. In an exemplary embodiment, an activity's fingerprint can be stored in the activities database 222. In general, as discussed further below, a user's fingerprint can be compared with the fingerprints of activities to help determine which one or more of the activities should be suggested to the user.

The system 10 can be configured to adjust one or more of the characteristics that make up the user's fingerprint each time the user makes a decision, e.g., when the user selects one or more activities to pursue from a presented list, when the user does not select one or more activities to pursue from a presented list, when the user indicates likeability of a performed activity, when the user indicates that a certain action should never be presented to the user as an option, when the user indicates that a certain class of actions should never be presented to the user as options, when the user indicates that a certain class of actions can be presented to the user as options, when the user indicates that an activity previously indicated as one being pursued is no longer being pursued, etc. The user's decision indicating B-DNA information of the user can be overt (e.g., the user inputs data into the system in reply to a presented question, etc.) or can be covert (e.g., the user chooses an activity to pursue). The specific one or more characteristics of the user's fingerprint that the system 10 updates based on any one specific user decision can be predetermined, e.g., an algorithm can be run with respect to a characteristic of enjoyment of outdoor activities when the user selects or chooses not to select an outdoor activity, an algorithm can be run with respect to wanting to perform activities in a group when the user inputs an answer to a presented question asking if the user enjoys group activities, etc. The user's fingerprint can thus dynamically change over time as the user's life, objectives, physical health, etc. change without the user even having to specifically input any of these changes into the system 10. The system 10 can instead be configured to infer such changes with respect to the user based on the user's interaction with the system 10 and can be configured to update the user's B-DNA accordingly. The system 10 can thus be continually attuned to a specific user's preferences regardless of how many other users are using the system 10, of how many other users having profiles similar to the user are using the system 10, and of how often the user updates his/her demographic information.

The system's creation and continual updating of a user's fingerprint based on the user's choices (which can include the user's positive selection of an action to pursue as well as the user's choice to not select an action presented to the user as an option) can allow the system 10 to create a behavioral profile of the user, e.g., create the fingerprint, in a data agnostic way. In other words, the system 10 does not need to reference and/or create a database of the user's current and/or past choices to infer preferences of the user or to determine which one or more actions to present to a user as options that are consistent with the user's objectives regarding health, wellness, and prevention. Instead, the system 10 can use the user's fingerprint.

The analysis module 202 can be configured to determine activities to recommend to the user based on fingerprints associated with activities stored in the activities database 222. These fingerprints can be pre-stored, which can allow the system 10 to provide recommendations to a user when the user is a new user and/or if there are not any or many other user fingerprints available for comparison with the user's fingerprint.

Alternatively or in addition to the analysis module 202 being configured to determine activities to recommend to the user based on fingerprints associated with activities stored in the activities database 222, the analysis module 202 can be configured to determine activities to recommend activities to a user by comparing the user's fingerprint, e.g., the fingerprint stored for the user in the individual database 216, with the fingerprints of other users, e.g., the plurality of fingerprints stored for the system's users in the population database 218. In other words, the analysis module 202 can be configured to determine activities to recommend to the user based on the experiences of other users. The fingerprints can thus allow the analysis module 202 to choose activities that the user is likely to enjoy and/or likely to effectively address the risk factors identified by the user based on the choices made and/or results achieved by other users as indicated by their fingerprints. The algorithms database 224 can include one or more algorithms that cause such comparison. An algorithm to perform such a comparison of multiple elements with one another can have a variety of configurations, as will be appreciated by a person skilled in the art.

A fingerprint can include a plurality of characteristics (e.g., a plurality of activity factors) that can each have one of three values. Each of the characteristics can represent a feature of the user, such as the user's preference with respect to activities and/or an aspect of the user's demographic. A first value (e.g., a positive number such as "1") can indicate a first condition of the user with respect to that characteristic, a second value (e.g., a negative number such as "−1") can indicate a second condition of the user with respect to that characteristic, and a third value (e.g., a null "0") can indicate a third condition of the user with respect to that characteristic. The first and second conditions can be mutually exclusive of one another, which can help allow the fingerprint to clearly identify the user's preferences with respect to a certain characteristic by either being "positive" (first condition), e.g., the user enjoys or otherwise achieved a positive result with respect to that characteristic, or "negative" (second condition), e.g., the user dislikes or otherwise experienced a negative result with respect to that characteristic. Non-limiting examples of mutually exclusive first and second conditions include indoor and outdoor for preferred location of activities, solo and group for preferred number of people involved in an activity, yes and no for whether a user has a dog, yes and no for whether a user prefers activities that involve walking, yes and no for whether a user prefers activities that involve water, and religious and non-religious for types of affirmations that the user chooses to access and/or read. The third condition can be neutral because the user's activity choices do not indicate a preference to the first condition or the second condition or because adequate data has not yet been gathered for the user with respect to that characteristic. Each of the fingerprint's characteristics can be defaulted to the third condition so as to start in a neutral position. In order for a characteristic to change from the third condition, the user has to provide some input to the system 10 that affects that characteristic so as to cause the analysis module 202 to change that characteristic from the third condition to either the first condition or the second condition. The fingerprint can thus evolve over time with the user and reflect his/her current life stage, current goals, etc.

Each of the characteristics in the B-DNA can be classified based on their rate of change over time. For non-limiting example, characteristics can be classified as "Static" or "Dynamic" to correspond to whether they are likely to change over the "short term" use of the system 10. The "Static" classification can generally refer to items that reflect long-term or permanent characteristics, and the "Dynamic" classification can generally refer to items more transient in nature or more likely to change over time.

As discussed further below, the analysis module 202 can use various scaling factors in a user's fingerprint to capture more nuanced importance of behavioral elements and include the ability to randomly test for evolutionary changes over time in the B-DNA.

An individual's fingerprint can be changed by the system 10, e.g., by the analysis module 202, in various ways. One way that the system 10 can be configured to change an individual's fingerprint is by changing one or more of the fingerprint's characteristics (e.g., one or more of its variables) in response to direct input to the system 10 via the input module 200 by the individual or by a person authorized to input data for the individual. The ones of the characteristics that change in response to direct input can include "Static" characteristics that are likely to remain static so as to vary little over time, such as demographic information, personal limitations ("risk factors"), personal focus areas, etc. The data input to the system 10 can be entered as binary data directly into the individual's fingerprint by the analysis module 202 (e.g., response X changes a specific characteristic to the first condition if not already so set and opposite response X' changes the specific characteristic to the second condition if not already so set), or the analysis module 202 can be configured to calculate using an algorithm in the algorithms database 224 whether the first or second condition is appropriate for a specific characteristic based on the user's input. Some characteristics of the fingerprint can be configured to be directly changed while other characteristics of the fingerprint can be configured to change based on algorithmic result.

Another way that the system 10 can be configured to change an individual's fingerprint is by indirect inference from user input to the system 10. The ones of the characteristics that change by indirect inference can include "Dynamic" characteristics that are likely to change over time. The analysis module 202 can be configured to make indirect inferences from user input by comparing the fingerprint characteristics of an activity users chooses with the user's existing fingerprint, or by comparing a composite fingerprint of several of the user's activity choices with the user's existing fingerprint.

The analysis module 202 can be configured to compensate for possible bias favoring suggestions of related items as a consequence of choosing one item. For example, once an individual has chosen an activity (e.g., walking more often), the analysis module 202 can be configured to intuit that similar choices involving opportunities to walk may also be selected by the individual in the future and could introduce a bias in the development of the B-DNA that would result in disproportionately more walking related suggestions being presented to the individual by the system 10. By downgrading the value of related suggestions, the analysis module 202 can be configured to provide the individual with a more balanced set of recommendations and can be configured to develop a B-DNA that is more truly reflective of the individual. The analysis module 202 can, however, also be configured to provide recommendations to an individual without reference to the user's fingerprint, which can help introduce the user to new and potentially enjoyable and/or beneficial activities and/or can help the system 10 gather more varied data via the user's selection or non-selection of such recommendations.

Figures 32, 33, 34, 35:
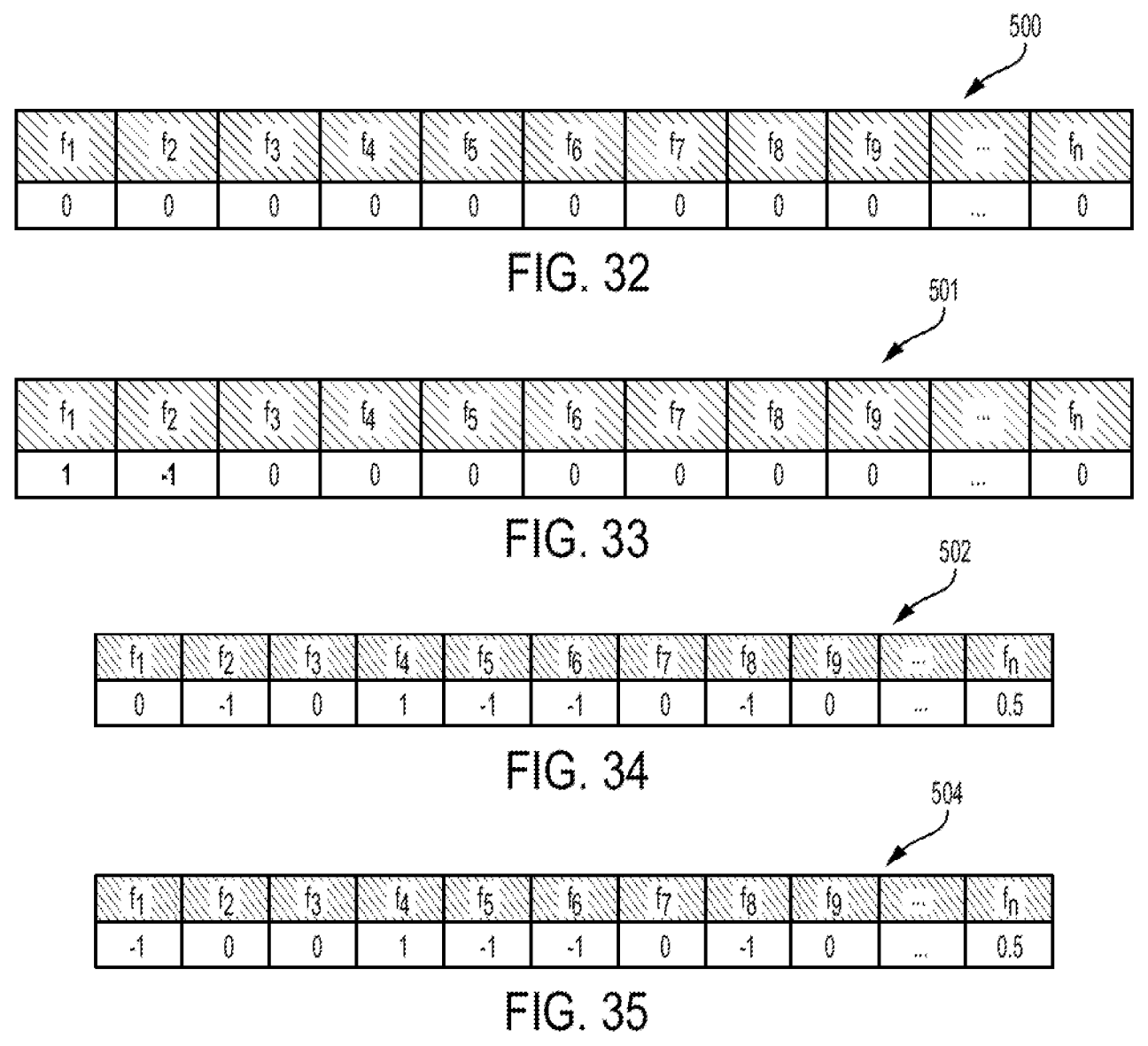

FIG. 32 illustrates one embodiment of a user fingerprint 500 including a plurality of characteristics $f_1$, $f_2$, $f_3$, $f_4$, $f_5$, $f_6$, $f_7$, $f_8$, $f_9$, ... $f_n$. The fingerprint 500 in this embodiment can be a user's initial fingerprint, with all of its characteristics $f_1$, $f_2$, $f_3$, $f_4$, $f_5$, $f_6$, $f_7$, $f_8$, $f_9$, ... $f_n$ being neutral, e.g., each set to the third condition, as represented by the number zero. As the user interacts with the system 10 by providing data input thereto via the input module 200 as related to Static characteristics, e.g., by inputting responses to demographics questions, etc., the analysis module 202 can be configured to change the Static characteristics based on the user's input as discussed above. FIG. 33 illustrates an updated fingerprint 501 as the user's now-current fingerprint having two "Static" characteristics $f_1$, $f_2$ thereof changed to the first and second conditions, respectively, in response to user input related to those characteristics $f_1$, $f_2$ as predetermined by the system 10, with a remainder of the characteristics $f_3$, $f_4$, ... $f_n$ remaining neutral.

As mentioned above, each activity can have associated therewith a fingerprint, the characteristics of which do not change over time, e.g., each of the characteristics remains at its predefined one of the first, second, and third conditions (absent an authorized administrator's intervention changing an activity's fingerprint). The analysis module 202 can be configured to compare the user's fingerprint and the fingerprint of an activity selected by the user to pursue and to change the user's fingerprint based on the comparison. The analysis module 202 can be configured to use a weighting factor, also referred to herein as a "scaling factor," to adjust the magnitude of that selected activity's fingerprint impact on the user's fingerprint. The scaling factor can be based on a choice of the user with respect to the selected activity. Scaling factors can be configured to temper the effect of certain user choices over time to lessen the effect of type I errors (false positives) and type II errors (false negatives). Table 1 below indicates one embodiment of scaling factors that can be predetermined (e.g., preprogrammed into the system 10) for various activity choices.

TABLE 1

| User Choice With Respect To Selected Activity | Scaling Factor |
| --- | --- |
| Decision to engage in the activity immediately | 0.1 |
| Decision to engage in an activity at some later point | 0.05 |
| Engaging in the activity | 0.05 |
| Successfully "Ritualizing" the activity | 0.05 |
| Abandoning the activity | −0.05 |
| Beneficial experience as a result of engaging in the activity | 0.1 |
| Negative experience as a result of engaging in the activity | −0.1 |

Figure 36:
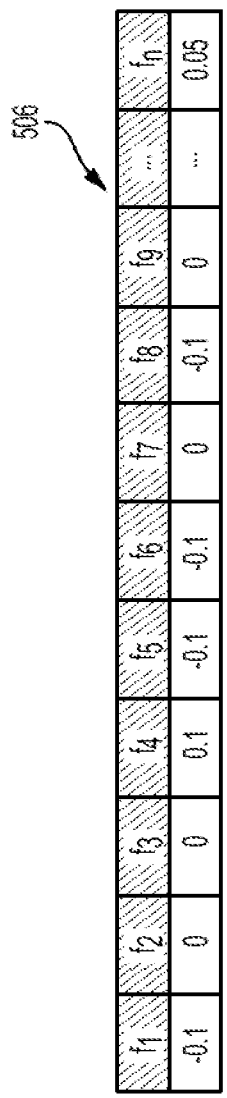
FIG. 36 is a diagram showing an embodiment of a weighted distance array of the system of FIG. 32.
Figure 37:
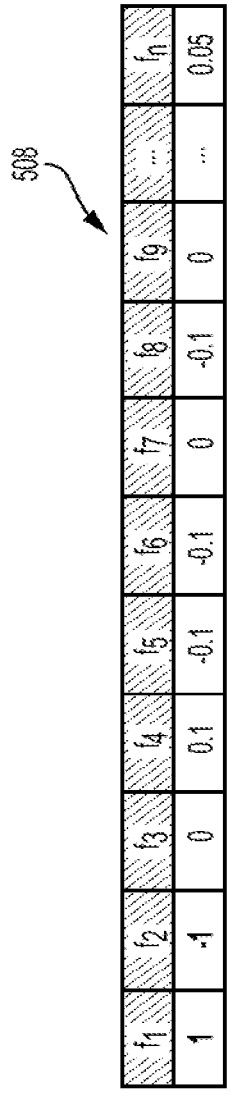
FIG. 37 is a diagram showing an updated version of the user fingerprint of FIG. 33.

FIG. 34 illustrates one embodiment of a fingerprint 502 for an activity. The analysis module 202 can be configured to calculate a distance array between the user fingerprint 500 and the activity fingerprint 502 by simple subtraction of the user's current fingerprint 501 from the activity fingerprint 502. FIG. 35 illustrates a distance array 504 calculated by subtracting the user's current fingerprint 501 of FIG. 33 from the activity fingerprint 502 of FIG. 34, e.g., subtracting user characteristic $f_1$ from activity characteristic $f_1$ to result in distance array characteristic $f_1$, etc. The analysis module 202 can be configured to multiply the distance array 504 with the scaling factor associated with the user's input regarding the activity. FIG. 36 illustrates a weighted distance array 506 calculated by the analysis module 202 by multiplying the distance array 504 by a scaling factor of 0.1 (e.g., multiplying each of the distance array's characteristics by 0.1) which, in the non-limiting example of Table 1, reflects that the user decided to engage in the selected activity immediately. The analysis module 202 can be configured to add the weighted distance array 506 to the user's current fingerprint 501 for all the "Dynamic" characteristics $f_3$, $f_4$, ... $f_n$ thereof to create the user's new current fingerprint 508, shown in FIG. 37. The analysis module 202 thereby changed the user's current fingerprint from the fingerprint 501 of FIG. 33 to the fingerprint 508 of FIG. 37 in response to the user inputting to the input module 200 an indication to engage immediately in the activity associated with the activity fingerprint of FIG. 34. The analysis module 202 can thus be configured to make recommendations of activities to the user based on the current fingerprint 508 of FIG. 37 so as to make recommendations that reflect the user's actual actions as reflected by a particular activity's selection by the user and the user's decision to engage in the activity immediately.

The analysis module 202 can be configured to apply a non-linear effect to the weighted distance array 506 to help prevent a user's decision (e.g., the user selecting to immediately perform the activity associated with the activity fingerprint 502) from having too overwhelming an effect on the user's current fingerprint and thereby skewing the user's current fingerprint too much from the user's actual choices. In other words, the weighted distance array 506 can be dampened or accelerated. The analysis module 202 can be configured to modify the weighted distance array 506 to magnify a user's choice so as to amplify its effect on the user's current fingerprint, and/or the analysis module 202 can be configured to modify the weighted distance array 506 to dampen a user's choice so as to reduce its effect on the user's current fingerprint. In an exemplary embodiment, the analysis module 202 can be configured to amplify some user choices and dampen other user choices.

Figure 38:
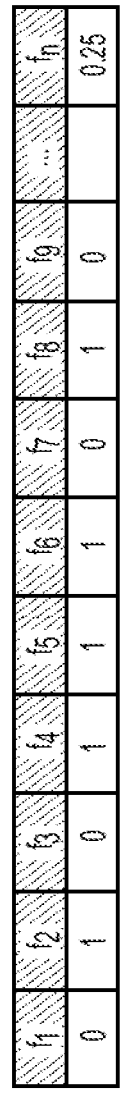
FIG. 38 is a diagram showing an embodiment of a secondary scaling array of the system of FIG. 32.
Figure 39:
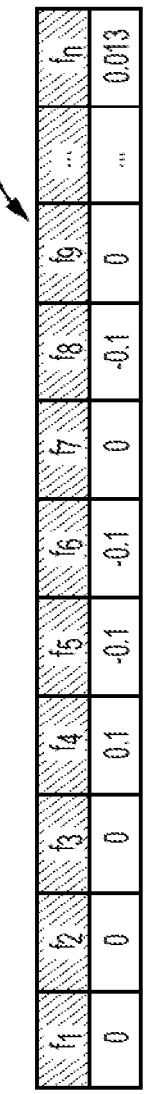
FIG. 39 is a diagram showing an embodiment of a secondary weighted scaling array of the system of FIG. 32.
Figure 40:
FIG. 40 is a diagram showing an updated version of the user fingerprint of FIG. 37.

The analysis module 202 can be configured to apply the non-linear effect in a variety of ways. In an exemplary embodiment, the analysis module 202 can be configured to apply the non-linear effect using a secondary scaling factor to attenuate disproportionate effects calculated from the absolute value (Abs) or the square of the weighted distance array 506 for the chosen activity. FIG. 38 illustrates a secondary scaling array 510 calculated by the analysis module 202 by squaring the activity fingerprint 502 and adding a predetermined secondary scaling factor for the selected activity thereto, with the predetermined secondary scaling factor equaling zero in this illustrated embodiment. FIG. 39 illustrates a secondary weighted distance array 512 calculated by the analysis module 202 by multiplying the weighted distance array 506 by the secondary scaling array 510. The analysis module 202 can be configured to add the secondary weighted distance array 512 to the user's current fingerprint 501 for all characteristics $f_1$, $f_2$, ... $f_n$ thereof to create the user's new current fingerprint 514, shown in FIG. 40.

In another embodiment, the analysis module 202 can be configured to calculate a secondary scaling array by taking an absolute value of the activity fingerprint 502 and adding the predetermined secondary scaling factor for the selected activity thereto. The analysis module 202 can be configured to then calculate the user's new current fingerprint as discussed above with respect to FIGS. 39 and 40.

In yet another embodiment, the analysis module 202 can be configured to calculate a secondary scaling array by taking the square root of the activity fingerprint 502 and adding the predetermined secondary scaling factor for the selected activity thereto. The analysis module 202 can be configured to then calculate the user's new current fingerprint as discussed above with respect to FIGS. 39 and 40.

The analysis module 202 can be configured to modify a characteristic of the user's current fingerprint based on a mean of the characteristic over the user's last N activity choices, where N is a positive integer greater than one. The analysis module 202 can be configured to calculate a mean value of the characteristic over the user's last N activity choices. If the mean value is above a predetermined threshold value then the characteristic can be assigned a predetermined set value and can be assigned a lower predetermined set value if the mean value is below the predetermined threshold value. For non-limiting example, if the mean value is above 0.5 then the characteristic can be assigned the value 1.1 (value range 1.01-1.5) and can be assigned the value 0.9 (value range 0.95 to 0.8) if the mean value is below 0.5.

The analysis module 202 can be configured to change a characteristic's rate of change in a calculation of the user's new current fingerprint. As the user makes various choices as input to the system 10, the user's current fingerprint can change, as discussed herein. A certain one or more of the characteristics of the user's fingerprint may change more often and/or at a different magnitude than other ones of the characteristics. The analysis module 202 can be configured to identify such trends in changing characteristics and reflect that trend in calculating the user's new current fingerprint. For non-limiting example, if a characteristic has been going in a certain direction for several change iterations (e.g., repeating increasing in positive number), its velocity in that direction can be accelerated or reduced by the analysis module 202.

The analysis module 202 can be configured to maintain the user's current fingerprint despite the user making a choice such as choosing to pursue a certain activity. The system 10 can thus be configured to introduce activity suggestions to test receptivity and inform future choice offerings without corrupting the current B-DNA. For non-limiting example, some activities may offer "Learn about nutrition and diet" as opposed to "Eat more fruits and vegetables." The user accepting the "Learn" activity can be captured by the system 10 as guidance for what other suggestions to offer related to diet and nutrition but not be reflected as an incremental change in the user's current B-DNA. Conversely, the user accepting "Eat more fruits and vegetables" can be a concrete action that causes the analysis module 202 to change the user's B-DNA as described herein and thereby increase or decrease priority for other related recommendations.

The analysis module 202 can be configured to discern behavioral attributes of the user from the user's fingerprint that are aligned to certain products, services, educational materials, etc. The system 10 can thus be configured to provide recommendations of consumable products that work within the behavior patterns of the user rather than to abruptly change the user's behavior to conform to the consumable product. For non-limiting example, a user's B-DNA may reflect a propensity for individual, private, physical activity, as interpreted by the analysis module 202. The analysis module 202 can be configured to provide recommendations to the user reflective of this identified propensity, such as offer a link to a fitness app for the user's personal training. For another non-limiting example, a user's B-DNA may reflect that the user has an interest in nutrition and energy, as interpreted by the analysis module 202. The analysis module 202 can be configured to provide recommendations to the user reflective of this identified interest, such as offering links for purchase of consumable products in the form of nutrition products that support energy.

The system 10 can be configured to share at least some elements of an individual's fingerprint among several domains accessible by the system 10, thereby allowing learning of one domain from "successful" user choices (e.g., choices incorporated into a user's routine behavior) to improve the appropriateness of choices presented to that individual in a different domain. For non-limiting example, choices of a user with respect to a domain directed to wellness through exercise can be applied to a domain directed to the user's health.

Figure 41:
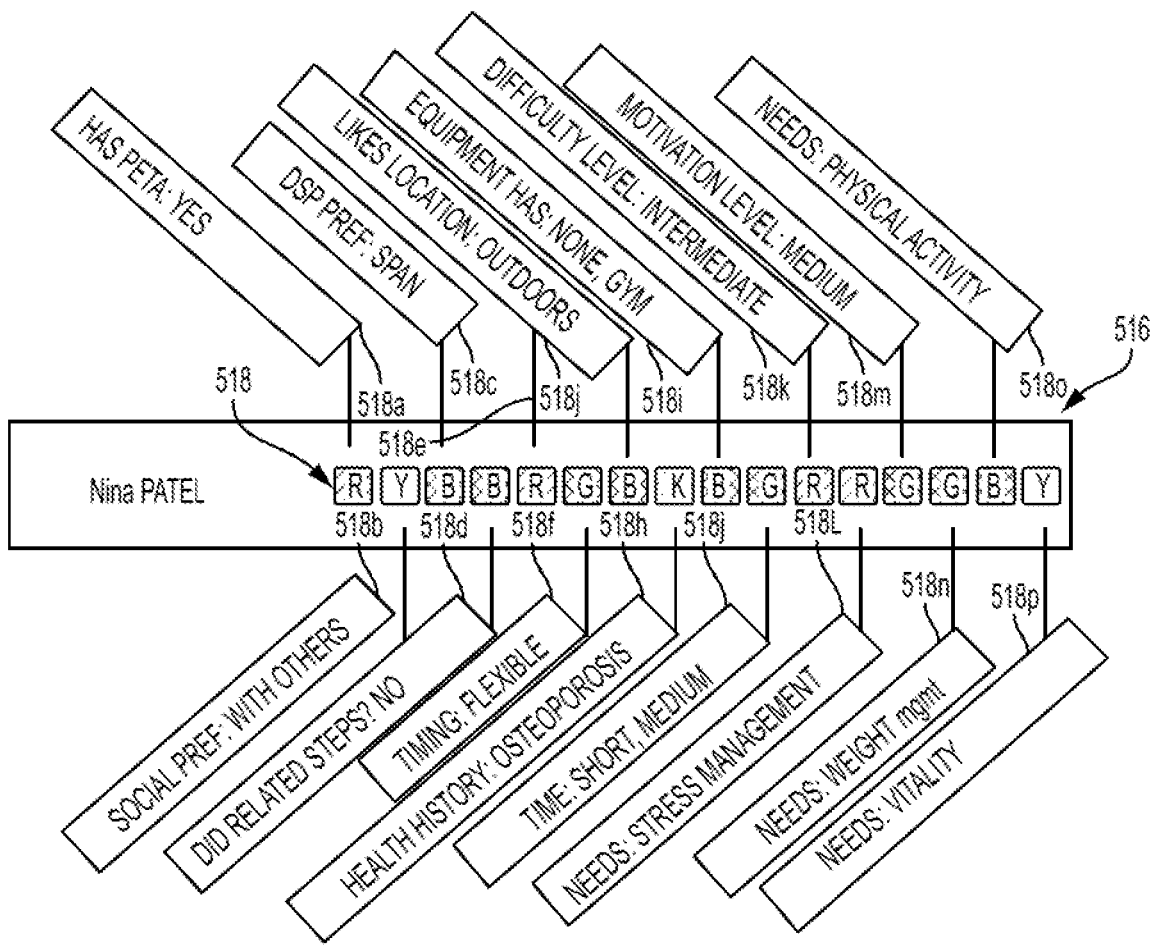
FIG. 41 is a diagram showing another embodiment of a user fingerprint of a wellness, health, and lifestyle planning, tracking, and maintenance system.
Figure 42:
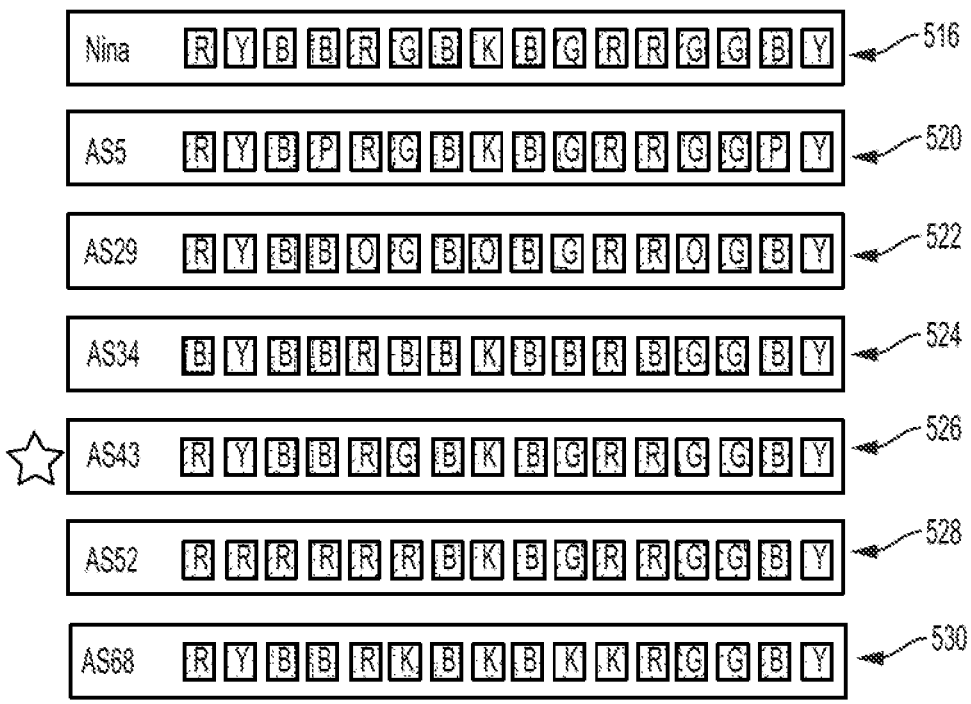
FIG. 42 is a diagram showing the fingerprint of FIG. 41 and embodiments of a plurality of activity fingerprints of the system of FIG. 41.

FIGS. 41 and 42 illustrate another embodiment of a user fingerprint 516, named Nina Patel in this illustrated embodiment. Each of a plurality of characteristics 518 of the fingerprint 516 can indicate the user's preference with respect to activities and/or indicates an aspect of the user's demographic. The fingerprint 516 include sixteen characteristics 518 in this illustrated embodiment, but a fingerprint can include any number of characteristics. Any number and any type of activities and demographics can be represented in the B-DNA 516. As in this illustrated embodiment, the fingerprint 516 can include characteristics 518 representing demographic information (whether the user has pets 518$a$, what equipment the user has access to 518$i$ (e.g., none, gym, home weights, etc.), health history with respect to osteoporosis 518$h$), and can include characteristics 518 representing activities information (whether the user prefers social activities 518$b$ (e.g., with a group or solo), user DSP preference 518$c$ (e.g., dot, span, etc.), whether the user performed related steps for actions 518$d$, activity sequence progress 518$e$ (e.g., how many activities in a set sequence of activities the user has completed), the user's preferred timing for performing activities 518$f$ (e.g., flexible, early morning, morning, afternoon, evening, late night, lunchtime, etc.), whether the user prefers indoor or outdoor activities 518$g$, activity duration preference 518$j$ (e.g., short, medium, long, 15 minutes, 30 minutes, etc.), activity difficulty level preference 518$k$ (e.g., easy, intermediate, hard, etc.), user motivation level 518$m$ (e.g., low, medium, high, etc.), stress management goal data 518L (e.g., whether or not the user has indicated an interest in stress management), weight management goal data 518$n$ (e.g., whether or not the user has indicated an interest in weight management), vitality goal data 518$p$ (e.g., whether or not the user has indicated an interest in increasing vitality), physical activity goal data 518$o$ (e.g., whether or not the user has indicated an interest in engaging in physical activity). The characteristics 518 forming the fingerprint 516 can all be input by the user via the input module 200 (e.g., input of demographics information, input of whether the user is concerned with weight management, input of whether the user prefers indoor or outdoor activities, etc.), can all be determined by the analysis module 202 (e.g., determining that the user does not perform related action steps, determining that the user tends to perform actions of intermediate difficulty, determining that the user tends to select actions that are performed outdoors, etc.), or can include one or more characteristics input by the user and one or more characteristics determined by the analysis module 202. FIG. 42 also shows this user B-DNA 516 in a first row thereof.

FIG. 42 also illustrates a plurality of activity fingerprints 520, 522, 524, 526, 528, 530, which each represent a different activity and that each include a plurality of characteristics. The user fingerprint 516 and the activity fingerprints 520, 522, 524, 526, 528, 530 can each have an equal number of characteristics, as in this illustrated embodiment, thereby facilitating comparison of the user fingerprint 516 with the activity fingerprints 520, 522, 524, 526, 528, 530. Each of the activity fingerprint's characteristics can thus correspond to the user fingerprint's characteristics 518. Thus, in this illustrated embodiment, each of the activity fingerprints 520, 522, 524, 526, 528, 530 has characteristics relating demographic information to the activity (whether the activity involves pets, what equipment the activity requires, whether having health history with respect to osteoporosis makes the activity unsuitable) and characteristics reflective of the activity itself such as actions required for the activity, environment of the activity, and probable effects on the user engaging in the activity (whether the activity is social, activity DSP, related steps for the activity, where the activity falls in a set sequence of activities, timing during the day for performing the activity, whether the activity is indoor or outdoor, activity duration, activity difficulty level, user motivation level best suited to the activity, activity's effect on stress management, activity's effect on weight management, activity's effect on vitality, physical activity level of the activity).

In FIGS. 41 and 42, the characteristics 518 making up the user fingerprint 516 and characteristics making up each of a plurality of activity fingerprints 520, 522, 524, 526, 528, 530, which each represent a different activity, that have the same identity are identified by color: blue ("B"), red ("R"), yellow ("Y"), orange ("O"), black ("K"), purple ("P"), and green ("G"). In other words, one characteristic in a fingerprint is identified by the color blue, another characteristic is identified by the color red, etc. For non-limiting example, "Health History: Osteoporosis" being black can indicate that the user has no osteoporosis history, as in the user fingerprint 516 and five of the activity fingerprints 520, 524, 526, 528, 530, while "Health History: Osteoporosis" being orange can indicate osteoporosis history, as with one of the activity fingerprints 522. A third color, not shown, can indicate that no data is available for a user's osteoporosis health history. "Health History: Osteoporosis" is an example of a fingerprint element that is binary with one or two possible options ("yes" or "no" for this element), with an option also being available for no data available. For another non-limiting example, "Time" being green can indicate a preference for activities of short and medium durations, as with the user fingerprint 516 and four of the activity fingerprints 520, 522, 526, 528, "Time" being blue can indicate a preference for activities of short duration, as with one of the activity fingerprints 524, and "Time" being black can indicate no time preference established, as with one of the activity fingerprints 530. Other colors can represent other time duration preferences, e.g., red indicating a preference for medium and long duration activities, black indicating no time duration preference data being available, etc. "Time" is an example of a fingerprint element that is not binary since more than two possible options are available in addition to a choice for no data being available. As will be appreciated by a person skilled in the art, the analysis module 202 can be configured to analyze characteristics of user and activity fingerprints that can be represented by colors when displayed, viewed, printed, etc. using numeric representations instead of colors, e.g., "0" representing the color black, "1" representing the color orange, "2" representing the color red, etc., to facilitate electronic analysis. The characteristics being color-coded can facilitate visual presentation of fingerprints to users, e.g., on a display of the system 10, which can allow a user to review his/her associated profile via characteristics recorded in his/her fingerprint.

FIG. 42 shows a result of a comparison performed by the analysis module 202 comparing the user fingerprint 516 with the activity fingerprints 520, 522, 524, 526, 528, 530 associated with activities stored in the activities database 222. Only six activity fingerprints 520, 522, 524, 526, 528, 530 are shown as being compared with the user fingerprint 516 in this illustrated embodiment, but any number of activity fingerprints can be compared with a particular user's fingerprint. In an exemplary embodiment, a user's fingerprint can be compared with hundreds or thousands of other fingerprints, which can help the analysis module 202 find best matches. As indicated by the star in FIG. 42, the activity module 202 in this illustrated embodiment determines that the user fingerprint 516 most closely matches the activity fingerprint 526 for activity 43 ("AS43"), which in this illustrated embodiment is setting aside fifteen minutes in the middle of your day for a walk outside and to do this four times this week. The closest match is an identical match in this illustrated embodiment, but the closest match may in some instances not be an identical match.

The analysis module 202 can use various metrics to determine a closest match of an activity for a particular user when no activity's fingerprint identically matches the user's fingerprint. For non-limiting example, the analysis module 202 can be configured to have a predetermined prioritization of characteristics such that characteristics are ranked in order of importance, thereby allowing the analysis module 202 to determine best activity matches based on best matches to the highest ranked characteristics. For another non-limiting example, if one activity's fingerprint matches more characteristics with the user's fingerprint than any other activity's fingerprint, the analysis module 202 can be configured to choose that activity. If multiple activity fingerprints each have a same highest number of characteristics matched with the user's fingerprint, the analysis module 202 can be configured to randomly choose a predetermined number of activities from among the multiple activities, to choose any one or more of the activities not yet recommended to the user, or to choose any one or more of the activities previously recommended to but not yet performed by the user. For yet another non-limiting example, if multiple activity fingerprints each have a same highest number of characteristics matched with the user's fingerprint, the analysis module 202 can be configured to choose one or more of the most popularly performed ones of the activities based on a rate of successful completion of the activities by other users of the system 10.

Figure 43:
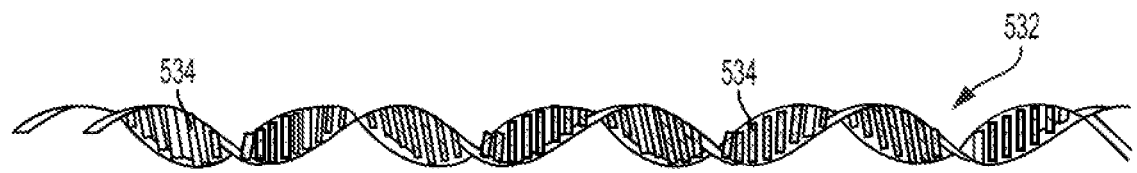
FIG. 43 is a diagram showing another embodiment of a user fingerprint of a wellness, health, and lifestyle planning, tracking, and maintenance system.
Figure 44:
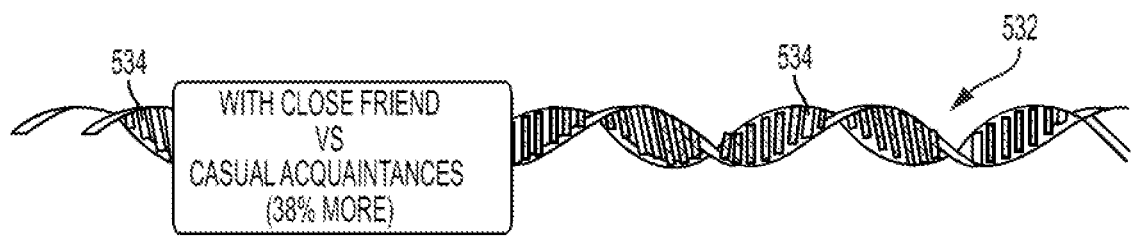
FIG. 44 is a diagram showing the user fingerprint of FIG. 43 with a characteristic thereof selected.

FIG. 43 illustrates another embodiment of a user fingerprint 532 that includes a plurality of characteristics 534, which are each a bar in the DNA-like helix configuration of this fingerprint 532 embodiment. Each of the bars can be color-coded, as in this illustrated embodiment, similar to the color-coding of the fingerprints 516, 520, 522, 524, 526, 528, 530 of FIGS. 41 and 42. As in this illustrated embodiment, a color of the characteristic 534 can indicate a degree of confidence for the characteristic. In this illustrated embodiment, dark red represents the third condition (e.g., that information for the user is unknown with respect to that characteristic or that the user is neutral with respect to that characteristic), dark green is at the other end of the spectrum from dark red and represents that one of the two binary choices for the characteristics fully dominates the other choice, shades of red represent that one of the two binary choices for the characteristics does not dominate the other choice but has some significance, and shades of green represent that one of the two binary choices for the characteristics does not yet dominate the other choice but is closer to dominating. As illustrated in FIG. 44, the user fingerprint 532 can be configured to show information for one of the characteristics 534 when a user hovers a pointer over the characteristic, which in this illustrated embodiment is a characteristic for whether the user prefers activities performed with a close friend or activities performed with casual acquaintances.

Figure 45:
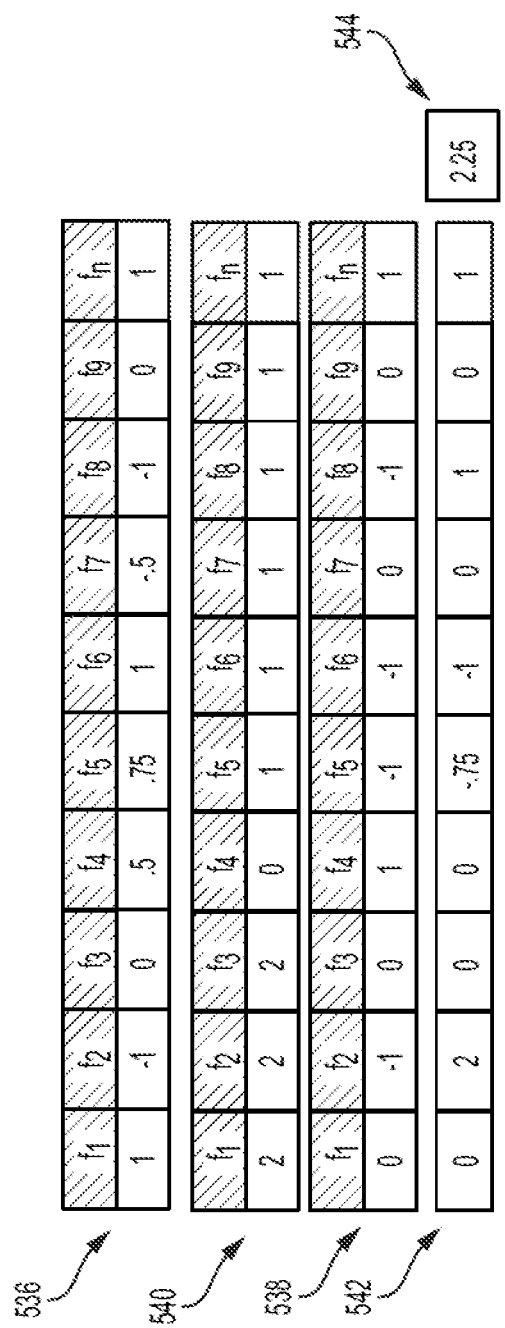
FIG. 45 is a diagram showing other embodiments of a user fingerprint, an activity fingerprint, a weighting array, a score array, and a score of a wellness, health, and lifestyle planning, tracking, and maintenance system.

FIG. 45 illustrates another embodiment of a user fingerprint 536 and another embodiment of an activity fingerprint 538. Similar to the user fingerprint 500 of FIG. 32, the user and activity fingerprints 534, 536 in this illustrated embodiment each include a plurality of characteristics $f_1, f_2, f_3, f_4, f_5, f_6, f_7, f_8, f_9, \ldots f_n$. FIG. 45 also illustrates an embodiment of a weighting array 540 that includes a scaling factor for each of the plurality of characteristics $f_1, f_2, f_3, f_4, f_5, f_6, f_7, f_8, f_9, \ldots f_n$, e.g., "2" for $f_1$, "2" for $f_2$, etc. that can be used by the analysis module 202 to weigh certain characteristics of the user and activity fingerprints 536, 538 more heavily than others. The scaling factors can thus be different for different characteristics, which can allow certain ones of the characteristics to have more importance than others, e.g., a user's age being weighted more than a user's preference to exercise in the morning instead of at night, a user's focus on weight loss being weighted more than a user's preference to engage in social activities with other people, a health condition of the user (e.g., osteoporosis, arthritis, sprain, asthma, etc.) being weighted more than a user's preference to engage in more strenuous activities. Because the weighting array 540 can help magnify similarities between user and activity fingerprints, the analysis module 202 can be more likely to recommend appropriate activities for a particular user when using the weighting array 540 in determining activities to recommend to the user.

In at least some embodiments, the analysis module 202 can be configured to use the weighting array 540 in updating a user's current fingerprint. Similar to that discussed above, the analysis module 202 can be configured to multiply a weighted distance array calculated by the analysis module 202 by the weighting array 540 in the process of updating the user fingerprint 536 in view of the user's selection of the activity associated with the activity fingerprint 538.

In at least some embodiments, the analysis module 202 can be configured to use the weighting array 540 in determining which one of a plurality of activities, with the activity associated with the activity fingerprint 538 being one of the plurality of activities, to recommend to the user associated with the user fingerprint 536. The analysis module 202 can be configured to multiply the user fingerprint 536 by each of the plurality of activity's fingerprints so as to calculate a plurality of intermediate score arrays (not shown). The analysis module 202 can be configured to multiply each of the intermediate score arrays by the weighting array 540 so as to calculate a plurality of score arrays (not shown, except for a score array 542 arrived at by multiplying the user fingerprint 536, the activity fingerprint 538, and the weighting array 540). The analysis module 202 can be configured to calculate a score for each of the plurality of activities by summing the values in that activity's score array. A score 544 of 2.25 for the score array 542 is shown in FIG. 45. The analysis module 202 can be configured to determine which of the plurality of activities to recommend to the user based on which one or more of the activities have the highest score. If multiple ones of the activities have a same highest score, the analysis module 202 can be configured to recommend all of those activities or can be configured to "break the tie" in a way similar to any of the ways discussed above for choosing an activity among activities having a same highest number of characteristics matched with a user fingerprint.

In at least some embodiments, the analysis module 202 can be configured to calculate a score for each of a plurality of activities without using a weighting array and use that score as discussed herein to choose one or more activities to recommend to a user.

Figure 46:
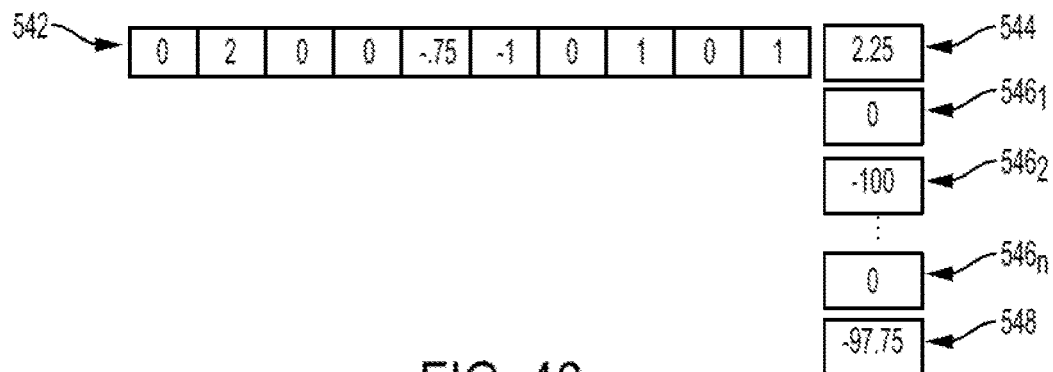
FIG. 46 is a diagram showing the score array of FIG. 45, a plurality of filter factors of the system of FIG. 45, and a final score of the system of FIG. 45.

In an least some embodiments, the analysis module 202 can be configured to filter recommendations out that would otherwise be selected by the analysis module 202 to be presented to the user as recommended activities based on the scores summed from each activity's score array. The analysis module 202 can thus be configured to provide more relevant recommendations to the user. The analysis module 202 can be configured to apply any number of filters. Non-limiting examples of filters include a filter to exclude activities previously selected by the user, a filter to exclude activities previously completed by the user, a filter to exclude activities that require a prerequisite unmet by the user, a filter to exclude activities that are contra-indicated for the user, and a filter to exclude activities the user previously indicated as being of no interest to them. Each of the filters can have a filter factor associated therewith. The analysis module 202 can be configured to calculate a final score for each of the plurality of activities that has a score summed from the activity's score array by summing all of the filter factors and the activity's score. The analysis module 202 can be configured to use the final score to select one or more activities to recommend to the user, similar to that discussed above. For non-limiting example, as shown in FIG. 46, the analysis module 202 can be configured to apply a plurality of filter factors $546_1, 546_2, \ldots 546_n$ to the score 544 of FIG. 45 to arrive at a final score 548 for the activity associated with the activity fingerprint 538. The first and last filter factors $546_1, 546_n$ in this illustrated embodiment each have a value of zero, thereby indicating that these filter factors configured to be applied by the analysis module 202 are inapplicable to the user, e.g., the user has not already performed the activity associated with the activity fingerprint 538, the user has no unmet prerequisite for the activity associated with the activity fingerprint 538, etc. The second filter factor $546_2$ in this illustrated embodiment has a negative value, thereby indicating that the activity to which it is being applied should be downgraded for the user, e.g., the user has already performed the activity associated with the activity fingerprint 538, the user is excluded from activities involving running due to a health condition, etc. A filter factor can have a positive value, thereby indicating that the activity to which it is being applied should be upgraded for the user, e.g., the activity is seasonal and is in season, the activity is among the most highly rated activities in the system 10, etc. The analysis module 202 can be configured to up-weight a final score, such as by applying a positive filter factor as a random one of the filter factors, which can help prevent final scores from converging on a local minimum.

Figure 47:
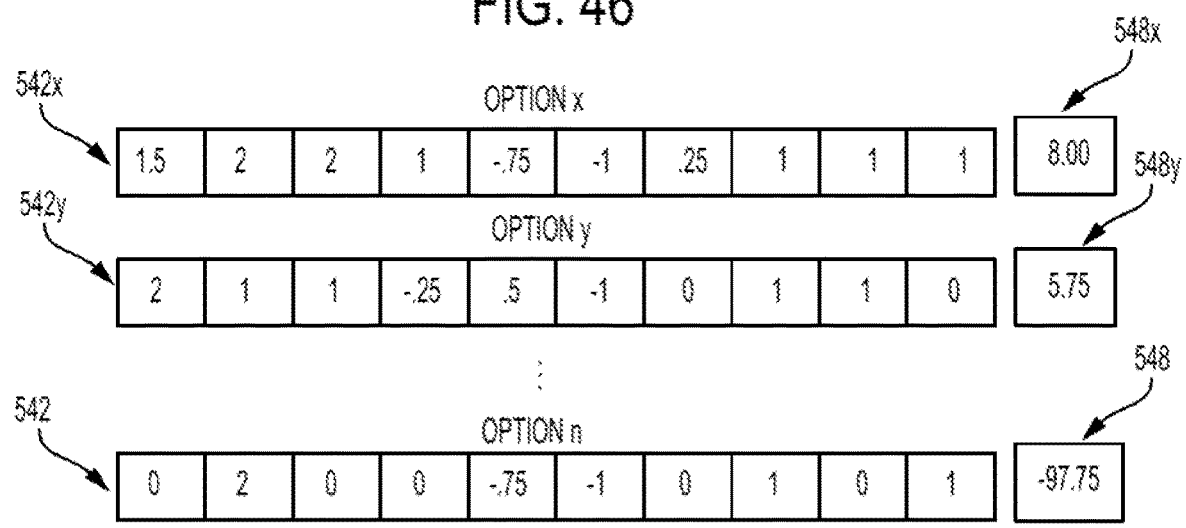
FIG. 47 is a diagram showing the score array of FIG. 45 and a plurality of other score arrays and final scores of the system of FIG. 45.

FIG. 47 shows a list including the score array 542 of FIGS. 45 and 46 and the final score 548 along with a plurality of other score arrays 542x, 542y and final scores

548x, 548y associated therewith calculated by the analysis module 202 for other activities. The list is sorted in descending final score order, thus indicating that Option x having the final score 548x of 8.00 is the activity with the highest final score from among the plurality of activities considered by the analysis module 202 and that Option n having the final score 538 of −97.75 is the activity with the lowest final score among the considered activities. The analysis module 202 can thus be configured to select Option x as the one activity to recommend to the user. Alternatively, as discussed herein, the analysis module 202 can be configured to select a predetermined number of activities having the highest final score, e.g., choose the Options having the top three final scores to present to the user.

In an exemplary embodiment, the analysis module 202 can be configured to determine activities to recommend to the user based on all of the user's demographics information, the user's activity information, pre-stored fingerprints for activities, and the experiences of other users, which can help allow the system 10 to provide well-informed, well-rounded activity recommendations to the user.

The analysis module 202 can be configured to determine activities to recommend to the user using an algorithm, e.g., an algorithm stored in the algorithms database 224, that in one embodiment first selects activities as a function of user preferences (articulated and derived), risk factors, focus area, demographic factors, previous activities (attempted, success and failure, and rejections). The algorithm can then remove activities that are very similar or where a prerequisite activity has not been completed, removes activities that not relevant to any risk factor or goal or where they conflict with a demographic factor, and remove activities that are already in progress. The algorithm can then add one or more random activities, which can help avoid user preferences from becoming self-fulfilling, and some activities can be removed to assure the presented list has a balance among activity types. Removal of an activity does not indicate removal of the activity from the activities database 222. Removal of an activity indicates that the activity is removed from a list of possible activities to be suggested to the user and/or that the activity is moved lower down a list of possible activities to be suggested to the user.

The analysis module 202 can be configured to provide recommendations other than activity recommendations. These other recommendations can be related to activities, e.g., can be resources that facilitate achievement of one or more activities. The analysis module 202 can be configured to suggest care providers experienced with particular wellness, health, and/or lifestyle issues of relevance to the user, can be configured to suggest facilities that allow the user to participate in certain activities at the facilities (e.g., climbing gyms, swimming pools, dog parks, yoga studios, mental health counseling, massage studios, dance studios, adult education centers, etc.), can be configured to suggest groups that the user can join to participate in certain activities (e.g., community sports teams, book clubs, dog owner groups, etc.), and/or can be configured to suggest stores where the user can purchase materials that can facilitate performance of certain activities (e.g., health food stores, supermarkets, pet stores, athletic equipment stores, etc.). The care providers database 220 can store information regarding a plurality of care providers that the analysis module 202 can use in determining care provider(s) to suggest to the user. The system 10 can include a facilities database (not shown) that can facilitate suggestion of facilities, a groups database (not shows) that can facilitate suggestion of groups, and/or a stores database (not shown) that can facilitate suggestion of stores (e.g., retail stores), similar to the care providers database 220 facilitating suggestion of care providers.

The analysis module 202 can include an assessment module 212 and a recommendations module 214. In general, the assessment module 212 can be configured to execute algorithms related to assessing the user's performance of activities (e.g., generating fingerprints, etc.) and/or related to the user's preferences (e.g., determining whether input information has become stale and thus prompting the user to update the information, etc.), and the recommendations module 214 can be configured to determine recommended activities for the user (e.g., comparing the user's B-DNA to other users' B-DNA, etc.). The assessment module 212 can be configured to assess that data may be stale based on determining whether a predetermined amount of time has passed since a date/time stamp indicating when the data was input. For non-limiting example, the assessment module 212 can be configured to prompt a user to update his/her work status after a certain amount of time if the user indicated that his/her occupation was a college student. For another non-limiting example, the assessment module 212 can be configured to prompt a user to update the status of an activity as being in progress, complete, or abandoned if the activity was added to the user's list a certain predetermined amount of time ago.

System Use

The systems and methods of using the systems described herein can be useful in managing personal wellness, health, and/or lifestyle, such as in a wellness and prevention phase of a traditional model for managing personal health. The system can be flexibly implemented using any one or more modules thereof in any combination. The system can thus be configured to accommodate different monetary cost constraints, different availabilities of computer infrastructure, and different end user needs. For example, an analysis module can be provided with an assessment module but not a recommendations module, which can allow the system to focus on an individual's wellness, health, and/or lifestyle. Such a system can be available at a lower monetary cost than a system that also includes a recommendations module since, e.g., fewer processing resources need be used to manage an individual's wellness, health, and/or lifestyle. Such a system can be available for use without requiring a network connection, e.g., since the system need not access data regarding other people, which can allow for more versatility and/or for the system to be available to people without any network access.

EXAMPLES

As mentioned above, the systems and methods described herein can be used in a variety of contexts related to any one or more of wellness, health, and lifestyle. The Examples discussed below are non-limiting examples of such systems and methods in various contexts.

Example A

Figure 48:
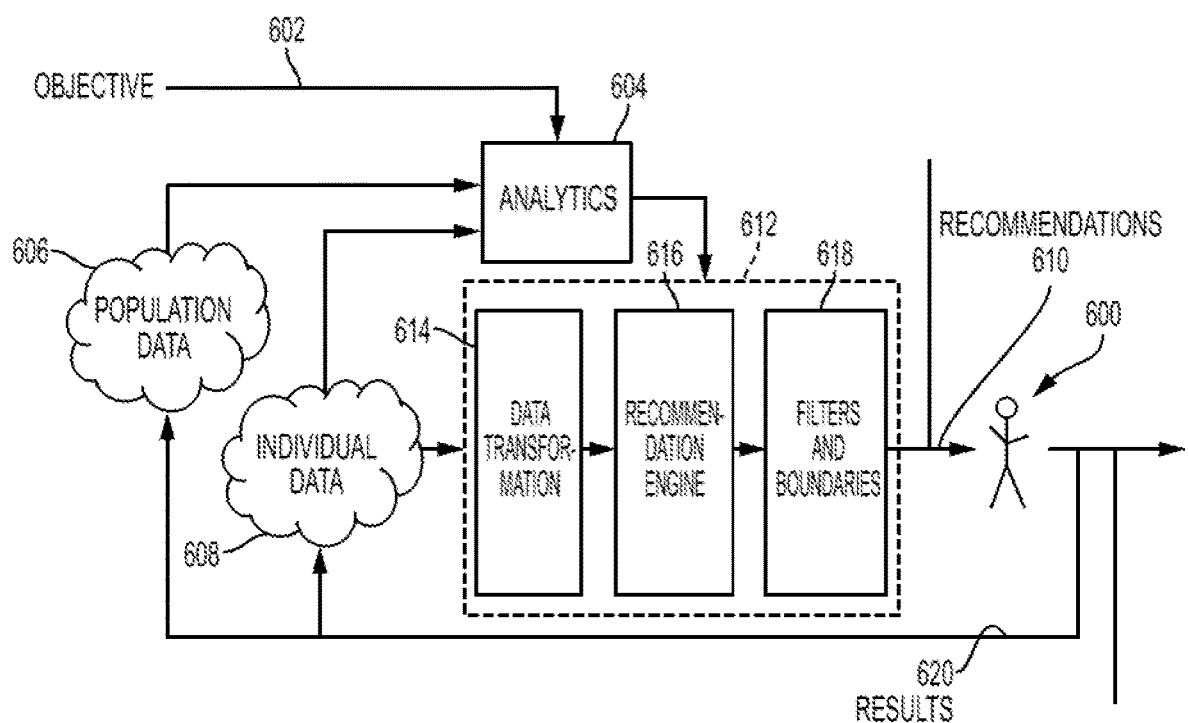
FIG. 48 is a schematic flow diagram of another embodiment of a wellness, health, and lifestyle planning, tracking, and maintenance system.

FIG. 48 illustrates an embodiment of a system for wellness, health, and/or lifestyle planning, tracking, and maintenance for a user 600. The system can be configured to receive objective data 602 from the user 600, e.g., via an input module, indicating one or more goals of the user 600. The system can be configured to analyze the objective data 602 using analytics 604, e.g., an assessment module of an analysis module. The analytics 604 can be configured to include population data 606, e.g., data regarding other users of the system, and individual data 608, e.g., data regarding the user 600, in its analysis. The population data 606 and the individual data 608 can each be stored in at least one database, e.g., a population database and an individual database. The analysis performed by the analytics 604 using the objective data 602 can include updating a fingerprint of the user 600. The user's fingerprint being updated can be included in the individual data 608 accessed by the analytics 604.

The system can be configured to provide recommendations 610 to the user 600 based on the user's fingerprint and, hence, in consideration of the input objective data 602. The system can include algorithms 612, e.g., in an algorithms database, configured to facilitate determination of the recommendations 610. The algorithms 612 can be executed in a variety of ways, such as by being executed by an analysis module (e.g., a recommendations module thereof) of the system, which as discussed herein can include processing by a processor. The algorithms 612 can include a data transformation algorithm 614 configured to prepare data regarding the user for evaluation with respect to data regarding a plurality of possible recommendations (e.g., possible activities), a recommendation engine 616 configured to determine which one or more of the recommendations are a best match for the user 600, and a filters and boundaries algorithm 618 configured to filter recommendations out of the recommendations determined to be best matches. The filtered recommendation results can be output to the user 600 as the recommendations 610.

Result data 620 of the user 600 with respect to the recommendations 610 output thereto can be configured to be fed back to the population data 606, as being indicative of a result of one of the users of the system, and can be configured to be fed back to the individual data, as being indicative of a result of this particular user 600. The analytics 604, and hence the algorithms 612, can thus consider the results data 620 in future analysis, thereby allowing for future recommendations to the user 600 and to other users of the system to be more appropriate for the user to which they are output.

One non-limiting example of a context in which the system of FIG. 48 can be used is a maternal health context. The objective data 602 can include a goal of improved pregnancy outcomes and a goal of reduced negative experience with pre-natal vitamins. In analyzing the input objective data 602, the analytics 604 can consider population data 606, such as evidence based requirements for pre-natal vitamins across a pregnancy term, and individual data 608, such as data regarding the user's diet, current drug and vitamin use, lifestyle, medical history, segmentation, previously input goals, and previous results 620. The system can be configured to execute the algorithms 612 and output recommendations 610 based thereon, such as a specific pre-natal vitamin product for the user 600 to try and a tailored pre-natal vitamin compliance program for the user 600. The results 620 of such recommendations 610 can include the user's nutritional adequacy measurements, health outcomes, side effects, and compliance with the program. In the maternal health context, the user's current situation is changing in some ways that the system can be configured to predict because certain symptoms tend to appear at certain times during pregnancy and can consider these typical changes in determining recommended activities for a user. In the maternal health context, the system can be configured to ask for the user's symptoms and focus areas more frequently than in other contexts, such as weight loss or diabetes, because the user's health changes beyond her control during pregnancy. Thus, symptoms and focus areas can change more frequently and/or more unpredictably than in other contexts such that the system can benefit from more frequent status updates from the user. In the maternal health context, scaling factors for the user's demographics (e.g., the user's pregnancy month, the user's symptoms, etc.) can be scaled higher than in other contexts because activities appropriate for an expectant mother are generally more dependent on the user's demographics than in other contexts. The system can thus be more likely to recommend activities that the user should do rather than activities geared toward what the user likes to do.

Another non-limiting example of a context in which the system of FIG. 48 can be used is a diabetes context. The objective data 602 can include a goal of optimized diabetes outcomes. In analyzing the input objective data 602, the analytics 604 can consider population data 606, such as population studies of people with diabetes, and individual data 608, such as data regarding the user's diet, current drug and vitamin use, lifestyle, medical history, segmentation, previously input goals, and previous results 620. The system can be configured to execute the algorithms 612 and output recommendations 610 based thereon, such as pharmaceutical recommendations (e.g., a specific pharmaceutical for the user 600 to try), activities directed to improving lifestyle, activities involving socialization, and recommendations of health care providers in the user's geographic area who work with diabetes patients. The results 620 of such recommendations 610 can include the user's glycated hemoglobin (HbA1C), glucose tolerance, quality of life measures, health risks, and compliance with recommended activities.

Example B

Figure 49:
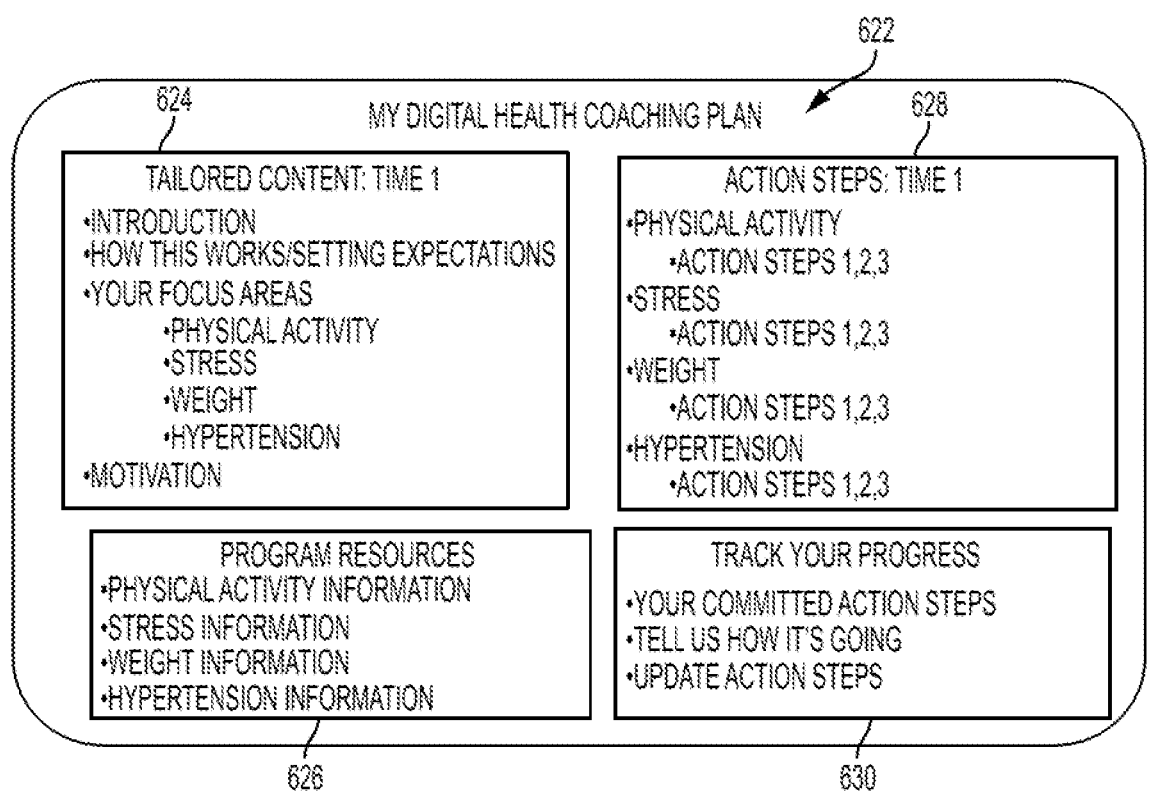
FIG. 49 is a diagram of an embodiment of a graphical user interface of a wellness, health, and lifestyle planning, tracking, and maintenance system.

FIG. 49 illustrates another embodiment of a system for wellness, health, and/or lifestyle planning, tracking, and maintenance for a user. The system can be configured to provide digital health coaching to a user (not shown) but can be used similarly in other contexts. The system can be configured to provide a graphical user interface (GUI) 622 to the user, e.g., on a display, through which the user can access various information available through the system. The GUI 622 can be configured to show tailored content 624 including information specific to the user (in this illustrated embodiment, an introduction to the system, how the system works/setting expectations, the user's focus areas (physical activity, stress, weight, and hypertension in this illustrated embodiment), and motivation), program resources 626 including information related to the user's focus areas, action step data 628 including information regarding actions (activities) the user can engage in to address the user's various focus areas, and progress data 630 including information related to the progress of the user's actions (e.g., actions selected by the user to pursue, input of progress data, and updating actions). The GUI 622 in this illustrated embodiment is at a "Time 1" when the user initially logs onto the system. Future logins can affect the information shown on the GUI 622, e.g., not including an introduction to the system in the tailored content 624 after a predetermined number of logins, showing current actions, etc.

Figure 50:
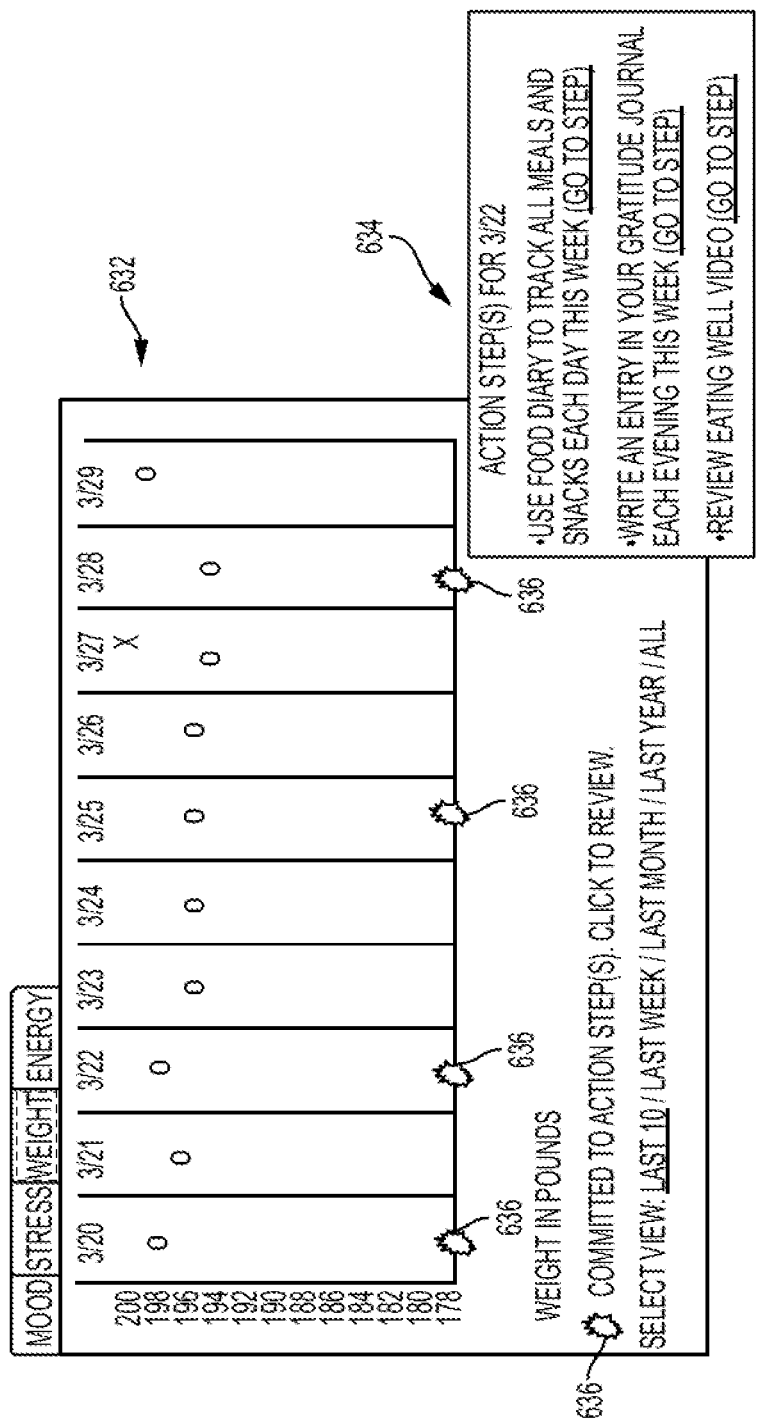
FIG. 50 is a diagram showing an embodiment of a progress screen of the system of FIG. 49.

Clicking on text in the various areas of the GUI 622 can show information related thereto to the user, as will be appreciated by a person skilled in the art. FIG. 50 illustrates one embodiment of a progress screen 632 that the system can be configured to display in response to the user clicking on the "Track Your Progress" text in the progress data 630 area of the GUI 622. A "Weight" tab is selected on the progress screen 626, with mood, stress, and energy tabs also being selectable to show data related thereto similar to data shown on the progress screen 626 for weight. FIG. 50 also shows a pop-up detail box 634 accessible by clicking on an action step starburst icon 636 for a specific date, March 22 in this illustrated embodiment. The detail box 634 can include action information for the selected date, e.g., the actions the user previously committed to performing on that date.

The system can be configured to gather information regarding the user's health by the user inputting the information directly into the system, e.g., via an input module, and/or by the system electronically communicating with one or more sensors, e.g., sensors of health monitoring devices. Receiving information from sensors can help the system gather data that the user may not remember accurately (e.g., due to delay in inputting data to the system, due to the user not using a timer to time a length of exercise, etc.), may forget to input, and/or may be too difficult and/or time-consuming for the user to input (e.g., all food and drink consumed by the user every day, etc.). For non-limiting example, a sensor configured to monitor the user's physical activity, such as a sensor of a fitness watch, heart rate monitor, etc., can be configured to provide data to the system regarding the user's energy expenditure regardless of whether the user remembers the physical activity or not, remembers to input data regarding the physical activity, and/or is too hard for the user to input into the system. For another non-limiting example, a health monitoring device can be configured to provide bioimpedance data to the system, from which the system can be configured to infer body weight of the user, as will be appreciated by a person skilled in the art. For yet another non-limiting example, a health monitoring device can be configured to measure a user's blood-sugar level on a continuous basis and provide such measurements to the system, which the system can be configured to consider in evaluating the user's performance of accepted activities and/or in determining activities to recommend to the user.

Example C

Figure 51:
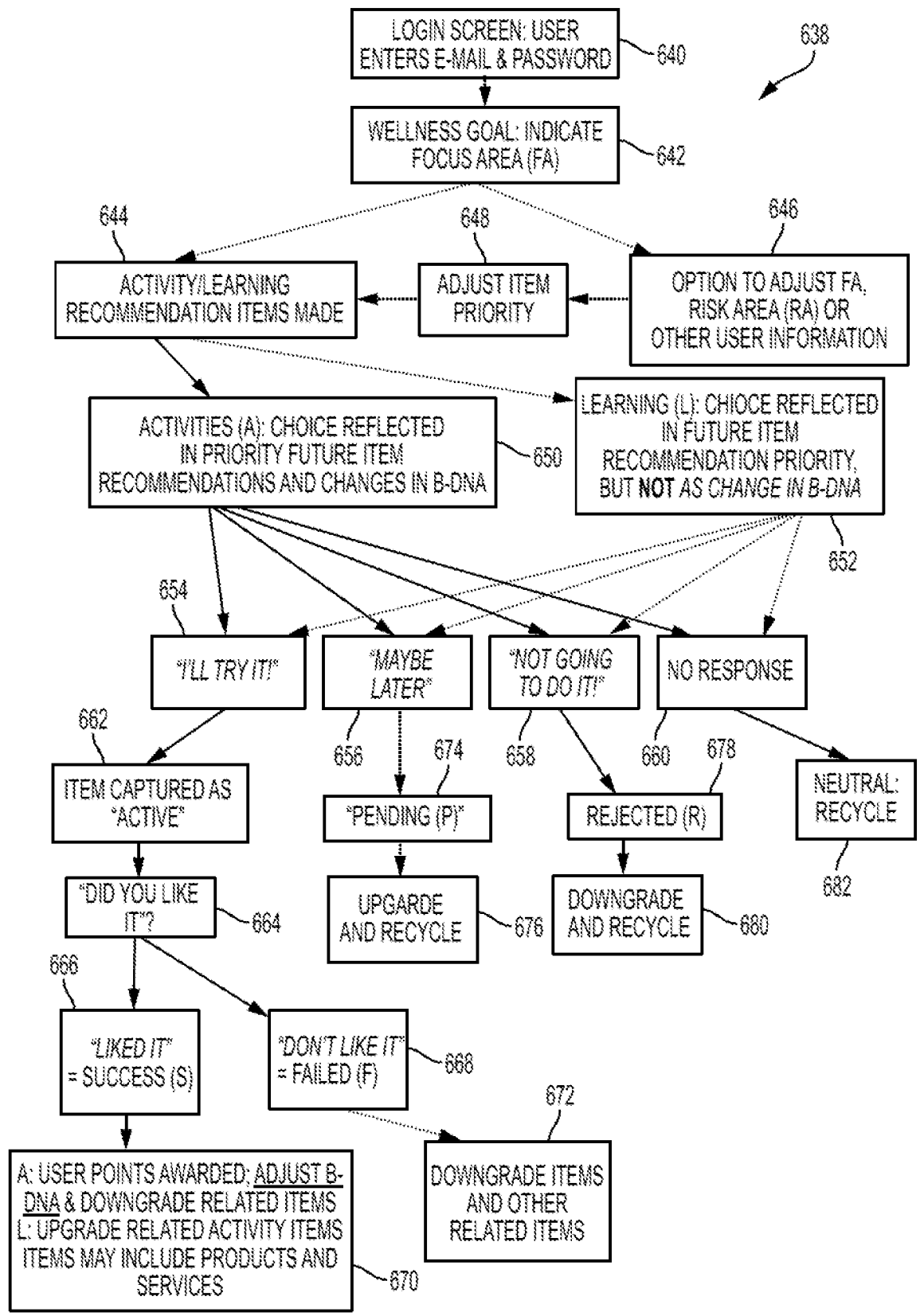
FIG. 51 is a flowchart showing an embodiment of a method of using a wellness, health, and/or lifestyle planning, tracking, and maintenance system.

FIG. 51 illustrates one embodiment of a method 638 of using a system (e.g., the system 10 of FIG. 2 or other systems described herein) for wellness, health, and/or lifestyle planning, tracking, and maintenance. In this illustrated embodiment, dotted lines in the method 638 indicate optional steps.

The method 638 can include a user logging in 640 to the system via a login screen, such as by using an e-mail address and password. Once logged in, the user can indicate 642 a focus area, such as weight, mood, stress, hypertension, etc., that the user would like to address. The indication 642 can be input to the system via an input module using an I/O interface. The system, e.g., an analysis module thereof, can be configured to determine activity recommendations (which can include learning activities, as discussed above) for the user based on the user's indicated 642 focus area and to provide 644 the determined recommendations to the user, e.g., by displaying the recommendations on a display. Before and/or after providing 644 the recommendations, the system, e.g., an analysis module thereof, can be configured to prompt 646 the user to adjust information used in determining the recommendations, such as by inputting data to adjust the indicated 642 focus area, change risk areas of concern to the user, or change other information related to the user (e.g., demographics information, indication of successfully completed activities, etc.). The system can be configured to adjust 648 priority of activities for the user by adjusting the user's fingerprint in view of the adjusted information provided by the user.

The system can be configured to receive 650 input from the user regarding a choice of a recommended one of the activities (non-learning) and to receive 652 input from the user regarding a choice of a recommended one of the learning activities. The system can be configured to adjust the user's fingerprint in view of selected non-learning activities and to not adjust the user's fingerprint in view of selected learning activities. Selected learning activities can be excluded from being reflected in the user's B-DNA because learning activities can help inform the user's performance of non-learning activities so as to be indirectly reflected in the B-DNA through the non-learning activities and/or because learning activities can generally reflect a desire to improve some aspect of daily life but generally do not reflect specific actions being performed that can change daily life.

The user can indicate a preference for each of the recommended activities (learning and non-learning). In this illustrated embodiment, preferences that the user can choose from for each recommended activity include the user selecting 654 the activity to perform, choosing 656 to maybe perform the activity later, and choosing 658 to not perform the activity. User non-response 660 can also be logged as a preference in an instance where the user does not select one of the other three options 654, 656, 658 for an activity.

In response to the user selecting 654 the activity to perform, the system can be configured to capture 662 that activity as an "active" activity, e.g., a current activity of the user. The system can be configured to prompt 664 the user to indicate whether the user liked 666 performing the "active" activity or did not like 668 performing the "active" activity either by not enjoying the activity during full or partial performance thereof or by not starting the activity at all. In response to a "liked" response, the activity can be considered a success for the user. The system can be configured to update 670 the user's information based on the "liked" response. The updating 670 can include awarding points to the user for performance of the activity (e.g., adding the predetermined number of points associated with the activity to the user's running point total), adjusting the user's fingerprint, downgrading related activities (such as in the case of non-learning activities, since repetition of similar activities may not provide the user with as well-rounded an experience), and upgrading related activities (such as in the case of learning activities, since related educational materials can help expand the user's knowledge in an area of interest to the user). In response to a "did not like" response, the activity can be considered a failure for the user. The system can be configured to reflect this negative experience by downgrading 672 related activities so the user is less likely to receive recommended activities in the future that the user will not like.

In response to the user choosing 656 to maybe perform the activity later, the system can be configured to capture 674 that activity as a "pending" activity, e.g., a possible current activity of the user. The system can be configured to upgrade and recycle 676 the "pending" activity such that the user is more likely to receive that activity as a recommendation again, at which time the user may decide to perform the activity (i.e., select 654 to perform the activity). Upgrading an activity can include, for non-limiting example, assigning a higher scaling factor to that activity.

In response to the user choosing 658 to not perform the activity, the system can be configured to capture 678 that activity as a "rejected" activity, e.g., an activity that the user is not interested in performing. The system can be configured to downgrade and recycle 680 the "rejected" activity such that the user is less likely to receive that activity as a recommendation again since the user is, at least in the near term, unlikely to decide to perform that activity. Downgrading an activity can include, for non-limiting example, assigning a lower scaling factor to that activity.

In response to the user not responding 660 to the recommended activity, the system can be configured to recycle 682 the activity as a possible activity to present as a recommendation to the user in the future. In other words, the user's non-response 660 can cause the system to treat that activity as a "neutral" activity that the user may or may not want to perform at some future point.

Example D

Figure 52:
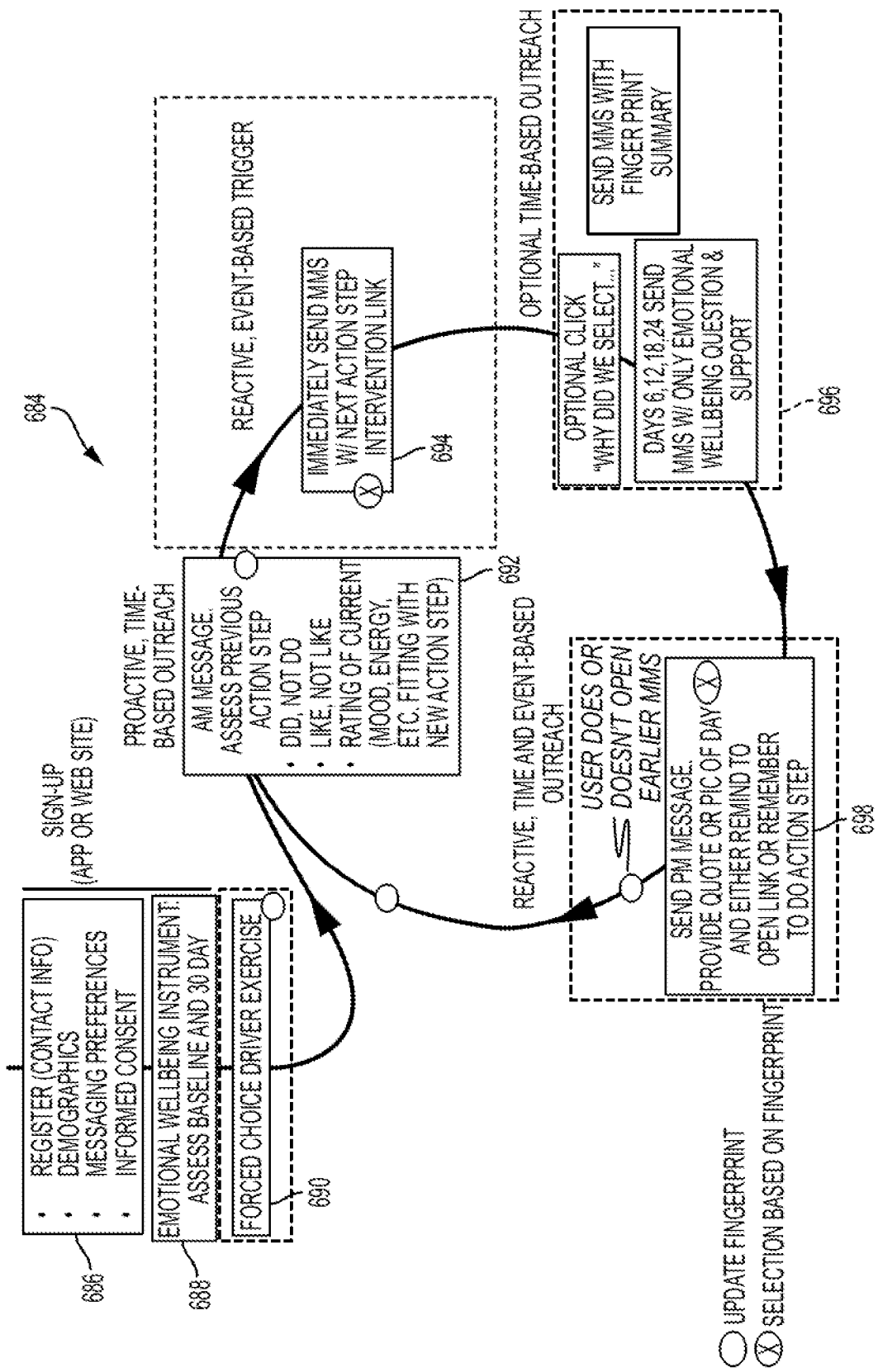
FIG. 52 is a schematic flow diagram of another embodiment of a wellness, health, and lifestyle planning, tracking, and maintenance system.

FIG. 52 illustrates another embodiment of a method 684 of using a system (e.g., the system 10 of FIG. 2 or other systems described herein) for wellness, health, and/or lifestyle planning, tracking, and maintenance. This illustrated embodiment is in the context of happiness, e.g., an aspect of the user's wellness, but can be used similarly in other contexts. In this illustrated embodiment, dotted lines in the method 684 indicate optional steps.

The method 684 can include a user registering 686 with the system, e.g., via an input module accessed through an app or at a website. The registration 686 can include the user providing contact information, demographic information, messaging preferences, and informed consent. The system can be configured to establish 688 a baseline of happiness for the user, which can help the system track the user's happiness level quantitatively over time, similar to tracking a user's weight using numbers that can change over time. Establishing 688 the baseline can include assessing an initial baseline of happiness for the user and adjusting the baseline over a thirty day period to better capture the user's overall happiness rather than a snapshot at the time the user registered with the system. The assessment can include presenting the user with a series of questions that the system, e.g., an analysis module thereof, can be configured to use to establish an initial user fingerprint.

The user can be presented 690 with a forced choice driver exercise, which can help the system adjust the user's fingerprint based on the user's response to the exercise. The forced choice driver exercise can include presenting the user with a series of questions whose responses thereto can be used to adjust the user's fingerprint. The exercise questions can be presented to the user all at once or over a series of days. The exercise questions can require the user to make binary choices, thereby providing concrete yes/no, 0/1, etc. data that the system can use to adjust the user's fingerprint in specific ways, e.g., by answers to specific questions affecting certain ones of the fingerprint's characteristics either positively or negatively.

The method 684 can include providing 692 proactive, time-based outreach to the user, which can help the system plan, track, and maintain the user's happiness without the user having to remember on his/her own to provide inputs to the system, can help prevent the user from avoiding the system at times less happy than others, and/or can help prevent the user from avoiding working on improving or maintaining his/her happiness by delaying the providing of inputs to the system. The system can be configured to update the user's fingerprint based on the user's response to the outreach. Non-limiting examples of the outreach include providing a morning message to the user that can help uplift the user at the start of a day, prompting the user to assess previously accepted activities, and prompting the user to indicate his/her current mood, energy, etc.

The system can be configured to provide 694 reactive, event-based triggers to the user in response to the occurrence of certain predetermined events. The triggers provided 694 can be related to the user's selected activities and can be configured to prompt the user to perform a previously accepted activity. For non-limiting example, a trigger can be provided 694 at a time of day that the user has indicated is a time for exercise. For another non-limiting example, a trigger can be provided 694 reminding the user to perform a certain action upon the system determining that the user is at a particular location (e.g., a gym, a restaurant, etc.) using GPS of the user's mobile client terminal.

The system can be configured to provide 696 time-based outreach to the user in response to it being a certain day and/or a certain time. The outreach can be configured to prompt the user to provide information regarding a previously provided 694 event-based trigger, to provide the user with questions for the user to reply to regarding his/her current emotional wellbeing, to provide the user with uplifting messages, and/or to provide the user with a snapshot of his/her current fingerprint to help the user understand his/her happiness progress.

The system can be configured to provide 698 reactive, time and event-based outreach to the user in response to the occurrence of certain predetermined events and it being a certain day and/or a certain time. This provided 698 outreach can follow up on the previously provided 696 triggers and/or the previously provided 696 outreach, which can help the system gather information regarding the previously provided 696 triggers and/or the previously provided 696 outreach and/or can help ensure that the user receives the previously provided 696 triggers and/or the previously provided 696 outreach. For non-limiting example, if the user does not access the previously provided outreach 696, e.g., does not open a previously sent text message, etc., the system can be configured to again reach out to the user after a predetermined amount of time has passed since the outreach was provided and remains unaccessed.

The providing 694, 696, 698 can be iterative so as to repeat over the course of time, thereby continually furthering the user's happiness goals.

Example E

Figure 53A:
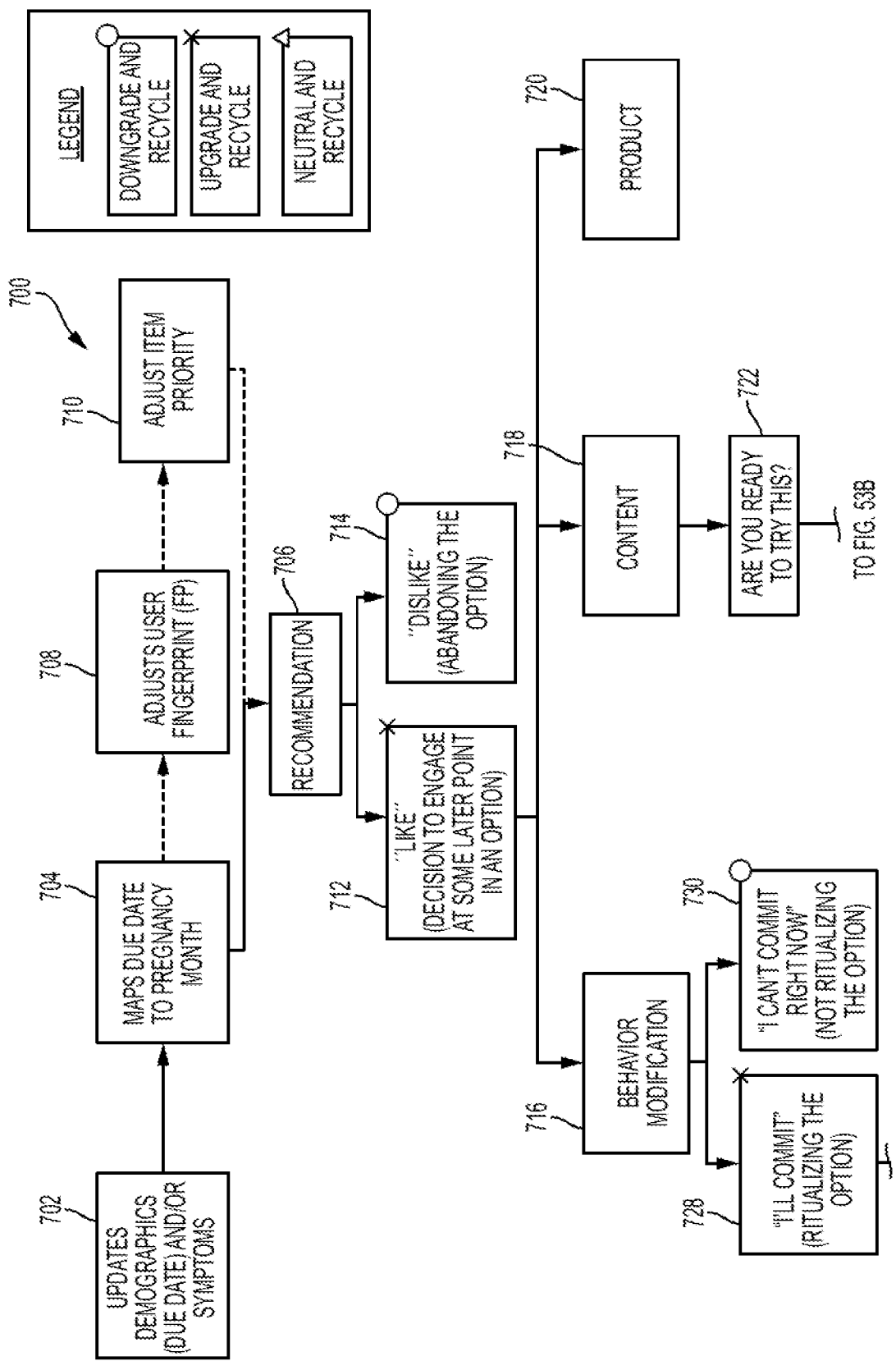
FIG. 53A is a portion of a flowchart showing another embodiment of a method of using a wellness, health, and/or lifestyle planning, tracking, and maintenance system.
Figure 53B:
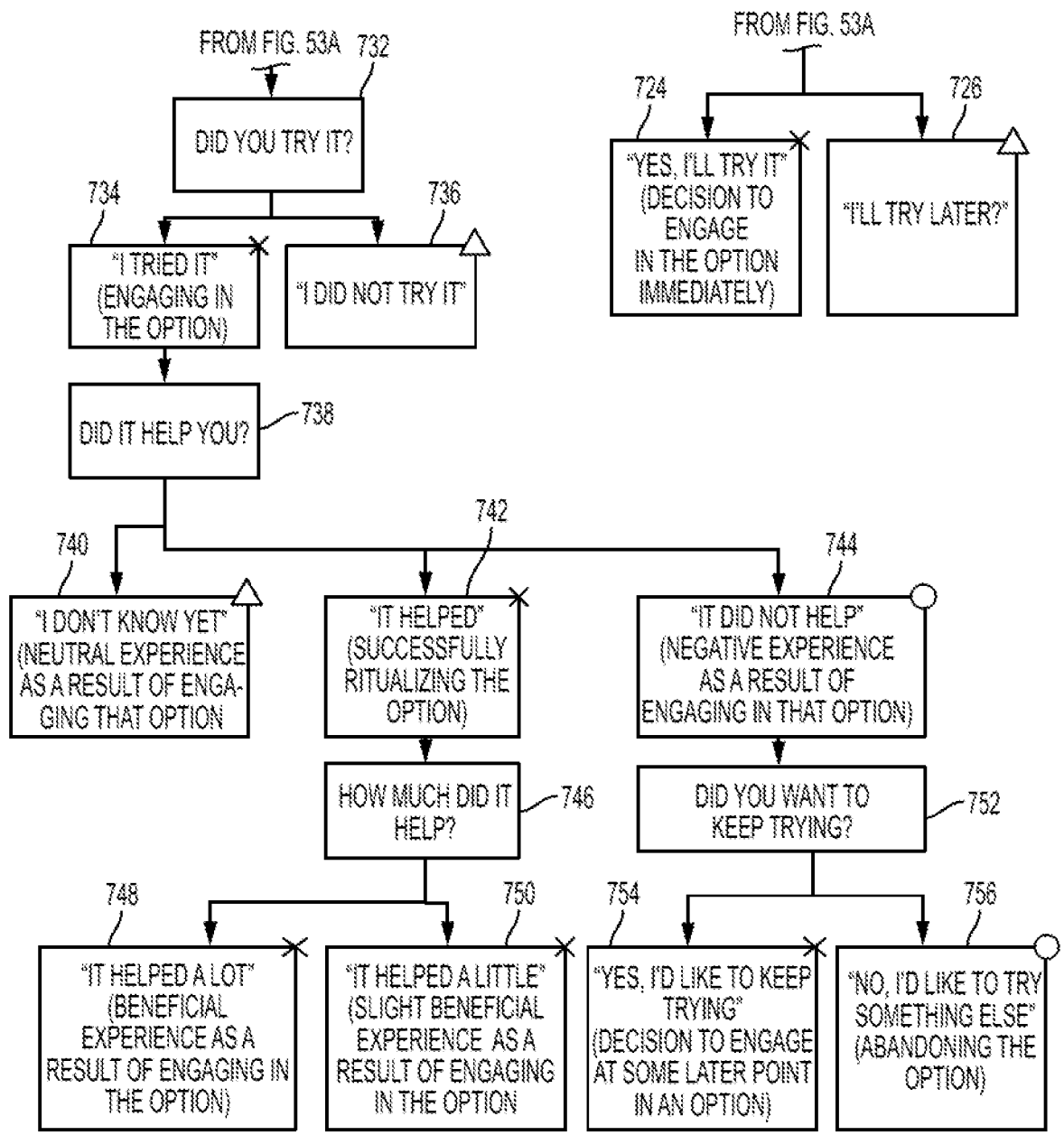
FIG. 53B is another portion of the flowchart of FIG. 53A.

FIGS. 53A and 53B illustrate another embodiment of a method 700 of using a system (e.g., the system 10 of FIG. 2 or other systems described herein) for wellness, health, and/or lifestyle planning, tracking, and maintenance. In this illustrated embodiment, steps with a ● (solid circle) symbol in the upper right corner thereof indicate that the system at that step is configured to downgrade and recycle the activity related to that step, steps with an "x" in the upper right corner thereof indicate that the system is configured at that step to upgrade and recycle the activity related to that step, and steps with a ▲ (solid triangle) symbol in the upper right corner thereof indicate that the system is configured at that step to consider as neutral and recycle the activity related to that step. This illustrated embodiment is in the context of maternal health but can be used similarly in other contexts.

The method 700 can include the system, e.g., an analysis module thereof, updating 702 demographics of a user (who is an expectant mother in a maternal health embodiment such as in FIGS. 53A and 53B) including the due date of the user and other demographics information, e.g., symptoms of the user, age of the user, etc. The system can be configured to map 704 the received due date to a pregnancy month of the user (e.g., the user is three months pregnant). The system can be configured to automatically map 704 the user's pregnancy month every time the user accesses the system, which can help the system provide recommendations appropriate for the user's stage of pregnancy throughout the pregnancy.

Having at least due date information for the user, and hence able to know how far along the user is in pregnancy, the system can be configured to provide 706 one or more activity recommendations of to the user as customized for the user as described herein. Prior to providing 706 the recommendation(s), the system can be configured to adjust 708 the user's fingerprint in view of the received demographics information and the mapped pregnancy month, which can help the recommendation(s) be more tailored and hence more likely to be of interest to the user, as opposed the recommendation(s) being tailored generally for an expectant mother. In view of the updated user fingerprint, the system can be configured to adjust 710 priority of activities available for recommendation to the user.

For each of the provided 706 activity recommendations, the user can indicate whether the user accepts 712 the activity or declines 714 the activity. In response to the user accepting 712 an activity, the system can be configured to perform different steps based on a type of the activity. As in this illustrated embodiment, types of activities can include activities that affect the user's behavior 716 (e.g., are capable of being ritualized into the user's daily life), activities that provide the user with content 718 (e.g., learning activities), and activities that involve purchase of one or more consumable products 720. For provided content 718, the system can be configured to confirm 722 the user's timing with respect to the activity. The system can be configured to receive the user's reply with respect to timing as the user being interested in pursuing the activity now 724 (e.g., watching an educational video now, being directed to an article on a particular subject, etc.) or at some point in the future 726 (e.g., receiving a link to a video later, saving the article in a library of a user for later reading, etc.).

For an activity that can result in behavior modification 716, the system 10 can be configured to receive a response from the user indicating that the user commits 728 to the activity (e.g., accept the activity) or indicating that the user does not commit 730 to the activity (e.g., decline the activity at least for now). In response to the user committing 728 to the activity, the system can be configured to prompt 732 the user for a response indicating whether the user did perform 734 the activity or did not 736 perform the activity. The prompting 732 can occur at a time after acceptance of the activity, with the time being a predetermined amount of time specific to that activity, being a standard predetermined amount of time for activities, or being based on when the user next logs onto the system. In response to the user indicating that the activity was performed 734, the system can be configured to prompt 738 the user to indicate whether the activity was helpful to the user or not. The question can ask generally about helpfulness or can be directed to a specific area of help, e.g., "Did engaging in the activity help you sleep more?", "Did engaging in the activity help you feel less nauseous during the day?", "Did engaging in the activity improve your skin?", etc. The system can be configured to prompt 738 the user to reply that the activity's helpfulness is currently unknown 740 (e.g., due to not enough time passing for the user to yet know, the user not being able to associate benefits specifically with that activity, etc.), that the activity was helpful 742, or that the activity was not helpful 744. In response to receiving a positive reply of the activity being helpful 742, the system can be configured to ask 746 the user to indicate how helpful the activity was to the user. The system can be configured to ask 746 the user to reply that the activity helped a lot 748 or helped a little 750. In response to receiving a negative reply of the activity not being helpful 744, the system can be configured to ask 752 the user to indicate whether the user would like to continue engaging in the activity, e.g., because it may be helpful in the future, the user did not put forth maximum effort when engaging in the activity, etc. The system can be configured to ask 752 the user to reply in the affirmative 754 or in the negative 756.

Example F

Figure 54A:
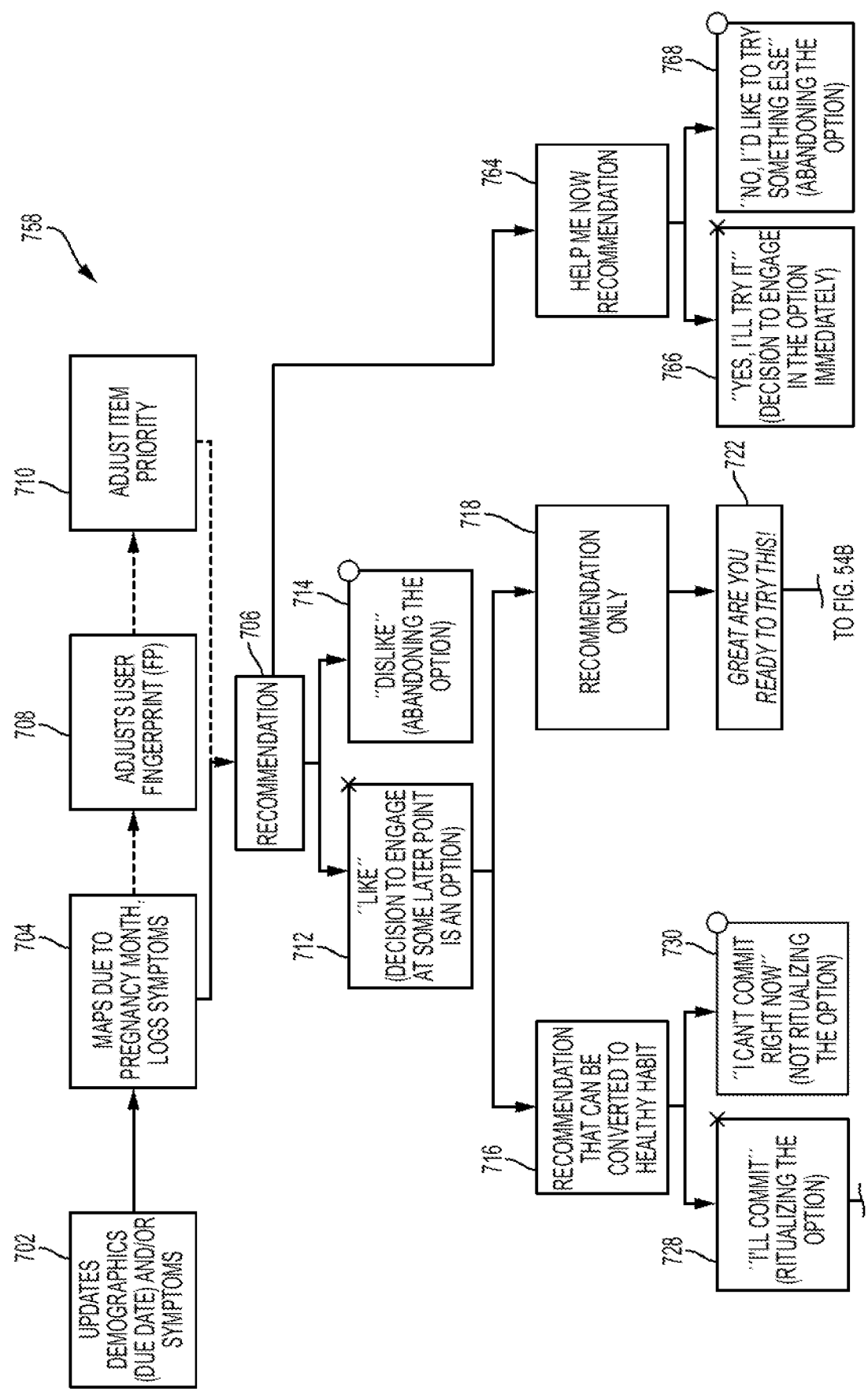
FIG. 54A is a portion of a flowchart showing yet another embodiment of a method of using a wellness, health, and/or lifestyle planning, tracking, and maintenance system.
Figure 54B:
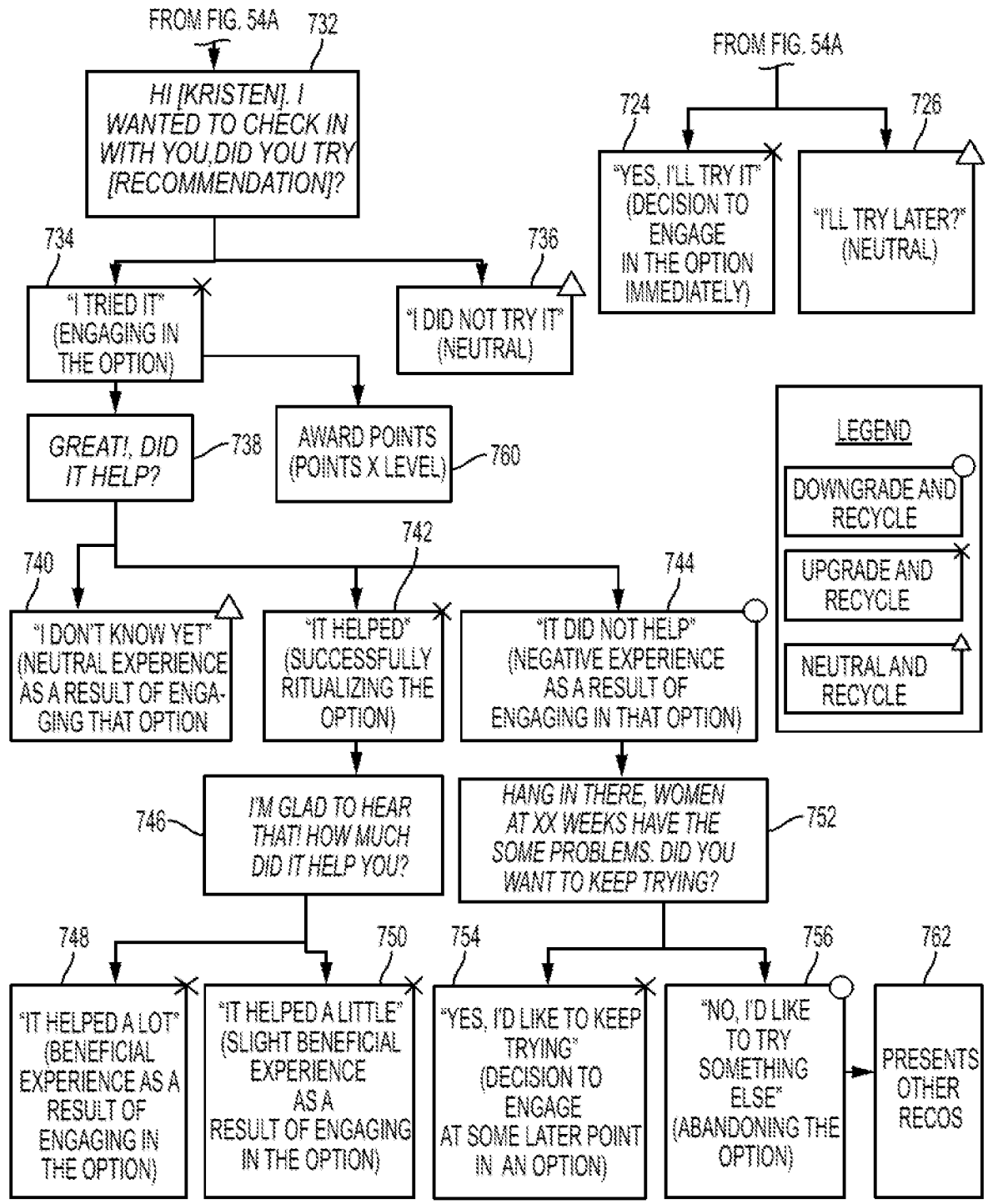
FIG. 54B is another portion of the flowchart of FIG. 54A.

FIGS. 54A and 54B illustrate another embodiment of a method 758 of using a system (e.g., the system 10 of FIG. 2 or other systems described herein) for wellness, health, and/or lifestyle planning, tracking, and maintenance. In this illustrated embodiment, steps with a ● (solid circle) symbol in the upper right corner thereof indicate that the system at that step is configured to downgrade and recycle the activity related to that step, steps with an "x" in the upper right corner thereof indicate that the system is configured at that step to upgrade and recycle the activity related to that step, and steps with a ▲ (solid triangle) symbol in the upper right corner thereof indicate that the system is configured at that step to consider as neutral and recycle the activity related to that step. This illustrated embodiment is in the context of maternal health but can be used similarly in other contexts.

The method 758 of FIGS. 54A and 54B is similar to the method 700 of FIGS. 53A and 53B, with similar steps numbered similarly. In the method 758 of FIGS. 54A and 54B, for activities that can be ritualized, e.g., that can be converted to a healthy habit, the system can be configured to update 760 the user's running point total based on the user indicating 734 that the user engaged in the activity and can be configured to present 762 other recommended activities to the user in response to the user indicating 756 that she would not like to continue engaging in an activity that was unhelpful.

In the method 758 of FIGS. 54A and 54B, the system can be configured to provide 764 activity recommendations to the user that are intended to provide immediate help to the user. In other words, the system can be configured to provide 764 activity recommendations to the user that address a specific characteristic of the user, e.g., activities that address a specific symptom the user is experiencing (e.g., eating a certain food to address nausea, doing a certain experience to alleviate discomfort, etc.). The system can be configured to receive an indication from the user indicating that the user is interested in pursuing the activity now 766 or not at this time 768.

Example G

Figure 55A:
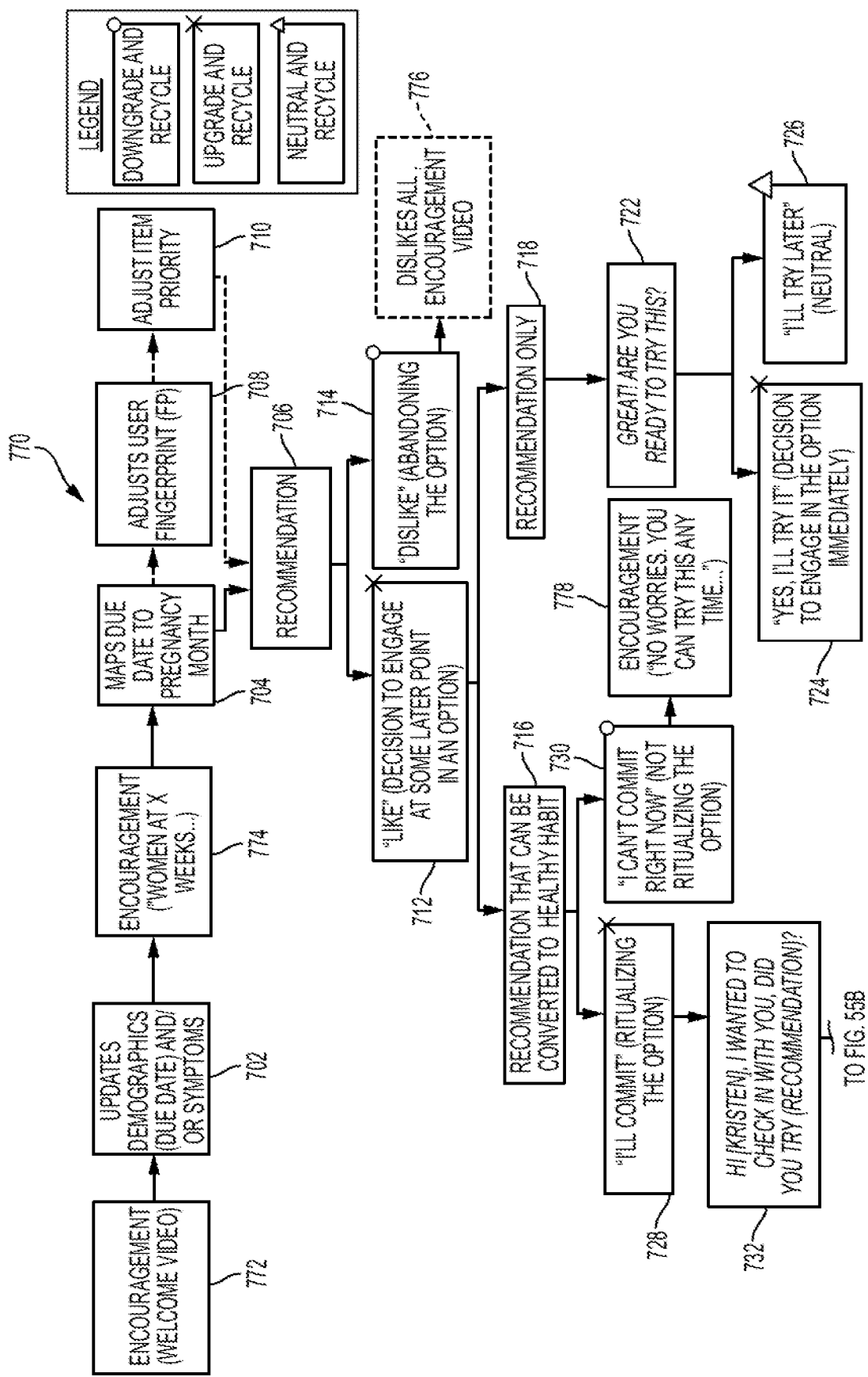
FIG. 55A is a portion of a flowchart showing still another embodiment of a method of using a wellness, health, and/or lifestyle planning, tracking, and maintenance system.
Figure 55B:
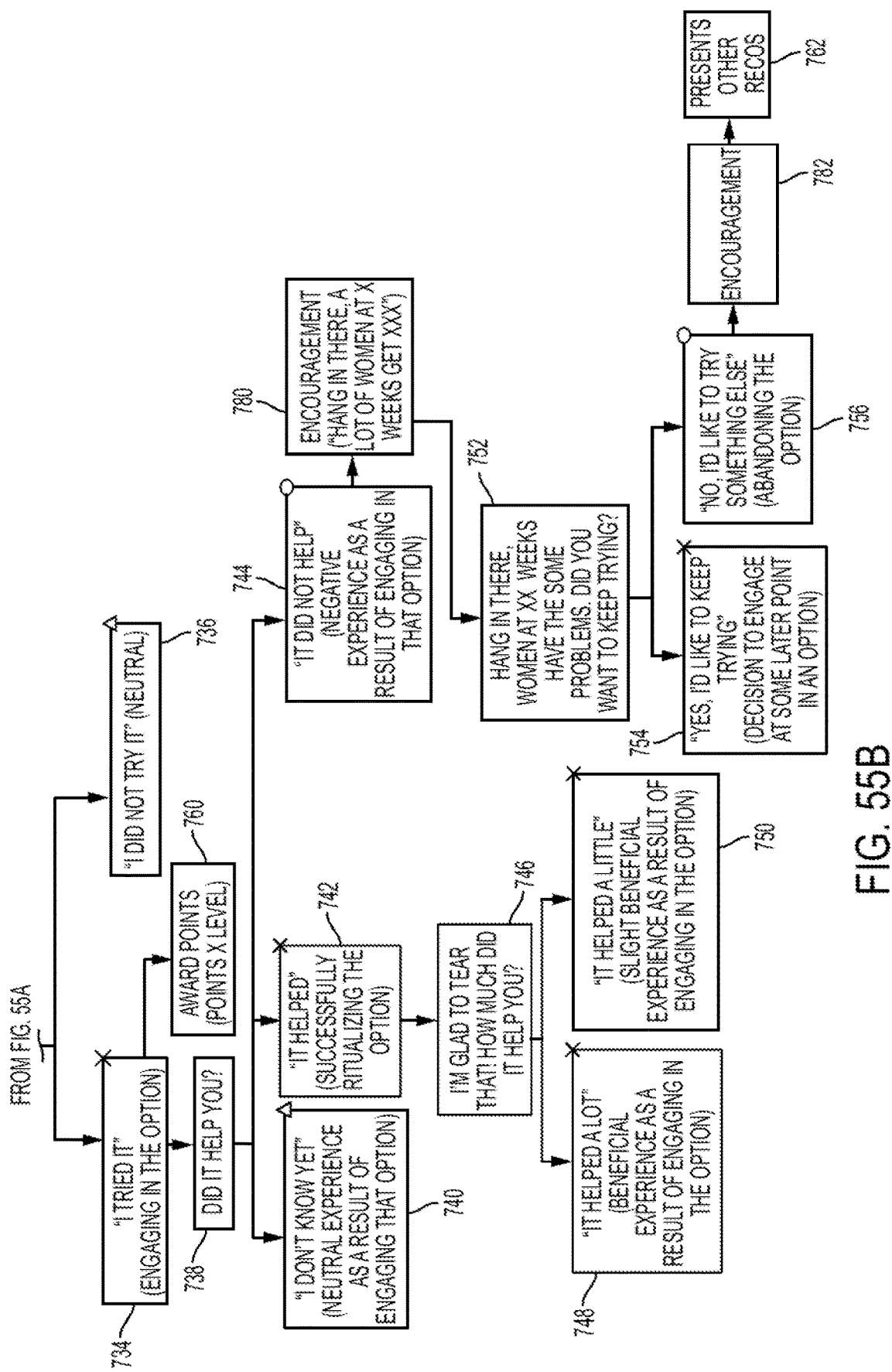
FIG. 55B is another portion of the flowchart of FIG. 55A.

FIGS. 55A and 55B illustrates another embodiment of a method 770 of using a system (e.g., the system 10 of FIG. 2 or other systems described herein) for wellness, health, and/or lifestyle planning, tracking, and maintenance. In this illustrated embodiment, steps with a ● (solid circle) symbol in the upper right corner thereof indicate that the system at that step is configured to downgrade and recycle the activity related to that step, steps with an "x" in the upper right corner thereof indicate that the system is configured at that step to upgrade and recycle the activity related to that step, and steps with a ▲ (solid triangle) symbol in the upper right corner thereof indicate that the system is configured at that step to consider as neutral and recycle the activity related to that step. This illustrated embodiment is in the context of maternal health but can be used similarly in other contexts.

The method 770 of FIGS. 55A and 55B is similar to the methods 700, 758 of FIGS. 53A, 53B, 54A, and 54B, with similar steps numbered similarly. In general, the method 770 of FIGS. 55A and 55B includes providing encouragement to the user at various points in the method 770. In general, the encouragements can be configured to help keep the user engaging in activities and selecting new activities, to help engage the user with the system, to help the user feel a sense of community by indicating consistencies of the user's experience with the experiences of other expectant mothers, and/or to help make the system more user-friendly. Non-limiting examples of encouragements can include encouraging text, motivational videos, and positive images.

Before updating 702 the demographics of the user, the system can be configured to provide 772 initial encouragement to the user, such as by showing a welcome video, displaying a welcome image, thanking the user for logging into the system again, etc. Such encouragement can help make the system more enjoyable to use.

The system can be configured to provide 774 encouragement to user based on the user's due date and hence on the user's stage of pregnancy. Such encouragement can help the user understand that they are feeling and/or are having experiences similar to other expectant mothers. Such encouragement can be provided at a point, e.g., between updating 702 the demographics of the user and mapping 704 the received due date to a pregnancy month of the user.

In response to the user providing a negative response to a query posed by the system, the system can be configured to provide encouragement to the user. As in this illustrated embodiment, the system can be configured to provide 776 encouragement if the user declines 714 all recommended activities, can be configured to provide 778 encouragement if the user does not commit to a recommended activity that can be converted to a healthy habit, can be configured to provide 780 encouragement if the user indicates that an accepted activity that can be converted to a healthy habit was not helpful 744, and can be configured to provide 782 encouragement if the user indicates 756 that she would not like to continue trying an accepted activity that can be converted to a healthy habit that was not helpful to the user.

In other embodiments of, one or more encouragements in addition to those in this illustrated embodiment can be provided at points in a method, only a subset of the encouragements in this illustrated embodiment can be provided at points in a method, or one or more encouragements instead of any shown in this method can be provided at points in a method.

Example H

FIGS. 56A-58 illustrate another embodiment of a method 784 of using a system (e.g., the system 10 of FIG. 2 or other systems described herein) for wellness, health, and/or lifestyle planning, tracking, and maintenance. In this illustrated embodiment, steps with a ● (solid circle) symbol in the upper right corner thereof indicate that the system at that step is configured to downgrade and recycle the activity related to that step, steps with an "x" in the upper right corner thereof indicate that the system is configured at that step to upgrade and recycle the activity related to that step, and steps with a ▲ (solid triangle) symbol in the upper right corner thereof indicate that the system is configured at that step to consider as neutral and recycle the activity related to that step. This illustrated embodiment is in the context of maternal health but can be used similarly in other contexts.

The method 784 of FIGS. 56A-58 is similar to the methods 700, 758, 770 of FIGS. 53A-55B, with similar steps numbered similarly. In general, the method 784 of FIGS. 56A-58 includes providing a conversational message to the user at various points in the method 784. In general, the conversational messages, also referred to herein as "feedback messages," can be configured to help provide the user with feedback in response to input by the user indicative of a decision (e.g., deciding to engage in an activity, deciding to not try an unhelpful activity again in the future, etc.), which can help keep the user engaging in activities and selecting new activities, help engage the user with the system, and/or help make the system more user-friendly. Non-limiting examples of conversational messages can include encouraging text, text confirming a user decision, audio messages, and video messages.

The system can be configured to provide 786, 788 a feedback message to the user confirming 722 timing with respect to a non-ritualizing activity. A thank you feedback message can be provided 786 to the user in response to the user indicating that she wants to pursue the activity now 724. A reassuring feedback message can be provided 788 to the user in response to the user indicating that she does not want to pursue the activity now 726.

In response to the user indicating that the user commits 728 to an activity that can be converted to a healthy habit, the system can be configured to ask 790 the user if a reminder should be set to later remind the user about the accepted activity. In response to the user's reply 792 of "yes" or "no," the system can be configured to, for a "yes" response, set the reminder and provide a confirmation feedback message to the user that the reminder is set, and for a "no" response, provide a reassuring feedback message.

The system can be configured to provide 794 a reassuring feedback message to the user in response to the user indicating that the user has not 736 tried an accepted activity that can be converted to a healthy habit.

The system can be configured to provide 796 an understanding feedback message to the user in response to the user indicating that the user does not know yet 740 the helpfulness of engaging in an accepted activity that can be converted to a healthy habit. The system can be configured to provide 798 a congratulatory feedback message to the user in response to the user indicating the helpfulness 742 of engaging in an accepted activity that can be converted to a healthy habit. In response to the user's reply that the accepted activity that can be converted to a healthy habit has helped a lot or a little, the system can be configured to provide 800 a congratulatory feedback message, which can include information relating the user's indicated level of helpfulness to users at a similar pregnancy term. In response to the user indicating 754 a willingness to keep trying a so-far unhelpful accepted activity that can be converted to a healthy habit, the system can be configured to provide 802 an encouraging feedback message.

In other embodiments of, one or more conversations in addition to those in this illustrated embodiment can be provided at points in a method, only a subset of the conversations in this illustrated embodiment can be provided at points in a method, or one or more conversations instead of any shown in this method can be provided at points in a method.

Figure 56A:
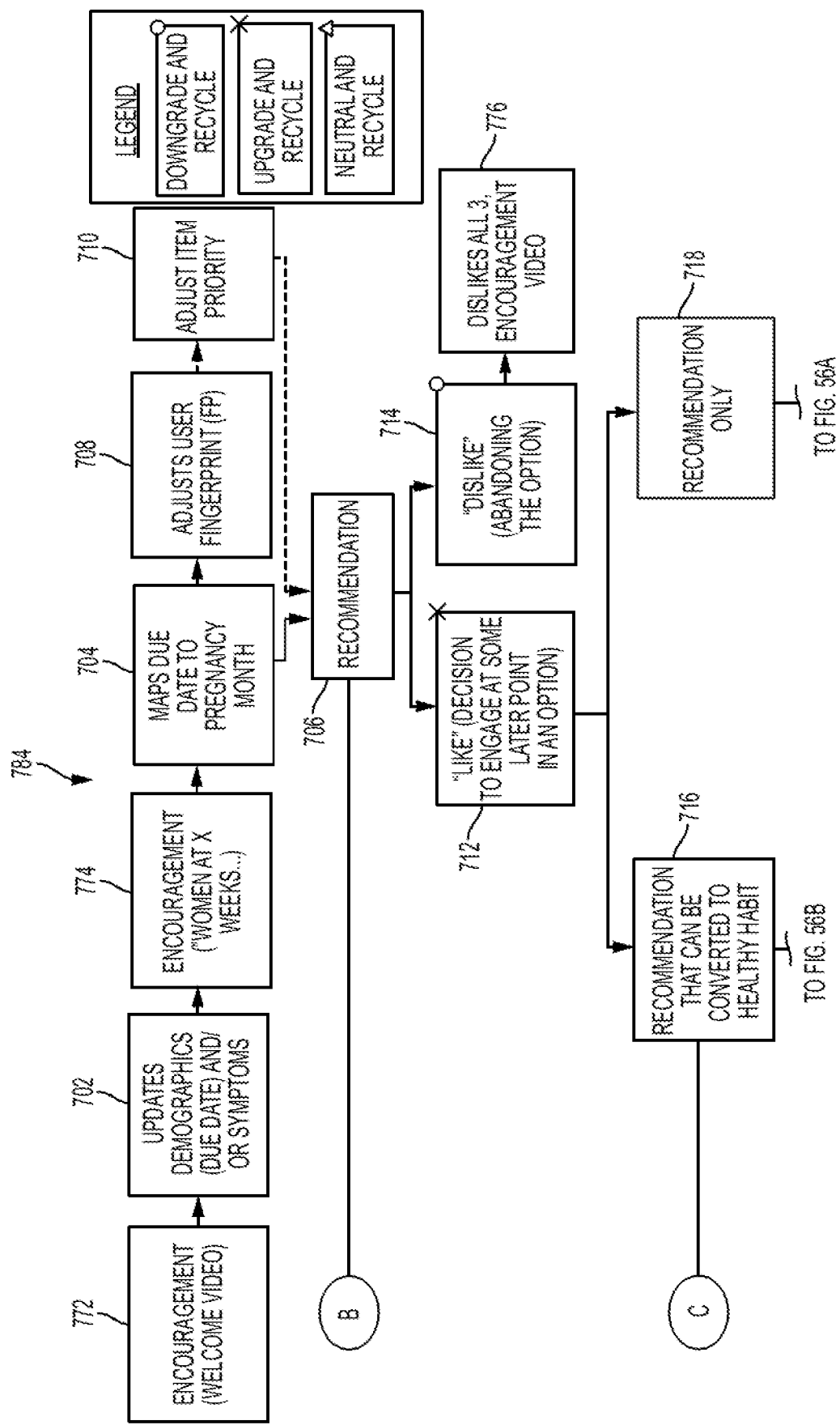
FIG. 56A is a portion of a flowchart showing a portion of another embodiment of a method of using a wellness, health, and/or lifestyle planning, tracking, and maintenance system.
Figure 56B:
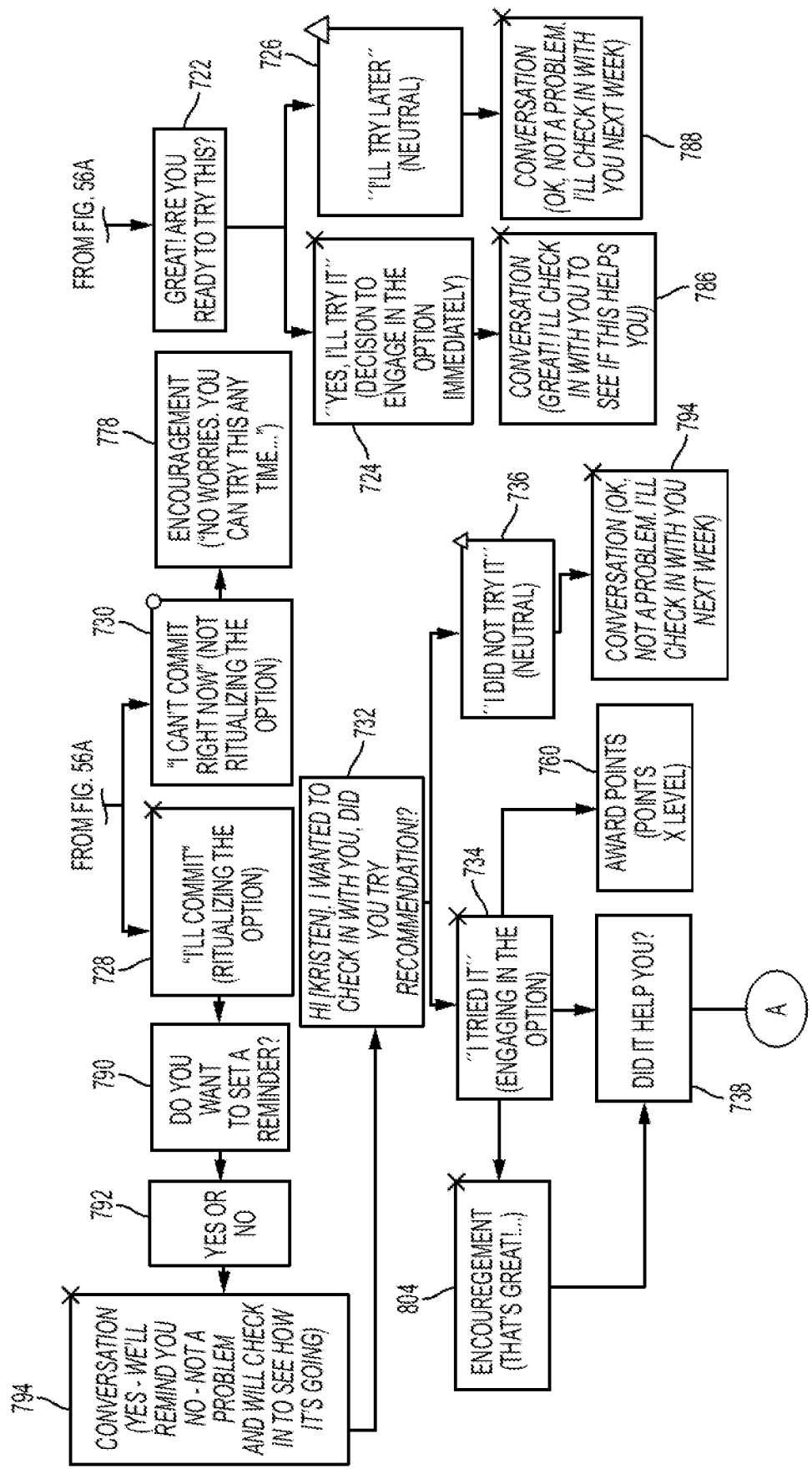
FIG. 56B is another portion of the flowchart of FIG. 56A.
Figure 57:
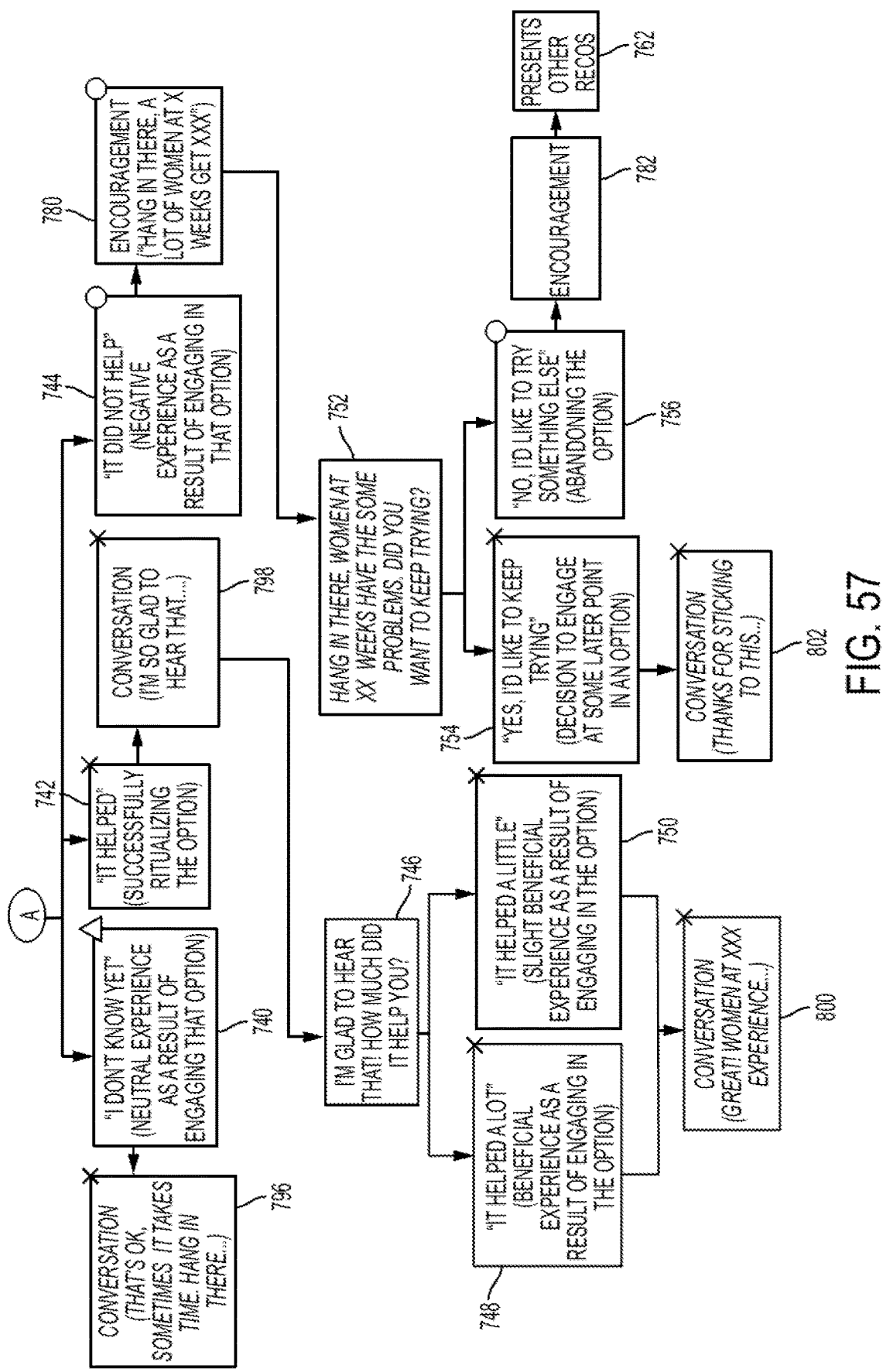
FIG. 57 is a flowchart showing still another portion of the method of FIGS. 56A and 56B.
Figure 58:
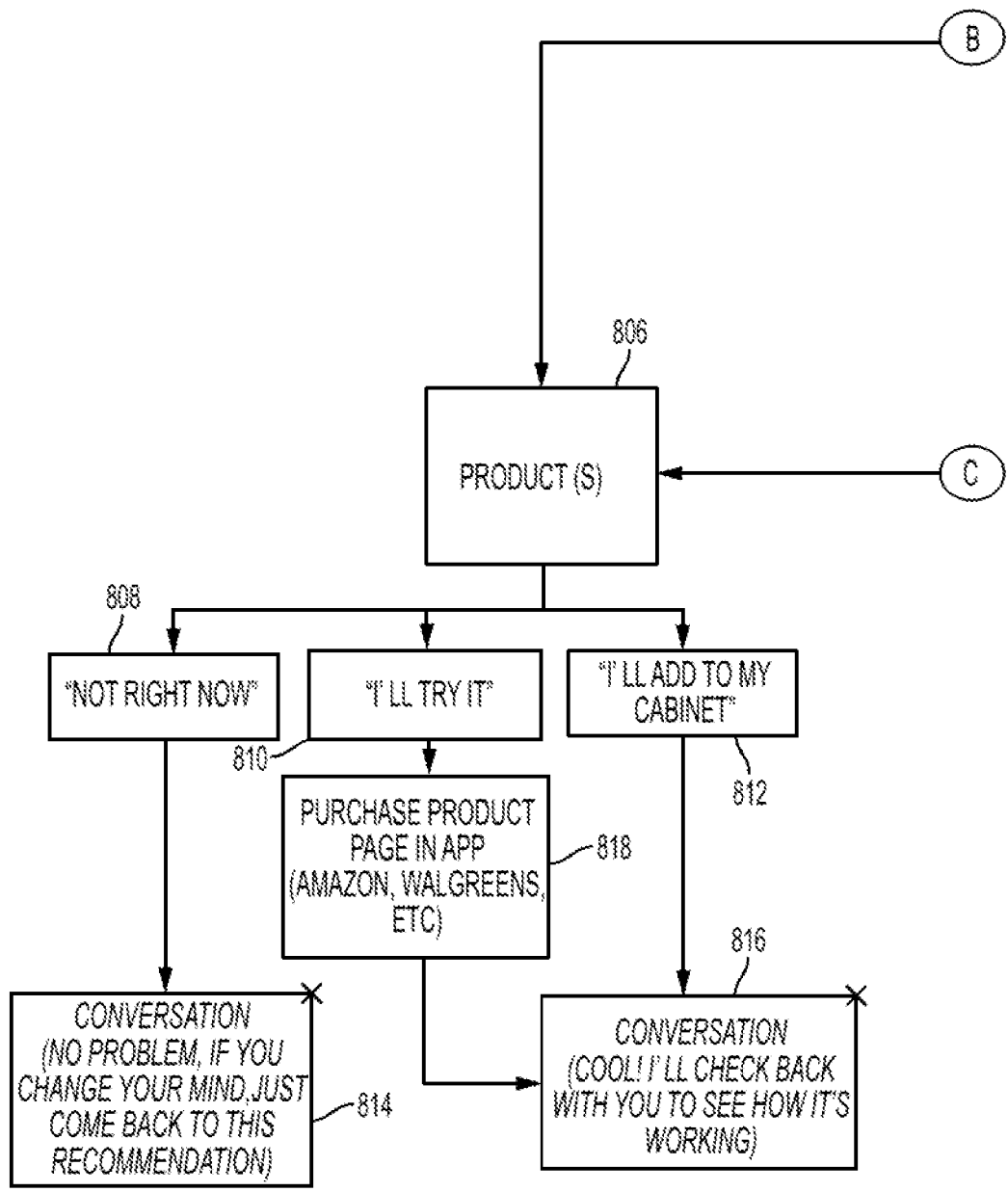
FIG. 58 is a flowchart showing yet another portion of the method of FIGS. 56A and 56B.

FIGS. 56A and 56B also illustrate that the system can be configured to provide 804 encouragement to the user between the user indicating that the user did perform 734 an accepted activity that can be converted to a healthy habit and prompting 738 the user to indicate whether the activity was helpful to the user or not.

As in this illustrated embodiment, a method can be configured to recommend 806 one or more consumable products to the user for each of the provided 706 one or more activity recommendations and/or for each of the activities that can be converted to a healthy habit that the user has accepted 712. The one or more consumable products recommended 806 to the user for an accepted 712 activity can be the same product recommendations provided 806 to the user before the user's acceptance 712 or can be different (e.g., based on a newly performed analysis). The system can be configured to receive a response from the user with respect to each recommended 806 product, such as the user deciding not to try the product now 808, the user deciding to try the product now 810, or the user deciding to save the product to the user's cabinet 812 (e.g., to a list of the user's physical products in use in relation to the system). In at least some embodiments, the system can be configured to require the user to provide a response to each of the recommended products, which can help the system gather information regarding the user's consumer preferences. In other embodiments, the system can be configured to allow the user to not provide a response to each of the recommended products, which can help the user focus on other activities and providing input to the system related thereto. In response to the user indicating that the user would not like to try the product now 808, the system can be configured to provide 814 an understanding feedback message. In response to the user indicating that the user would like to try the product now 810 or later 812, the system can be configured to provide 816 a thank you feedback message. In response to the user indicating that the user would like to try the product now 810, the system can be configured to facilitate immediate purchase 818 of the product, such as by allowing purchase of the product through an online retailer using the app or web page identifying the product to the user.

Example I

FIGS. 59-77 illustrate another embodiment of a method of using a system (e.g., the system 10 of FIG. 2 or other systems described herein) for wellness, health, and/or lifestyle planning, tracking, and maintenance. FIGS. 59 and 61-77 illustrate various aspects of the method, indicating which actions in this illustrated embodiment involve actions by a user of the system, e.g., involve the user inputting data using an input module, and which actions in this illustrated embodiment involve actions by the system in response to the user's actions, e.g., which actions involve analysis using an analysis module such as updating the user's fingerprint (the fingerprint also being referred to herein as a "learning engine"). This illustrated embodiment is in the context of maternal health but can be used similarly in other contexts.

Figure 59:
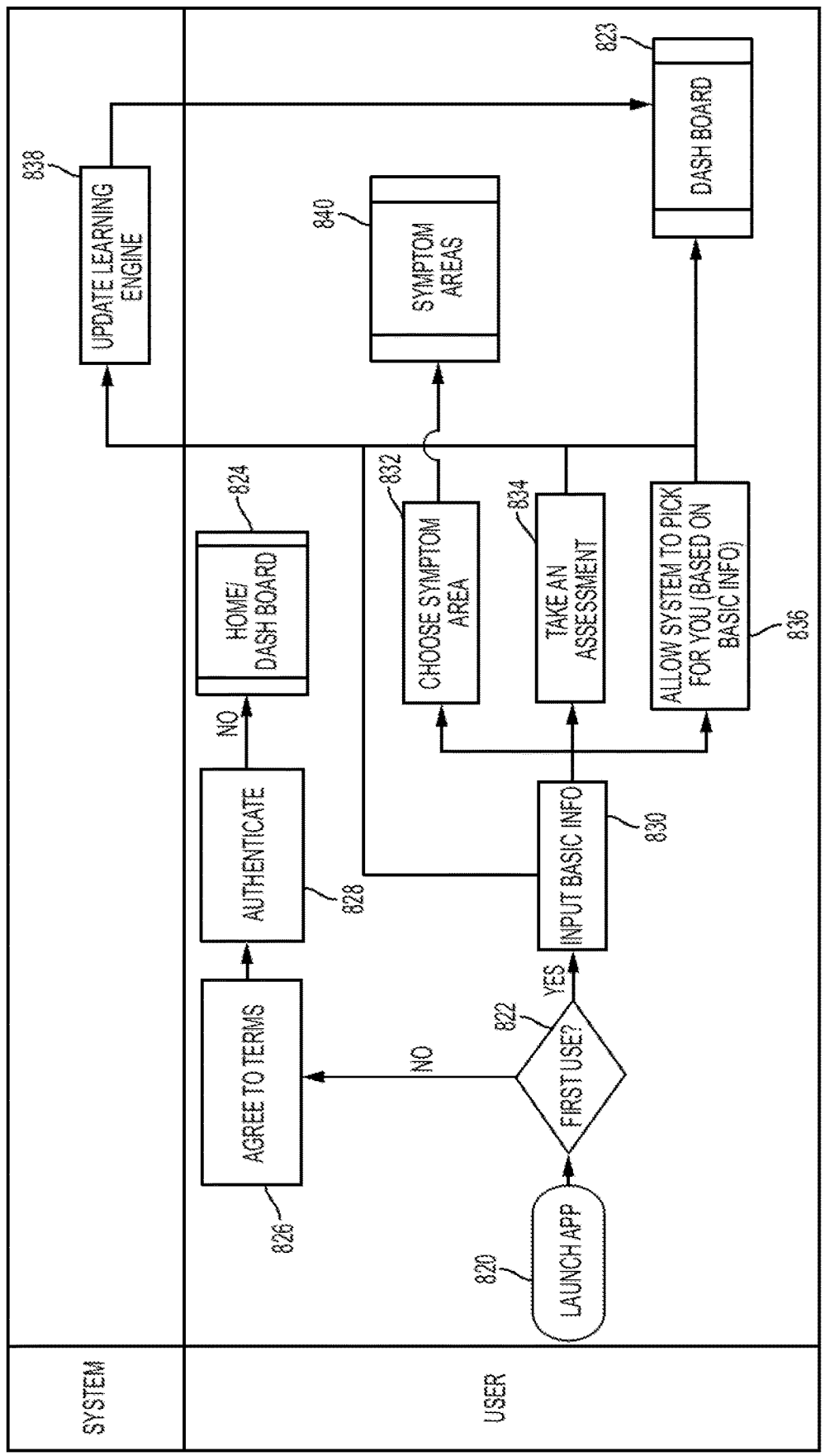
FIG. 59 is a flowchart showing another embodiment of a method of using a wellness, health, and/or lifestyle planning, tracking, and maintenance system.

FIG. 59 illustrates the user accessing the system, which in this illustrated embodiment includes the user accessing the system by launching 820 an app. As discussed herein, a user can access systems in various other ways, such as by visiting a website. Whether or not this is the user's first use 822 of the system, the user's logon to the system can allow the user to access a dashboard 823 of the system after the user satisfies various initial requirements. The initial requirements when it is not the user's first use 822 can include agreeing 826 to terms of the system (e.g., privacy terms, etc.) and authenticating 828 the user's identity. The initial requirements when it is the user's first use 822 can include inputting 830 basic information about the user (e.g., demographics information, etc.), choosing 832 symptom areas from among a plurality of provided possible symptoms, taking 834 an assessment (e.g., answering questions about the user's pregnancy), and allowing 836 the system to pick focus areas for the user. The system can be configured to update 838 its learning engine (e.g., update the user's fingerprint) based on the user's inputs 820, 832, 834, 836. The system can be configured to allow the user to access a symptoms area 840, which can identify symptoms currently known for the user that the user can update as symptoms change.

Figure 60:
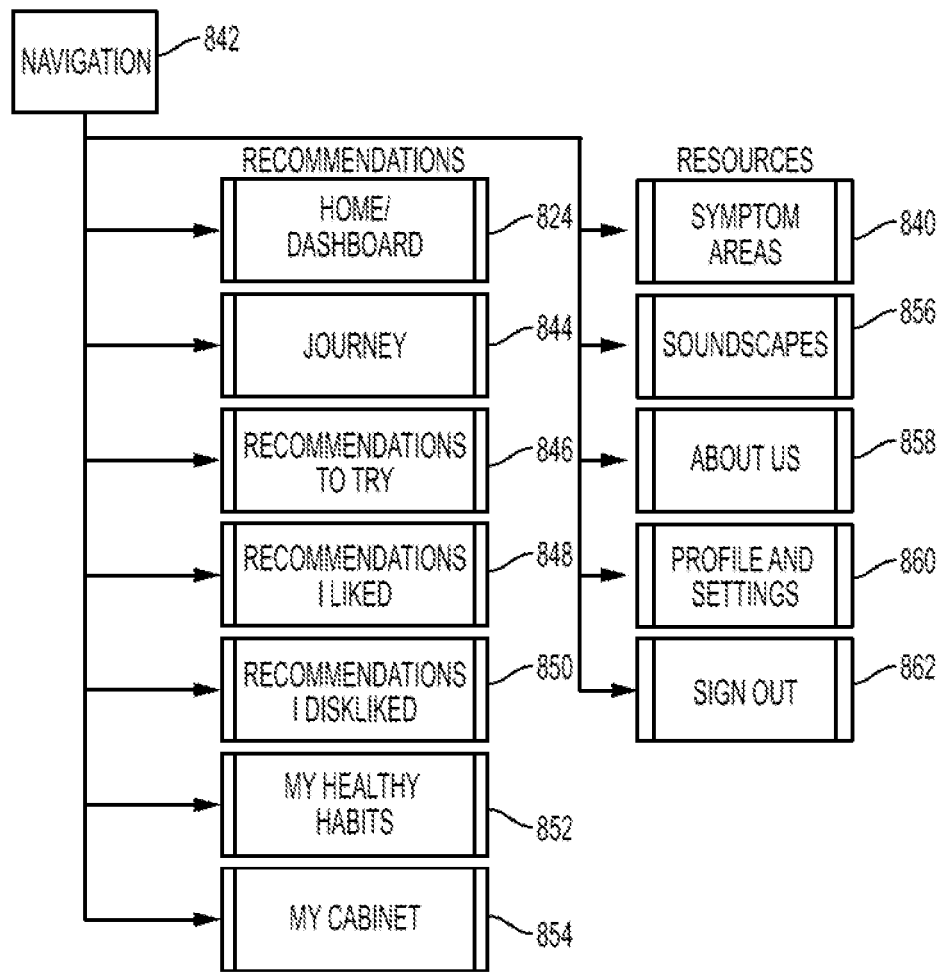
FIG. 60 is a schematic diagram showing a navigation menu of the method of FIG. 59.

The system can be configured to provide a navigation menu 842 to the user, illustrated in FIG. 60, after the user logins in to the system. The menu 842 can include various options (e.g., a home/dashboard 824 (e.g., a home page), the symptom areas 840, a journey of the user 844 (e.g., user history, progress graphs, etc.), recommended activities 846 (e.g., activities that the system determines to recommend to the user based on the user's fingerprint), recommended activities liked by the user 848 but not yet accepted as activities to engage in, recommended activities disliked by the user 850, the user's healthy habits 852, the user's cabinet 854, soundscapes 856 (e.g., available audio that can be played by the system, such as available white noise audio), an "about us" section 858 for the system, user profile and settings 860, and a sign out 862) that the user can select to access various types of information related to the user and/or the system. These various options are discussed further below.

Figure 61:
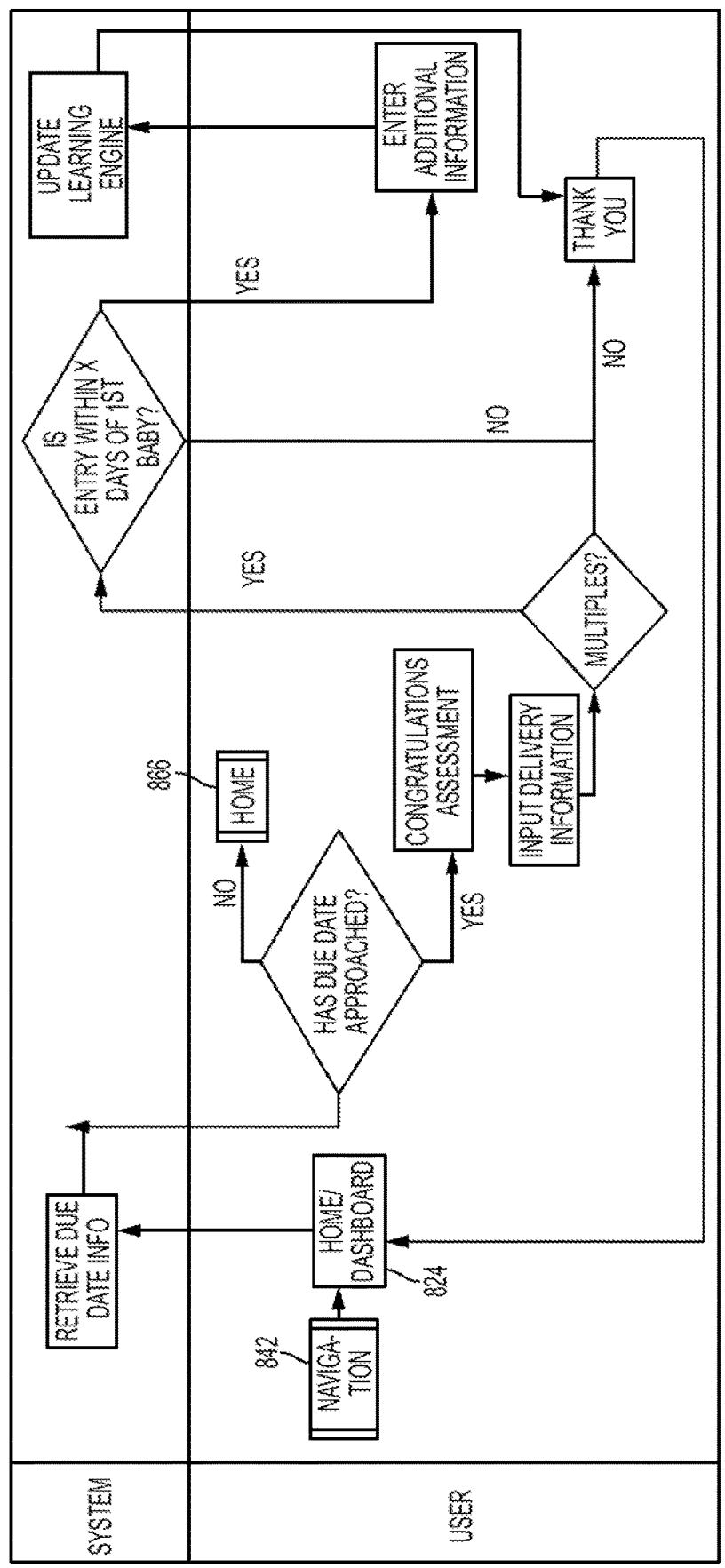
FIG. 61 is a flowchart showing another portion of the method of FIG. 59.
Figure 62:
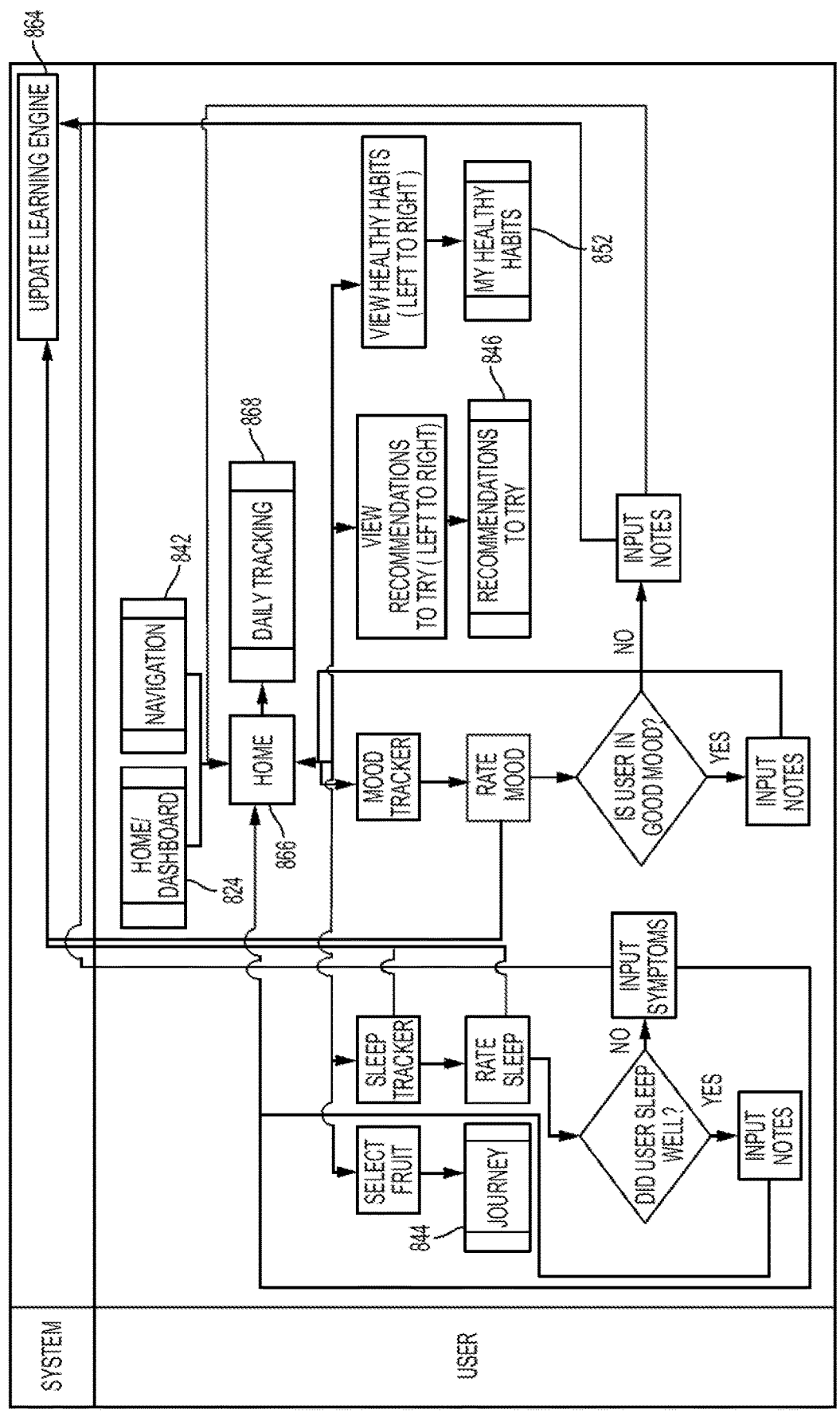
FIG. 62 is a flowchart showing yet another portion of the method of FIG. 59.
Figure 63:
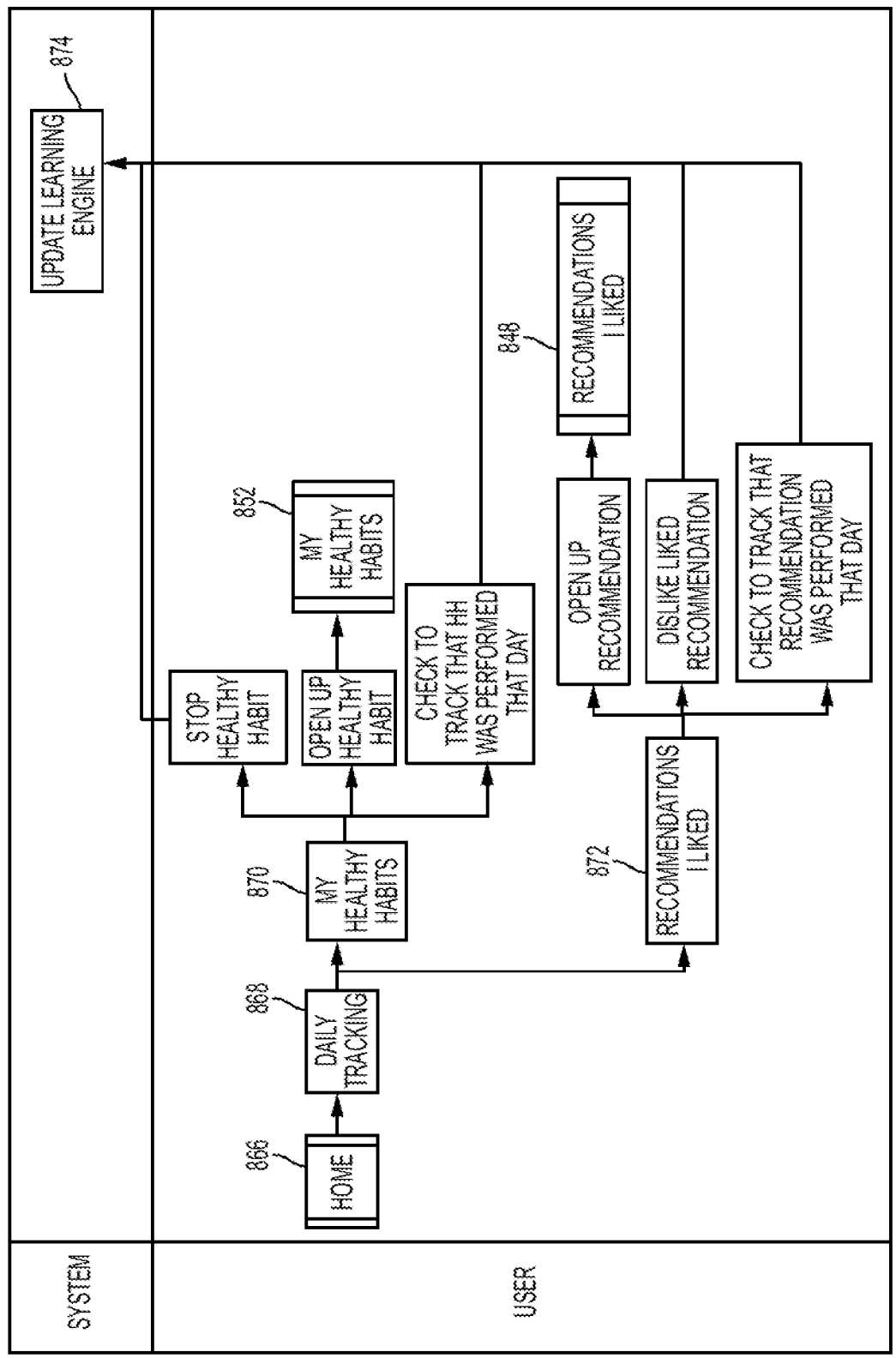
FIG. 63 is a flowchart showing still another portion of the method of FIG. 59.

FIG. 61 illustrates how the system can check the user's due date from the home/dashboard 824. FIG. 62 illustrates how the system can receive data from the user that the system can use to update 864 the user's fingerprint. Such data can include mood information, sleep information, food intake information, and symptoms information. From home 866, the user can access Daily Tracking 868, also shown in FIG. 63, which can allow the user to view information for the user that is relevant to the user's daily life, such as the user's healthy habits 870 and the user's previously liked recommendations 872 (e.g., recommendations previously accepted by the user as activities to engage in). Based on the user's inputs related to her healthy habits 870 and/or to her liked recommendations 872, the system can update 874 the user's fingerprint.

Figure 64:
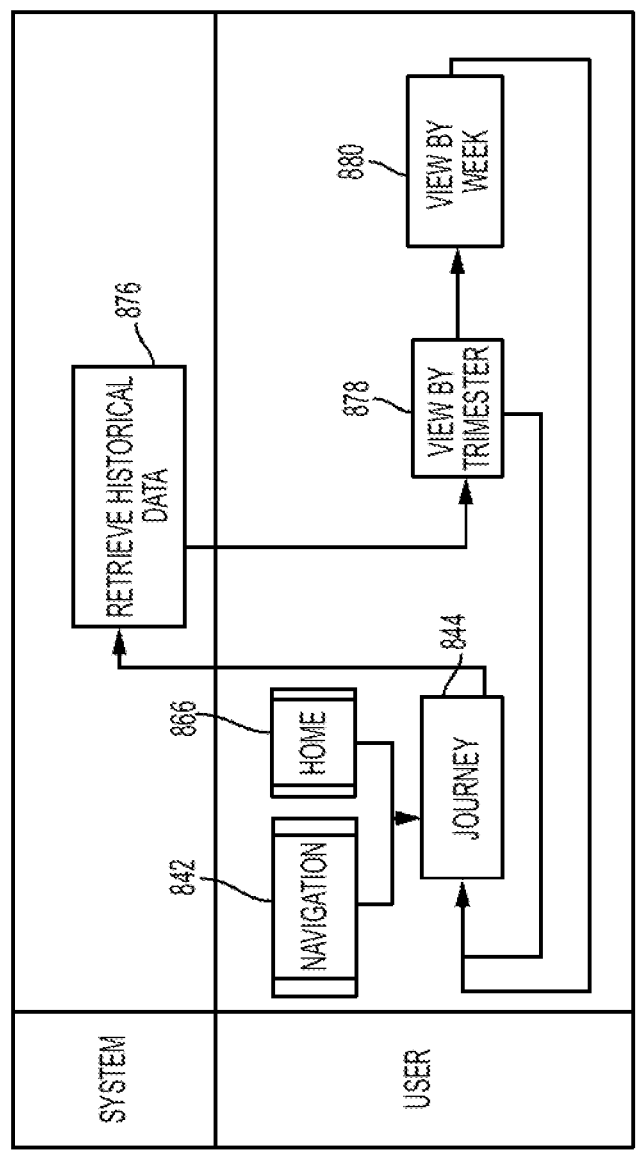
FIG. 64 is a flowchart showing another portion of the method of FIG. 59.

FIG. 64 illustrates user access of the user's journey 844. The user's journey 844 access can cause the system to retrieve 876 historical data related to the user (e.g., access an individual database) and to present the retrieved historical data to the user by trimester 878 and by week 880. The system can be configured to present the retrieved historical data in any one or more ways, text, image, audio, etc. The system can be configured to allow the user to select which one or both of the trimester 878 and week 880 retrieved historical data is presented.

Figure 65:
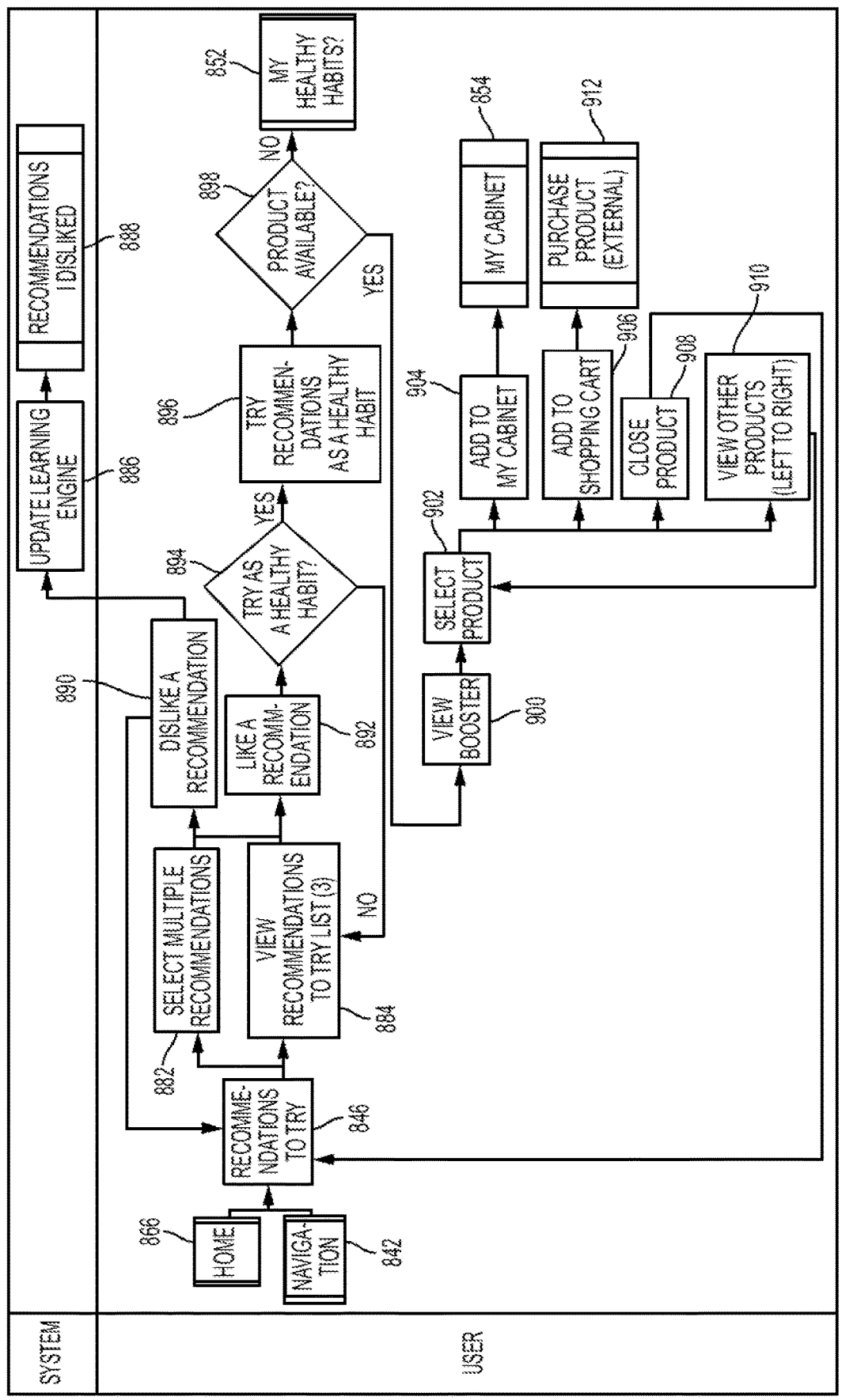
FIG. 65 is a flowchart showing still another portion of the method of FIG. 59.

FIG. 65 illustrates user access of the recommended activities 846, which can allow the user to select 882 multiple ones of the recommendations and to view 884 a list of recommendations. If the user indicates 890 a dislike (e.g., by clicking on a "dislike" check box for an activity, by sliding a slide bar to "dislike" for an activity, etc.) for any of the selected 882 recommendations or any of the listed 884 recommendations, the system can 886 update the user's fingerprint to reflect the dislike and can add 888 the disliked activity to the user's disliked activities. If the user indicates 892 a like (e.g., by clicking on a "like" check box for an activity, by sliding a slide bar to "like" for an activity, etc.) for any of the selected 882 recommendations or any of the listed 884 recommendations, the system can prompt 894 the user to indicate whether the user would like to try that activity as a healthy habit (e.g., whether the user would like to attempt ritualizing that activity). If so 896, the system can check 898 whether any consumable products are available for that activity. If not, the user can view his/her healthy habits 852 including the newly selected activity. If so, the user can view 900 a list of the products, from which the user can select 902 any one or more of the products to try. In response to the user making a selection 902, the system can add 904 the selected product(s) to the user's cabinet, can add 906 the selected product(s) to the user's shopping cart, can close 908 the product (e.g., remove the product from the list since it has already been selected), and can allow 910 the user to scroll through additional products. From the shopping cart, the can purchase 912 the products therein, such as through an external seller.

Figure 66:
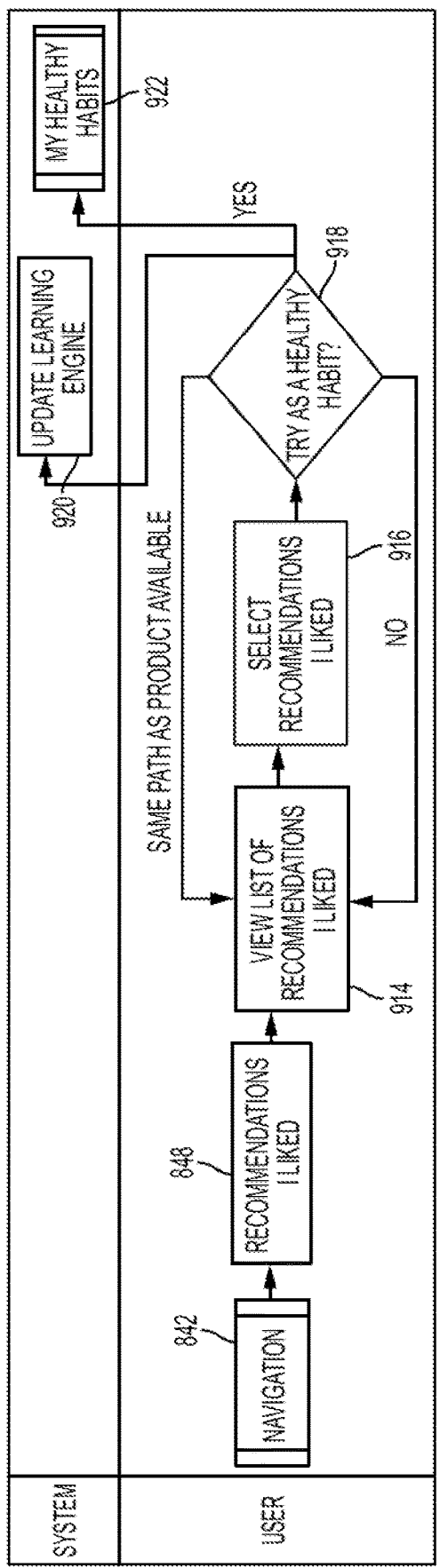
FIG. 66 is a flowchart showing yet another portion of the method of FIG. 59.

FIG. 66 illustrates user access of the recommended activities liked by the user 848, which can allow the user to view 914 a list of recommendations previously liked by the user. From the list, the user can select 916 any one or more of the liked recommendations and indicate 918 whether the user would like to try those selections as a healthy habit. If so, the system can update 920 the user's fingerprint to reflect the accepted one or more activities and can add 922 the liked activity to the user's healthy habits.

Figure 67:
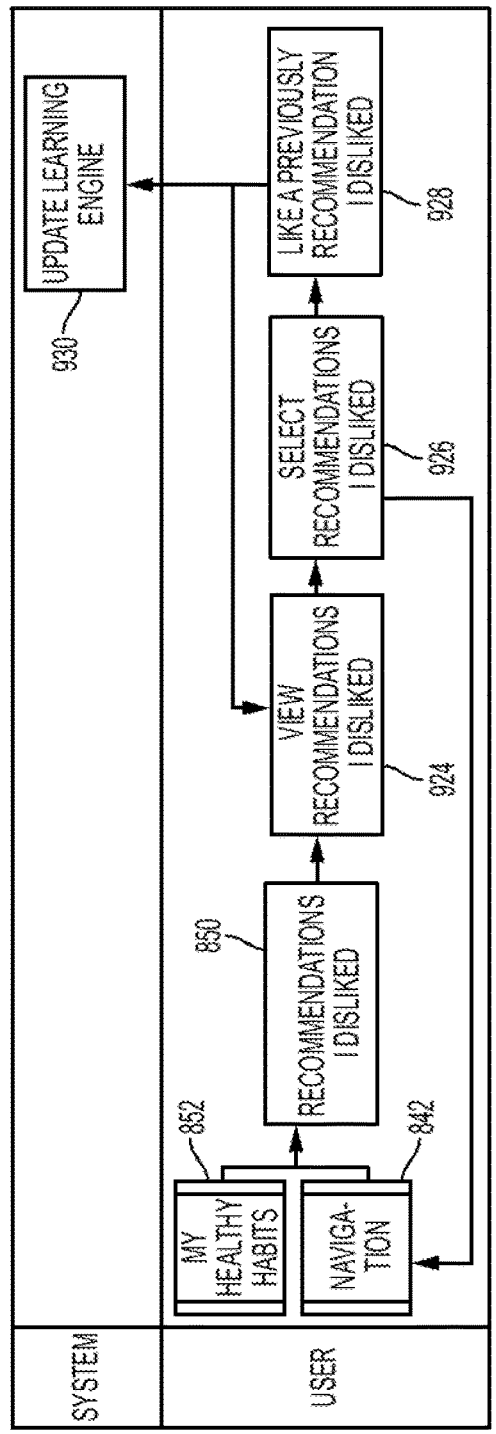
FIG. 67 is a flowchart showing still another portion of the method of FIG. 59.

FIG. 67 illustrates user access of the recommended activities disliked by the user 850, which can allow the user to view 924 a list of recommendations previously liked by the user. From the list, the user can select 926 any one or more of the disliked recommendations and indicate 928 whether the user now likes the recommendation (e.g., due to a change in circumstance such as geographic location, purchase of exercise equipment, job change, etc.). If so, the system can update 930 the user's fingerprint to reflect the accepted one or more activities and can add the liked activity to the user's recommended liked activities.

Figure 68:
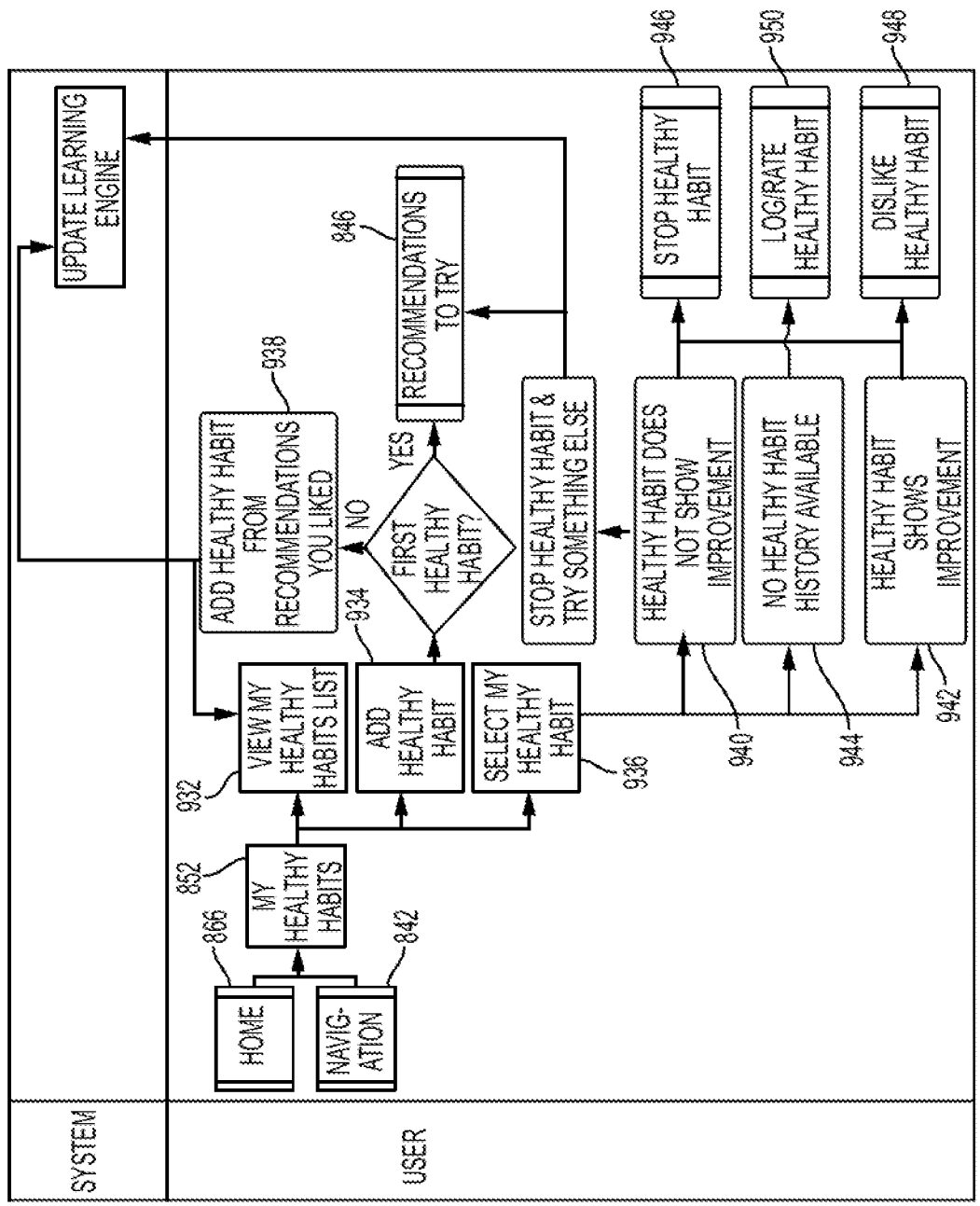
FIG. 68 is a flowchart showing another portion of the method of FIG. 59.
Figure 69:
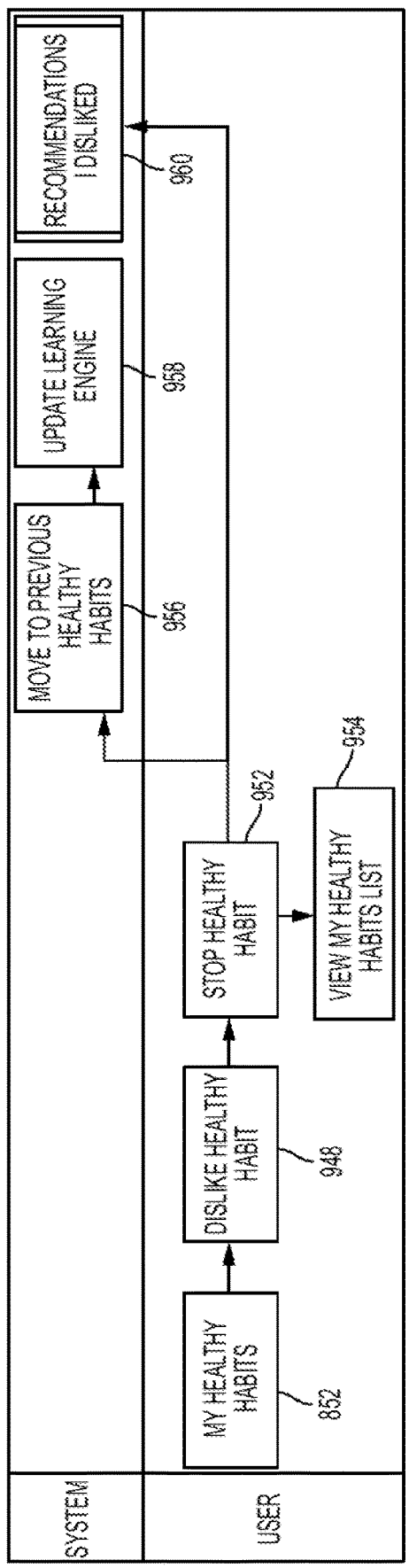
FIG. 69 is a flowchart showing yet another portion of the method of FIG. 59.
Figure 70:
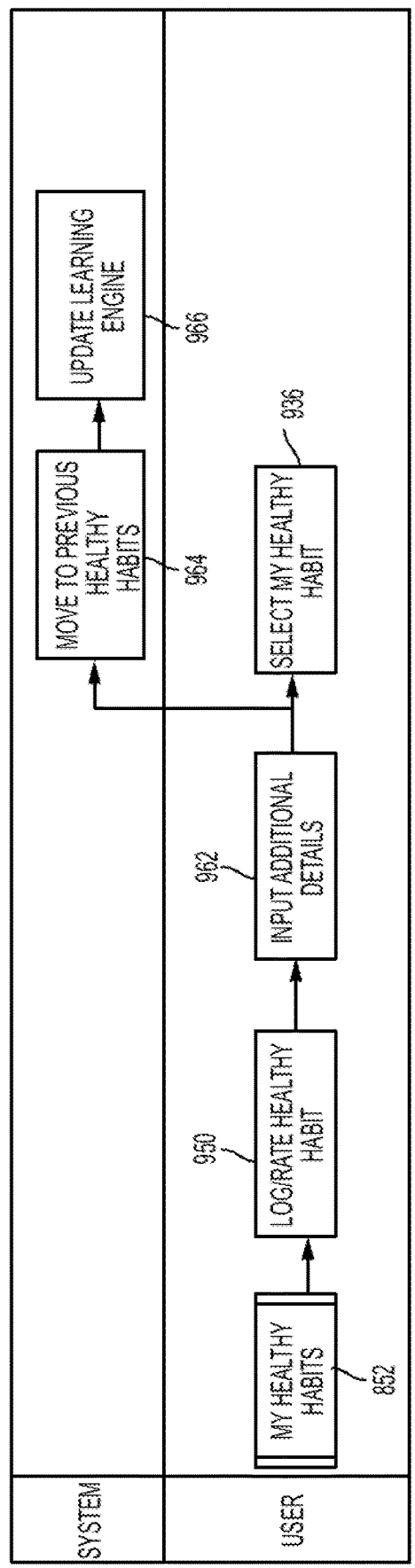
FIG. 70 is a flowchart showing still another portion of the method of FIG. 59.
Figure 71:
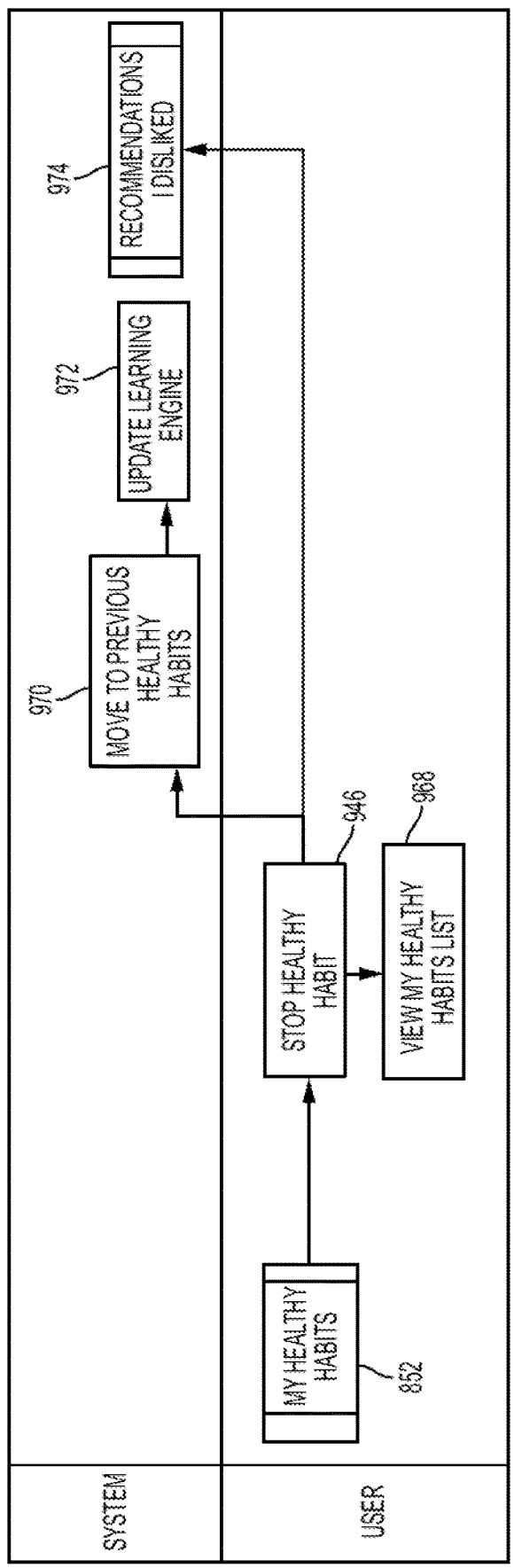
FIG. 71 is a flowchart showing another portion of the method of FIG. 59.

FIG. 68 illustrates user access of the user's healthy habits 852, which can allow the user to view 932 a list of the user's current healthy habits, add 934 one or more healthy habits to his/her current list, and select 936 any one or more of his/her current healthy habits. If the added 934 healthy habit(s) have not already been liked by the user, the system can add those healthy habit(s) to the user's recommendations to try 846. If not, the system can add 938 those healthy habit(s) to the user's healthy habits list from the user's previously liked activities. The system can allow the user to indicate with respect to the selected 936 healthy habit(s) that those habit(s) have not shown improvement 940, that those habit(s) have shown improvement 942, that those habit(s) have been completed 944, that the user would like to stop 946 engaging in those habit(s) before completion thereof, that the user dislikes 948 those habit(s), and results 950 of those healthy habit(s). For disliked 948 healthy habits, as shown in FIG. 69, the user can stop 952 engaging in the disliked 948 healthy habits and can view 954 her current healthy habits, and the system can move 956 the disliked 948 healthy habits from the user's current healthy habits list to the user's list of past healthy habits, update 958 the user's fingerprint in view of dislike, and add 960 the disliked 948 healthy habits to the user's disliked recommended activities. For the completed habit(s) 944, as shown in FIG. 70, the user can input 960 additional details related thereto (e.g., whether the user liked the activity, whether the user disliked the activity, whether the user would like more activities like this one, etc.) and can select 936 any one or more of his/her current healthy habits, and the system can move 964 the completed healthy habit(s) from the user's current healthy habits list to the user's list of past healthy habits and update 966 the user's fingerprint in view of the completion and the input 960 details. For stopped 946 habits, as shown in FIG. 71, the user can view 968 her current healthy habits, and the system can move 970 the stopped 946 healthy habits from the user's current healthy habits list to the user's list of past healthy habits, update 972 the user's fingerprint in view of stopping, and add 960 the stopped 946 healthy habits to the user's disliked recommended activities.

Figure 72:
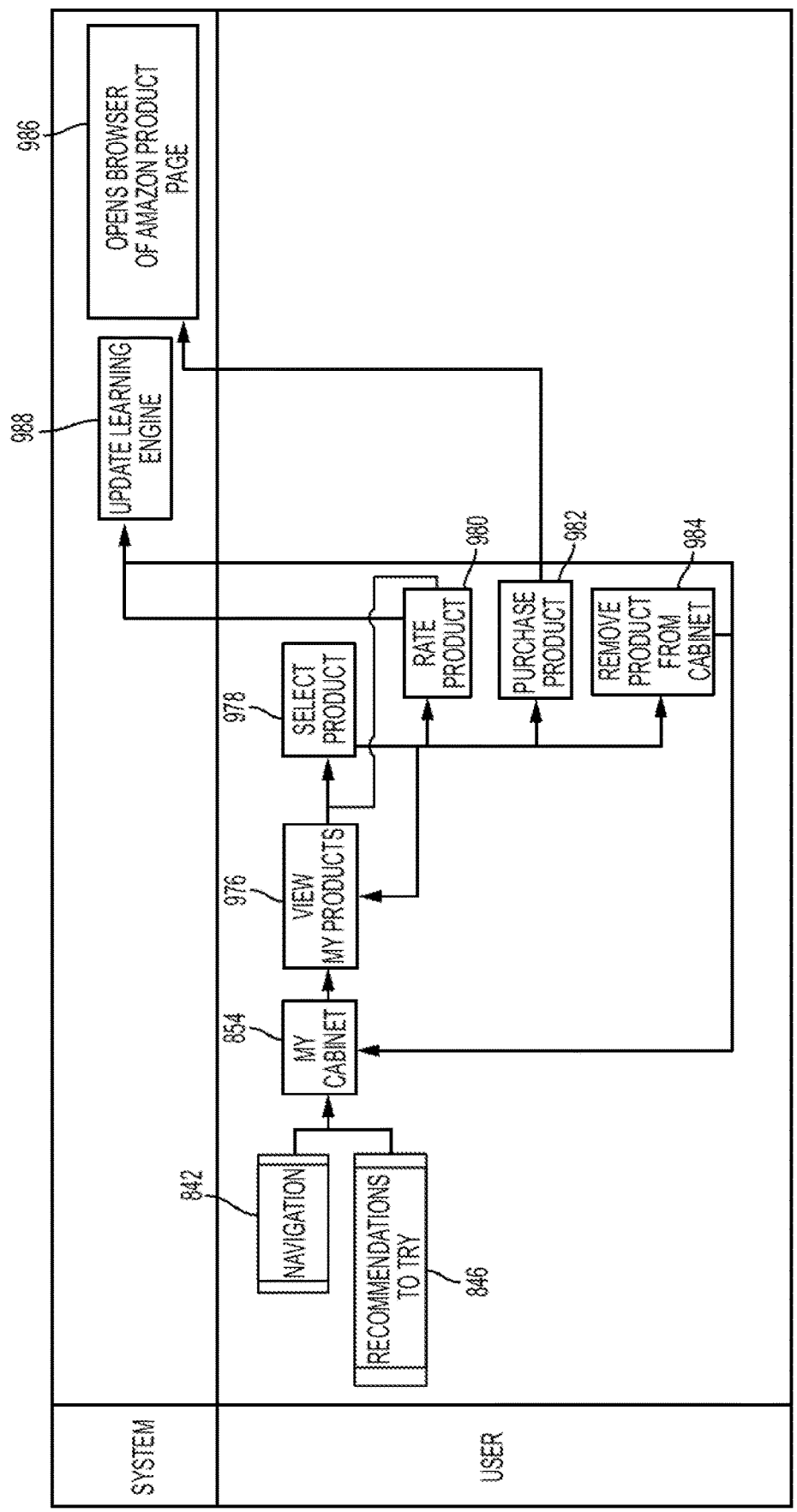
FIG. 72 is a flowchart showing still another portion of the method of FIG. 59.

FIG. 72 illustrates user access of the user's cabinet 854, which can allow the user to view 976 contents of her cabinet and select 978 one or more consumable products stored therein. The user can rate 980 any of the products in the cabinet (e.g., rate based on the user's use of the product), purchase 982 any of the products in the cabinet (e.g., purchase 986 through an online retailer, reserve for pick-up at a store, etc.), and delete 984 any of the products in the cabinet (e.g., because the user is no longer interested in them). In response to the user's deletion 984 of any products from the cabinet, the system can update 988 the user's fingerprint to reflect the user's disinterest in the product(s).

Figure 73:
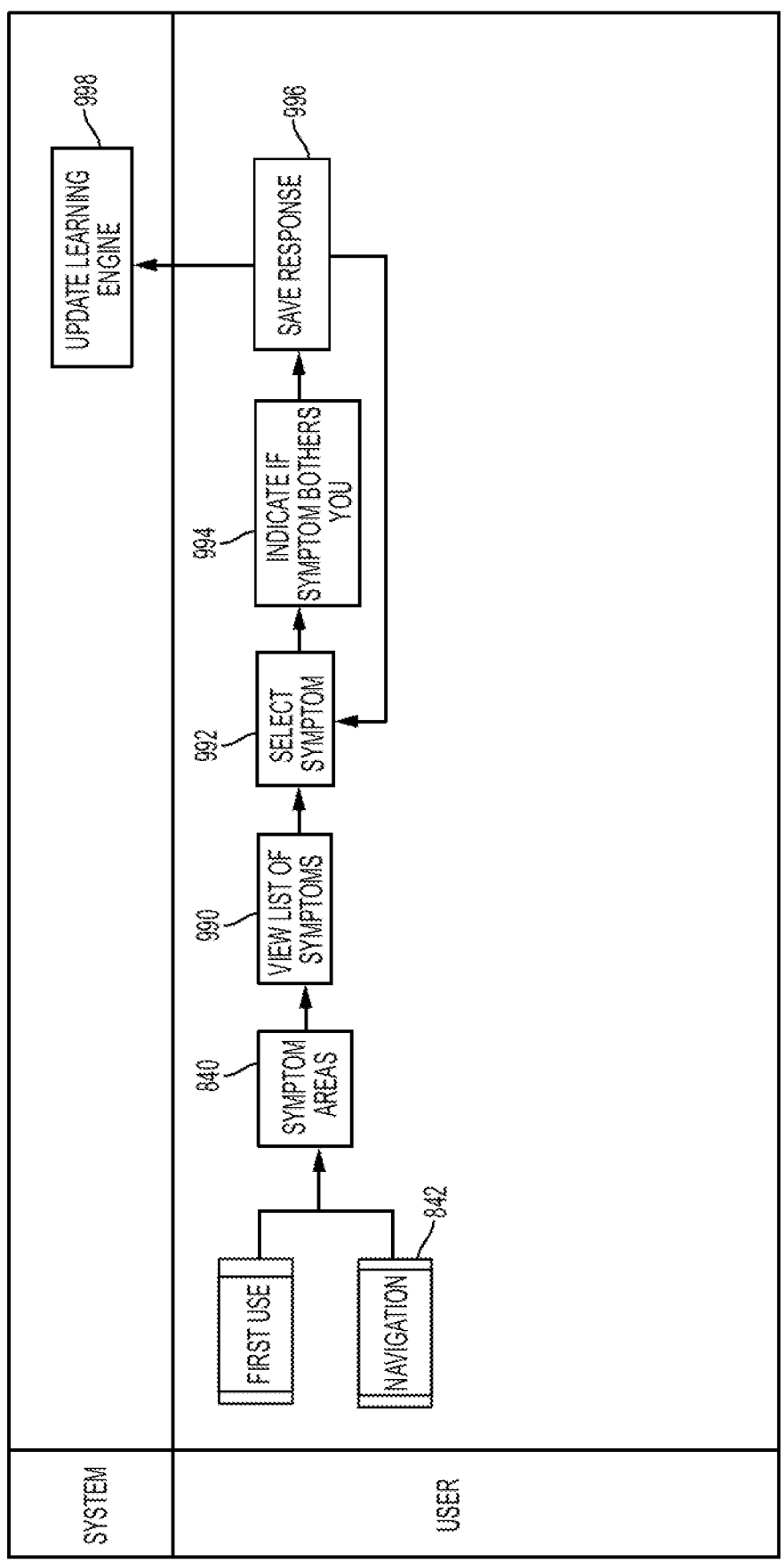
FIG. 73 is a flowchart showing another portion of the method of FIG. 59.

FIG. 73 illustrates user access of the user's symptom areas 840, which can allow the user to view 990 a list of symptoms, select 992 one or more of those symptoms, indicate 994 whether the selected 992 symptoms are bothering the user, and save 996 the indication. The system can update 998 the user's fingerprint to reflect the symptoms that the user is currently experiencing.

Figure 74:
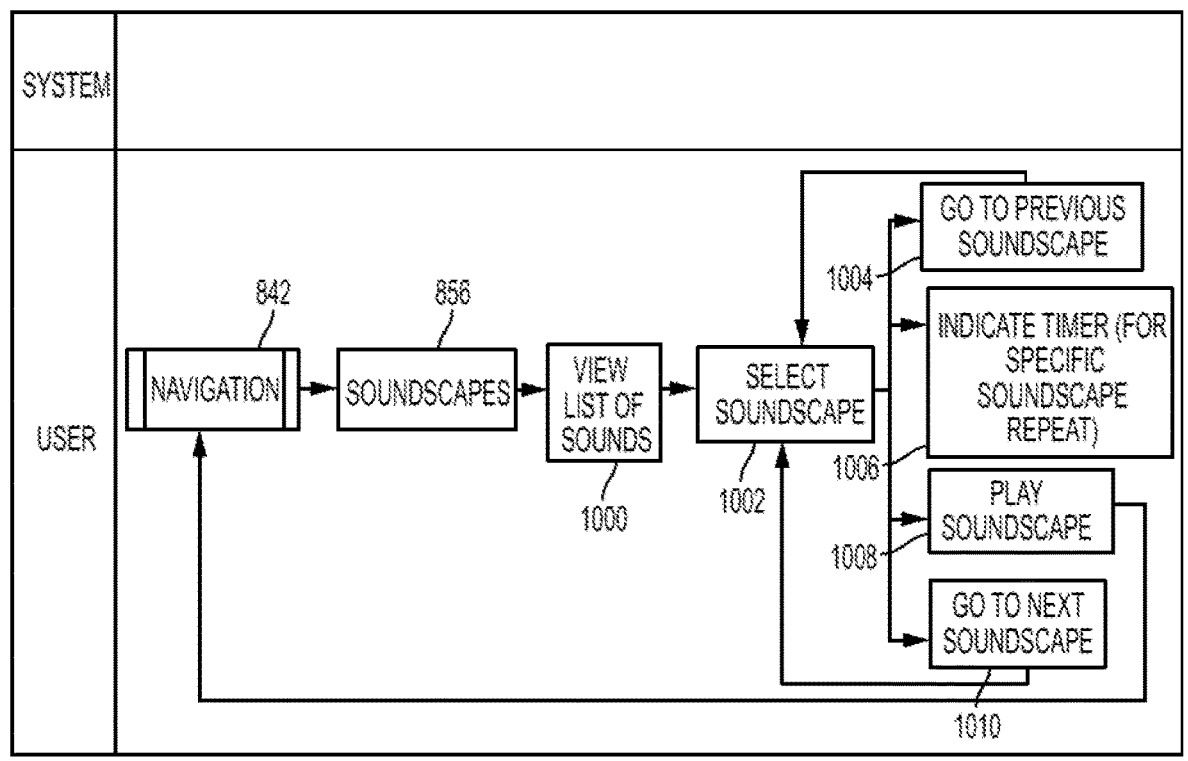
FIG. 74 is a flowchart showing yet another portion of the method of FIG. 59.

FIG. 74 illustrates user access of soundscapes 856, which can allow the user to view 1000 a list of available soundscapes (e.g., relaxing audio available for streaming and/or download, such as white noise soundscapes) and select 1002 a soundscape, which can provide more information to the user about the selected audio. For the selected 1002 soundscape, the user can decide to scroll 1004 to the next soundscape in the list, can indicate 1006 a timer in accordance with the soundscape should be played (e.g., play one time, play on repeat, play 1008 for the next thirty minutes, play every day at 8:00 am for ten minutes, etc.), play 1008 the soundscape, or scroll 1010 to the previous soundscape in the list.

Figure 75:
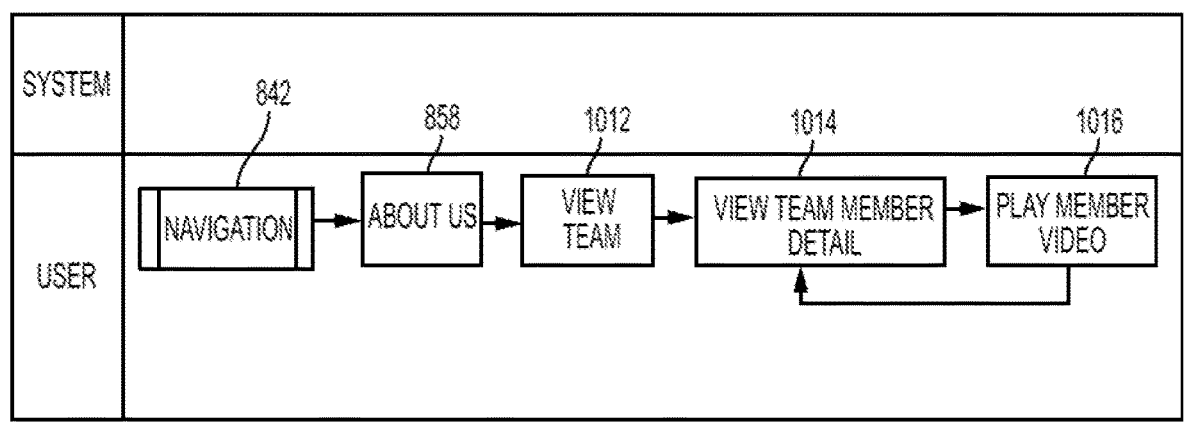
FIG. 75 is a flowchart showing still another portion of the method of FIG. 59.

FIG. 75 illustrates user access of the "About Us" 858, which can allow the user to view 1012 information about the system including information about the system's team, e.g., members of the system's team including personnel running the system, medical experts who appear in educational videos available through the system, etc. The user can select any of the team members to view 1014 more information about that selected team member, such as a video that can be played 1016.

Figure 76:
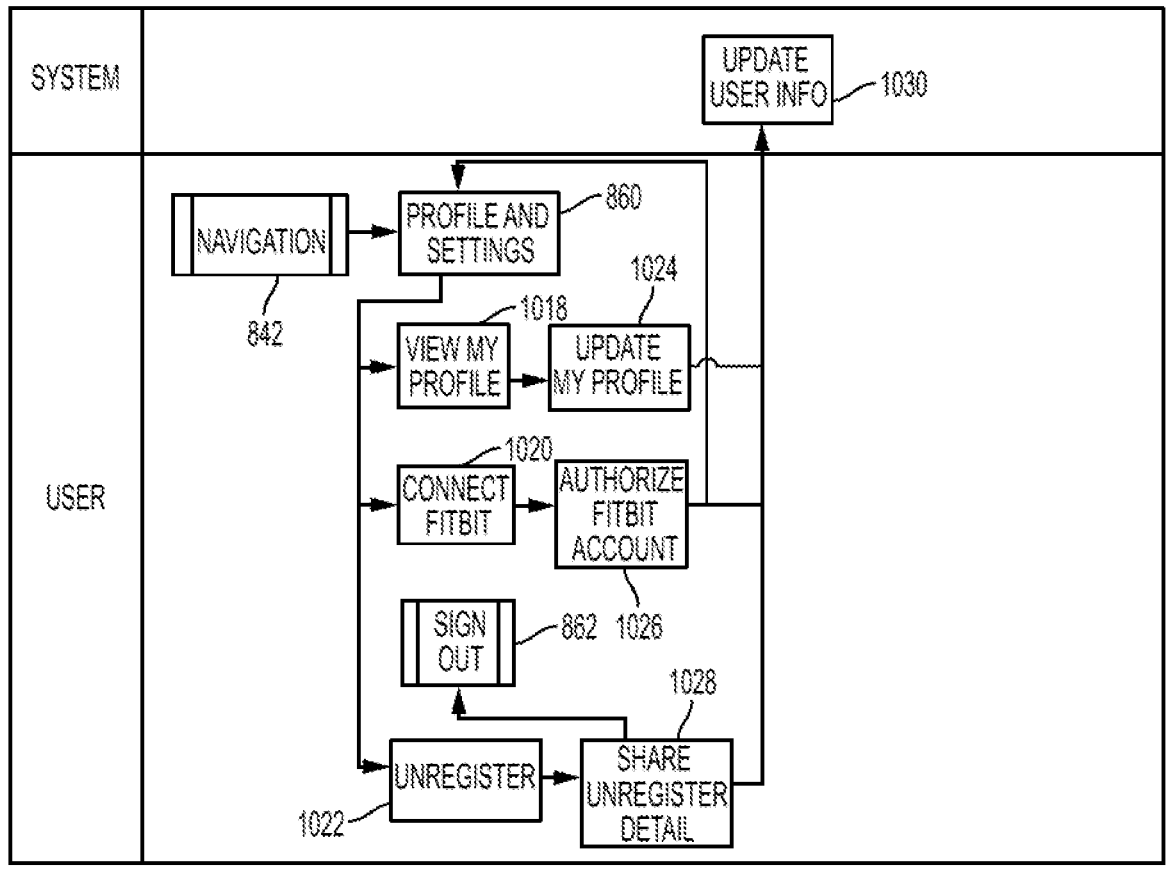
FIG. 76 is a flowchart showing another portion of the method of FIG. 59.
Figure 77:
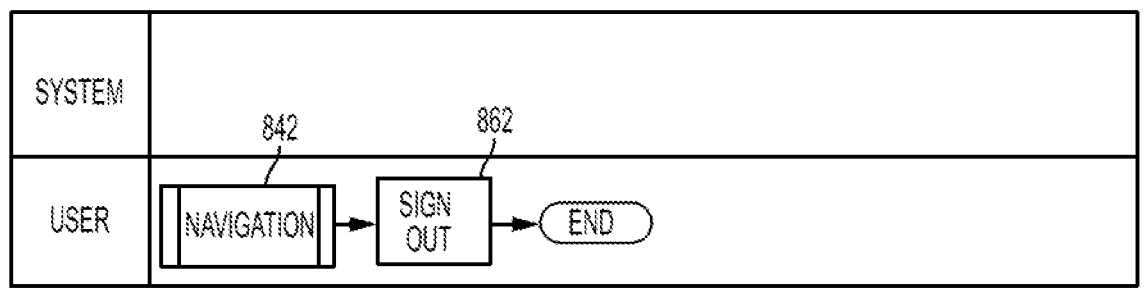
FIG. 77 is a flowchart showing yet another portion of the method of FIG. 59.

FIG. 76 illustrates user access of the user profile and settings 860, which can allow the user to view 1018 her profile, connect 1020 a health monitoring device (in this illustrated embodiment, a Fitbit device available from Fitbit Inc. of San Francisco, Calif.), sign out 862 of the system (as illustrated in FIG. 77), and unregister 1022 from the system. From viewing 1018 her profile, the user can update 1024 the profile, e.g., change email address, add a mobile phone number, etc. The user can authorize 1026 the connected 1020 the health monitoring device to be in electronic communication with the system, e.g., transmit data to and/or receive data from the system. The user can indicate 1028 reason(s) for the user's unregistration 1022, which can help the system be improved for other users, and then the user can be signed out 862. The system can update 1030 the user's fingerprint in view of the user's updated 1024 profile, authorized 1026 health monitoring device, and unregistration 1028. Updating 1030 the user's fingerprint in the case of unregistration 1028 can include removing the user's fingerprint from an individual database of the system while keeping the user's fingerprint in a population database of the system, which can allow the system to consider the user's experiences when analyzing other users, e.g., determining recommended activities for other users, determining encouragements to provide to other users, etc.

Example J

FIGS. 78-104 illustrate embodiments of screens that can be configured to be provided by a system (e.g., the system 10 of FIG. 2 or other systems described herein) for wellness, health, and/or lifestyle planning, tracking, and maintenance. This illustrated embodiment is in the context of maternal health but can be used similarly in other contexts.

Figure 78:
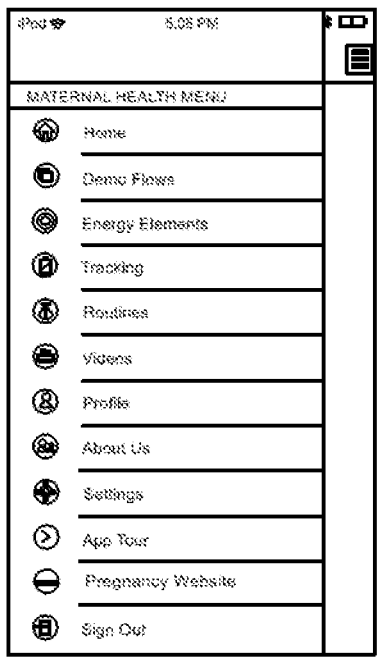
FIG. 78 is a diagram showing an embodiment of a menu screen of a wellness, health, and lifestyle planning, tracking, and maintenance system.

FIG. 78 illustrates an embodiment of a menu screen indicating a variety of options for selection by a user of the system, e.g., "Home" to access a home screen, "Demo Flows" to access examples of the system's features, "Energy Elements" to access information about various symptoms that can affect the user's energy level, "Tracking" to access information about the user's progress, "Routines" to access information about the user's selected activities, "Videos" to access informational videos, "Profile" to access information related to the user's registration with the system, "About Us" to access information about the system itself and/or about people, "Settings" to access information about the user's system preferences, "App Tour" to access help for the system, "Pregnancy Website" to access a website associated with the system, and "Sign Out" to sign out of the system.

Figure 79:
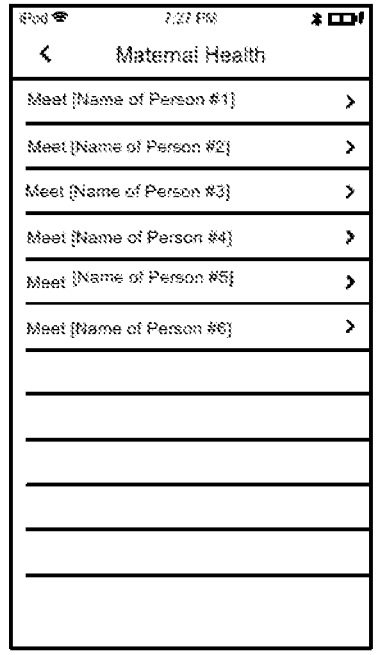
FIG. 79 is a diagram showing an embodiment of an about screen of the system of FIG. 78.
Figure 79A:
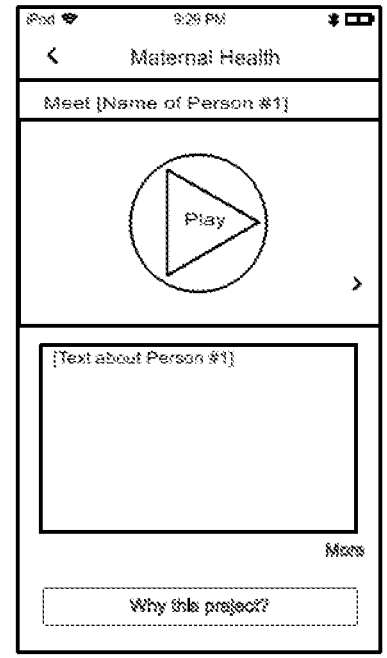
FIG. 79A is a diagram showing an embodiment of an about detail screen of the system of FIG. 78.

FIG. 79 illustrates an embodiment of an about screen that the system can be configured to provide upon the user's selection of the "About Us" option on the menu screen. As in this illustrated embodiment, the about screen can include a list of people associated with features provided by the system, each of which the user can select to learn more information. FIG. 79A illustrates an embodiment of an about detail screen that the system can be configured to provide upon the user's selection of one of the people in the list on the about screen.

Figure 80:
FIG. 80 is a diagram showing an embodiment of a flow screen of the system of FIG. 78.

FIG. 80 illustrates an embodiment of a flow screen that the system can be configured to provide upon the user's selection of the "Demo Flows" option on the menu screen. In general, the flow screen can identify flows that the user can select to learn by example about how various features of the system work. Five example flows are listed on the flow screen, but any number of demo flows can be provided.

Figure 81:
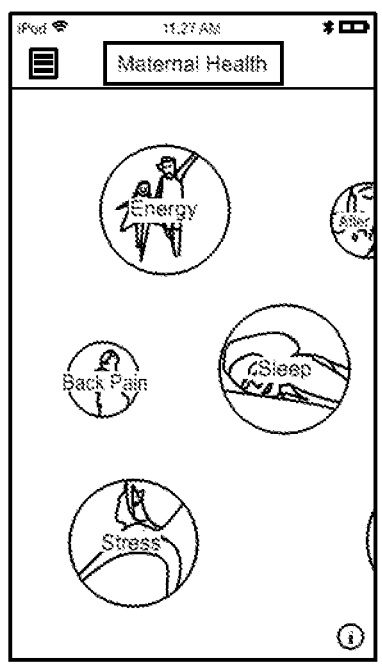
FIG. 81 is a diagram showing a portion of an embodiment of a home screen of the system of FIG. 78.
Figure 82:
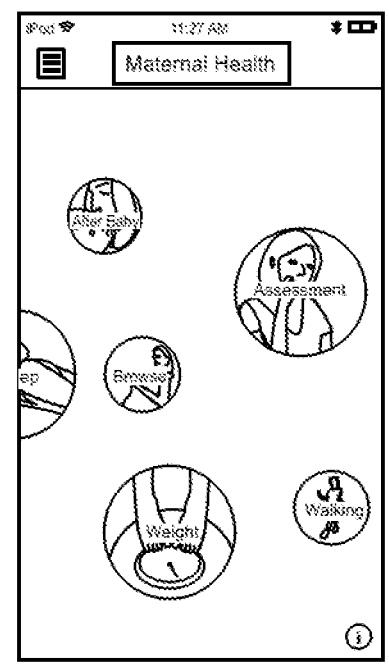
FIG. 82 is a diagram showing another portion of the home screen of FIG. 81.

FIGS. 81 and 82 illustrate an embodiment of a home screen that the system can be configured to provide upon the user's selection of the "Home" option on the menu screen. FIG. 81 shows a left side of the home screen, and FIG. 82 shows a right side of the home screen. As will be appreciated by a person skilled in the art, the user can switch between viewing the left and right sides of the home screen by sliding between the two via touchscreen. In some embodiments, a home screen can be provided as a single screen that does not need sliding to access a whole thereof. In general, the home screen can identify various aspects of the system that the user can select to direct the user to various components of the system for further information, e.g., to access activities related to maternal health. In general, the home screen and the selectable aspects thereon can enable the user to access information quickly and conveniently as needed. Non-limiting examples of selectable aspects that can be included on the home screen include "Energy," "Back Pain," "Sleep," "Stress," "After Baby," "Assessment," "Resource Library," "Current Progress," "Immediate Needs," "Solicit Recommendations," "Weight," and "Walking."

Figure 83:
FIG. 83 is a diagram showing an embodiment of an energy screen of the system of FIG. 78.
Figure 84:
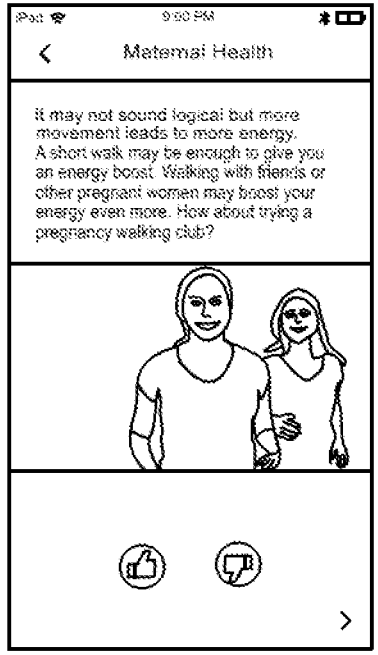
FIG. 84 is a diagram showing an embodiment of a movement screen of the system of FIG. 78.
Figure 85:
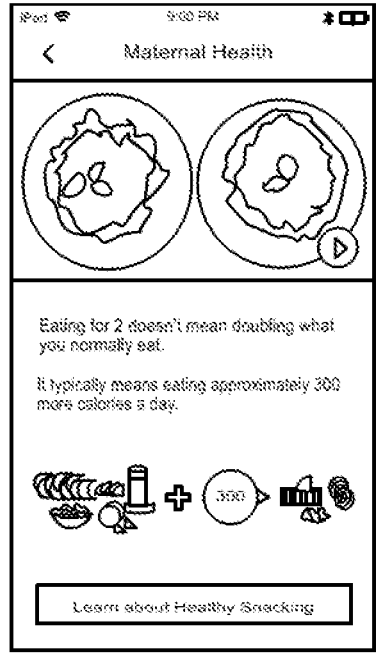
FIG. 85 is a diagram showing an embodiment of a nutrition screen of the system of FIG. 78.
Figure 86:
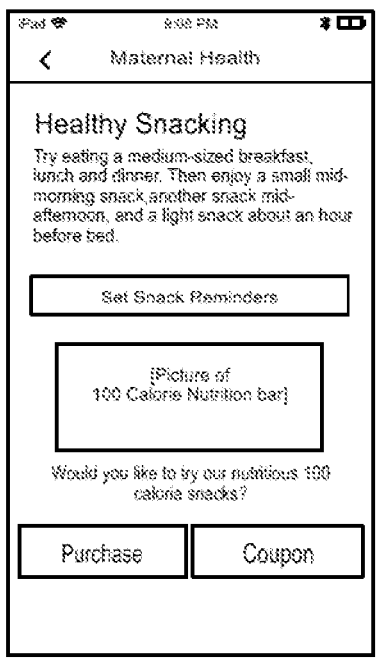
FIG. 86 is a diagram showing an embodiment of a supplemental nutrition screen of the system of FIG. 78.

FIG. 83 illustrates an embodiment of an energy screen that the system can be configured to provide upon the user's selection of the "Energy Elements" option on the menu screen. In general, the energy screen can identify various aspects related to elements that affect an expectant mother's energy level. Each of the various aspects can be selectable by a user to learn more about that selected aspect. As in this illustrated embodiment, the energy screen can include selectable aspects of "Nutrition," "Sleep," "Mood," and "Movement." Selection of an aspect on the energy screen can cause the system to present the user with one or more recommended activities related to that aspect. As discussed herein, the one or more recommended activities can be customized for the user, e.g., based upon analysis by an analysis module of the system, and the user can be prompted to accept or decline each of the one or more recommended activities. FIG. 84 illustrates an embodiment of a movement screen that the system can be configured to provide upon the user's selection of the "Movement" option on the energy screen. In this illustrated embodiment, the user can choose to accept or decline the recommended activity (trying a pregnancy walking club in this non-limiting example) by selecting a thumbs up icon (accept) or on a thumbs down icon (decline). Instead of clicking on one of the accept or decline icons, the user may instead navigate away from the screen, e.g., via a button of his/her client terminal, etc., in which case the system can be configured to recycle that recommended activity without updating the user's fingerprint, as discussed herein. The movement screen can provide any one or more of text, audio, video, and images that help explain the recommended activity, e.g., explain what the activity is and how it can help the user. FIG. 85 illustrates an embodiment of a nutrition screen that the system can be configured to provide upon the user's selection of the "Nutrition" option on the energy screen. As in this illustrated embodiment, the nutrition screen can include explanatory information (text in this illustrated embodiment, but images, audio, and/or video can be provided in addition to or in alternative to text) related to nutrition for expectant mothers and can include an option for the user to learn more about nutrition, such as about healthy snacking. If the user selected the "learn more" option, the system can be configured to provide the user with a supplemental nutrition screen, an embodiment of which is shown in FIG. 86. As in this illustrated embodiment, the supplemental nutrition screen can include one or more recommend activities, which in this illustrated embodiment includes a consumable product recommendation, which the user can choose to purchase or receive a coupon for use in a later purchase, and a recommendation to try eating a medium-sized breakfast, lunch, and dinner and to have a small snack mid-morning, another snack mid-afternoon, and a light snack an hour before bed, which the user can accept by selecting a "Set Snack Reminders" icon. The user's selection of the "Sleep" and "Mood" options on the energy screen can cause screens similar to the movement screen of FIG. 84 and the nutrition screen of FIG.

85 to be provided to the user. The user's selection of the "Energy" option of the home screen can cause the system to provide an energy screen.

Figure 87:
FIG. 87 is a diagram showing an embodiment of a prompt of the system of FIG. 78 on a screen.
Figure 88:
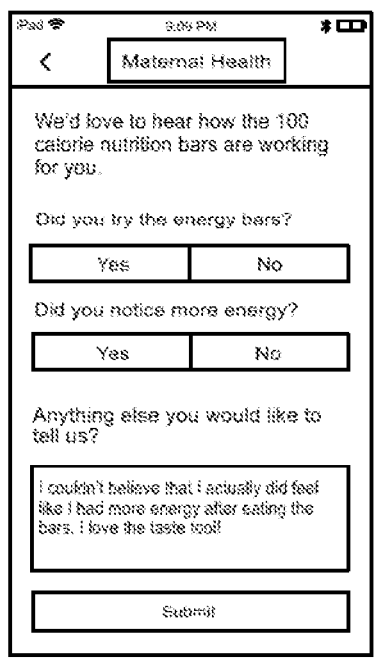
FIG. 88 is a diagram showing an embodiment of an evaluation screen of the system of FIG. 78.

FIG. 87 illustrates an embodiment of a prompt on a screen that the system can be configured to provide to the user to prompt the user to input information related to her selected activities. The system can be configured to prompt the user to input information related to her selected activities at any of a variety of times, as discussed herein (e.g., upon login to the system, upon login to the user's client terminal, after passage of a predetermined amount of time since the user accepted an activity, etc.). FIG. 88 illustrates an embodiment of an evaluation screen that the system can be configured to provide upon the user agreeing to input information in response to the prompt. In this illustrated embodiment, the evaluation screen is asking the user about use of the consumable product purchased through the supplemental nutrition screen of FIG. 86.

Figure 94:
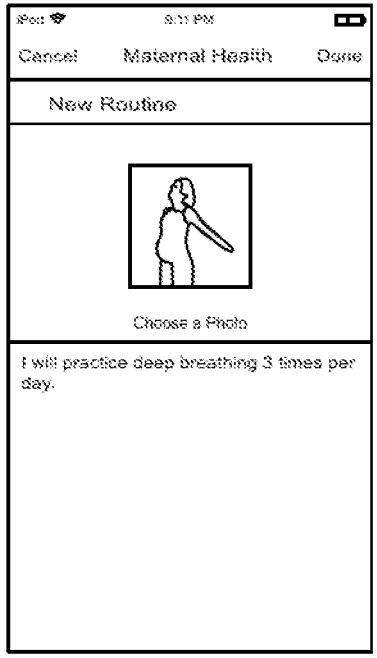
FIG. 94 is a diagram showing an embodiment of a deep breathing routine screen of the system of FIG. 78.

FIG. 89 illustrates an embodiment of a stress screen that the system can be configured to provide upon the user's selection of the "Stress" option on the home screen. In general, the stress screen can identify various aspects related to elements relevant to an expectant mother's stress level. Each of the various aspects can be selectable by a user to learn more about that selected aspect. As in this illustrated embodiment, the stress screen can include selectable aspects of "journaling," "deep breathing," "yoga," and "self massage." Selection of an aspect on the stress screen can cause the system to present the user with one or more recommended activities related to that aspect. As discussed herein, the one or more recommended activities can be customized for the user, e.g., based upon analysis by an analysis module of the system, and the user can be prompted to accept or decline each of the one or more recommended activities. FIG. 90 illustrates an embodiment of a journaling screen that the system can be configured to provide upon the user's selection of the "journaling" option on the stress screen. In this illustrated embodiment, similar to the movement screen discussed above, the user can choose to accept or decline the recommended activity (writing about a stressful situation in a notebook) by selecting a thumbs up icon (accept) or on a thumbs down icon (decline). The journaling screen in this illustrated embodiment explains the recommended activity using text and a video, but recommended activities can be explained in additional or alternative ways, as discussed herein. FIG. 91 illustrates an embodiment of a deep breathing screen that the system can be configured to provide upon the user's selection of the "deep breathing" option on the stress screen. As in this illustrated embodiment, the deep breathing screen can include a recommended activity of deep breathing, can include accept/decline selectable icons, and can include explanatory information thereof, which includes text and an image in this illustrated embodiment, but audio, and/or video can be provided in addition to or in alternative. If the user accepts the deep breathing recommendation, the system can be configured to provide the user with a supplemental deep breathing screen, an embodiment of which is shown in FIG. 92. As in this illustrated embodiment, the deep breathing screen can include one or more recommend activities, which in this illustrated embodiment includes creating a deep breathing routine, which the user can accept via accept icon or decline via decline icon, and a learning more about healthy habits. FIGS. 93 and 93A illustrate an embodiment of a healthy habits screen that the system can be configured to provide in response to the user indicating via the supplemental deep breathing screen that she would like to learn more about healthy habits. The healthy habits screen can be scrollable, as in this illustrated embodiment, similar to the scrollable home screen of FIGS. 81 and 82. FIG. 94 illustrates an embodiment of a deep breathing routine screen that the system can be configured to provide in response to the user indicating via the supplemental deep breathing screen that she would like to create a deep breathing routine. The user's selection of the "yoga" and "self massage" options on the stress screen can cause screens similar to the journaling screen of FIG. 90 and the deep breathing screen of FIG. 91 to be provided to the user.

Figure 95:
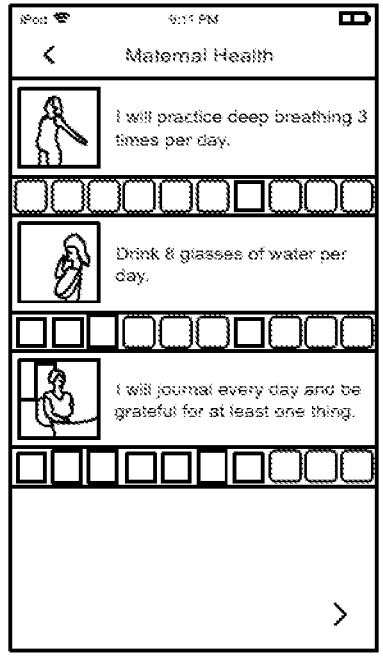
FIG. 95 is a diagram showing an embodiment of a routines screen of the system of FIG. 78.

The user accepting an activity can cause a routines screen to be displayed, thereby allowing the user to identify all his/her current activities and see how the most recently-accepted activity fits into her regular routine. The system can be configured to provide a routines screen upon the user's selection of the "Routines" option on the menu screen. FIG. 95 illustrates an embodiment of a routines screen. In general, the routines screen can identify the activities that the user has previously accepted, which in this illustrated embodiment include practicing deep breathing three times a day, drinking eight glasses of water per day, and journaling every day and being grateful for at least one thing.

Figure 96:
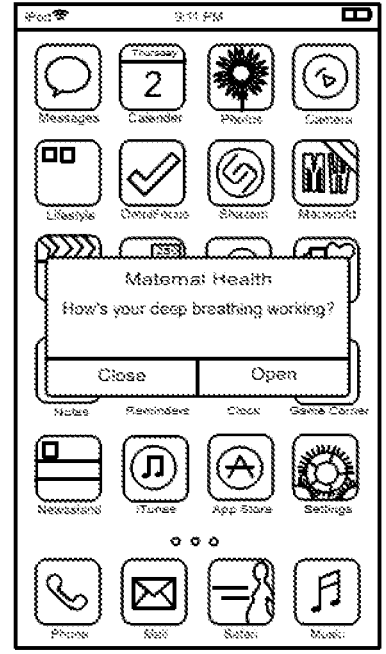
FIG. 96 is a diagram showing another embodiment of a prompt of the system of FIG. 78 on a screen.
Figure 97:
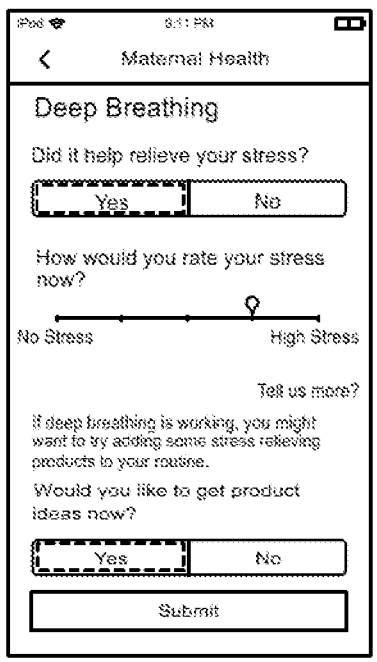
FIG. 97 is a diagram showing another embodiment of an evaluation screen of the system of FIG. 78.
Figure 98:
FIG. 98 is a diagram showing an embodiment of a products screen of the system of FIG. 78.
Figure 99:
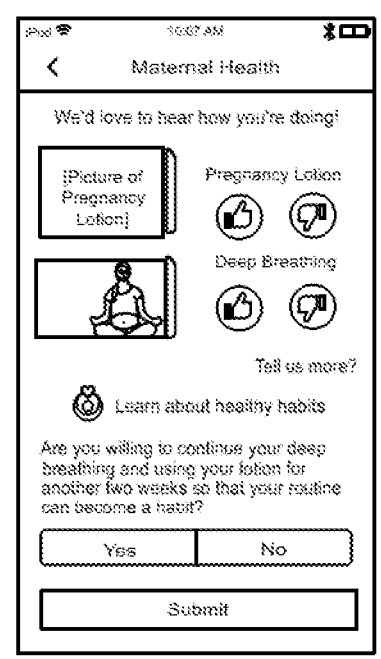
FIG. 99 is a diagram showing another embodiment of an evaluation screen of the system of FIG. 78.

FIG. 96 illustrates an embodiment of a prompt on a screen that the system can be configured to provide upon the user asking the user to provide input about a specific activity, which in this illustrated embodiment is the deep breathing routine created via the deep breathing routine screen of FIG. 94. FIG. 97 illustrates an embodiment of an evaluation screen that the system can be configured to provide upon the user agreeing to input information in response to the prompt of FIG. 96. As in this illustrated embodiment, the evaluation screen can ask the user whether the specific activity (e.g., deep breathing routine) helped the user, how the user thinks the specific activity affected her stress level (e.g., on a scale of the user having no stress to the user having high stress), and whether the user would like to receive consumable product recommendations that can help with his/her deep breathing routine (e.g., are products that can help reduce stress and/or that can make it easier for the user to perform and/or maintain the deep breathing routine). If the user indicates a desire to receive the consumable product recommendations, the system can be configured to provide the user with a products screen, an embodiment of which is shown in FIG. 98. As in this illustrated embodiment, a plurality of consumable products can be recommended, with the user having the option to scroll through the recommended products and to purchase or receive a coupon for each of the recommended products. FIG. 99 illustrates another embodiment of an evaluation screen that the system can be configured to provide at a time subsequent to the user's purchase of one or more of the consumable products recommended on the products screen (e.g., at a predetermined time after the user's purchase, at a predetermined time after the purchased product ships to the user, at a predetermined time related to the user's login to the system, etc.). As in the illustrated embodiments of FIGS. 97 and 99, an evaluation screen can be configured to receive input from the user about outcomes of one or more accepted activities and to provide the user with a reward (e.g., new activity recommendations (e.g., product purchase recommendations, etc.), free consumable products mailed to the user, coupons for consumable products, educational information regarding one or more of her activities, increasing her overall point total, unlocking of the next activity in a set sequence of activities, encouragements, conversational messages, etc.), which can help "train" the user to respond to prompts to provide information.

Figure 100:
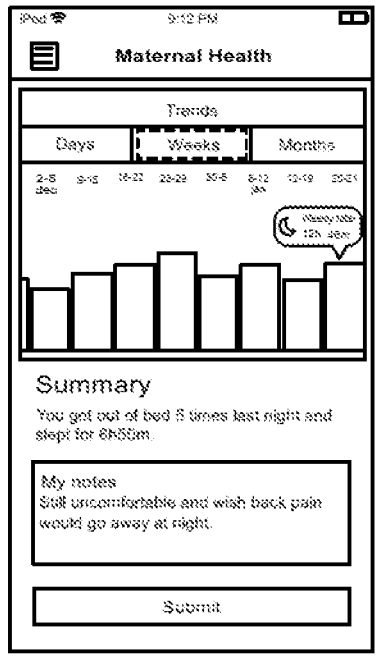
FIG. 100 is a diagram showing an embodiment of a sleep screen of the system of FIG. 78.
Figure 101:
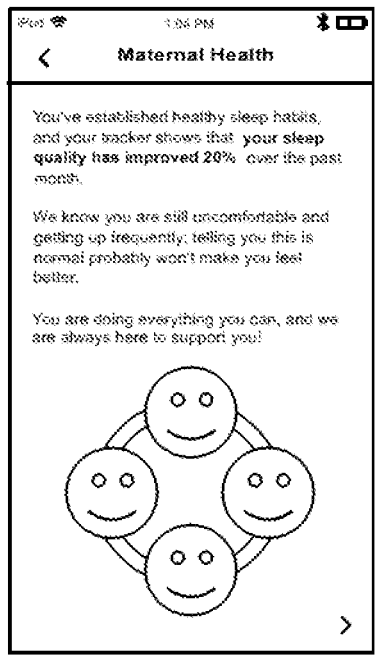
FIG. 101 is a diagram showing an embodiment of a supplemental sleep screen of the system of FIG. 78.

FIG. 100 illustrates an embodiment of a sleep screen that the system can be configured to provide upon the user's selection of the "Sleep" option on the home screen. In general, the sleep screen can provide the user with information regarding her sleep, such as information gathered via a sleep app. As in this illustrated embodiment, the sleep screen can provide the user with historical information about her sleep by day, week, and month graphs, can allow the user to input notes regarding sleep for specific days, weeks, or months, and can provide a summary of the user's sleep by day, week, and month. The system can be configured to provide additional summary information regarding the user's sleep upon the user's selection of the summary on the sleep screen. FIG. 101 illustrates an embodiment of a supplemental sleep screen that the system can be configured to provide upon the user's selection of the summary on the sleep screen. Each of the images on the supplemental sleep screen can be configured to be selected by the user, thereby triggering the playing of a video providing further information about maternal health and sleep.

Figure 102:
FIG. 102 is a diagram showing another embodiment of a prompt of the system of FIG. 78 on a screen.
Figure 103:
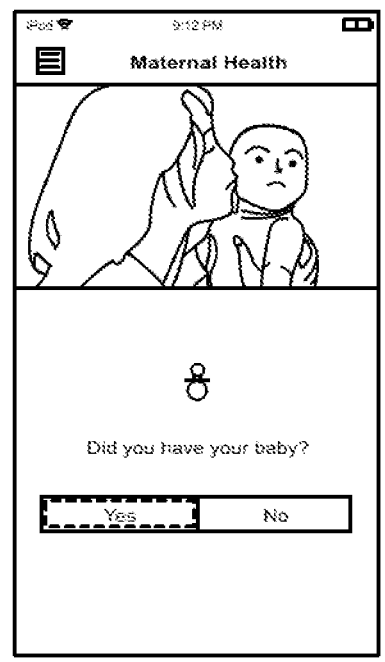
FIG. 103 is a diagram showing an embodiment of a delivery screen of the system of FIG. 78.
Figure 104:
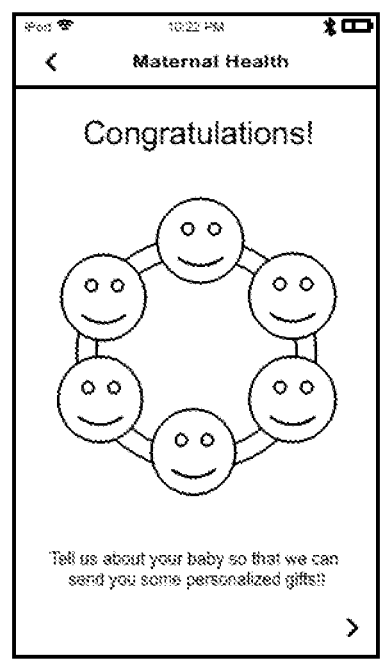
FIG. 104 is a diagram showing an embodiment of a supplemental delivery screen of the system of FIG. 78.

The system can be configured to track the user's due date so as to determine when the user is past her due date. The system can be configured to prompt the user for delivery information when the system determines that the user is past her due date. FIG. 102 illustrates an embodiment of a prompt on a screen that the system can be configured to provide to the user to prompt the user to input information related to being past her due date. FIG. 103 illustrates an embodiment of a delivery screen that the system can be configured to provide upon the user agreeing to input information in response to the prompt of FIG. 102. The delivery screen can ask the user whether she had her baby. In response to an affirmative response, the system can be configured to provide a supplemental delivery screen to the user, an embodiment of which is illustrated in FIG. 104. Each of the images on the supplemental delivery screen can be configured to be selected by the user, thereby triggering the playing of a video providing further information about maternal health post-delivery. The supplemental delivery screen can ask the user to provide information about her baby, e.g., name, birth date, gender, height, weight, etc., which can allow the system to trigger delivery of one or more consumable products to the user, such as trial size consumable products for baby care.

CONCLUSION

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A user management system, comprising:
   a storage device that stores
      a fingerprint that includes a plurality of characteristics unique to an individual, each of the plurality of characteristics being represented by one of a first variable, a second variable, and a third variable, the first variable indicating a first condition of the individual with respect to that characteristic, the second variable indicating a second condition of the individual with respect to that characteristic, and the third variable indicating a neutral position of the individual with respect to that characteristic, the first and second conditions being mutually exclusive, and each of the plurality of characteristics being defaulted to being represented by the third variable, and
      a profile for each of a plurality of activities providing a positive benefit to at least one of wellness, health, and lifestyle; and
   a processor configured to perform functions of
      displaying on a display a prompt to which a user can provide an input in response thereto,
      receiving the input,
      updating one or more of the variables representing the plurality of characteristics based on the received input, thereby updating the fingerprint so as to reflect the user's input,
      comparing the profiles of the plurality of activities with the fingerprint, thereby identifying at least one activity in the plurality of activities that has a profile corresponding to the fingerprint, and
      causing the identified at least one activity to be indicated on the display;
   wherein the received input indicates an opinion of the user with respect to the indicated at least one activity;
   wherein the plurality of characteristics unique to the individual include at least two of whether the individual has a pet, what exercise equipment the individual has access to, the individual's health history with respect to osteoporosis, whether the individual prefers social activities, how many activities in a set sequence of activities the individual has completed, the individual's preferred timing for performing activities, whether the individual prefers indoor or outdoor activities, the individual's activity duration preference, the individual's activity difficulty level preference, the individual's motivation level, whether the individual has indicated an interest in stress management, whether the individual has indicated an interest in weight management, and whether the individual has indicated an interest in engaging in physical activity;
   wherein the user input is received via a user input device that has a capability to make calls;
   wherein the plurality of activities include at least one of talking on the telephone to a family member and talking on the telephone to a friend; and
   wherein the processor is also configured to perform a function of automatically determining that the user engaged in the at least one of talking on the telephone to a family member and talking on the telephone to a friend, the automatic determination including accessing the user input device to determine if a call was made to at least one of the family member and the friend.

2. The system of claim 1, wherein each of the plurality of characteristics is limited to being represented by one of the first, second, and third variables.

3. The system of claim 1, wherein the storage device stores a profile for each of a plurality of consumable products;
   the processor is configured to perform functions of
      comparing the profiles of the plurality of consumable products with the fingerprint, thereby identifying at least one consumable product in the plurality of consumable products that has a profile corresponding to the fingerprint, and
      causing the identified at least one consumable product to be provided to the user;
   the received input indicates an opinion of the user with respect to the provided at least one consumable product;

the consumable products include at least two of a lotion, a soap, a vitamin, clothing, bedding, a computer accessory, a mobile phone accessory, an app, an exercise product, a shampoo, a conditioner, a face wash, and a face cream; and the plurality of characteristics unique to the individual include at least two of whether the individual has a pet, what exercise equipment the individual has access to, the individual's health history with respect to osteoporosis, whether the individual prefers social activities, how many activities in a set sequence of activities the individual has completed, the individual's preferred timing for performing activities, whether the individual prefers indoor or outdoor activities, the individual's activity duration preference, the individual's activity difficulty level preference, the individual's motivation level, whether the individual has indicated an interest in stress management, whether the individual has indicated an interest in weight management, and whether the individual has indicated an interest in engaging in physical activity.

4. The system of claim 3, wherein causing the identified at least one consumable product to be provided to the user includes mailing the at least one consumable product to the user for free.

5. The system of claim 1, wherein the updating includes changing the fingerprint by multiplying the variable of the one or more of the plurality of characteristics by a scaling factor that is dependent on a type of the received input.

6. The system of claim 5, wherein the type of the received input is selected from the group consisting of an indication of a decision to engage in an activity immediately, an indication of a decision to engage in an activity at a future point in time, engagement in an activity, repeated performance of an activity, an indication of a decision to not engage in an activity previously indicated as an activity that the user would engage in immediately, an indication of a decision to not engage in an activity previously indicated as an activity that the user would engage in at a future time, an indication of a beneficial experience as a result of engaging in an activity, and an indication of a negative experience as a result of engaging in an activity.

7. The system of claim 1, wherein each of the plurality of characteristics is classified as being of a first type of characteristic that changes over time at a first rate or as being of a second type of characteristic that changes over time at a second rate that is slower than the first rate; and the processor updates the one or more of the variables based on whether the characteristics represented by the one or more of the variables are classified as being of the first type or of the second type.

8. The system of claim 1, wherein the processor is also configured to perform functions of displaying on the display a second prompt to which the user can provide a second input in response thereto;

receiving the second input, the second input being indicative of the user acting on the identified at least one activity; and causing the variable of at least one of the first, second, and third variables to be modified to be closer to the values of the factors of the identified at least one activity in response to the second input being indicative of a positive benefit to at least one of the user's health, wellbeing, and lifestyle.

9. The system of claim 1, wherein each of the profiles includes a plurality of factors unique to the activity, each of the plurality of factors unique to the activity being represented by a numeric value;

each of the first, second, and third variables is represented by a numeric value; and the updating includes subtracting the numeric value of the one of the first, second, and third variables for each of the plurality of characteristics from the numeric value of a corresponding one of the plurality of factors, resulting in a first array of values, multiplying the first array by a scaling factor, resulting in a second array, and adding the second array to the fingerprint.

10. The system of claim 9, wherein the scaling factor is dependent on a type of the received input; and the type of the received input is selected from the group consisting of an indication of a decision to engage in an activity immediately, an indication of a decision to engage in an activity at a future point in time, engagement in an activity, repeated performance of an activity, an indication of a decision to not engage in an activity previously indicated as an activity that the user would engage in immediately, an indication of a decision to not engage in an activity previously indicated as an activity that the user would engage in at a future time, an indication of a beneficial experience as a result of engaging in an activity, and an indication of a negative experience as a result of engaging in an activity.

11. A user management system, comprising:

a storage device that stores a fingerprint that includes a plurality of characteristics unique to an individual, each of the plurality of characteristics being represented by one of a first variable, a second variable, and a third variable, the first variable indicating a first condition of the individual with respect to that characteristic, the second variable indicating a second condition of the individual with respect to that characteristic, and the third variable indicating a neutral position of the individual with respect to that characteristic, the first and second conditions being mutually exclusive, and each of the plurality of characteristics being defaulted to being represented by the third variable, and a plurality of suggestions that are described by two or more factors that each have a value, and each of the plurality of suggestions includes a suggestion for a specific activity that provides a positive benefit to at least one of health, wellbeing, and lifestyle; and a processor configured to perform functions of displaying on a display a prompt to which a user can provide an input in response thereto, receiving the input, updating one or more of the variables representing the plurality of characteristics based on the received input, thereby updating the fingerprint so as to reflect the user's input, after the updating, selecting at least one of the suggestions by comparing the values of the two or more factors with the variables of the plurality of characteristics unique to the individual and determining which one or more of the plurality of suggestions has factors with values that most closely match the variables of the plurality of characteristics, and causing the determined one or more of the suggestions to be communicated to the user;

wherein the input is received via a user input device that has a capability to make calls;

wherein the determined one or more of the suggestions include at least one of talking on the telephone to a family member and talking on the telephone to a friend; and wherein the processor is also configured to perform a function of automatically determining that the user engaged in the at least one of talking on the telephone to a family member and talking on the telephone to a friend, the automatic determination including accessing the user input device to determine if a call was made to at least one of the family member and the friend.

12. The system of claim 11, wherein the activities include at least two of an athletic activity, eating a healthy food, drinking a healthy drink, forming a healthy habit, engaging in an individual sport, engaging in a group sport, gardening, taking a walk, jogging, swimming, stretching, yoga, pilates, tai chi, meditation, doing housework, taking an in-person educational course regarding at least one of wellness, health, and lifestyle, taking an online educational course regarding at least one of wellness, health, and lifestyle, deep breathing, martial arts, making art, playing music, writing a handwritten letter, writing an electronic letter, talking on the telephone to a family member, talking on the telephone to a friend, bringing a meal to work, cooking a meal at home, sleeping, walking a dog, quitting smoking, reducing an amount of smoking per day, quitting drinking coffee, reducing an amount of coffee intake per day, stopping drinking coffee after a certain hour of the day, establishing a bed time, purchasing a device that assists in at least one of a wellness, health, or lifestyle behavior, using a device that assists in at least one of a wellness, health, or lifestyle behavior, reducing an intake amount of an unhealthy food, reducing an intake amount of an alcoholic beverage, and establishing a waking time; and the plurality of characteristics unique to the individual include at least two of whether the individual has a pet, what exercise equipment the individual has access to, the individual's health history with respect to osteoporosis, whether the individual prefers social activities, how many activities in a set sequence of activities the individual has completed, the individual's preferred timing for performing activities, whether the individual prefers indoor or outdoor activities, the individual's activity duration preference, the individual's activity difficulty level preference, the individual's motivation level, whether the individual has indicated an interest in stress management, whether the individual has indicated an interest in weight management, and whether the individual has indicated an interest in engaging in physical activity.

13. The system of claim 12, wherein the activities include at least two of an athletic activity, eating a healthy food, drinking a healthy drink, forming a healthy habit, engaging in an individual sport, engaging in a group sport, gardening, taking a walk, jogging, swimming, stretching, yoga, pilates, tai chi, meditation, doing housework, taking an in-person educational course regarding at least one of wellness, health, and lifestyle, taking an online educational course regarding at least one of wellness, health, and lifestyle, deep breathing, martial arts, making art, playing music, writing a handwritten letter, writing an electronic letter, talking on the telephone to a family member, talking on the telephone to a friend, bringing a meal to work, cooking a meal at home, sleeping, walking a dog, quitting smoking, reducing an amount of smoking per day, quitting drinking coffee, reducing an amount of coffee intake per day, stopping drinking coffee after a certain hour of the day, establishing a bed time, purchasing a device that assists in at least one of a wellness, health, or lifestyle behavior, using a device that assists in at least one of a wellness, health, or lifestyle behavior, reducing an intake amount of an unhealthy food, reducing an intake amount of an alcoholic beverage, and establishing a waking time.

14. The system of claim 12, wherein the activities include at least two of eating a healthy food, drinking a healthy drink, doing housework, taking an in-person educational course regarding at least one of wellness, health, and lifestyle, taking an online educational course regarding at least one of wellness, health, and lifestyle, deep breathing, making art, playing music, writing a handwritten letter, writing an electronic letter, talking on the telephone to a family member, talking on the telephone to a friend, bringing a meal to work, cooking a meal at home, sleeping, quitting smoking, reducing an amount of smoking per day, quitting drinking coffee, reducing an amount of coffee intake per day, stopping drinking coffee after a certain hour of the day, establishing a bed time, reducing an intake amount of an unhealthy food, reducing an intake amount of an alcoholic beverage, and establishing a waking time; and the plurality of characteristics unique to the individual include at least two of what exercise equipment the individual has access to, the individual's health history with respect to osteoporosis, whether the individual prefers social activities, how many activities in a set sequence of activities the individual has completed, and whether the individual has indicated an interest in stress management.

15. The system of claim 11, wherein the determined one or more of the suggestions each include a suggestion for a specific product within a specific product category.

16. The system of claim 15, wherein the specific product category includes at least one of lotions, soaps, vitamins, clothing, bedding, computer accessories, mobile phone accessories, apps, exercise products, shampoos, conditioners, face washes, and face creams.

17. The system of claim 16, wherein the processor is also configured to perform a function of causing the specific product to be mailed to the user for free.

18. The system of claim 11, wherein each of the values of the factors is a numeric value;

each of the first, second, and third variables is represented by a numeric value; and the updating includes
subtracting the numeric value of the one of the first, second, and third variables for each of the plurality of characteristics from the numeric value of a corresponding one of the factors, resulting in a first array of values,
multiplying the first array by a scaling factor, resulting in a second array, and
adding the second array to the fingerprint.

19. The system of claim 18, wherein the scaling factor is dependent on a type of the received input; and the type of the received input is selected from the group consisting of an indication of a decision to engage in an activity immediately, an indication of a decision to engage in an activity at a future point in time, engagement in an activity, repeated performance of an activity, an indication of a decision to not engage in an activity previously indicated as an activity that the user would engage in immediately, an indication of a decision to not engage in an activity previously indicated as an activity that the user would engage in at a future time, an indication of a beneficial experience as a result of engaging in an activity, and an indication of a negative experience as a result of engaging in an activity.

20. The system of claim 11, wherein the determined one or more suggestions are communicated to the user via the display.

21. A user management system of comprising:
a storage device that stores
   a fingerprint that includes a plurality of characteristics unique to an individual, each of the plurality of characteristics being represented by one of a first variable, a second variable, and a third variable, the first variable indicating a first condition of the individual with respect to that characteristic, the second variable indicating a second condition of the individual with respect to that characteristic, and the third variable indicating a neutral position of the individual with respect to that characteristic, the first and second conditions being mutually exclusive, and each of the plurality of characteristics being defaulted to being represented by the third variable, and
   a profile for each of a plurality of activities providing a positive benefit to at least one of wellness, health, and lifestyle; and
a processor configured to perform functions of
   displaying on a display a prompt to which a user can provide an input in response thereto,
   receiving the input,
   updating one or more of the variables representing the plurality of characteristics based on the received input, thereby updating the fingerprint so as to reflect the user's input,
   comparing the profiles of the plurality of activities with the fingerprint, thereby identifying at least one activity in the plurality of activities that has a profile corresponding to the fingerprint, and
   causing the identified at least one activity to be indicated on the display;
wherein the received input indicates an opinion of the user with respect to the indicated at least one activity;
wherein the plurality of characteristics unique to the individual include at least two of whether the individual has a pet, what exercise equipment the individual has access to, the individual's health history with respect to osteoporosis, whether the individual prefers social activities, how many activities in a set sequence of activities the individual has completed, the individual's preferred timing for performing activities, whether the individual prefers indoor or outdoor activities, the individual's activity duration preference, the individual's activity difficulty level preference, the individual's motivation level, whether the individual has indicated an interest in stress management, whether the individual has indicated an interest in weight management, and whether the individual has indicated an interest in engaging in physical activity;
wherein the user input is received via a user input device that has a capability to make calls;
wherein the plurality of activities include at least one of taking an in-person educational course regarding at least one of wellness, health, and lifestyle and taking an online educational course regarding at least one of wellness, health, and lifestyle; and
wherein the processor is also configured to perform a function of automatically assessing whether the user enrolled in at least one of the in-person educational course and the online educational course, the automatic assessing including accessing the user input device to determine if a call was made to a facility offering at least one of the in-person educational course and the online educational course.

22. The system of claim 21, wherein each of the plurality of characteristics is limited to being represented by one of the first, second, and third variables.

23. The system of claim 21, wherein the updating includes changing the fingerprint by multiplying the variable of the one or more of the plurality of characteristics by a scaling factor that is dependent on a type of the received input.

24. The system of claim 21, wherein each of the profiles includes a plurality of factors unique to the activity, each of the plurality of factors unique to the activity being represented by a numeric value;
each of the first, second, and third variables is represented by a numeric value; and
the updating includes
   subtracting the numeric value of the one of the first, second, and third variables for each of the plurality of characteristics from the numeric value of a corresponding one of the plurality of factors, resulting in a first array of values,
   multiplying the first array by a scaling factor, resulting in a second array, and
   adding the second array to the fingerprint.

25. A user management system comprising:
a storage device that stores
   a fingerprint that includes a plurality of characteristics unique to an individual, each of the plurality of characteristics being represented by one of a first variable, a second variable, and a third variable, the first variable indicating a first condition of the individual with respect to that characteristic, the second variable indicating a second condition of the individual with respect to that characteristic, and the third variable indicating a neutral position of the individual with respect to that characteristic, the first and second conditions being mutually exclusive, and each of the plurality of characteristics being defaulted to being represented by the third variable, and
   a plurality of suggestions that are described by two or more factors that each have a value, and each of the plurality of suggestions includes a suggestion for a specific activity that provides a positive benefit to at least one of health, wellbeing, and lifestyle; and
a processor configured to perform functions of
   displaying on a display a prompt to which a user can provide an input in response thereto,
   receiving the input,
   updating one or more of the variables representing the plurality of characteristics based on the received input, thereby updating the fingerprint so as to reflect the user's input,
   after the updating, selecting at least one of the suggestions by comparing the values of the two or more factors with the variables of the plurality of characteristics unique to the individual and determining which one or more of the plurality of suggestions has factors with values that most closely match the variables of the plurality of characteristics, and causing the determined one or more of the suggestions to be communicated to the user;

wherein the input is received via a user input device that has a capability to make calls;

wherein the determined one or more of the suggestions include at least one of taking an in-person educational course regarding at least one of wellness, health, and lifestyle and taking an online educational course regarding at least one of wellness, health, and lifestyle; and wherein the processor is also configured to perform a function of automatically assessing whether the user enrolled in at least one of the in-person educational course and the online educational course, the automatic assessing including accessing the user input device to determine if a call was made to a facility offering at least one of the in-person educational course and the online educational course.

* * * * *